United States Patent
Duan et al.

(10) Patent No.: US 9,771,320 B2
(45) Date of Patent: Sep. 26, 2017

(54) CARBOCYCLIC SULFONE RORγ MODULATORS

(71) Applicant: BRISTOL-MYERS SQUIBB COMPANY, Princeton, NJ (US)

(72) Inventors: Jingwu Duan, Yardley, PA (US); T. G. Murali Dhar, Newtown, PA (US); Bin Jiang, Bryn Mawr, PA (US); Zhonghui Lu, King of Prussia, PA (US); Ananta Karmakar, Bangalore (IN); Arun Kumar Gupta, Bangalore (IN); Carolyn A. Weigelt, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/109,741

(22) PCT Filed: Jan. 5, 2015

(86) PCT No.: PCT/US2015/010085
§ 371 (c)(1),
(2) Date: Jul. 5, 2016

(87) PCT Pub. No.: WO2015/103508
PCT Pub. Date: Jul. 19, 2015

(65) Prior Publication Data
US 2016/0326103 A1  Nov. 10, 2016

Related U.S. Application Data

(60) Provisional application No. 61/923,911, filed on Jan. 6, 2014.

(51) Int. Cl.
C07C 317/14 (2006.01)
C07D 213/81 (2006.01)
C07D 401/04 (2006.01)
C07D 237/08 (2006.01)
C07C 317/20 (2006.01)
C07C 317/30 (2006.01)
C07C 317/46 (2006.01)
C07D 471/04 (2006.01)
(Continued)

(52) U.S. Cl.
CPC .......... *C07C 317/14* (2013.01); *C07C 317/20* (2013.01); *C07C 317/22* (2013.01); *C07C 317/30* (2013.01); *C07C 317/32* (2013.01); *C07C 317/44* (2013.01); *C07C 317/46* (2013.01); *C07C 317/50* (2013.01); *C07D 205/04* (2013.01); *C07D 211/36* (2013.01); *C07D 211/62* (2013.01); *C07D 213/30* (2013.01); *C07D 213/40* (2013.01); *C07D 213/56* (2013.01); *C07D 213/75* (2013.01); *C07D 213/81* (2013.01); *C07D 213/85* (2013.01); *C07D 231/12* (2013.01); *C07D 237/08* (2013.01); *C07D 239/38* (2013.01); *C07D 241/12* (2013.01); *C07D 257/04* (2013.01); *C07D 261/08* (2013.01); *C07D 263/32* (2013.01); *C07D 271/06* (2013.01); *C07D 285/06* (2013.01); *C07D 295/108* (2013.01); *C07D 295/155* (2013.01); *C07D 295/18* (2013.01); *C07D 295/185* (2013.01); *C07D 295/20* (2013.01); *C07D 295/22* (2013.01); *C07D 303/06* (2013.01); *C07D 303/34* (2013.01); *C07D 305/14* (2013.01); *C07D 309/04* (2013.01); *C07D 309/14* (2013.01); *C07D 317/44* (2013.01); *C07D 319/20* (2013.01); *C07D 401/04* (2013.01); *C07D 471/04* (2013.01); *C07D 471/10* (2013.01); *C07C 2601/02* (2017.05); *C07C 2601/04* (2017.05); *C07C 2601/08* (2017.05); *C07C 2601/10* (2017.05); *C07C 2601/14* (2017.05); *C07C 2601/16* (2017.05); *C07C 2602/08* (2017.05)

(58) Field of Classification Search
None
See application file for complete search history.

(56) References Cited

U.S. PATENT DOCUMENTS 9,458,171 B2  10/2016  Duan et al.

FOREIGN PATENT DOCUMENTS

WO   WO 2013/169588   11/2013
WO   WO 2014/028669    2/2014
(Continued)

*Primary Examiner* — Samantha Shterengarts
(74) *Attorney, Agent, or Firm* — Elliott Korsen

(57) ABSTRACT

Described are RORγ modulators of the formula (I), or stereoisomers, tautomers, pharmaceutically acceptable salts, solvates, or prodrugs thereof, wherein all substituents are defined herein. Also provided are pharmaceutical compositions comprising the same. Such compounds and compositions are useful in methods for modulating RORγ activity in a cell and methods for treating a subject suffering from a disease or disorder in which the subject would therapeutically benefit from modulation of RORγ activity, for example, autoimmune and/or inflammatory disorders.

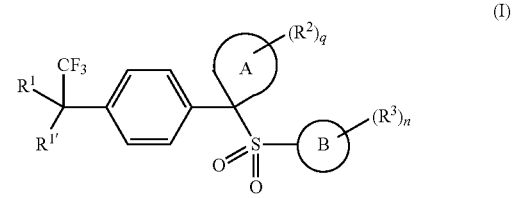

15 Claims, No Drawings

(51) Int. Cl.

| | | |
|---|---|---|
| *C07D 213/30* | (2006.01) | |
| *C07D 213/56* | (2006.01) | |
| *C07D 309/04* | (2006.01) | |
| *C07D 309/14* | (2006.01) | |
| *C07D 317/44* | (2006.01) | |
| *C07D 231/12* | (2006.01) | |
| *C07D 239/38* | (2006.01) | |
| *C07D 241/12* | (2006.01) | |
| *C07D 471/10* | (2006.01) | |
| *C07D 257/04* | (2006.01) | |
| *C07D 261/08* | (2006.01) | |
| *C07D 263/32* | (2006.01) | |
| *C07D 271/06* | (2006.01) | |
| *C07D 211/36* | (2006.01) | |
| *C07D 295/16* | (2006.01) | |
| *C07D 295/20* | (2006.01) | |
| *C07D 303/06* | (2006.01) | |
| *C07D 305/14* | (2006.01) | |
| *C07D 205/04* | (2006.01) | |
| *C07D 211/62* | (2006.01) | |
| *C07D 213/40* | (2006.01) | |
| *C07D 213/75* | (2006.01) | |
| *C07D 295/155* | (2006.01) | |
| *C07D 295/108* | (2006.01) | |
| *C07D 319/20* | (2006.01) | |
| *C07D 285/06* | (2006.01) | |
| *C07D 295/18* | (2006.01) | |
| *C07D 295/22* | (2006.01) | |
| *C07D 303/34* | (2006.01) | |
| *C07C 317/22* | (2006.01) | |
| *C07C 317/44* | (2006.01) | |
| *C07C 317/32* | (2006.01) | |
| *C07C 317/50* | (2006.01) | |
| *C07D 213/85* | (2006.01) | |
| *C07D 295/185* | (2006.01) | |

(56) References Cited

FOREIGN PATENT DOCUMENTS

| | | |
|---|---|---|
| WO | WO2014/062938 | 4/2014 |
| WO | WO2015/035278 | 3/2015 |
| WO | WO2015/042212 | 3/2015 |
| WO | WO2015/103507 | 7/2015 |
| WO | WO2015/103508 | 7/2015 |
| WO | WO2015/103509 | 7/2015 |
| WO | WO2015/103510 | 7/2015 |

CARBOCYCLIC SULFONE RORγ MODULATORS

CROSS-REFERENCE TO RELATED APPLICATIONS

This application claims the benefit of U.S. Provisional Application No. 61/923,911, filed Jan. 6, 2014, the disclosure of which is incorporated herein by reference in its entirety.

FIELD OF THE INVENTION

This invention relates to modulators of the retinoid-related orphan receptor RORγ and methods for using such modulators. The compounds described herein can be particularly useful for diagnosing, preventing, or treating a variety of diseases and disorders in humans and animals. Exemplary disorders include, but are not limited to, psoriasis, rheumatoid arthritis, inflammatory bowel disease, Crohn's disease, ulcerative colitis, acute graft-versus-host disease, psoriatic arthritis, ankylosing spondylitis and multiple sclerosis.

BACKGROUND OF THE INVENTION

The retinoid-related orphan receptors RORα, RORβ, and RORγ play an important role in numerous biological processes including organ development, immunity, metabolism, and circadian rhythms. See, for example, Dussault et al. in Mech. Dev. (1998) vol. 70, 147-153; Andre et al. in EMBO J. (1998) vol. 17, 3867-3877; Sun et al. in Science (2000) vol. 288, 2369-2373; and Jetten in Nucl. Recept. Signal. (2009) vol. 7, 1-32.

RORγ is expressed in several tissues including the thymus, kidney, liver, and muscle. Two isoforms of RORγ have been identified: RORγ1 and RORγ2 (also known, respectively, as RORγ and RORγt). See, for example, Hirose et al. in Biochem. Biophys. Res. Commun. (1994) vol. 205, 1976-1983; Oritz et al. in Mol. Endocrinol. (1995) vol. 9, 1679-1691; and He et al. in Immunity (1998) vol. 9, 797-806. Expression of RORγt is restricted to lymphoid cell types including CD4+CD8+ thymocytes, IL-17 producing T helper (Th17) cells, lymphoid tissue inducer (LTi) cells, and γδ cells. RORγt is essential for the development of lymph nodes and Peyer's patches and for the normal differentiation of Th17, γδ, and LTi cells. See, for example, Sun et al. in Science (2000) vol. 288, 2369-2373; Ivanov et al. in Cell (2006) vol. 126, 1121-1133; Eberl et al. in Nat. Immunol. (2004) vol. 5, 64-73; Ivanov et al. in Semin. Immunol. (2007) vol. 19, 409-417; and Cua and Tato in Nat. Rev. Immunol. (2010) vol. 10, 479-489.

Proinflammatory cytokines such as IL-17A (also referred to as IL-17), IL-17F, and IL-22 produced by Th17 cells and other RORγ+ lymphocytes activate and direct the immune response to extracellular pathogens. See, for example, Ivanov et al. in Semin. Immunol. (2007) vol. 19: 409-417; and Marks and Craft in Semin. Immunol. (2009) vol. 21, 164-171. RORγ directly regulates IL-17 transcription and disruption of RORγ in mice attenuates IL-17 production. See, for example, Ivanov et al. in Cell (2006) vol. 126, 1121-1133.

Dysregulated production of IL-17 has been implicated in several human autoimmune and inflammatory diseases including multiple sclerosis, rheumatoid arthritis, psoriasis, inflammatory bowel disease (IBD), and asthma. See, for example, Lock et al. in Nat. Med. (2002) vol. 8, 500-508; Tzartos et al. in Am. J. Pathol. (2008) vol. 172, 146-155; Kotake et al. in J. Clin. Invest. (1999) vol. 103, 1345-1352; Kirkham et al. in Arthritis Rheum. (2006) vol. 54, 1122-1131; Lowes et al. in J. Invest. Dermatol. (2008) vol. 128, 1207-1211; Leonardi et al. in N. Engl. J. Med. (2012) vol. 366, 1190-1199; Fujino et al. in Gut (2003) vol. 52, 65-70; Seiderer et al. in Inflamm. Bowel Dis. (2008) vol. 14, 437-445; Wong et al. in Clin. Exp. Immunol. (2001) vol. 125, 177-183; and Agache et al. in Respir. Med. (2010) 104: 1131-1137. In murine models of these diseases, inhibition of IL-17 function by neutralizing antibodies or genetic disruption of IL-17 or IL-17 receptor ameliorates the disease course or clinical symptoms. See, for example, Hu et al. in Ann. N.Y. Acad. Sci. (2011) vol. 1217, 60-76.

Disruption of RORγ in mice also attenuates disease progression or severity in animal models of autoimmunity and inflammation including experimental autoimmune encephalomyelitis (EAE), imiquimod induced psoriasis, colitis, and allergic airway disease. See, for example, Ivanov et al. in Cell (2006) vol. 126, 1121-1133; Yang et al. in Immunity (2008) vol. 28, 29-39; Pantelyushin et al. in J. Clin. Invest. (2012) vol. 122, 2252-2256; Leppkes et al. in Gastroenterology (2009) vol. 136, 257-267; and Tilley et al. in J. Immunol. (2007) vol. 178, 3208-3218.

Each of the references in this Background section is hereby incorporated herein by reference in its entirety for all purposes.

Therapeutic agents exist to treat a variety of inflammatory and autoimmune diseases, but there still remains a significant unmet medical need in these therapeutic areas. Given the role of IL-17 in human disease and the validation of IL-17 and RORγ as targets in murine disease models, compounds capable of modulating RORγt activity are contemplated to provide a therapeutic benefit in the treatment of multiple immune and inflammatory disorders.

SUMMARY OF THE INVENTION

In one aspect, the invention comprises compounds of the formula (I),

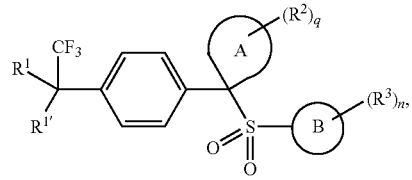

or pharmaceutically acceptable salts thereof, wherein all substituents are defined herein. The invention includes stereoisomers, tautomers, pharmaceutically acceptable salts, solvates, or prodrugs thereof.

In another aspect, the invention comprises pharmaceutical compositions comprising a compound according to formula (I), stereoisomeric form or pharmaceutically acceptable salt, as described herein, and a pharmaceutically acceptable carrier, excipient, or diluent.

In another aspect, the invention comprises methods for antagonizing RORγ in a cell comprising contacting the cell with an effective amount of a compound according to formula (I), stereoisomeric form or pharmaceutically acceptable salt, as described herein. This aspect may be conducted in vitro or in vivo.

3

In another aspect, the invention comprises methods for treating a subject suffering from a disease or disorder modulated by RORγ, the method comprising administering to a subject a therapeutically effective amount of compound according to formula (I), stereoisomeric form, pharmaceutically acceptable salt or pharmaceutical composition as described herein.

In another aspect, the invention comprises a method for treating a disease or disorder selected from an inflammatory disease or disorder, an autoimmune disease or disorder, an allergic disease or disorder, a metabolic disease or disorder, and/or cancer in a subject, the method comprising administering to the subject a therapeutically effective amount of compound according to formula (I), or a stereoisomeric form, pharmaceutically acceptable salt or pharmaceutical composition as described herein.

DETAILED DESCRIPTION OF THE INVENTION

In one aspect, the invention comprises compounds of formula (I),

I

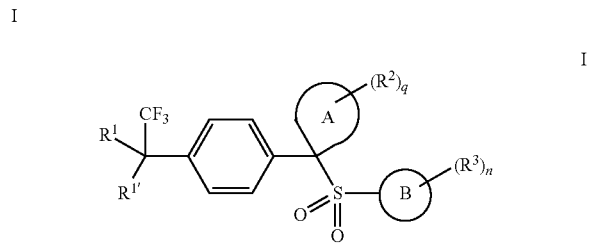

or stereoisomers, tautomers, pharmaceutically acceptable salts, solvates, or prodrugs thereof, wherein:

A is a 3-, 4- or 5-membered cycloalkyl or cycloalkenyl ring;

B is a, —(CH$_2$)$_r$-3-14 membered carbocycle, or —(CH$_2$)$_r$-5-12 membered heterocycle comprising carbon atoms, and 1-4 heteroatoms selected from N, O, and S(O)$_p$;

$R^1$ and $R^{1'}$ are, independently at each occurrence, hydrogen, halo, CF$_3$, OCF$_3$, CN, NO$_2$, —(CH$_2$)$_r$OR$^{1b}$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^{1a}$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;

$R^{1a}$ is, independently at each occurrence, hydrogen, =O, halo, OCF$_3$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;

4

$R^{1b}$ is, independently at each occurrence, hydrogen, CF$_3$, —(CH$_2$)$_r$OR$^b$, —(CH$_2$)$_r$S(O)$_p$R$^b$, —(CH$_2$)$_r$C(O)R$^{1d}$, —(CH$_2$)$_r$C(O)OR$^b$, —(CH$_2$)$_r$OC(O)R$^b$, —(CH2)rNR$^{11}$R$^{11}$, —(CH$_2$)$_r$C(O)NR$^{11}$R$^{11}$, —(CH2)rNR$^b$C(O)R$^{1c}$, —(CH2)rNR$^b$C(O)OR$^c$, —(CH2)rNR$^b$C(O)NR$^{11}$R$^{11}$, —(CH2)rS(O)$_2$NR$^{11}$R$^{11}$, —(CH2)rNR$^b$S(O)$_2$R$^c$, C$_{1-6}$ alkyl substituted with 0-2 R$^a$, C$_{1-6}$ haloalkyl, —(CH$_2$)$_p$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-2 R$^a$;

$R^2$ is, independently at each occurrence, hydrogen, C$_{1-6}$ alkyl substituted with 0-3 R$^{2a}$, =CR$^{2a}$R$^{2a}$, C$_{2-6}$ alkenyl substituted with 0-3 R$^{2a}$, —(CH$_2$)$_r$OR$^{2b}$, —(CH$_2$)$_r$C(O)R$^{2b}$, —(CH$_2$)$_r$C(O)OR$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)NR$^{11}$R$^{11}$, —(CH$_2$)$_r$C(O)NR$^{11}$R$^{11}$, —(CH$_2$)$_r$NR$^{2b}$C(O)R$^{2c}$, —(CH$_2$)$_r$NR$^{2b}$C(O)OR$^{2c}$, —(CH$_2$)$_r$NR$^{11}$R$^{11}$, —NR$^{2b}$S(O)$_p$R$^c$, —(CH$_2$)$_r$NR$^{2b}$S(O)$_p$NR$^{11}$R$^{11}$, —(CH2)r-3-10 membered carbocycle substituted with 0-3 R2a or —(CH$_2$)$_r$-4-10 membered heterocycle comprising carbon atoms, and 1-4 heteroatoms selected from N, O, and S(O)$_p$ substituted with 0-3 R$^{2a}$; or one R$^2$ together with an R$^2$ on an adjacent carbon combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, and S(O)$_p$ substituted with 0-3 R$^{2a}$;

$R^{2a}$ is, independently at each occurrence, hydrogen, =O, halo, OCF$_3$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;

$R^{2b}$ is, independently at each occurrence, hydrogen, CF$_3$, —(CH$_2$)$_r$OR$^b$, —(CH$_2$)$_r$S(O)$_p$R$^b$, —(CH$_2$)$_r$C(O)R$^{1d}$, —(CH$_2$)$_r$C(O)OR$^b$, —(CH$_2$)$_r$OC(O)R$^b$, —(CH2)rNR$^{11}$R$^{11}$, —(CH$_2$)$_r$C(O)NR$^{11}$R$^{11}$, —(CH2)rNR$^b$C(O)R$^{1c}$, —(CH2)rNR$^b$C(O)OR$^c$, —(CH2)rNR$^b$C(O)NR$^{11}$R$^{11}$, —(CH2)rS(O)$_2$NR$^{11}$R$^{11}$, —(CH2)rNR$^b$S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-2 R$^a$;

$R^{2c}$ is, independently at each occurrence, hydrogen, C$_{1-6}$ alkyl substituted with 0-3 R$^a$, C$_{2-6}$ alkenyl substituted with 0-3 R$^a$, C$_{3-10}$ cycloalkyl substituted with 0-3 R$^a$, C$_{6-10}$ aryl substituted with 0-3 R$^a$, or —(CH$_2$)$_r$ 5-10 membered heterocycle comprising carbon atoms and 1-4 heteroatoms selected from N, O, and S(O)p, substituted with 0-3 R$^a$;

$R^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, C$_{3-6}$ cycloalkyl substituted with 0-2 R$^d$, or (CH$_2$)$_r$-phenyl substituted with 0-2 R$^a$, a 5-10 membered heterocycle comprising carbon atoms and 1-4 heteroatoms selected from N, O, and S(O)p, substituted with 0-3 R$^a$;

$R^3$ is selected from hydrogen, halo, N$_3$, CN, —(CH$_2$)$_r$OR$^{3b}$, —(CH$_2$)$_r$NR$^{11}$R$^{11}$, C$_{1-6}$ alkyl substituted with 0-3 R$^{3a}$, and C$_{3-10}$ cycloalkyl substituted with 0-3 R$^{3a}$; 4-10 membered heterocycle comprising carbon atoms and 1-4 heteroatoms selected from N, O, and S(O)$_p$, substituted with 0-3 R$^a$, or together with the carbon atoms to which they are attached, one $R^3$ combines with a second $R^3$ located on an adjacent atom to form a 5-7 membered carbocycle or a 5-7 membered heterocycle comprising carbon atoms and 1-4 heteroatom selected from N, O and S(O)p, each optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and S(O)$_p$ substituted with 0-3 $R^a$;

$R^{3b}$ is, independently at each occurrence, hydrogen, $CF_3$, —$(CH2)rOR^b$, —$(CH_2)_rS(O)_pR^b$, —$(CH_2)_rC(O)R^{1a}$, —$(CH_2)_rC(O)OR^b$, —$(CH2)rOC(O)R^b$, —$(CH2)rNR^{11}R^{11}$, —$(CH_2)_rC(O)NR^{11}R^{11}$, —$(CH_2)_rNR^bC(O)R^{1c}$, —$(CH_2)_rNR^bC(O)OR^c$, —$(CH_2)_rNR^bC(O)NR^{11}R^{11}$, —$(CH_2)_rS(O)_2NR^{11}R^{11}$, —$(CH2)r\ NR^bS(O)_2R^c$, $C_{1-6}$ alkyl substituted with 0-3 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and S(O)$_p$ substituted with 0-3 $R^a$;

$R^{11}$ is, independently at each occurrence, hydrogen, $C_{1-6}$ alkyl substituted with 0-3 $R^d$, $CF_3$, $C_{3-10}$ cycloalkyl substituted with 0-3 $R^d$, (CH)$_r$-phenyl substituted with 0-3 $R^d$, or —$(CH_2)_r$-5-7 membered heterocycle comprising carbon atoms and 1-4 heteroatoms selected from N, O, and S(O)$_p$ substituted with 0-3 $R^d$; or, together with the nitrogen atom to which they are attached, one $R^{11}$ combines with a second $R^{11}$ to form a 4-12 membered heterocycle comprising carbon atoms and 1-4 heteroatoms selected from N, O, and S(O)$_p$ substituted with 0-3 $R^d$;

$R^d$ is, independently at each occurrence, hydrogen, =O, halo, $OCF_3$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^f$, $C_{2-6}$ alkynyl substituted with 0-3 $R^f$, —$(CH_2)_r$-3-14 membered carbocycle substituted with 0-3 $R^f$, or —$(CH_2)_r$-5-7 membered heterocycle comprising carbon atoms and 1-4 heteroatoms selected from N, O, and S(O)$_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{2-6}$ alkenyl substituted with 0-3 $R^d$, $C_{3-6}$ cycloalkyl substituted with 0-3 $R^d$, —$(CH_2)_r$-5-7 membered heterocycle comprising carbon atoms and 1-4 heteroatoms selected from N, O, and S(O)$_p$ substituted with 0-3 $R^f$, or (CH$_2$)$_r$-6-10 atom carbocycle substituted with 0-3 $R^d$;

$R^c$ is, independently at each occurrence, $C_{1-6}$ alkyl substituted with 0-3 $R^f$, (CH$_2$)$_r$—$C_{3-6}$ cycloalkyl substituted with 0-3 $R^f$, —$(CH_2)_r$-5-7 membered heterocycle comprising carbon atoms and 1-4 heteroatoms selected from N, O, and S(O)$_p$ substituted with 0-3 $R^f$, or (CH$_2$)$_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CH_2)_rC(O)R^c$, —$NR^eR^e$, —$NR^eC(O)OR^c$, $C(O)NR^eR^e$, —$NR^eC(O)R^c$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, (CH$_2$)$_r$-phenyl substituted with 0-3 $R^f$ or —$(CH_2)_r$-5-7 membered heterocycle comprising carbon atoms and 1-4 heteroatoms selected from N, O, and S(O)$_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, or (CH$_2$)$_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl)$_2$, $SO_2(C_{1-6}$ alkyl), $CO_2H$, $CO_2(C_{1-6}$ alkyl), OH, $C_{3-6}$ cycloalkyl, $CF_3$ or $O(C_{1-6}$ alkyl);

or $R^f$ is, independently at each occurrence, an optionally substituted —$(CH_2)_r$-5-10 membered heterocycle comprising carbon atoms and 1-4 heteroatoms selected from N, O, and S(O), phenyl or $C_{3-6}$ cycloalkyl, each group optionally substituted with 1-3 groups selected from halo, CN, $CF_3$, $C_{1-6}$ alkyl and $O(C_{1-6}$ alkyl);

q and n are independently selected from 0, 1, 2 and 3;
p is 0, 1, or 2; and
r is 0, 1, 2, 3, or 4.

In another aspect, there is provided a compound of Formula (I), or stereoisomers, tautomers, pharmaceutically acceptable salts, solvates, or prodrugs thereof, wherein B is a phenyl ring.

In another aspect, there is provided a compound of Formula (I), or stereoisomers, tautomers, pharmaceutically acceptable salts, solvates, or prodrugs thereof, wherein:
$R^{1'}$ is halo, $CF_3$, or $C_{1-6}$ alkyl; and
$R^1$ is hydrogen, $NH_2$, $CF_3$, halo, $C_{1-6}$ alkyl substituted with 0-3 $R^{1a}$, —$(CH_2)_rOR^{1b}$, or (CH$_2$)$_r$-phenyl substituted with 0-3 $R^{1a}$.

In another aspect, there is provided a compound of Formula (I), or stereoisomers, tautomers, pharmaceutically acceptable salts, solvates, or prodrugs thereof, wherein:
$R^3$ is hydrogen, halo, $N_3$, CN, $OR^{3b}$, —$NH_2$, $NH(C_{1-6}$ alkyl), $N(C_{1-6}$alkyl)$_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$ $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, a —$(CH_2)_r$-5-7 membered heteroaryl comprising carbon atoms and 1-4 heteroatoms selected from N, S or O substituted with 0-3 $R^a$, or a —$(CH_2)_r$-5-10 membered heterocycle comprising carbon atoms and 1-4 heteroatoms selected from N, O, and S(O)$_p$ substituted with 0-3 $R^a$; and $R^{3b}$ is, independently at each occurrence, hydrogen, $C_{1-6}$ alkyl substituted with 0-3 $R^a$ or phenyl substituted with 0-3 $R^a$.

In another aspect, there is provided a compound having the following formula:

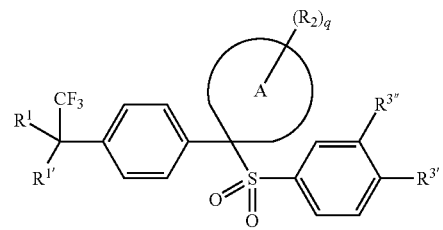

or stereoisomers, tautomers, pharmaceutically acceptable salts, solvates, or prodrugs thereof, wherein:

A is a 3-, 4- or 5-membered cycloalkyl or cycloalkenyl ring;

$R^{1'}$ is halo, $CF_3$, or $C_{1-6}$ alkyl;

$R^1$ is hydrogen, $NH_2$, $CF_3$, halo, $C_{1-6}$ alkyl substituted with 0-3 $R^{1a}$, —$(CH_2)_rOR^{1b}$, or $(CH_2)_r$-phenyl substituted with 0-3 $R^{1a}$;

$R^{1a}$ is, independently at each occurrence, hydrogen, =O, halo, $OCF_3$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, $CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{1b}$ is, independently at each occurrence, hydrogen, $CF_3$, —$(CH_2)_rOR^b$, —$(CH_2)_rS(O)_pR^b$, —$(CH_2)_rC(O)R^{1d}$, —$(CH_2)_rC(O)OR^b$, —$(CH_2)_rOC(O)R^b$, —(CH2)rNR$^{11}$R$^{11}$, —$(CH_2)_rC(O)NR^{11}R^{11}$, —(CH2)rNR$^b$C(O)R$^{1c}$, —(CH2)rNR$^b$C(O)OR$^c$, —(CH2)rNR$^b$C(O)NR$^{11}$R$^{11}$, —(CH2)rS(O)$_2$NR$^{11}$R$^{11}$, —(CH2)rNR$^b$S(O)$_2$R$^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-2 $R^a$;

$R^2$ is, independently at each occurrence, hydrogen, $C_{1-6}$ alkyl substituted with 0-3 $R^{2a}$, =$CR^{2a}R^{2a}$, $C_{2-6}$ alkenyl substituted with 0-3 $R^{2a}$, —$(CH_2)_rOR^{2b}$, —$(CH_2)_rC(O)R^{2b}$, —$(CH_2)_rC(O)OR^{2b}$, —$(CH_2)_rOC(O)OR^{2b}$, —$(CH_2)_rOC(O)NR^{11}R^{11}$, —$(CH_2)_rNR^{2b}C(O)NR^{11}R^{11}$, —$(CH_2)_rC(O)NR^{11}R^{11}$, —$(CH_2)_rNR^{2b}C(O)R^{2c}$, —$(CH_2)_rNR^{2b}C(O)OR^{2c}$, —$(CH_2)_rNR^{11}R^{11}$, —$NR^{2b}S(O)_pR^c$, or —$(CH_2)_r$-5-7 membered heterocycle comprising carbon atoms, and 1-4 heteroatoms selected from N, O, and $S(O)_p$ substituted with 0-3 $R^{2a}$; or one $R^2$ together with an $R^2$ on an adjacent carbon combine to form a fused ring substituted with 0-3 $R^{2a}$, wherein the fused ring is selected from 3-10 membered carbocycle substituted with 0-3 $R^{2a}$, or 3-7 membered heterocycle comprising carbon atoms and 1-4 heteroatoms selected from N, O, and $S(O)_p$ substituted with 0-3 $R^{2a}$;

$R^{2a}$ is hydrogen, $NR^{11}R^{11}$, or $C_{1-6}$ alkyl substituted with 0-3 $R^a$, or 3-10 membered carbocycle substituted with 0-3 $R^a$, $R^{2b}$ is hydrogen, $C_{1-6}$ alkyl substituted with 0-3 $R^a$, $C_{3-6}$ cycloalkyl substituted with 0-3 $R^a$, or 5-7 membered heterocycle comprising carbon atoms and 1-4 heteroatoms selected from N, O, and $S(O)_p$ substituted with 0-3 $R^a$, or $(CH_2)_r$-phenyl substituted with 0-3 $R^a$;

$R^{2c}$ is independently at each occurrence hydrogen, $C_{1-6}$ alkyl substituted with 0-3 $R^a$, $C_{2-6}$ alkenyl substituted with 0-3 $R^a$, $C_{3-6}$ cycloalkyl substituted with 0-3 $R^a$, $C_{6-10}$ aryl substituted with 0-3 $R^a$, or a 5-10 membered heterocycle comprising carbon atoms and 1-4 heteroatoms selected from N, O, and S, substituted with 0-3 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $C_{3-6}$ cycloalkyl substituted with 0-2 $R^d$, or $(CH_2)_r$-phenyl substituted with 0-2 $R^a$, a 5-10 membered heterocycle comprising carbon atoms and 1-4 heteroatoms selected from N, O, and S, substituted with 0-3 $R^a$;

$R^{3'}$ and $R^{3''}$ are, independently, hydrogen, halo, $N_3$, CN, $OR^{3b}$, —$NH_2$, $NH(C_{1-6}$ alkyl), $N(C_{1-6}$ alkyl)$_2$, $C_{1-6}$ alkyl substituted with 0-3 $R^{3a}$ or $C_{3-10}$ cycloalkyl substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $C_{1-6}$ alkyl substituted with 0-3 $R^a$ or phenyl substituted with 0-3 $R^a$;

$R^{11}$ is, independently at each occurrence, hydrogen, $C_{1-6}$ alkyl substituted with 0-3 $R^d$, $CF_3$, $C_{3-10}$ cycloalkyl substituted with 0-3 $R^d$, $(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$; or, together with the nitrogen atom to which they are attached, one $R^{11}$ combines with a second $R^{11}$ to form a 4-7 membered heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^f$, $C_{2-6}$ alkynyl substituted with 0-3 $R^f$, —$(CH_2)_r$-3-14 membered carbocycle, or —$(CH_2)_r$-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{3-6}$ cycloalkyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^f$, or $(CH_2)_r$-6-10 carbocycle substituted with 0-3 $R^d$;

$R^c$ is, independently at each occurrence, $C_{1-6}$ alkyl substituted with 0-3 $R^f$, $(CH_2)_r$—$C_{3-6}$ cycloalkyl substituted with 0-3 $R^f$, —$(CH_2)_r$-5-7 membered heterocycle comprising carbon atoms and 1-4 heteroatoms selected from N, O, and $S(O)_p$ substituted with 0-3 $R^f$, or $(CH_2)_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CH_2)_rC(O)R^c$, —$NR^eR^e$, —$NR^eC(O)OR^c$, —$C(O)NR^eR^e$, —$NR^eC(O)R^c$, $CO_2R^c$, —$NR^eSO_2R^c$, $SO_2R^c$, $C_{1-6}$ alkyl substituted with 0-3 $R^f$, $C_{3-6}$ cycloalkyl substituted with 0-3 $R^f$, $(CH_2)_r$-phenyl substituted with 0-3 $R^f$ or —$(CH_2)_r$-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, and $(CH_2)_r$-phenyl substituted with 0-3 $R^f$;

$R^f$ is, independently at each occurrence, hydrogen, =O, halo, CN, $NH_2$, $NH(C_{1-6}alkyl)$, $N(C_{1-6}alkyl)_2$, $SO_2(C_{1-6}alkyl)$, $CO_2H$, $CO_2(C_{1-6}alkyl)$, OH, $C_{3-6}$ cycloalkyl, $CF_3$ or $O(C_{1-6}alkyl)$;

or $R^f$ is, independently at each occurrence, an optionally substituted —$(CH_2)_r$-5-10 membered heterocycle comprising carbon atoms and 1-4 heteroatoms selected from N, O, and S(O), phenyl or $C_{3-6}$ cycloalkyl, each group optionally substituted with 1-3 groups selected from halo, CN, $CF_3$, $C_{1-6}$ alkyl or $O(C_{1-6}alkyl)$;

p and q are, independently at each occurrence, 0, 1, or 2; and r is 0, 1, 2, 3, or 4.

In another aspect, there is provided a compound of Formula (I), or stereoisomers, tautomers, pharmaceutically acceptable salts, solvates, or prodrugs thereof, wherein:

$R^{1'}$ is F, $CF_3$, $CH_3$, and $CH_2CH_3$; and $R^1$ is:

OH, OMe, F, Cl, $NH_2$, $CH_3$, Ph, Bz, $(CH_2)_2Ph$,

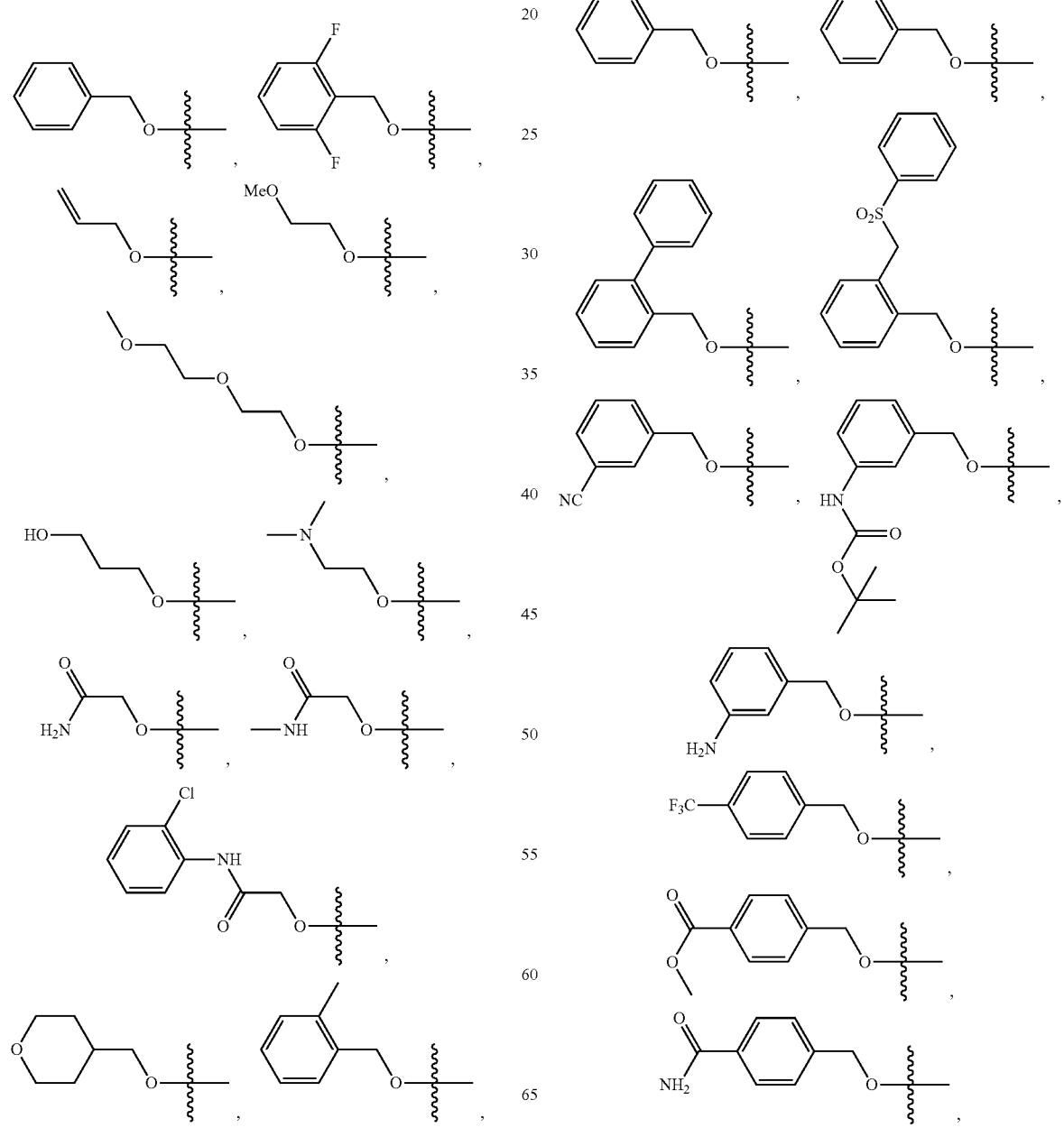

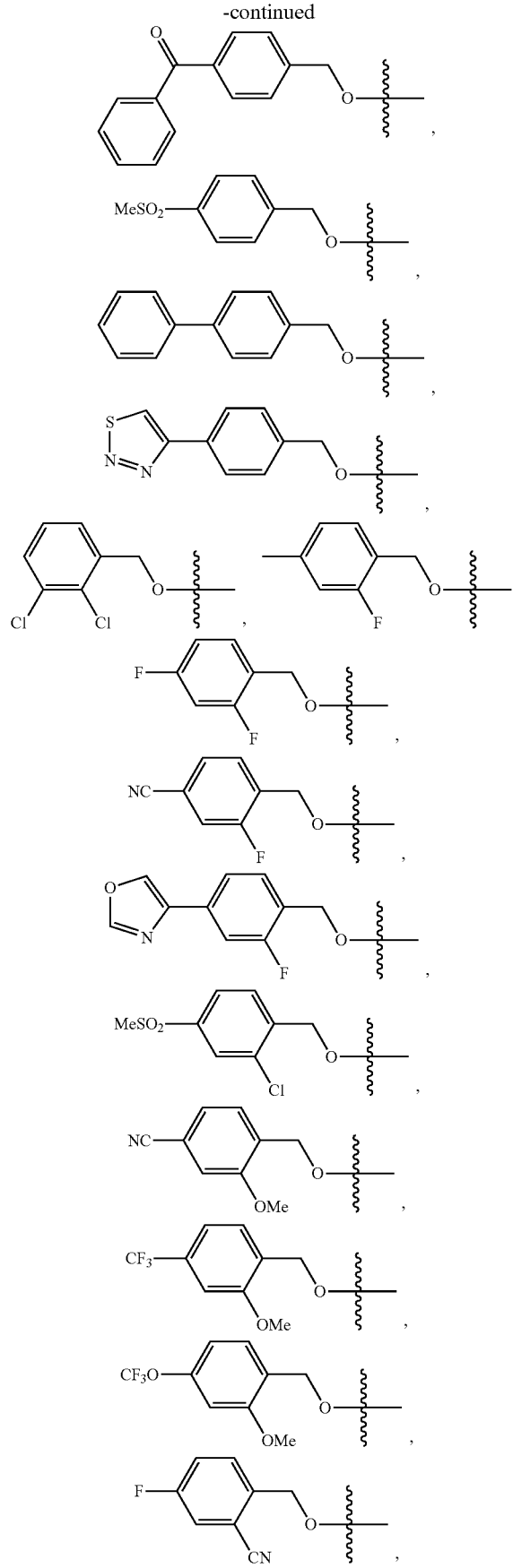
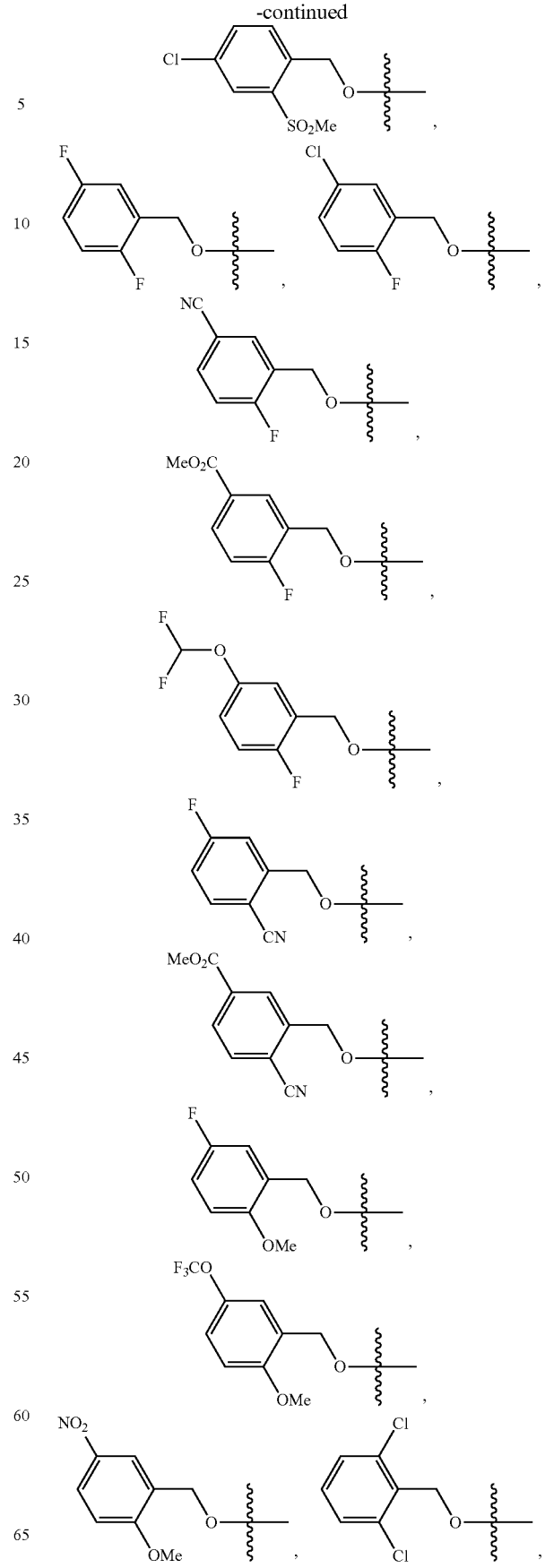

-continued
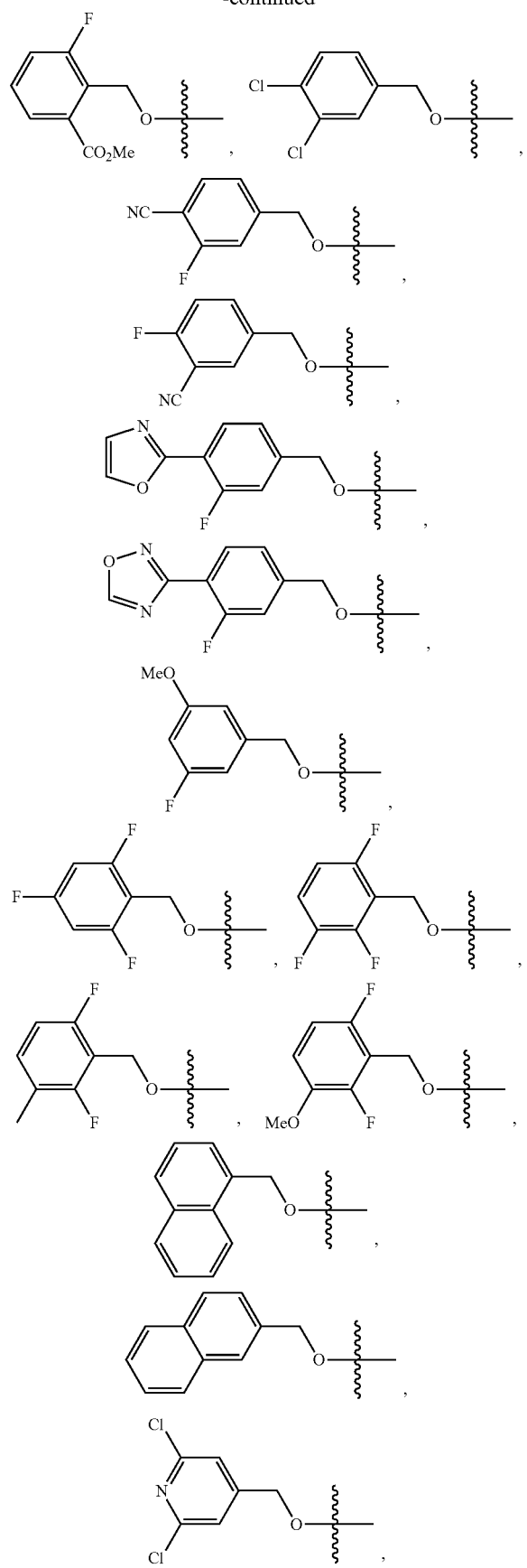
-continued
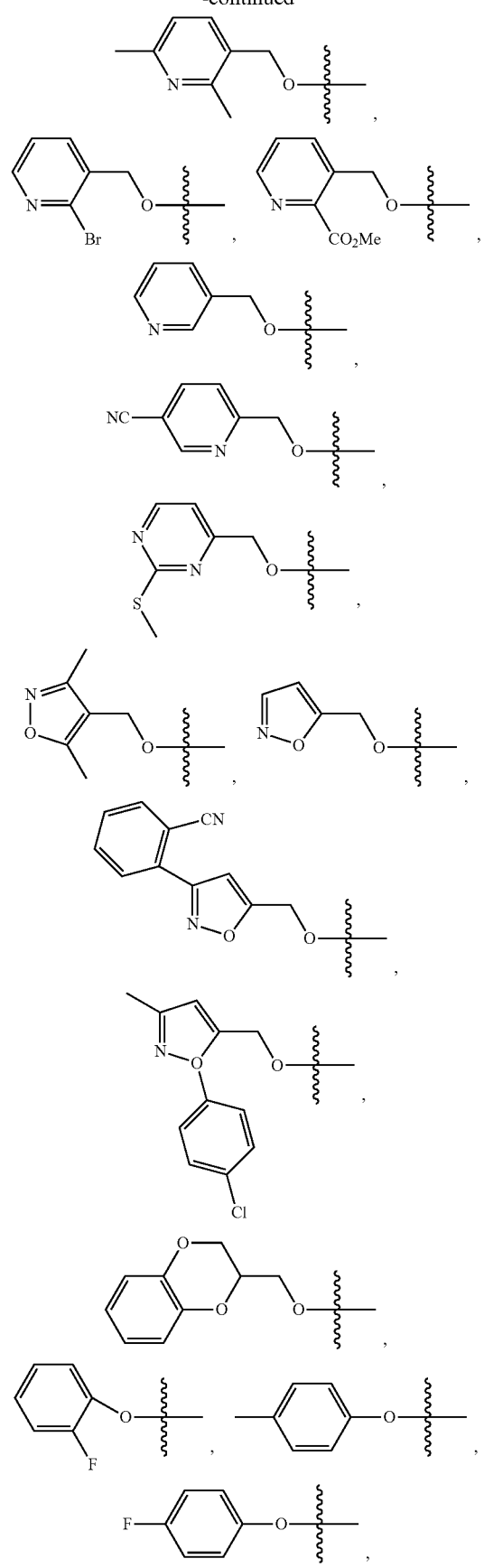

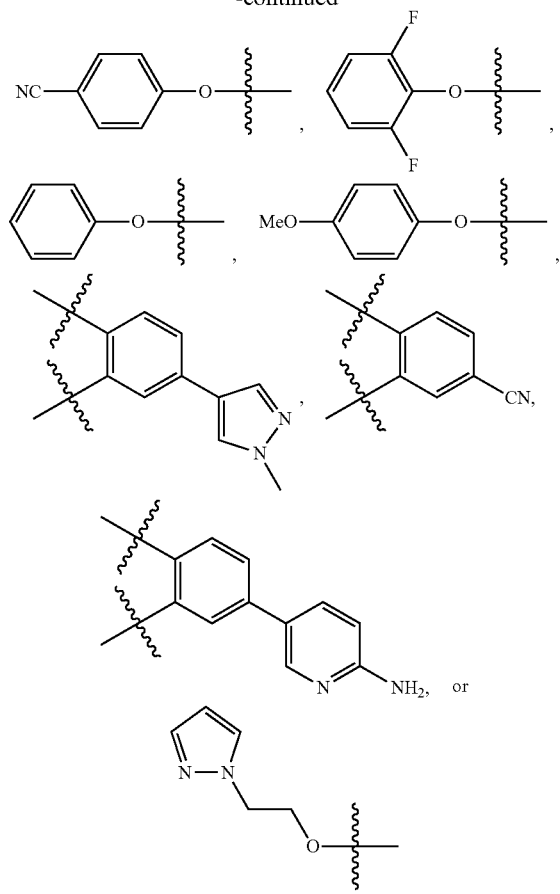

In another aspect, there is provided a compound of Formula (I), or stereoisomers, tautomers, pharmaceutically acceptable salts, solvates, or prodrugs thereof, wherein:

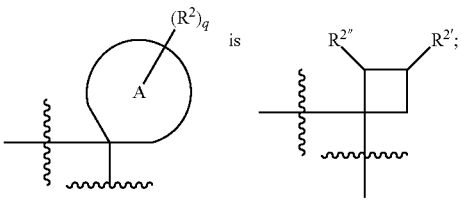

and $R^{2'}$ and $R^{2''}$ are, independently at each occurrence, hydrogen, $=CR^{2a}R^{2a}$, $-(CH_2)_rOR^{2b}$, $-(CH_2)_rC(O)R^{2b}$, $-(CH_2)_rC(O)OR^{2b}$, $-(CH_2)_rOC(O)OR^{2b}$, $-(CH_2)_rOC(O)NR^{11}R^{11}$, $-(CH_2)_rNR^{2b}C(O)NR^{11}R^{11}$, $-(CH_2)_rC(O)NR^{11}R^{11}$, $-(CH_2)_rNR^{2b}C(O)R^{2c}$, $-(CH_2)_rNR^{2b}C(O)OR^{2c}$, $-(CH_2)_rNR^{11}R^{11}$, $-NR^{2b}S(O)_pR^c$, or $-(CH_2)_r$-5-7 membered heterocycle comprising carbon atoms, and 1-4 heteroatoms selected from N, O, and $S(O)_p$ substituted with 0-3 $R^{2a}$; or together with the atoms to which they are attached, $R^{2'}$ and $R^{2''}$ combine to form a fused ring substituted with 0-3 $R^{2a}$, wherein the fused ring is selected from 3-10 membered carbocycle substituted with 0-3 $R^{2a}$, or 3-7 membered heterocycle comprising carbon atoms and 1-4 heteroatoms selected from N, O, and $S(O)_p$ substituted with 0-3 $R^{2a}$.

In another aspect, there is provided a compound of Formula (I), or stereoisomers, tautomers, pharmaceutically acceptable salts, solvates, or prodrugs thereof, wherein:

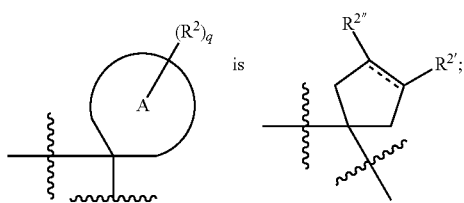

and $R^{2'}$ and $R^{2''}$ are, independently at each occurrence, hydrogen, $=CR^{2a}R^{2a}$, $-(CH_2)_rOR^{2b}$, $-(CH_2)_rC(O)R^{2b}$, $-(CH_2)_rC(O)OR^{2b}$, $-(CH_2)_rOC(O)OR^{2b}$, $-(CH_2)_rOC(O)NR^{11}R^{11}$, $-(CH_2)_rNR^{2b}C(O)NR^{11}R^{11}$, $-(CH_2)_rC(O)NR^{11}R^{11}$, $-(CH_2)_rNR^{2b}C(O)R^{2c}$, $-(CH_2)_rNR^{2b}C(O)OR^{2c}$, $-(CH_2)_rNR^{11}R^{11}$, $-NR^{2b}S(O)_pR^c$, or $-(CH_2)_r$-5-7 membered heterocycle comprising carbon atoms, and 1-4 heteroatoms selected from N, O, and $S(O)_p$ substituted with 0-3 $R^{2a}$; or together with the atoms to which they are attached, $R^{2'}$ and $R^{2''}$ combine to form a fused ring substituted with 0-3 $R^{2a}$, wherein the fused ring is selected from 3-10 membered carbocycle substituted with 0-3 $R^{2a}$, or 3-7 membered heterocycle comprising carbon atoms and 1-4 heteroatoms selected from N, O, and $S(O)_p$ substituted with 0-3 $R^{2a}$.

In another aspect, there is provided a compound of Formula (I), or stereoisomers, tautomers, pharmaceutically acceptable salts, solvates, or prodrugs thereof, wherein:

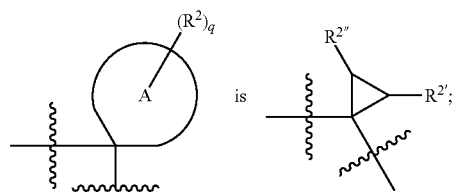

and $R^{2'}$ and $R^{2''}$ are, independently at each occurrence, hydrogen, $=CR^{2a}R^{2a}$, $-(CH_2)_rOR^{2b}$, $-(CH_2)_rC(O)R^{2b}$, $-(CH_2)_rC(O)OR^{2b}$, $-(CH_2)_rOC(O)OR^{2b}$, $-(CH_2)_rOC(O)NR^{11}R^{11}$, $-(CH_2)_rNR^{2b}C(O)NR^{11}R^{11}$, $-(CH_2)_rC(O)NR^{11}R^{11}$, $-(CH_2)_rNR^{2b}C(O)R^{2c}$, $-(CH_2)_rNR^{2b}C(O)OR^{2c}$, $-(CH_2)_rNR^{11}R^{11}$, $-NR^{2b}S(O)_pR^c$, or $-(CH_2)_r$-5-7 membered heterocycle comprising carbon atoms, and 1-4 heteroatoms selected from N, O, and $S(O)_p$ substituted with 0-3 $R^{2a}$; or together with the atoms to which they are attached, $R^{2'}$ and $R^{2''}$ combine to form a fused ring substituted with 0-3 $R^{2a}$, wherein the fused ring is selected from 3-10 membered carbocycle substituted with 0-3 $R^{2a}$, or 3-7 membered heterocycle comprising carbon atoms and 1-4 heteroatoms selected from N, O, and $S(O)_p$ substituted with 0-3 $R^{2a}$.

In another aspect, there is provided a compound of Formula (I), or stereoisomers, tautomers, pharmaceutically acceptable salts, solvates, or prodrugs thereof, wherein: $R^1$ is

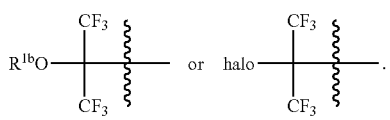

In another aspect, there is provided a compound of Formula (I), or stereoisomers, tautomers, pharmaceutically acceptable salts, solvates, or prodrugs thereof, wherein $R^{2''}$ is hydrogen.

In another aspect, there is provided a compound of Formula (I), or stereoisomers, tautomers, pharmaceutically acceptable salts, solvates, or prodrugs thereof, wherein wherein $R^{1'}$ is $CF_3$; and $R^1$ is $OR^{1b}$ or halo. Preferably, $OR^{1b}$ is

or OH; and halo is F.

In another aspect, there is provided a compound of Formula (I), or stereoisomers, tautomers, pharmaceutically acceptable salts, solvates, or prodrugs thereof, wherein wherein $R^{2''}$ is hydrogen and $R^{2'}$ is $CO_2R^{2b}$, $C(O)NR^{11}R^{11}$, $-NR^{11}R^{11}$, $-NR^{2b}C(O)R^{2c}$, $-NR^{2b}C(O)OR^{2c}$, or $-NR^{2b}C(O)NR^{11}R^{11}$.

In another aspect, there is provided a compound of Formula (I), or stereoisomers, tautomers, pharmaceutically acceptable salts, solvates, or prodrugs thereof, wherein $R^{2'}$ is:

hydrogen, OH, $NH_2$, $=CH_2$, $CO_2H$, $-C(O)OMe$, $-NHSO_2Me$,

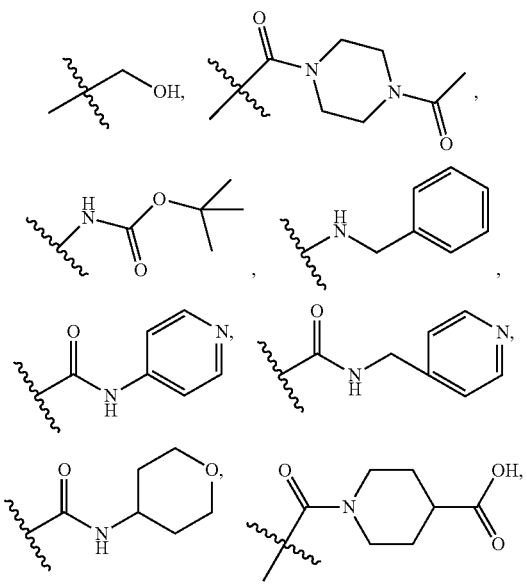

-continued

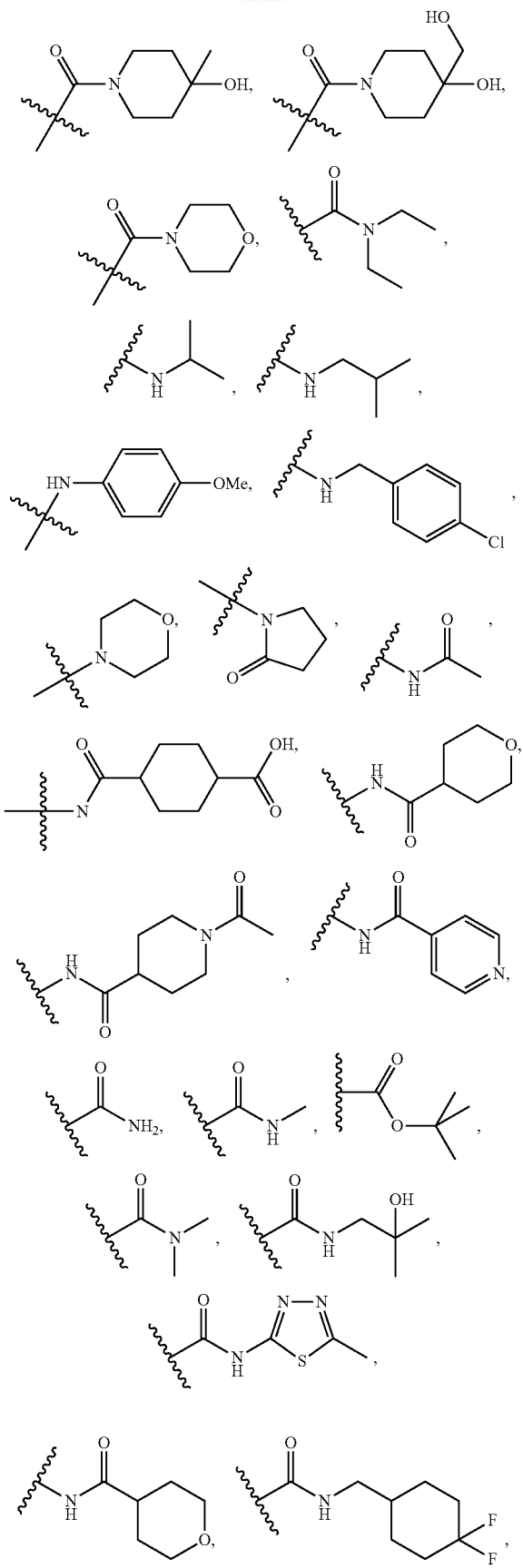

-continued
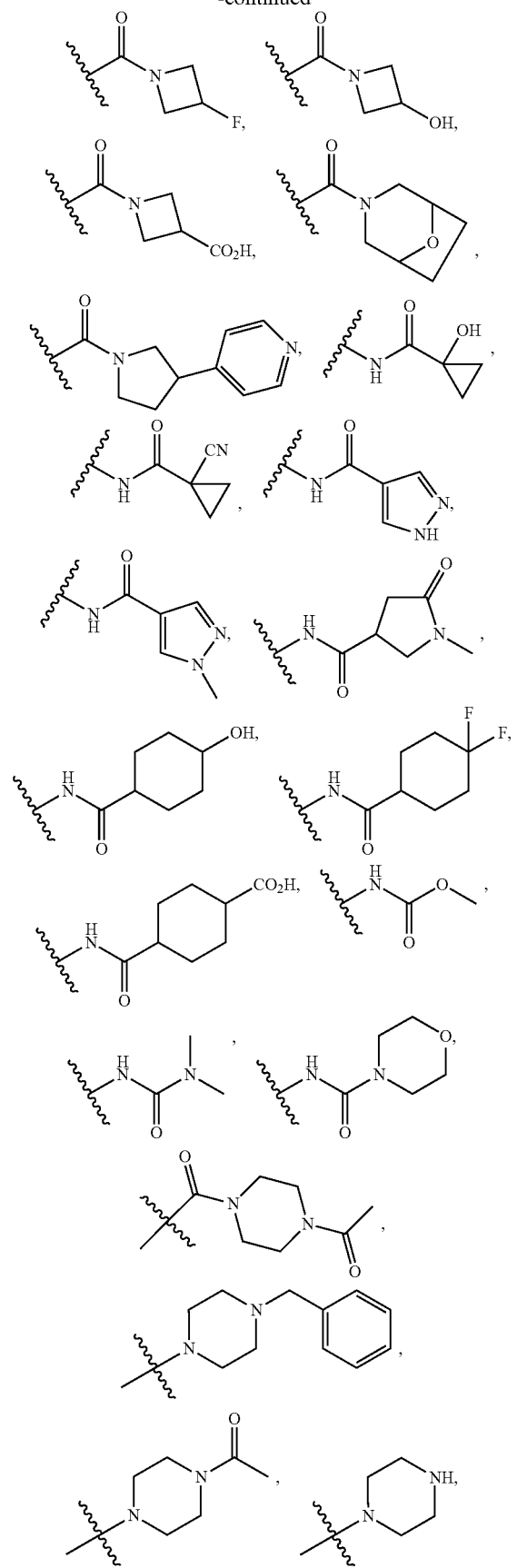
-continued
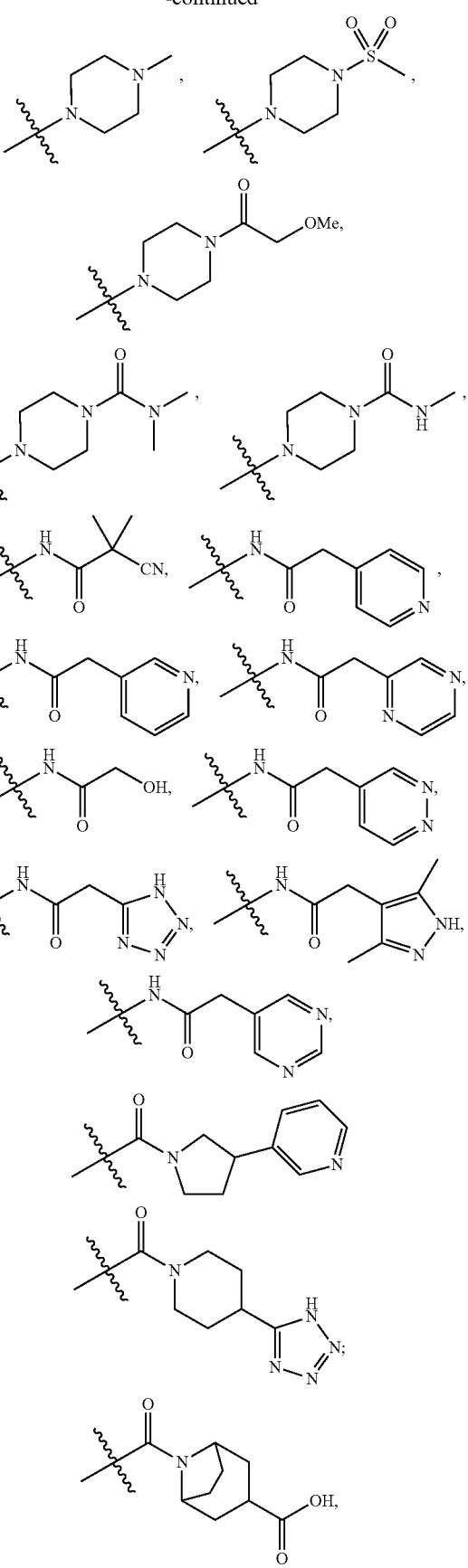

-continued

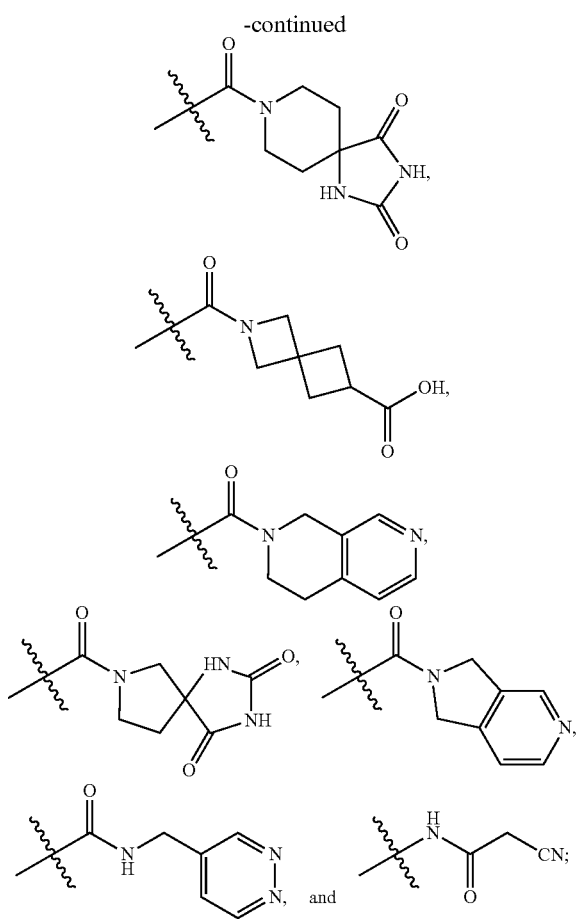

or together with the atoms to which they are attached R²' is combined with R²'' to form a fused ring selected from

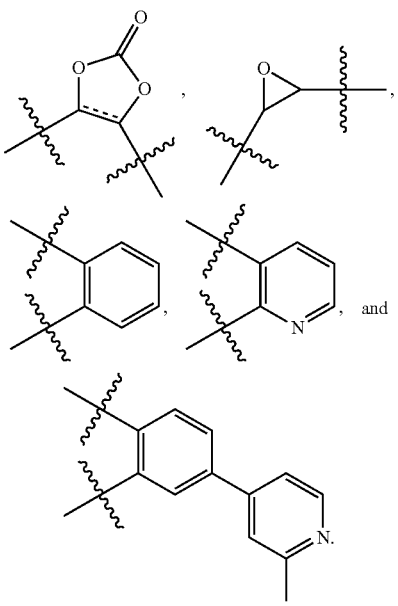

In another aspect, there is provided a compound of Formula (I), or stereoisomers, tautomers, pharmaceutically acceptable salts, solvates, or prodrugs thereof, wherein R³''' and R³' are, independently, hydrogen, halo, $N_3$, CN, —O(phenyl), —$NH_2$, —NH($C_{1-6}$ alkyl), —N($C_{1-6}$ alkyl)$_2$, $C_{1-6}$ alkyl or $C_{3-6}$ cycloalkyl. Preferably, $R^3$ is F, H, OMe, $NH_2$, $N_3$, CN, OPh, cyclopropyl, or $CH_3$, and $R^{3'}$ is hydrogen. More preferably $R^3$ is F and $R^{3'}$ is hydrogen.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

In another embodiment, the invention provides a compound of the present invention for use in treating diseases (or a method of treating diseases) in which inflammation is a component including, without limitation, diseases such as psoriasis, rheumatoid arthritis, inflammatory bowel disease, Crohn's disease, ulcerative colitis, acute graft-versus-host disease, psoriatic arthritis, ankylosing spondylitis and multiple sclerosis.

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

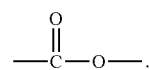

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

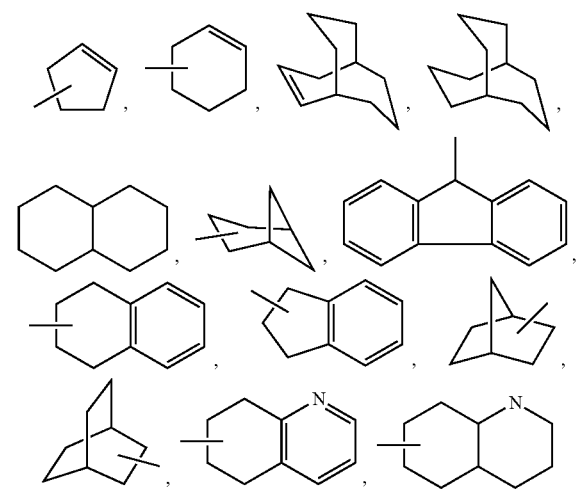

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, di, and trifluoromethyl.

The term "haloalkoxy" means an alkoxy group having one or more halo substituents. For example, "haloalkoxy" includes $OCF_3$.

Thus, examples of aryl groups include:

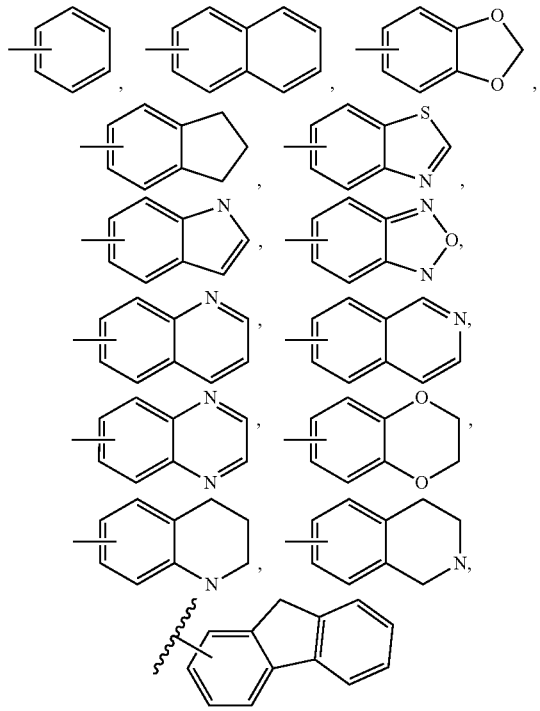

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

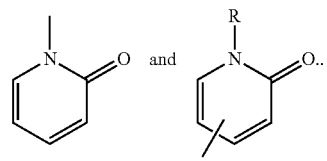

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

In compounds of formula I, preferred heteroaryl groups include

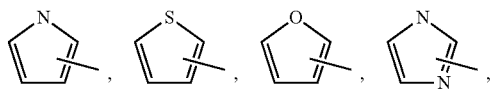

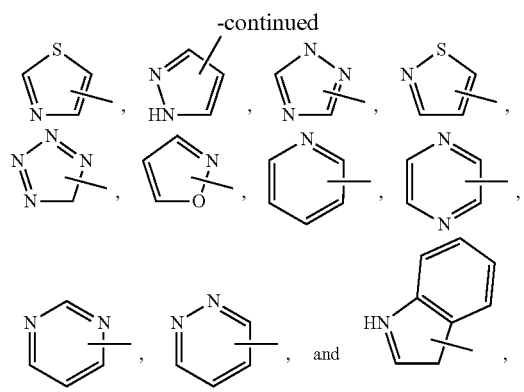

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The terms "carbocycle, carbocyclyl or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Enzymology*, 112:309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers.

It should further be understood that solvates (e.g., hydrates) of the compounds of Formula I are also with the scope of the present invention. Methods of solvation are generally known in the art.

Another aspect of the invention is a pharmaceutical composition including a compound, stereoisomeric form, pharmaceutical salt, solvate or hydrate as described herein. The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by U.S. regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the subject by employing procedures known in the art.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a subject will vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the subject, and the like.

The compositions administered to a subject can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the subject, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular subject, the relative biological efficacy of the compound selected, formulation of the excipient, and its route of administration. Effective doses can be extrapolated from dose-response curves derived from in vitro or animal model test systems.

The compounds of the present invention are useful to prevent, diagnose, and treat various medical disorders in humans or animals. The compounds are used to inhibit or reduce one or more activities associated with RORγ receptors, relative to RORγ receptors in the absence of the same compounds. Thus, in one aspect of the invention, a method for treating a disease or disorder selected from an autoimmune disease or disorder, asthma, an allergic disease or disorder, a metabolic disease or disorder, and cancer in a subject comprises administering to the subject a therapeutically effective amount of compound according to formula (I), stereoisomeric form, N-oxide, pharmaceutically acceptable salt, solvate, hydrate or pharmaceutical composition as described herein. See, e.g., L. A. Solt et al., "Action of RORs and their ligands in (patho)physiology," *Trends Endocrinol Metab.*, preprint available online Jul. 11, 2012 at http://www.sciencedirect.com/science/article/pii/S1043276012000926; M. S. Maddur et al., "Th17 cells: biology, pathogenesis of autoimmune and inflammatory diseases, and therapeutic strategies," *Am. J. Pathol.* 2012 July; 181(1):8-18; and A. M. Jetten, "Retinoid-related orphan receptors (RORs): critical roles in development, immunity, circadian rhythm, and cellular metabolism," *Nucl. Recept. Signal.* 2009; 7:e003, each of which is hereby incorporated herein by reference in its entirety, as well as the references discussed in the Background section. In certain embodiments, the autoimmune disease or disorder is selected from rheumatoid arthritis, ankylosing spondylitis, psoriasis and psoriatic arthritis, multiple sclerosis, inflammatory bowel diseases and lupus. In certain embodiments, the allergic disease or disorder is selected from allergic rhinitis and dermatitis. In certain embodiments, the metabolic disease or disorder is selected from obesity, obesity-induced insulin resistance and type II diabetes.

In certain embodiments, the disease or disorder is rheumatoid arthritis. See, e.g., L. A. Solt et al., referenced above, as well as the references discussed in the Background section.

In other embodiments, the disease or disorder is multiple sclerosis. See, e.g., L. Codarri et al., "RORγt drives production of the cytokine GM-CSF in helper T cells, which is essential for the effector phase of autoimmune neuroinflammation," *Nat. Immunol.,* 2011 June; 12(6):560-7, which is hereby incorporated herein by reference in its entirety, as well as the references discussed in the Background section.

In other embodiments, the disease or disorder is ankylosing spondylitis. See, e.g., E. Toussirot, "The IL23/Th17 pathway as a therapeutic target in chronic inflammatory diseases," *Inflamm. Allergy Drug Targets,* 2012 April; 11(2): 159-68, which is hereby incorporated herein by reference in its entirety, as well as the references discussed in the Background section.

In other embodiments, the disease or disorder is inflammatory bowel disease. See, e.g., M. Leppkes et al., "ROR-gamma-expressing Th17 cells induce murine chronic intestinal inflammation via redundant effects of IL-17A and IL-17F," *Gastroenterology*, 2009 January; 136(1):257-67, which is hereby incorporated herein by reference in its entirety, as well as the references discussed in the Background section.

In other embodiments, the disease or disorder is lupus. See, e.g., K. Yoh et al., "Overexpression of RORγt under control of the CD2 promoter induces polyclonal plasmacytosis and autoantibody production in transgenic mice," *Eur. J. Immunol.*, 2012 August; 42(8):1999-2009, which is hereby incorporated herein by reference in its entirety, as well as the references discussed in the Background section.

In other embodiments, the disease or disorder is psoriasis. See, e.g., S. Pantelyushin et al., "RORγt+ innate lymphocytes and γδ T cells initiate psoriasiform plaque formation in mice," *J. Clin. Invest.*, 2012 Jun. 1; 122(6):2252-6; and S. P. Raychaudhuri, "Role of IL-17 in Psoriasis and Psoriatic Arthritis," Clin. Rev. Allergy Immunol., preprint available online Feb. 24, 2012 at http://rd.springer.com/article/10.1007/s12016-012-8307-1 (PubMed PMID: 22362575), each of which is hereby incorporated herein by reference in its entirety, as well as the references discussed in the Background section.

In other embodiments, the disease or disorder is psoriatic arthritis. See, e.g., S. P. Raychaudhuri, referenced above, as well as the references discussed in the Background section.

In other embodiments, the disease or disorder is graft-vs.-host disease (GVHD). Y. Yu et al., "Prevention of GVHD while sparing GVL effect by targeting Th1 and Th17 transcription factorT-bet and RORγt in mice," *Blood,* 2011 Nov. 3; 118(18):5011-20, which is hereby incorporated by reference in its entirety, as well as the references discussed in the Background section.

In other embodiments, the disease or disorder is autoimmune uveitis. See, e.g., R. Horai et al., "Cytokines in autoimmune uveitis," *J. Interferon Cytokine Res.*, 2011 October; 31(10):733-44, which is hereby incorporated herein by reference in its entirety, as well as the references discussed in the Background section.

In other embodiments, the disease or disorder is obesity and/or insulin resistance. See, e.g., B. Meissburger et al., "Adipogenesis and insulin sensitivity in obesity are regulated by retinoid-related orphan receptor gamma," *EMBO Mol. Med.*, 2011 November; 3(11):637-51, which is hereby incorporated herein by reference in its entirety, as well as the references discussed in the Background section.

In other embodiments, the disease or disorder is melanoma. See, e.g., Purwar R, et al. Robust tumor immunity to melanoma mediated by interleukin-9-producing T cells. Nat. Med., 2012 July: 18:1248-53, which is hereby incorporated herein by reference in its entirety, as well as the references discussed in the Background section.

In certain aspects, the medical disorder being diagnosed, treated, or prevented by use of the presently disclosed compounds can be, for example, an autoimmune disorder. In other embodiments, the disorder being diagnosed, treated or prevented by use of the presently disclosed compounds can be an inflammatory disorder. For example, in certain embodiments, the disorder is selected from arthritis, diabetes, multiple sclerosis, uveitis, rheumatoid arthritis, psoriasis, asthma, bronchitis, allergic rhinitis, chronic obstructive pulmonary disease, atherosclerosis, *H. pylori* infection and inflammatory bowel disease. In other embodiments, the disorder is selected from Crohn's disease, ulcerative colitis, sprue and food allergies. In other embodiments, the disorder is experimental autoimmune encephalomyelitis, imiquimod-induced psoriasis, colitis or allergic airway disease.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; or (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; (ii) eliciting the biological or medicinal response that is being sought in a tissue, system, animal, individual or human by a researcher, veterinarian, medical doctor or other clinician; or (iii) inhibiting the referenced disease state; for example, inhibiting a disease, condition or disorder in an individual who is experiencing or displaying the pathology or symptomatology of the disease, condition or disorder.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

Scheme 1 illustrates a general synthesis of intermediates 4 and 7. Appropriately functionalized benzyl halide 1 can be reacted with functionalized thiophenol 2 using a base such as potassium carbonate or sodium hydroxide in a solvent such as tetrahydrofuran, ethanol or N,N-dimethylformamide to provide sulfide intermediate 3. Oxidation of 3 to sulfone 4 can be accomplished with mCPBA or other oxidant such as oxone and sodium tungstate. Sulfone 4 can also be synthesized in one step by treating 1 with sodium benzenesulfinate 5 in a solvent such as N,N-dimethylformamide. Upon treatment with n-butyllithium, the resulting anion derivative of 4 can be reacted with Eschenmoser's salt (dimethylmethylideneammonium iodide) to yield amine derivative 6, which can be converted to vinyl sulfone 7 after heating in acetic anhydride and toluene. Vinyl sulfone 7 can also be synthesized directly from 4 by heating with N,N,N',N'-tetramethylmethylenediamine and acetic anhydride in N,N-dimethylformamide. Intermediate 4 and 7 can be useful intermediates for further functionaliztion using conditions described below for Schemes 3-5.

can be selectively brominated with N-bromosuccinimide in refluxing carbon tetrachloride using AIBN as a radical initiator to yield bromide 9. Reaction of 9 with sodium benzenesulfinate 5 in a solvent such as N,N-dimethylformamide could lead to sulfone product 10. The hydroxyl group in 10 can be protected as a benzyl ether using conditions such as benzyl bromide and potassium carbonate in N,N-dimethylformamide to give 11. Treatment of 11 with appropriately functionalized di-halide 12 (such as 1,2-di-halo-ethane, 1,3-di-halo-propane, and 1,4-di-halo-butane) with a base such as sodium hydride can lead to a series of 3 to 5-membered cycloalkane product 13. Debenzylation of 13 using palladium(II) hydroxide catalyzed hydrogenolysis

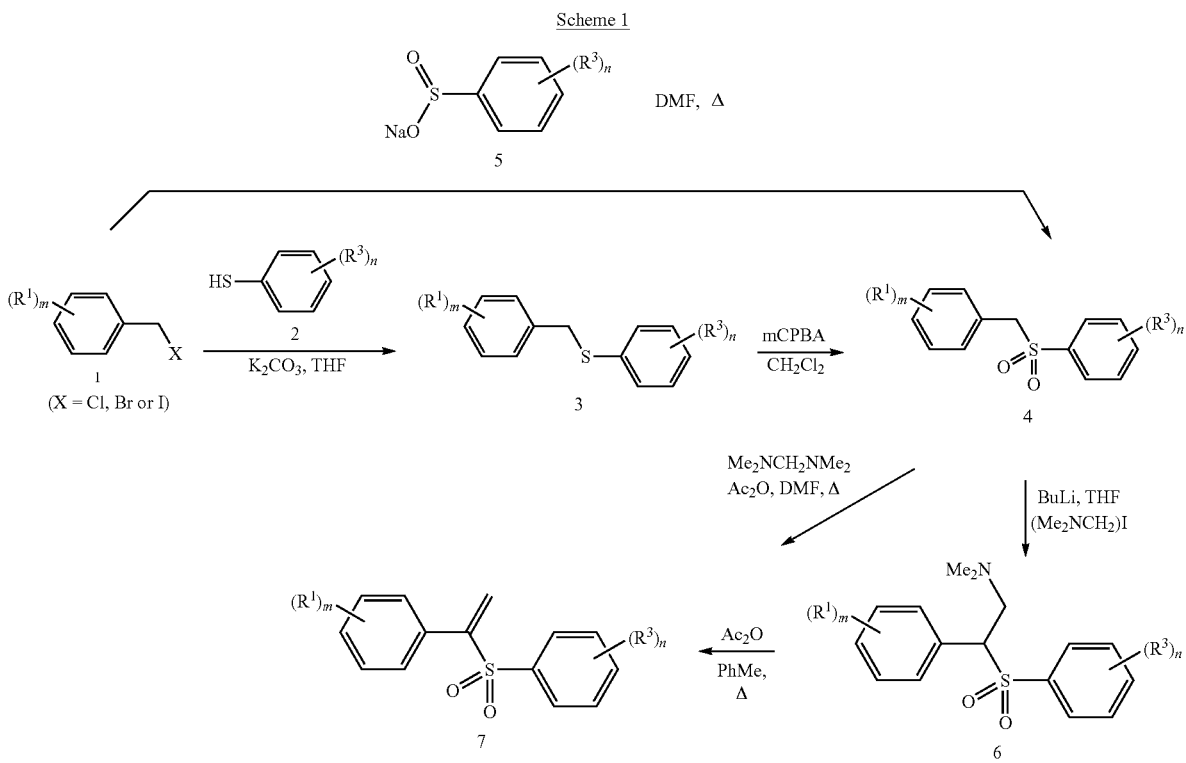

Scheme 1

Scheme 2 illustrates a synthesis of a series of compounds 13 and 14 and intermediate 15, where $R^1$ is 1,1,1,3,3,3-hexafluoro-2-hydroxypropan-2-yl group. Commercially available 1,1,1,3,3,3-hexafluoro-2-(p-tolyl)propan-2-ol (8)

conditions can provide alcohol 14. Intermediate 11 can also be used to synthesize vinyl sulfone intermediate 15 by heating with N,N,N',N'-tetramethylmethylenediamine and acetic anhydride in N,N-dimethylformamide.

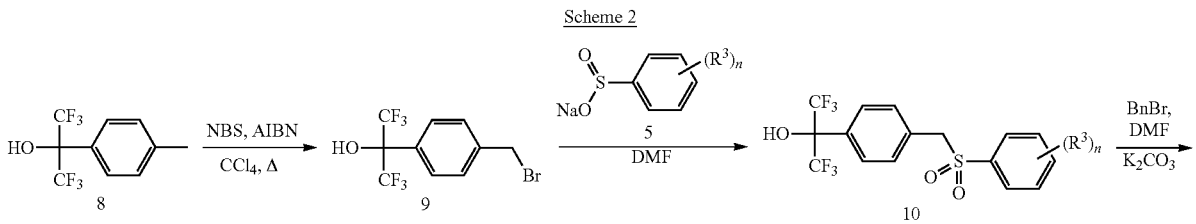

Scheme 2

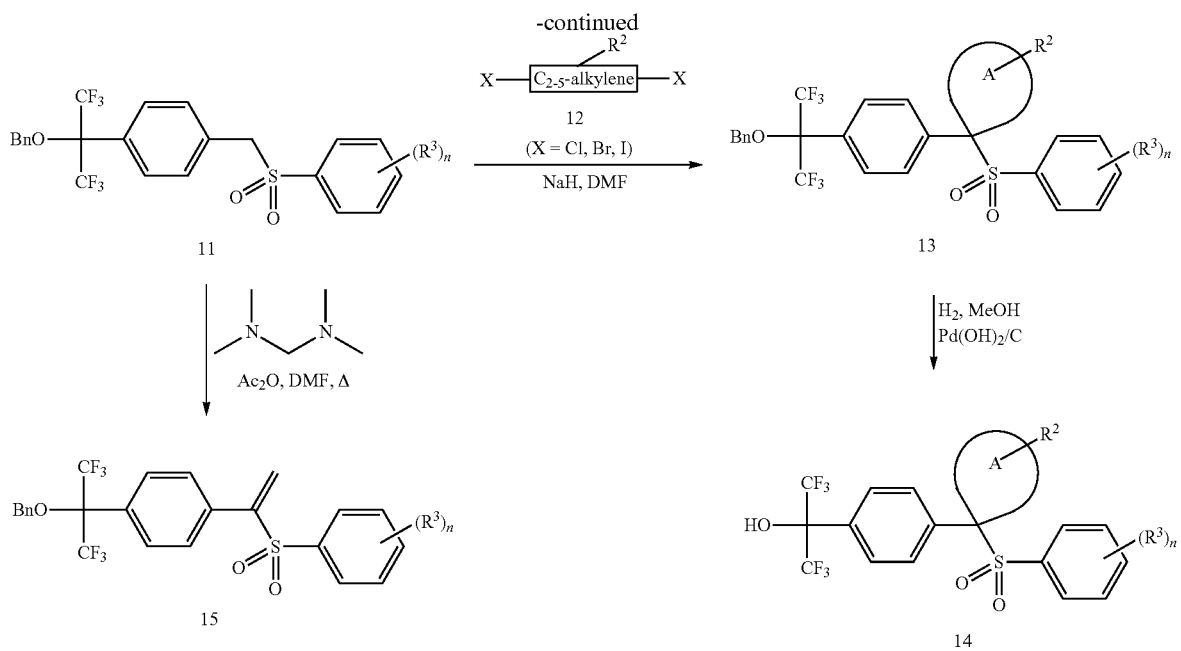

Scheme 3 depicts a synthesis of a series of cyclobutane compounds. Treatment of sulfone 11 with 3-chloro-2-(chloromethyl)prop-1-ene with a base such as sodium hydride in N,N-dimethylformamide can produce cyclobutane analogue 16. After hydroboration with a reagent such as borane-tetrahydrofuran complex, the resulting alcohol 17 can be oxidized to carboxylic acid 18 using Jone's oxidation (chromium trioxide/sulfuric acid mixture). Curtius rearrangement of acid 18 can be accomplished with diphenylphosphoryl azide and triethylamine at elevated temperature to provide carbamate 19 after quenching the isocyanate intermediate with 2-(trimethylsily)ethanol. Finally, the Teoc protecting group can be removed with trifluoroacetic acid to yield amine 20.

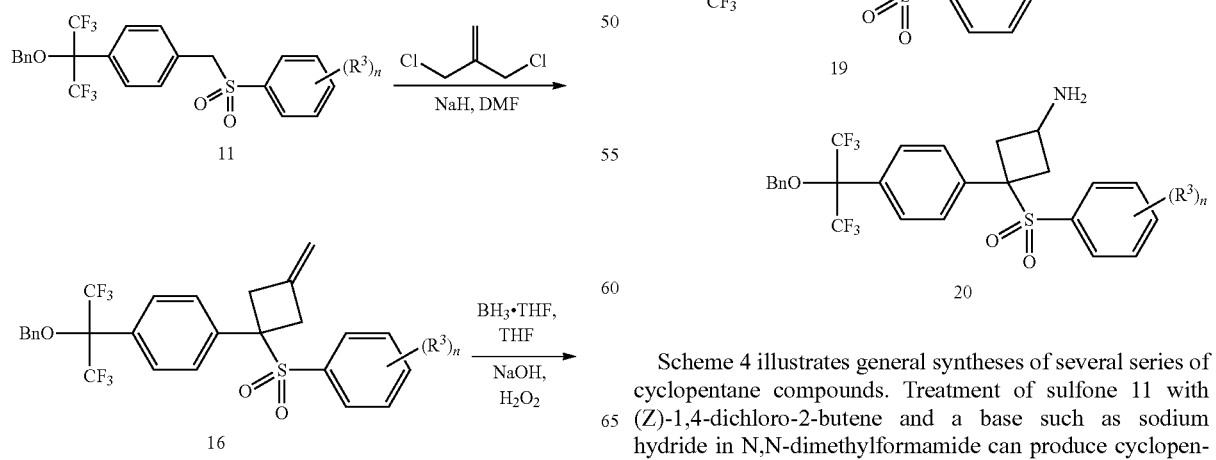

Scheme 4 illustrates general syntheses of several series of cyclopentane compounds. Treatment of sulfone 11 with (Z)-1,4-dichloro-2-butene and a base such as sodium hydride in N,N-dimethylformamide can produce cyclopentene 21. Osmium tetroxide-catalyzed dihydroxylation using 4-methylmorpholine-N-oxide as a co-oxidant can provide diol 22, which in turn can be converted to cyclic carbonate 23 using a reagent such as triphosgene. The cyclopentene 21 can also be converted to epoxide 24 using a reagent such as 3-chloroperbenzoic acid. The epoxide ring of 24 can react with Grignard reagent in the presence of copper bromide-dimethyl sulfide complex to provide alcohol 25. Conversion of 25 to ether 26 can be carried out using halide $R^{2b}$—X (X=Cl, Br, or I) and a base such as sodium hydride in N,N-dimethylformamide. Alternatively, cyclopentene 21 can undergo hydroboration using reagent such as borane-dimethyl sulfide complex to yield alcohol 27, after oxidative work up with hydrogen peroxide and sodium hydroxide. Alcohol 27 can be converted to 28 using conditions similar to synthesis of 26.

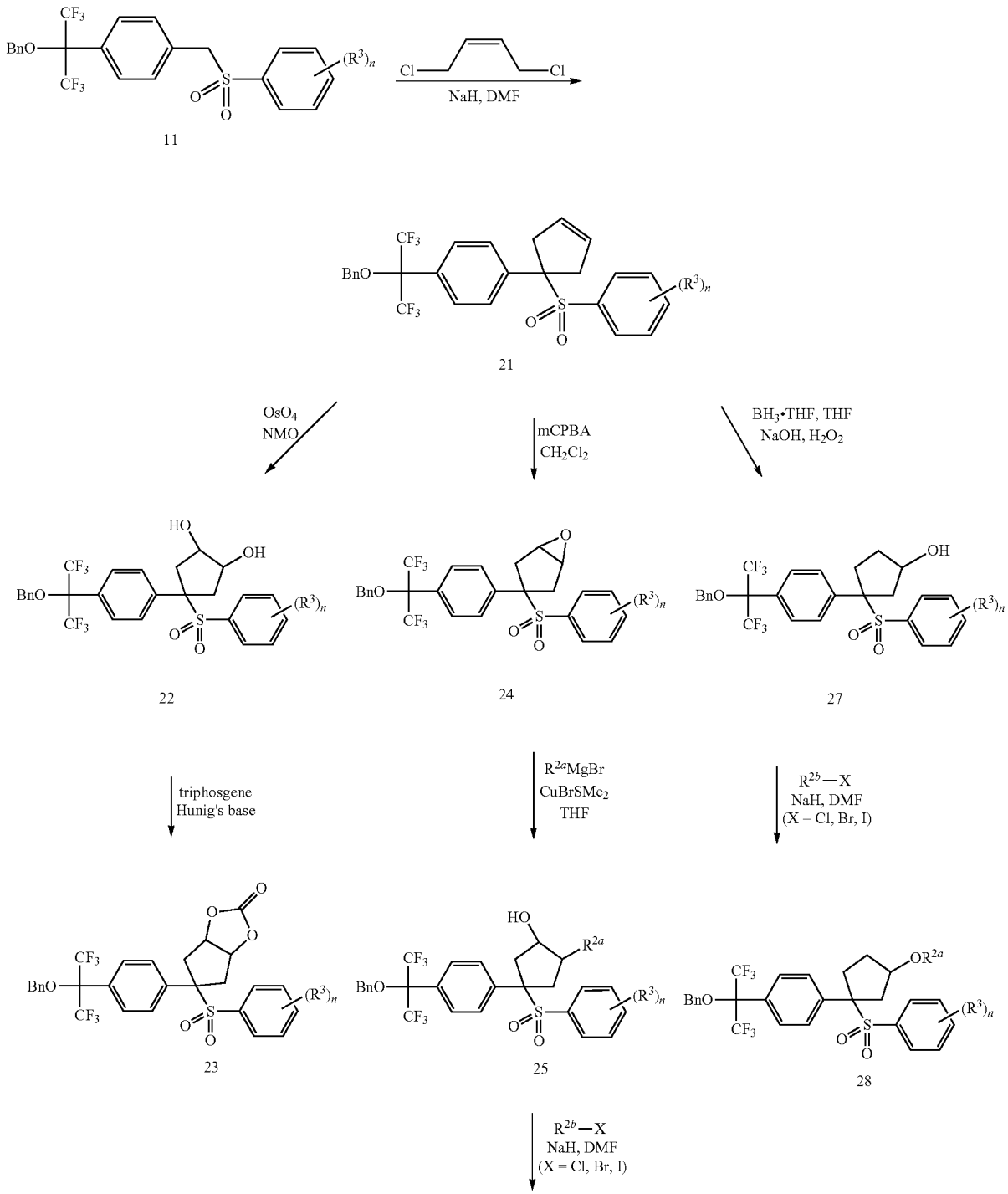

-continued

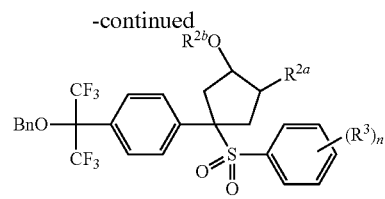

26

Scheme 5 illustrates general syntheses of cyclopropane analogue 30 and cyclopentane analogues 34 and 36 using vinyl sulfone intermediate 15. Cyclopropanation of 15 can be accomplished with (2-(tert-butoxy)-2-oxoethyl)dimethylsulfonium bromide and DBU to give ester 29. Hydrolysis of the tert-butyl ester in 29 with trifluoroacetic acid can provide product 30. The cyclopentane intermediate 32 can be synthesized from vinyl sulfone 15 via a palladium catalyzed reaction with 2-((trimethylsilyl)methyl)allyl acetate (31). Following conditions described for Scheme 3, the olefin group in 32 can be converted to carboxylic acid 34 via hydroboration and Jone's oxidation, and subsequently to amine 36 via Curtius rearrangement and deprotection of Teoc group.

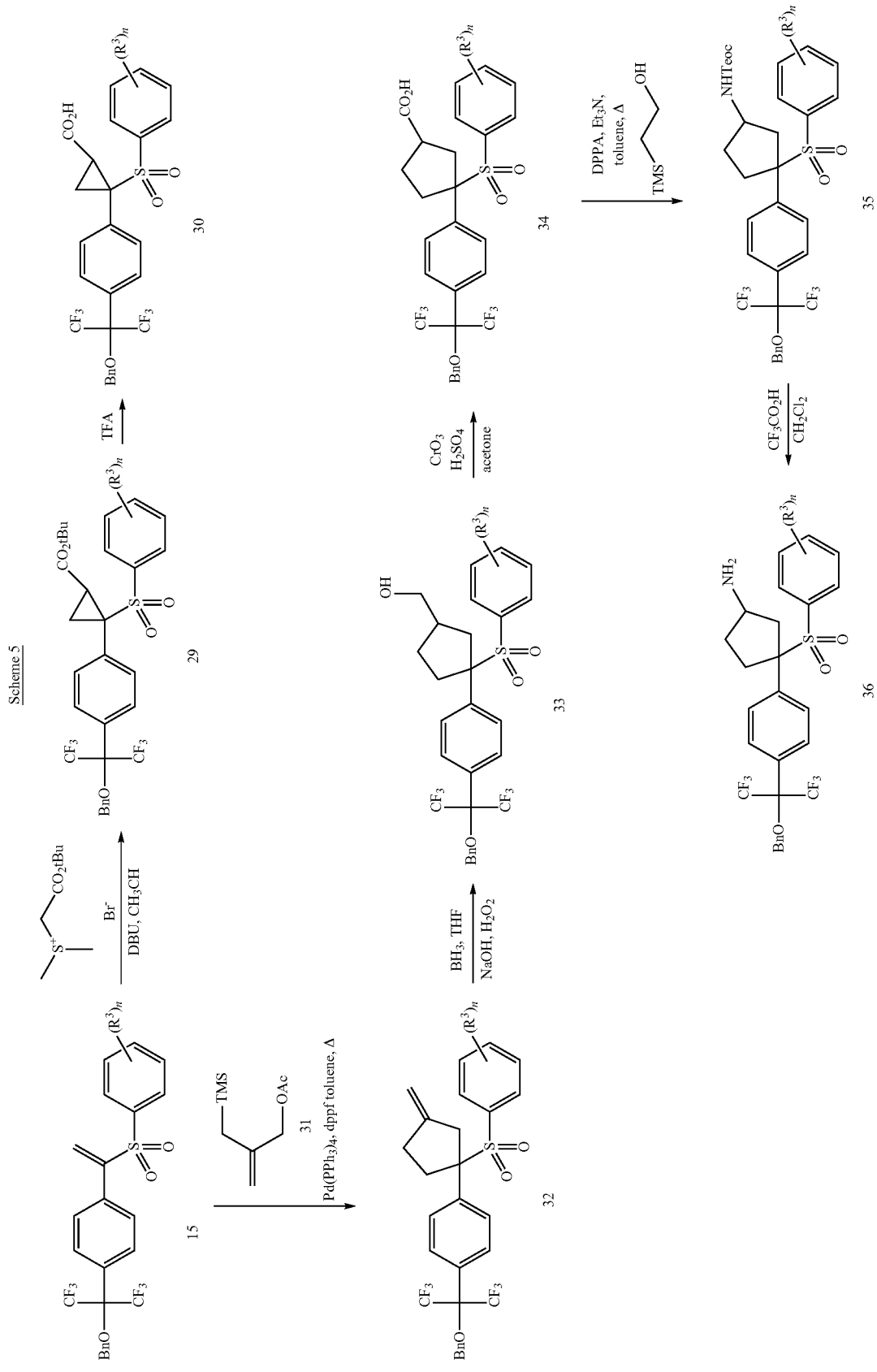

Most of the compounds in Schemes 3-5 can be converted to the corresponding 1,1,1,3,3,3-hexafluoro-2-hydroxypropan-2-yl analogues by cleavage of the benzyl ether group via palladium hydroxide-catalyzed hydrogenolysis. In addition, the synthesis described in Schemes 3-5 can be used to prepare analogues where $R^1$ is other than the 1,1,1,3,3,3-hexafluoro-2-hydroxypropan-2-yl group using intermediates 4 and 7 in place of 11 and 15, respectively.

Carboxylic acid 37 (such as 18, 30 and 34, as well as the corresponding analogues prepared from intermediates 4 and 7) can be coupled with amine $R^{2a}R^{2b}NH$ using well-known amide coupling reagents such as HOBt/EDC or BOP to provide amide analogue 38 (Scheme 6). In addition, amine 39 (for example, 20, 36 and the corresponding amines prepared from intermediates 4 and 7) can be functionalized using various well known transformations to give 40. Examples of these transformations include, but are not limited to, alkylation reaction with alkyl halide and a base such as Hunig's base, reductive alkylation with aldehyde/ketone and a reducing reagent such as sodium triacetoxyborohydride, coupling reaction with carboxylic acid using an activating agent such as BOP or HOBt/EDC, and other acylation reactions using acid chloride, anhydride, chloroformate, isocyanate, and sulfonyl chloride.

Scheme 6

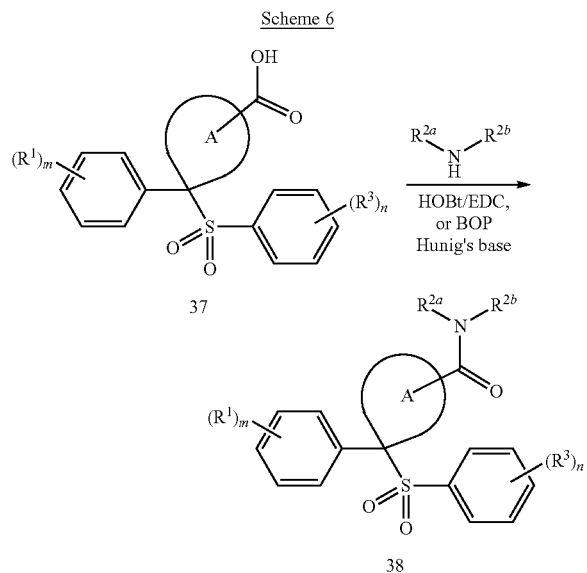

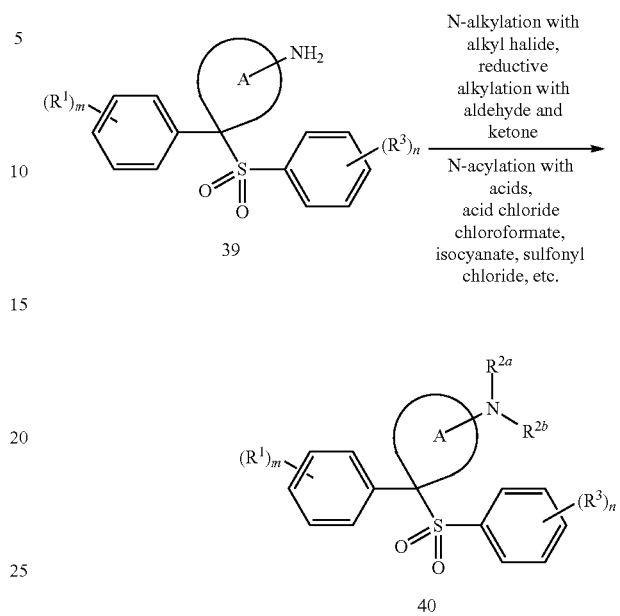

Compound 41, prepared following synthetic description for Schemes 1-6, can also be useful intermediate for further derivatization (Scheme 7). For example, it can be alkylated with $R^{1a}$-halide (chloride, bromide or iodide) under basic conditions such as potassium carbonate or sodium hydride to give 42. Alternatively, compound 42 can be synthesized from 41 and alcohol $R^{1a}$—OH using Mitsunobu conditions involving an azodicarboxylate such as diethyl azodicarboxylate (DEAD) and a phosphine ligand such as triphenylphosphine or tributylphosphine. The hydroxyl group in 41 can also be replaced with a fluoro group using (diethylamino) sulfur trifluoride (DAST) to give perfluoroisopropyl analogue 43. In addition, the OH group in 41 can be arylated with diphenyliodonium iodide 44 using a base such as potassium methoxide or sodium hydride to give phenyl ether 45.

Scheme 7

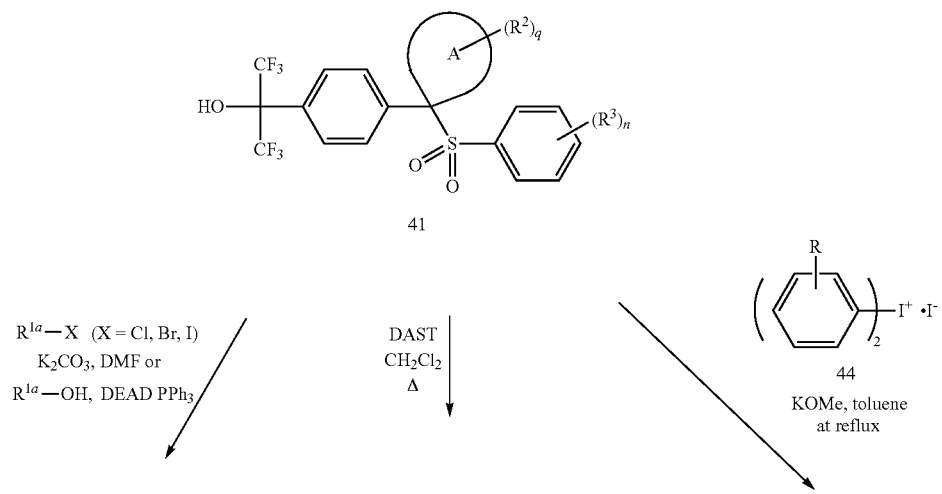

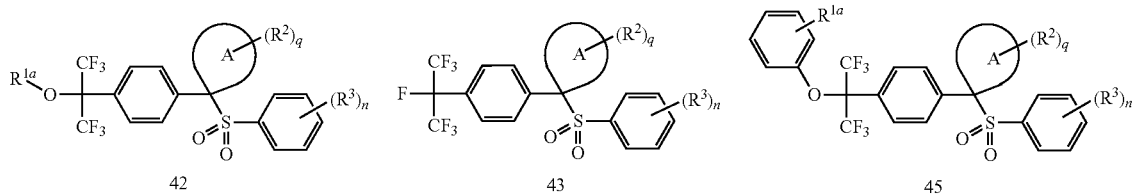

Iodide 46, prepared from the sequence outlined in Schemes 1-6, can be a useful intermediate for further diversification to prepare 48, 50 and 51 (Scheme 8). It can be reacted with aryl/heteroaryl boronic acid (or ester) 47 under well-known Suzuki coupling conditions using a catalyst such as palladium tetrakis(triphenylphosphine) or Pd(dppf)Cl$_2$ to give compound 48. Compound 48 can also be obtained under Stille coupling conditions using aryl/heteroaryltin in place of the boronic acid 47. Iodide 46 can also be treated with tert-butyllithium or ethylmagensium bromide to produce the corresponding aryllithium or arylmagnesium species, which can react with ketone 49 to produce alcohol 50. Compound 50 can in turn be converted to ether 51 using previously described conditions.

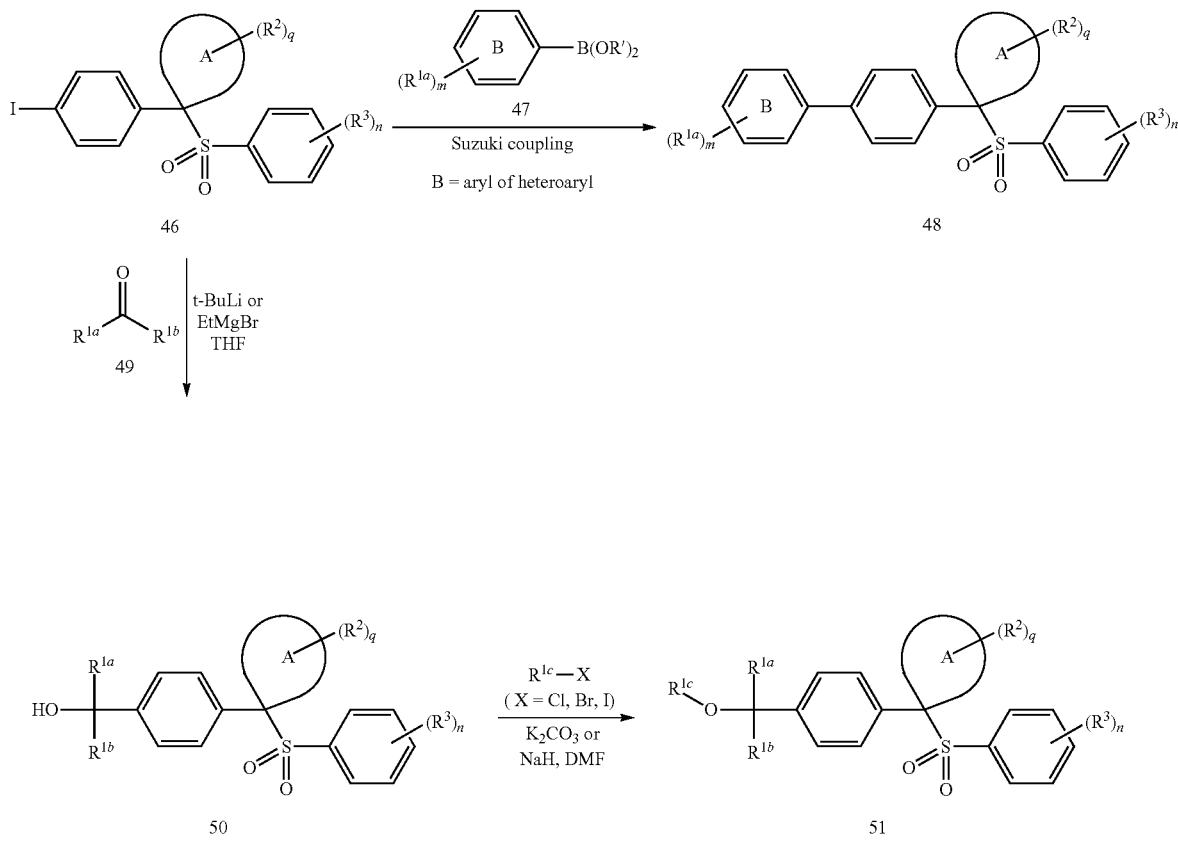

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

HPLC Conditions

Condition A:
Column: YMC Combiscreen ODS-A 4.6×50 mm (4 min.); Linear gradient of 0 to 100% solvent B over 4 min with 1 min hold at 100% B; UV visualization at 220 nm; Solvent A=10% MeOH, 90% $H_2O$, 0.2% $H_3PO_4$; Solvent B=90% MeOH, 10% $H_2O$, 0.2% $H_3PO_4$; Flow: 4 mL/min.

Condition B:
Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min.

Condition C:
Column: Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Condition D:
Column: XBridge Phenyl, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition E:
Column: ZORBAX CN, 4.6×150 mm, 5 micron; Mobile Phase A: 5:95 acetonitrile:water with 10 mM ammonium acetate; Mobile Phase B: 95:5 acetonitrile:water with 10 mM ammonium acetate; Gradient: 10-100% B over 25 minutes, then a 5-minute hold at 100% B; Flow: 1 mL/min.

Condition F:
Column: SUNFIRE C18, 4.6×150 mm, 3.5 micron; Mobile Phase A: 5:95 acetonitrile:water with 0.05% TFA; Mobile Phase B: 95:5 acetonitrile:water with 0.05% TFA; Gradient: 10-100% B over 25 minutes, then a 5-minute hold at 100% B; Flow: 1 mL/min.

Condition G:
Column: Ascentis Express C18 (4.6λ50) mm, 2.7 μm; Mobile Phase A: 5:95 acetonitrile:water with 10 mM ammonium acetate; Mobile Phase B: 95:5 acetonitrile:water with 10 mM ammonium acetate; Temperature: 45° C.; Gradient: 0-100% B over 4 minutes; Flow: 4.00 mL/min.

Condition H:
Column: Ascentis Express C18 (2.1λ50) mm, 2.7 μm; Mobile Phase A: 5:95 acetonitrile:water with 10 mM ammonium acetate; Mobile Phase B: 95:5 acetonitrile:water with 10 mM ammonium acetate; Gradient: 0-100% B over 3.4 minutes; Flow: 1.11 mL/min.

Condition I:
Waters Acquity UPLC BEH C18 (2.1×50) mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 2-98% B over 1 minutes, then a 0.5-minute hold at 98% B; Flow: 0.80 mL/min.

Intermediates 1 and 2

2-(4-((1s,3s)-3-amino-1-((4-fluorophenyl)sulfonyl) cyclobutyl)phenyl)-1,1,1,3,3,3-hexafluoropropan-2-ol and 2-(4-((1r,3r)-3-amino-1-((4-fluorophenyl) sulfonyl)cyclobutyl)phenyl)-1,1,1,3,3,3-hexafluoropropan-2-ol Step A: 2-(trimethylsilyl)ethyl (3-(4-(2-(benzyloxy)-1,1,1,3,3,3-hexafluoropropan-2-yl)phenyl)-3-((4-fluorophenyl)sulfonyl)cyclobutyl)carbamate

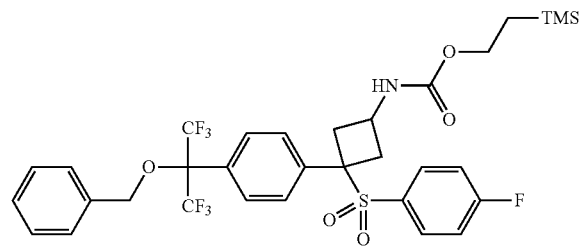 [SMILES: C[Si](C)(C)CCOC(=O)NC1CC(c2ccc(C(OCc3ccccc3)(C(F)(F)F)C(F)(F)F)cc2)(S(=O)(=O)c2ccc(F)cc2)C1]

In a 100 ml round-bottomed flask, 3-(4-(2-(benzyloxy)-1,1,1,3,3,3-hexafluoropropan-2-yl)phenyl)-3-((4-fluorophenyl)sulfonyl)cyclobutanecarboxylic acid (3.6 g, 6.10 mmol, from Step C of Example 44) was dissolved in toluene (75 mL) and cooled to 0° C. under inert atmosphere. Triethylamine (2.55 mL, 18.28 mmol) and diphenylphosphorylazide (5.04 g, 18.28 mmol) was then added successively and stirred at room temperature for 30 min. Reaction monitored by TLC. As soon as SM was found consumed, it was quenched with water (75 mL). The aqueous layer was extracted with EtOAc (3×75 ml), dried over anhydrous sodium sulphate, filtered and concentrated to produce brown colored liquid. The mass thus obtained was then dissolved in 2-(trimethylsilyl)ethanol (17.54 mL, 122.0 mmol) and stirred at 80° C. for 1 h. Reaction mass was concentrated as such to getting crude oil, which was diluted with water (75 mL) and extracted with ethyl acetate (3×100 mL). Combined organic layer was washed with saturated sodium-bicarbonate solution (100 mL), saturated brine solution (50 mL), dried over anhydrous sodium sulphate and concentrated to produce crude 2-(trimethylsilyl)ethyl (3-(4-(2-(benzyloxy)-1,1,1,3,3,3-hexafluoropropan-2-yl)phenyl)-3-((4-fluorophenyl)sulfonyl)cyclobutyl)carbamate (4.4 g) as brown colored gummy liquid.

Step B: 3-(4-(2-(benzyloxy)-1,1,1,3,3,3-hexafluoropropan-2-yl)phenyl)-3-((4-fluorophenyl)sulfonyl)cyclobutanamine

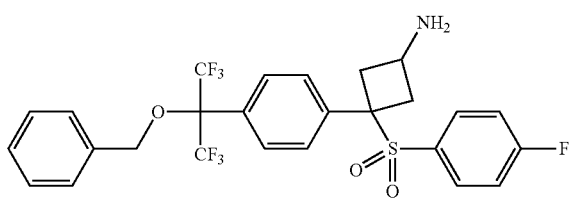 [SMILES: NC1CC(c2ccc(C(OCc3ccccc3)(C(F)(F)F)C(F)(F)F)cc2)(S(=O)(=O)c2ccc(F)cc2)C1]

Crude 2-(trimethylsilyl)ethyl (3-(4-(2-(benzyloxy)-1,1,1,3,3,3-hexafluoropropan-2-yl)phenyl)-3-((4-fluorophenyl)sulfonyl)cyclobutyl)carbamate was dissolved in 50 mL DCM and cooled to 0° C. under nitrogen atmosphere. TFA (4.80 mL, 62.4 mmol) was added in reaction mass and allowed to stir at room temperature for 2 hr. Then reaction mass was concentrated as such to get crude product (3.6 g) as a brown oil. Crude product was purified by preparative HPLC to produce 3-(4-(2-(benzyloxy)-1,1,1,3,3,3-hexafluoropropan-2-yl)-phenyl)-3-((4-fluorophenyl)-sulfonyl)cyclobutanamine as a mixture of two diastereomers (2.4 g, 4.26 mmol, 68.8% yield). LC/MS (M+1): 562.2.

Step C: 2-(4-((1s,3s)-3-amino-1-((4-fluorophenyl)sulfonyl)cyclobutyl)phenyl)-1,1,1,3,3,3-hexafluoropropan-2-ol and 2-(4-((1r,3r)-3-amino-1-((4-fluorophenyl)sulfonyl)cyclobutyl)phenyl)-1,1,1,3,3,3-hexafluoropropan-2-ol

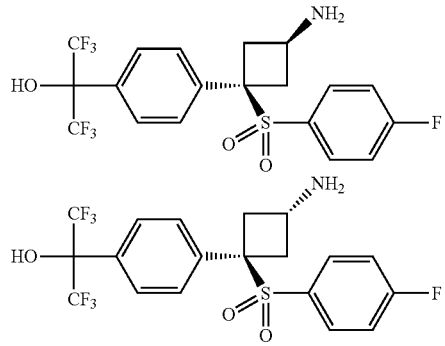

In a 250 ml round-bottomed flask 3-(4-(2-(benzyloxy)-1,1,1,3,3,3-hexafluoropropan-2-yl)-phenyl)-3-((4-fluorophenyl)-sulfonyl)cyclobutanamine (1.2 g, 2.13 mmol) was dissolved in methanol (80 mL), to that was added 10% Pd/C (100 mg, 0.940 mmol) and the reaction mixture was stirred at room temperature under hydrogen atmosphere (through bladder) for 3 h. Reaction mass was filtered through 1 inch celite bed, the bed was washed with methanol (3×50 ml). Combined organic layer was concentrated to get crude product as off white solid (1.0 g as a mix of two diastereomers). The crude material was purified by preparative-HPLC to yield 2-(4-(3-amino-1-((4-fluorophenyl)sulfonyl)cyclobutyl)phenyl)-1,1,1,3,3,3-hexafluoropropan-2-ol as a mixture of diastereomers (680 mg, 67% yield). The two diastereomers were further separated by preparative HPLC to yield 2-(4-((1s,3s)-3-amino-1-((4-fluorophenyl)sulfonyl)cyclobutyl)phenyl)-1,1,1,3,3,3-hexafluoropropan-2-ol (peak 1, 140 mg, 0.297 mmol, 14% yield) and 2-(4-((1r,3r)-3-amino-1-((4-fluorophenyl)sulfonyl)cyclobutyl)phenyl)-1,1,1,3,3,3-hexafluoropropan-2-ol (peak 2, 70 mg, 0.148 mmol, 7% yield).

Analytical data of 2-(4-((1s,3s)-3-amino-1-((4-fluorophenyl)sulfonyl) cyclobutyl)phenyl)-1,1,1,3,3,3-hexafluoropropan-2-ol: LC/MS (M+1): 472.2; LC retention time: 8.05 min (analytical HPLC Method D); 1H NMR (400 MHz, DMSO-d6): δ 8.78 (br-s, 1H), 7.53 (d, J=8.4 Hz, 2H), 7.27-7.21 (m, 6H), 3.23-3.04 (m, 1H), 2.90-2.83 (m, 2H), 2.77-2.70 (m, 2H).

Analytical data of 2-(4-((1r,3r)-3-amino-1-((4-fluorophenyl)sulfonyl) cyclobutyl)phenyl)-1,1,1,3,3,3-hexafluoropropan-2-ol: LC/MS (M+1): 472.0; LC retention time: 8.17 min (analytical HPLC Method D); 1H NMR (400 MHz, DMSO-d6): δ 8.82 (br-s, 1H), 7.53 (d, J=8.4 Hz, 2H), 7.35-7.32 (m, 2H), 7.23 (t, J=8.8 Hz, 2H), 7.03 (d, J=8.4 HZ, 2H), 3.58 (m, 1H), 3.33-3.24 (m, 2H), 2.41-2.33 (m, 2H).

Intermediate 3

(1s,3s)-3-((4-fluorophenyl)sulfonyl)-3-(4-(perfluoropropan-2-yl)phenyl)cyclobutanamine Step A: tert-butyl ((1s,3s)-3-((4-fluorophenyl)sulfonyl)-3-(4-(1,1,1,3,3,3-hexafluoro-2-hydroxypropan-2-yl)phenyl)cyclobutyl)carbamate

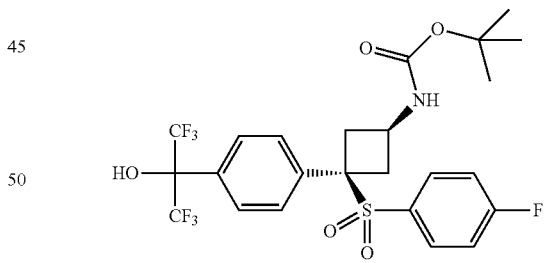

BOC₂O (0.056 mL, 0.243 mmol) and TEA (0.053 mL, 0.382 mmol) were added to a mixture of 2-(4-((1s,3s)-3-amino-1-((4-fluorophenyl)sulfonyl)cyclobutyl)phenyl)-1,1,1,3,3,3-hexafluoropropan-2-ol (90 mg, 0.191 mmol) in CH₂Cl₂ (2 mL) and THF (1 mL). After stirring for 1 h at room temperature, LCMS analysis showed that the reaction was complete. The mixture was concentrated and purified by ISCO (12 g silica gel cartridge, 0-50% EtOAc/hex) to give the desired product as white solid (90.5 mg, 83% yield). LC/MS (M−56+1): 516.1; LC retention time: 4.286 min (analytical HPLC Method A); 1H NMR (400 MHz, CDCl₃-CD₃OD) δ ppm 7.60 (d, J=8.3 Hz, 2H), 7.25-7.17 (m, 2H), 7.16-7.10 (m, 2H), 7.04-6.95 (m, 2H), 4.05-3.94 (m, 1H), 3.14-3.03 (m, 2H), 3.02-2.92 (m, 2H), 1.41 (s, 9H).

Step B: tert-butyl ((1s,3s)-3-((4-fluorophenyl)sulfonyl)-3-(4-(perfluoropropan-2-yl)phenyl)cyclobutyl)carbamate

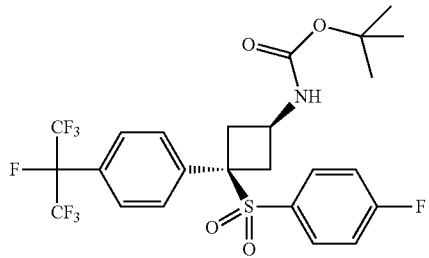 [SMILES: CC(C)(C)OC(=O)N[C@H]1C[C@@](c2ccc(C(F)(C(F)(F)F)C(F)(F)F)cc2)(S(=O)(=O)c2ccc(F)cc2)C1]

A mixture of tert-butyl ((1s,3s)-3-((4-fluorophenyl)sulfonyl)-3-(4-(1,1,1,3,3,3-hexafluoro-2-hydroxypropan-2-yl)phenyl)cyclobutyl)carbamate (90.5 mg, 0.158 mmol) and DAST (0.126 mL, 0.950 mmol) in 1,2-dichloroethane (0.5 mL) in a sealed vial was stirred at 60° C. for 16 h. The mixture was cooled to room temperature and purified by ISCO (12 g silica gel cartridge, 0-50% EtOAc/Hex) to give the desired product as brown solid (43.6 mg, 47% yield). 1H NMR (400 MHz, CDCl$_3$) δ ppm 7.50 (d, J=8.4 Hz, 2H), 7.26-7.22 (m, 2H), 7.17 (d, J=8.4 Hz, 2H), 7.01-6.95 (m, 2H), 5.46-5.31 (m, 1H), 4.24 (d, J=6.4 Hz, 1H), 3.16-3.01 (m, 4H), 1.46 (s, 9H).

Step C: (1s,3s)-3-((4-fluorophenyl)sulfonyl)-3-(4-(perfluoropropan-2-yl)phenyl)cyclobutanamine

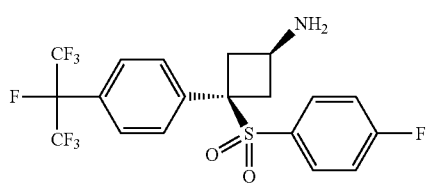 [SMILES: N[C@H]1C[C@@](c2ccc(C(F)(C(F)(F)F)C(F)(F)F)cc2)(S(=O)(=O)c2ccc(F)cc2)C1]

A mixture of tert-butyl ((1s,3s)-3-((4-fluorophenyl)sulfonyl)-3-(4-(perfluoropropan-2-yl)phenyl)cyclobutyl)carbamate (64.7 mg), 4 N dioxane solution of HCl (3 mL) and CH$_2$Cl$_2$ (3 mL) was stirred for 17 h at room temperature, concentrated and dried under vacuum to give desired (1s,3s)-3-((4-fluorophenyl)sulfonyl)-3-(4-(perfluoropropan-2-yl)phenyl)cyclobutanamine HCl salt as yellow solid (57.5 mg). LC/MS (M+1): 474.1; LC retention time: 3.713 min (analytical HPLC Method A); $^1$H NMR (400 MHz, CDCl$_3$-CD$_3$OD) δ ppm 7.53 (d, J=8.4 Hz, 2H), 7.31-7.25 (m, 2H), 7.23 (d, J=8.4 Hz, 2H), 7.09-7.01 (m, 2H), 3.71 (t, J=7.6 Hz, 1H), 3.39-3.33 (m, 2H), 3.16-3.07 (m, 2H).

Example 1

1-(2-(benzyloxy)-1,1,1,3,3,3-hexafluoropropan-2-yl)-4-(1-(phenylsulfonyl)cyclopent-3-en-1-yl)benzene

Step A: 2-(4-(bromomethyl)phenyl)-1,1,1,3,3,3-hexafluoropropan-2-ol

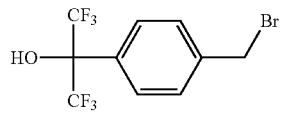

N-Bromosuccinimide (13.79 g, 77 mmol) and 2,2'-azobis(2-methylpropionitrile) (0.025 g, 0.155 mmol) were added to a solution of 1,1,1,3,3,3-hexafluoro-2-(p-tolyl)propan-2-ol (20.00 g, 77 mmol) in carbon tetrachloride (80 mL). The resulting suspension was heated to reflux under nitrogen for 4 h, cooled to room temperature and filtered through a celite pad. The filter cake was rinsed with ether and the filtrate was concentrated under reduced pressure. The residue was treated with ether (100 mL) and hexanes (50 mL), stirred for 15 min and filtered. The filtrate was concentrated under reduced pressure and dried under vacuum to give crude product as tan liquid (27.07 g). 1H NMR analysis showed a 69:15:16 molar ratio of the desired 2-(4-(bromomethyl)phenyl)-1,1,1,3,3,3-hexafluoropropan-2-ol, unreacted 1,1,1,3,3,3-hexafluoro-2-(p-tolyl)propan-2-ol and 2-(4-(dibromomethyl)phenyl)-1,1,1,3,3,3-hexafluoropropan-2-ol. The mixture was used without further purification, assuming ~70% purity of the desired 2-(4-(bromomethyl)phenyl)-1,1,1,3,3,3-hexafluoropropan-2-ol.

Step B: 1,1,1,3,3,3-hexafluoro-2-(4-((phenylsulfonyl)methyl)phenyl)propan-2-ol

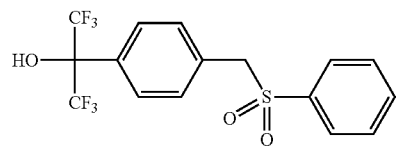 [SMILES: O=S(=O)(Cc1ccc(C(O)(C(F)(F)F)C(F)(F)F)cc1)c1ccccc1]

Sodium benzenesulfinate (3.36 g, 20.47 mmol) was added in small portions over 30 min to a stirred solution of impure 2-(4-(bromomethyl)phenyl)-1,1,1,3,3,3-hexafluoropropan-2-ol (5.00 g, 70% pure) in N,N-dimethylformamide (20 mL). The mixture warmed up slightly during the addition. After stirring at ambient temperature for 24 h, the mixture was diluted with ethyl acetate (150 mL), washed with water (2×100 mL), brine (50 mL), dried (magnesium sulfate), filtered and concentrated under reduced pressure. Silica gel chromatography, eluting with 5-35% ethyl acetate in hexanes, gave 1,1,1,3,3,3-hexafluoro-2-(4-((phenylsulfonyl)methyl)phenyl)propan-2-ol as white solid (3.929 g, 96% yield). LC/MS (M+23): 421.1; 1H NMR (400 MHz, CDCl$_3$) δ ppm 7.67-7.56 (m, 5H), 7.48-7.39 (m, 2H), 7.23-7.15 (m, 2H), 4.34 (s, 2H), 3.60 (s, 1H).

Step C: 1-(2-(benzyloxy)-1,1,1,3,3,3-hexafluoropropan-2-yl)-4-((phenylsulfonyl)methyl)benzene

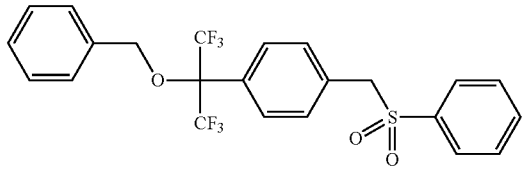 [SMILES: O=S(=O)(Cc1ccc(C(OCc2ccccc2)(C(F)(F)F)C(F)(F)F)cc1)c1ccccc1]

Benzyl bromide (0.588 mL, 4.95 mmol) was added dropwise to a mixture of 1,1,1,3,3,3-hexafluoro-2-(4-((phenylsulfonyl)methyl)phenyl)propan-2-ol (1.516 g, 3.81 mmol) and potassium carbonate (2.104 g, 15.22 mmol) in N,N-dimethylformamide (20 mL). After stirring for 15 h at room temperature, the mixture was diluted with ethyl acetate (180 mL), washed with water (3×50 mL), brine (50 mL), dried (magnesium sulfate), filtered and concentrated under reduced pressure. Silica gel chromatography, eluting with 10-25% ethyl acetate in hexanes, gave 1-(2-(benzyloxy)-1,1,1,3,3,3-hexafluoropropan-2-yl)-4-((phenylsulfonyl)methyl)benzene as white solid (1.602 g, 83% yield). LC/MS (M+18): 506.3; 1H NMR (400 MHz, CDCl$_3$) δ ppm 7.67-7.57 (m, 3H), 7.53 (d, J=8.1 Hz, 2H), 7.48-7.31 (m, 7H), 7.22 (d, J=8.6 Hz, 2H), 4.61 (s, 2H), 4.34 (s, 2H).

Step D: 1-(2-(benzyloxy)-1,1,1,3,3,3-hexafluoropropan-2-yl)-4-(1-(phenylsulfonyl)cyclopent-3-en-1-yl)benzene

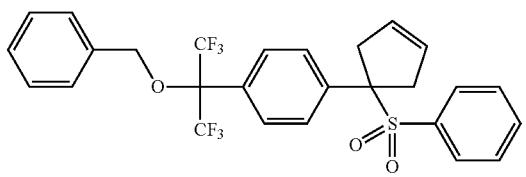 [SMILES: O=S(=O)(c1ccccc1)C1(c2ccc(C(OCc3ccccc3)(C(F)(F)F)C(F)(F)F)cc2)CC=CC1]

Sodium hydride (65.5 mg, 1.638 mmol, 60% in mineral oil) was added to a solution of 1-(2-(benzyloxy)-1,1,1,3,3,3-hexafluoropropan-2-yl)-4-((phenylsulfonyl)methyl)benzene (100 mg, 0.205 mmol) and (Z)-1,4-dichlorobut-2-ene (77 mg, 0.614 mmol) in N,N-dimethylformamide (2 mL). The resulting mixture was stirred under nitrogen over weekend, quenched with water (3 mL), diluted with ethyl acetate (30 mL), washed with water (2×10 mL), brine (10 mL), dried (magnesium sulfate), filtered and concentrated under reduced pressure. Silica gel chromatography, eluting with 5-25% ethyl acetate in hexanes, gave Example 1 as white solid (84 mg, 75% yield). LC/MS (M+18): 558.3; LC retention time: 4.690 min (analytical HPLC Method A); 1H NMR (400 MHz, CDCl$_3$) δ ppm 7.58-7.47 (m, 3H), 7.45-7.27 (m, 11H), 5.69 (s, 2H), 4.64 (s, 2H), 3.69 (d, J=16.1 Hz, 2H), 3.10 (d, J=16.3 Hz, 2H).

Example 2

1,1,1,3,3,3-hexafluoro-2-(4-(1-(phenylsulfonyl)cyclopentyl)phenyl)propan-2-ol

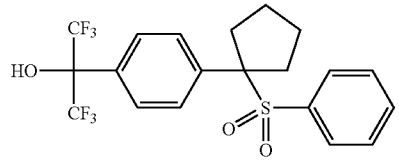 [SMILES: O=S(=O)(c1ccccc1)C1(c2ccc(C(O)(C(F)(F)F)C(F)(F)F)cc2)CCCC1]

A mixture of 1-(2-(benzyloxy)-1,1,1,3,3,3-hexafluoropropan-2-yl)-4-(1-(phenylsulfonyl)cyclopent-3-en-1-yl)benzene (82 mg, 0.152 mmol, from Example 1) and 20% palladium hydroxide on carbon (42.6 mg, 0.061 mmol) in methanol (10 mL) was stirred under balloon pressure hydrogen for 4 h. Additional 20% palladium hydroxide on carbon (42.6 mg, 0.061 mmol) was added. The mixture was hydrogenated at 40 psi hydrogen for 3 h using a Parr Shaker. LCMS analysis showed that the olefin was reduced, but the benzyl ether remained intact. The mixture was filtered to remove the catalyst. The filtrate was concentrated and purified by silica gel chromatography, eluting with 5-25% ethyl acetate in hexanes, to give 1-(2-(benzyloxy)-1,1,1,3,3,3-hexafluoropropan-2-yl)-4-(1-(phenylsulfonyl)cyclopentyl)benzene. A mixture of 1-(2-(benzyloxy)-1,1,1,3,3,3-hexafluoropropan-2-yl)-4-(1-(phenylsulfonyl)cyclopentyl)benzene, 20% palladium hydroxide on carbon (150 mg), methanol (10 mL) and ethyl acetate (5 mL) was hydrogenated at 40 psi hydrogen for 3 h using a Parr Shaker. LCMS analysis showed that the debenzylation was complete. The filtrate was concentrated. Silica gel chromatography, eluting with 10-30% ethyl acetate in hexanes, gave impure product. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation to give Example 2 (17.7 mg). LC/MS (M+1): 470.1; LC retention time: 1.732 min (analytical HPLC Method B); 1H NMR (400 MHz, 1:1 mixture of CDCl$_3$-CD$_3$OD) δ ppm 7.58-7.47 (m, 3H), 7.45-7.27 (m, 11H), 5.69 (s, 2H), 4.64 (s, 2H), 3.69 (d, J=16.1 Hz, 2H), 3.10 (d, J=16.3 Hz, 2H).

Example 3

1-(2-(benzyloxy)-1,1,1,3,3,3-hexafluoropropan-2-yl)-4-(1-((4-fluorophenyl)sulfonyl)cyclopent-3-en-1-yl)benzene Step A: 1,1,1,3,3,3-hexafluoro-2-(4-((phenylsulfonyl)methyl)phenyl)propan-2-ol

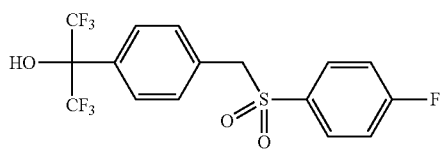

Sodium 4-fluorobenzenesulfinate (12.62 g, 69.3 mmol) was added in small portions to a stirred solution of 2-(4-(bromomethyl)phenyl)-1,1,1,3,3,3-hexafluoropropan-2-ol (20.00 g, ~70% pure from Step A of Example 1) in N,N-dimethylformamide (80 mL). The mixture warmed up slightly during the addition. After 6 h at ambient temperature, the mixture was diluted with ethyl acetate (1 L), washed with water (3×200 mL), brine (100 mL), dried (magnesium sulfate), filtered and concentrated under reduced pressure. The residue was dissolved in dichloromethane (40 mL), triturated with hexanes (400 mL), stirred for 30 min and filtered. The filter cake was washed with hexanes (100 mL) and dried under vacuum to give 1,1,1,3,3,3-hexafluoro-2-(4-((phenylsulfonyl)methyl)phenyl)propan-2-ol as white solid (14.84 g, 82% yield). LC/MS (M+23): 439.2; 1H NMR (400 MHz, CDCl₃) δ ppm 7.64 (d, J=8.1 Hz, 2H), 7.62-7.54 (m, 2H), 7.20 (d, J=8.6 Hz, 2H), 7.15-7.06 (m, 2H), 4.34 (s, 2H), 3.59 (s, 1H).

Step B: 1-(2-(benzyloxy)-1,1,1,3,3,3-hexafluoropropan-2-yl)-4-(((4-fluorophenyl)sulfonyl)methyl)benzene

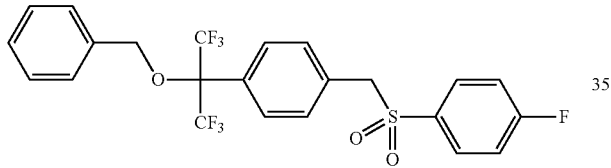

A mixture of 1,1,1,3,3,3-hexafluoro-2-(4-(((4-fluorophenyl)sulfonyl) methyl)phenyl)propan-2-ol (14.84 g, 35.6 mmol), benzyl bromide (6.71 g, 39.2 mmol) and potassium carbonate (14.78 g, 107 mmol) in N,N-dimethylformamide (150 mL) was stirred under nitrogen for 16 h at room temperature. The mixture was quenched with saturated ammonium chloride (100 mL), diluted with ethyl acetate (800 mL), washed with water (2×200 mL), brine (50 mL), dried (magnesium sulfate), filtered and concentrated under reduced pressure. The residue was dissolved in toluene (40 mL), triturated with hexanes (500 mL), stirred for 30 min and filtered. The filter cake was washed with hexanes (100 mL) and dried under vacuum to give first batch of 1-(2-(benzyloxy)-1,1,1,3,3,3-hexafluoropropan-2-yl)-4-(((4-fluorophenyl)sulfonyl)methyl)benzene as yellow solid (14.239 g). The filtrate was concentrated. Silica gel chromatography, eluting with 5-30% ethyl acetate in hexanes, gave the second batch of the desired product as white solid (1.480 g). The combined yield of the product is 87%. LC/MS (M+18): 524.3; LC retention time: 4.486 min (analytical HPLC Method A); 1H NMR (400 MHz, CDCl₃) δ ppm 7.67-7.60 (m, 2H), 7.56 (d, J=8.1 Hz, 2H), 7.45-7.31 (m, 5H), 7.23 (d, J=8.6 Hz, 2H), 7.11 (t, J=8.6 Hz, 2H), 4.62 (s, 2H), 4.34 (s, 2H).

Step C: 1-(2-(benzyloxy)-1,1,1,3,3,3-hexafluoropropan-2-yl)-4-(1-((4-fluorophenyl)sulfonyl)cyclopent-3-en-1-yl)benzene

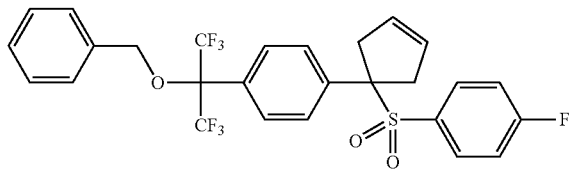 [SMILES: O=S(=O)(c1ccc(F)cc1)C1(c2ccc(C(OCc3ccccc3)(C(F)(F)F)C(F)(F)F)cc2)CC=CC1]

Sodium hydride (0.395 g, 9.87 mmol, 60% suspension in mineral oil) was added to a solution of 1-(2-(benzyloxy)-1,1,1,3,3,3-hexafluoropropan-2-yl)-4-(((4-fluorophenyl)sulfonyl)methyl)benzene (1.000 g, 1.975 mmol) and (Z)-1,4-dichlorobut-2-ene (0.444 g, 3.55 mmol) in N,N-dimethylformamide (30 mL) at 0° C. The resulting mixture was stirred at 0° C. under nitrogen for 1.5 h, quenched with saturated ammonium chloride (50 mL), diluted with ethyl acetate (150 mL), washed with water (2×50 mL), brine (25 mL), dried (magnesium sulfate), filtered and concentrated under reduced pressure. Silica gel chromatography, eluting with 5-25% ethyl acetate in hexanes, gave Example 3 as off-white solid (770.7 mg, 70% yield). LC/MS (M+18): 576.3; LC retention time: 4.715 min (analytical HPLC Method A); 1H NMR (400 MHz, CDCl₃) δ ppm 7.55 (d, J=8.4 Hz, 2H), 7.46-7.30 (m, 9H), 7.06-6.93 (m, 2H), 5.70 (s, 2H), 4.65 (s, 2H), 3.65 (d, J=16.3 Hz, 2H), 3.11 (d, J=16.3 Hz, 2H).

Example 4

1-(2-(benzyloxy)-1,1,1,3,3,3-hexafluoropropan-2-yl)-4-(1-((4-fluorophenyl)sulfonyl)cyclopentyl)benzene

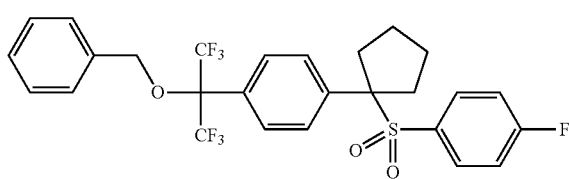

A mixture of 1-(2-(benzyloxy)-1,1,1,3,3,3-hexafluoropropan-2-yl)-4-(1-((4-fluorophenyl)sulfonyl)cyclopent-3-en-1-yl)benzene (20 mg, 0.036 mmol, from Example 3) and 20% palladium hydroxide on carbon (40.2 mg, 0.057 mmol) in methanol (8 mL) and ethyl acetate (4 mL) was stirred under balloon pressure hydrogen for 15 h. The mixture was filtered to remove the catalyst and the filtrate concentrated. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 45-100% B over 15 minutes, then a 5-minute hold at 100% B; Flow: 20 mL/min. Fractions containing the desired product were combined and dried via centrifugal evaporation to give Example 4 (9.9 mg, 47% yield). LC/MS (M+18): 578.1; LC retention time: 3.313 min (analytical HPLC Method B); 1H NMR (500 MHz, 1:1 mixture of CDCl₃-CD₃OD) δ ppm 7.52 (d, J=8.4 Hz, 2H), 7.44-7.40 (m, 2H), 7.39-7.32 (m, 5H), 7.30-7.22 (m, 2H), 7.05-6.96 (m, 2H), 4.63 (s, 2H), 2.91-2.79 (m, 2H), 2.45-2.33 (m, 2H), 2.13-2.02 (m, 2H), 1.83-1.70 (m, 2H).

Example 5

1,1,1,3,3,3-hexafluoro-2-(4-(1-((4-fluorophenyl)sulfonyl)cyclopentyl)phenyl)propan-2-ol

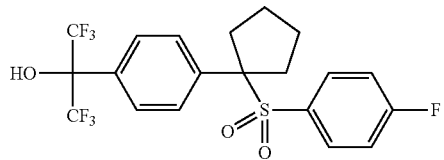 [SMILES: O=S(=O)(c1ccc(F)cc1)C1(c2ccc(C(O)(C(F)(F)F)C(F)(F)F)cc2)CCCC1]

A mixture of 1-(2-(benzyloxy)-1,1,1,3,3,3-hexafluoropropan-2-yl)-4-(1-((4-fluorophenyl)sulfonyl)cyclopent-3-en-1-yl)benzene (403 mg, 0.722 mmol, from Example 3) and 20% palladium hydroxide on carbon (1.267 g, 1.804 mmol) in methanol (10 mL) and ethyl acetate (5 mL) was hydrogenated at 40 psi hydrogen using a Parr Shaker for 18 h. The mixture was filtered and the filtrate concentrated. Silica gel chromatography, eluting with 5-30% ethyl acetate in hexanes, gave the desired impure product. The material was dissolved in dichloromethane (2 mL), triturated with hexanes (14 mL) and stirred for 30 min. The suspension was collected by filtration to give Example 5 as white solid (132.2 mg, 39% yield). LC/MS (M+23): 493.3; LC retention time: 4.208 min (analytical HPLC Method A); 1H NMR (400 MHz, CDCl₃) δ ppm 7.57 (d, J=8.4 Hz, 2H), 7.33-7.26 (m, 2H), 7.23-7.15 (m, 2H), 6.97-6.85 (m, 2H), 3.43 (s, 1H), 2.92-2.77 (m, 2H), 2.39-2.25 (m, 2H), 2.16-1.98 (m, 2H), 1.80-1.64 (m, 2H).

Example 6

1-[1-(4-fluorobenzenesulfonyl)cyclopentyl]-4-(1,1,1,3,3,3-hexafluoro-2-methoxypropan-2-yl)benzene

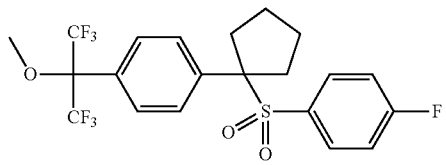 [SMILES: COC(c1ccc(C2(S(=O)(=O)c3ccc(F)cc3)CCCC2)cc1)(C(F)(F)F)C(F)(F)F]

A mixture of 1,1,1,3,3,3-hexafluoro-2-(4-(1-((4-fluorophenyl)sulfonyl)cyclopentyl)phenyl)propan-2-ol (20 mg, 0.043 mmol, from Example 5), iodomethane (18.1 mg, 0.128 mmol) and potassium carbonate (29.4 mg, 0.213 mmol) in N,N-dimethylformamide (1 mL) was stirred at room temperature for 15 h. The mixture was filtered and purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to give Example 6 (16.2 mg, 78% yield). LC/MS (M+18): 502.2; LC retention time: 2.437 min (analytical HPLC Method B); 1H NMR (500 MHz, 1:1 mixture of CDCl₃-CD₃OD) δ ppm 7.47 (d, J=8.4 Hz, 2H), 7.37-7.32 (m, 2H), 7.29-7.22 (m, 2H), 7.05-6.97 (m, 2H), 3.50 (s, 3H), 2.91-2.79 (m, 2H), 2.44-2.33 (m, 2H), 2.15-2.03 (m, 2H), 1.83-1.70 (m, 2H).

Example 7

1-[1-(4-fluorobenzenesulfonyl)cyclopentyl]-4-(heptafluoropropan-2-yl)benzene

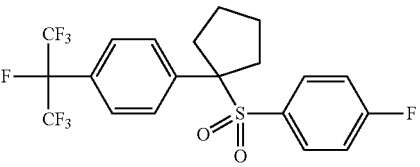 [SMILES: O=S(=O)(c1ccc(F)cc1)C1(c2ccc(C(F)(C(F)(F)F)C(F)(F)F)cc2)CCCC1]

(Diethylamino)sulfur trifluoride (0.025 mL, 0.191 mmol) was added to a solution of 1,1,1,3,3,3-hexafluoro-2-(4-(1-((4-fluorophenyl)sulfonyl) cyclopentyl)phenyl)propan-2-ol (30 mg, 0.064 mmol, from Example 5) in dichloromethane (1 mL) at room temperature. The reaction vial was sealed, stirred at room temperature for 15 h and at 85° C. for 15 h. After cooling to room temperature, the mixture was quenched with saturated sodium bicarbonate (1 mL), diluted with dichloromethane (60 mL), washed with water, brine, dried (magnesium sulfate), filtered and concentrated under reduced pressure. Silica gel chromatography, eluting with 0-20% ethyl acetate in hexanes, provided Example 7 (18.0 mg, 54% yield). LC/MS (M+18): 490.0; HPLC RT=4.58 min (analytical HPLC Method B); ¹H NMR (400 MHz, CDCl₃) δ ppm 7.47 (d, J=8.4 Hz, 2H), 7.33 (d, J=8.4 Hz, 2H), 7.26-7.09 (m, 2H), 6.98-6.84 (m, 2H), 3.01-2.75 (m, 2H), 2.46-2.22 (m, 2H), 2.18-1.96 (m, 2H), 1.82-1.61 (m, 2H).

Example 8

1-(2-chloro-1,1,1,3,3,3-hexafluoropropan-2-yl)-4-(1-((4-fluorophenyl)sulfonyl)cyclopentyl)benzene

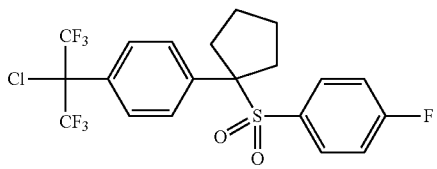 [SMILES: O=S(=O)(c1ccc(F)cc1)C1(c2ccc(C(Cl)(C(F)(F)F)C(F)(F)F)cc2)CCCC1]

Thionyl chloride (0.051 ml, 0.699 mmol) was added to a solution of 1,1,1,3,3,3-hexafluoro-2-(4-(1-((4-fluorophenyl)sulfonyl)cyclopentyl)phenyl)propan-2-ol (47 mg, 0.100 mmol, from Example 5) in pyridine (0.2 mL, 2.473 mmol) at room temperature. After 15 h at reflux, the mixture was cooled to room temperature and treated with 1 N hydrochloric acid (5 mL). After stirring for 10 min, the mixture was extracted with ethyl acetate (3×10 mL), washed with water, brine, dried (magnesium sulfate), filtered and concentrated under reduced pressure. Silica gel chromatography, eluting with 0-20% ethyl acetate in hexanes, provided the title compound (25.0 mg, 46% yield). LC/MS (M+18): 505.9; HPLC RT=4.63 min (analytical HPLC Method B); $^1$H NMR (400 MHz, CDCl$_3$) δ ppm 7.67 (d, J=8.6 Hz, 2H), 7.36-7.10 (m, 4H), 7.02-6.80 (m, 2H), 3.01-2.62 (m, 2H), 2.49-2.18 (m, 2H), 2.20-1.96 (m, 2H), 1.83-1.49 (m, 2H).

Example 9

1,1,1,3,3,3-hexafluoro-2-(4-(1-((4-fluorophenyl)sulfonyl)cyclopentyl)phenyl)propan-2-amine Step A: 1,1,1,3,3,3-hexafluoro-2-(4-(1-((4-fluorophenyl)sulfonyl)cyclopentyl)phenyl)propan-2-yl trifluoromethanesulfonate

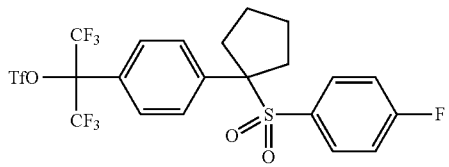 [SMILES: O=S(=O)(OC(c1ccc(C2(S(=O)(=O)c3ccc(F)cc3)CCCC2)cc1)(C(F)(F)F)C(F)(F)F)C(F)(F)F]

Potassium methoxide (19.68 mg, 0.281 mmol) was added to a solution of 1,1,1,3,3,3-hexafluoro-2-(4-(1-((4-fluorophenyl)sulfonyl)cyclopentyl)phenyl)propan-2-ol (120 mg, 0.255 mmol, from Example 5) in toluene (1 mL) at room temperature. The resulting mixture was stirred at room temperature for 1 h and concentrated. The residue was dissolved in toluene (1 mL) and cooled to 0° C. A 1.0 M dichloromethane solution of trifluoromethanesulfonic anhydride (0.332 mL, 0.332 mmol) was added. The resultant mixture was warmed to room temperature and stirred for 5 h. After addition of ethyl acetate (60 ml), the mixture was washed with water, brine, dried (magnesium sulfate), filtered and concentrated under reduced pressure. Silica gel chromatography, eluting with 0-20% ethyl acetate in hexanes, provided 1,1,1,3,3,3-hexafluoro-2-(4-(1-((4-fluorophenyl)sulfonyl)cyclopentyl) phenyl)propan-2-yl trifluoromethanesulfonate (65 mg, 42% yield). LC/MS (M+18): 619.9; $^1$H NMR (400 MHz, CDCl$_3$) δ ppm 7.58 (d, J=8.8 Hz, 2H), 7.43-7.29 (m, 2H), 7.26-7.04 (m, 2H), 7.04-6.81 (m, 2H), 2.99-2.76 (m, 2H), 2.34-2.24 (m, 2H), 2.16-1.97 (m, 2H), 1.80-1.60 (m, 2H).

Step B: 1-(2-azido-1,1,1,3,3,3-hexafluoropropan-2-yl)-4-(1-((4-fluorophenyl)sulfonyl)cyclopentyl) benzene

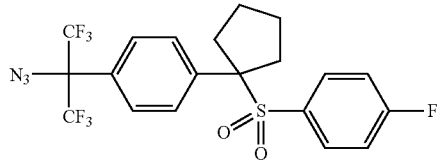 [SMILES: [N-]=[N+]=NC(c1ccc(C2(S(=O)(=O)c3ccc(F)cc3)CCCC2)cc1)(C(F)(F)F)C(F)(F)F]

Trifluoroacetic acid (0.5 mL, 6.49 mmol) was added to a mixture of 1,1,1,3,3,3-hexafluoro-2-(4-(1-((4-fluorophenyl)sulfonyl)cyclopentyl)phenyl)propan-2-yl trifluoromethanesulfonate (60 mg, 0.100 mmol) and sodium azide (19.42 mg, 0.299 mmol) at room temperature. After stirring for 4 h at room temperature, additional sodium azide (19.42 mg, 0.299 mmol) was added. After 2 h at 45° C., another portion of sodium azide (19.42 mg, 0.299 mmol) was added and the mixture stirred for additional 2 h at 45° C. The mixture was quenched with ammonium hydroxide (0.5 mL), diluted with dichloromethane (60 mL), washed with water, brine, dried (magnesium sulfate), filtered and concentrated under reduced pressure. Silica gel chromatography, eluting with 0 to 20% ethyl acetate in hexanes, provided 1-(2-azido-1,1,1,3,3,3-hexafluoropropan-2-yl)-4-(1-((4-fluorophenyl)sulfonyl)cyclopentyl) benzene (30 mg, 61% yield). $^1$H NMR (400 MHz, CDCl$_3$) δ ppm 7.65-7.45 (m, 2H), 7.34-7.27 (m, 2H), 7.27-7.10 (m, 2H), 7.03-6.80 (m, 2H), 3.00-2.62 (m, 2H), 2.35-2.21 (m, 2H), 2.11-1.96 (m, 2H), 1.82-1.58 (m, 2H).

Step C: 1,1,1,3,3,3-hexafluoro-2-(4-(1-((4-fluorophenyl)sulfonyl)cyclopentyl)phenyl)propan-2-amine

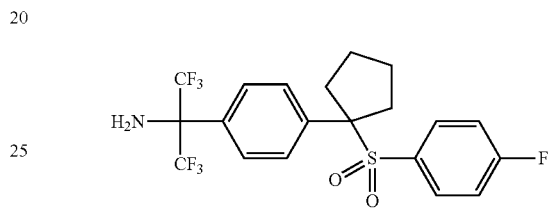

A mixture of 1-(2-azido-1,1,1,3,3,3-hexafluoropropan-2-yl)-4-(1-((4-fluorophenyl)sulfonyl)cyclopentyl)benzene (30 mg, 0.061 mmol) and 5% palladium on carbon (12.89 mg, 0.012 mmol) in dichloromethane (4 mL) and methanol (4 mL) was stirred under hydrogen (30 psi) for 3 h. The resulting mixture was filtered to remove the catalyst. The filtrate was concentrated to provide Example 9 (27 mg, 89% yield). LC/MS (M+23): 492.1; HPLC RT=4.25 min (analytical HPLC Method B); $^1$H NMR (400 MHz, CD$_3$OD) δ ppm 7.79-7.48 (m, 2H), 7.48-7.07 (m, 4H), 7.18-6.83 (m, 2H), 3.03-2.57 (m, 2H), 2.51-2.20 (m, 2H), 2.05-1.94 (m, 2H), 1.84-1.51 (m, 2H).

Example 10

1,1,1-trifluoro-2-(4-(1-((4-fluorophenyl)sulfonyl)cyclopentyl)phenyl)propan-2-ol Step A: 1-fluoro-4-((4-iodobenzyl)sulfonyl)benzene

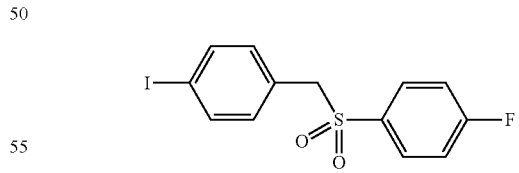

Sodium 4-fluorobenzenesulfinate (3.52 g, 19.33 mmol) was added in several portions to a stirred solution of 1-(bromomethyl)-4-iodobenzene (4.10 g, 13.81 mmol) in N,N-dimethylformamide (30 mL). The reaction was slightly exothermic. The resulting suspension was stirred under nitrogen for 15 h, diluted with water (120 mL), stirred for 15 min and filtered. The filter cake was washed with water (3×30 mL) and dried under vacuum to give 1-fluoro-4-((4-iodobenzyl)sulfonyl)benzene as white solid (5.130 g, 99% yield). LC/MS (M+23): 399.1; HPLC RT=3.773 min (analytical HPLC Method A); 1H NMR (400 MHz, CDCl₃) δ ppm 7.69-7.58 (m, 4H), 7.15 (t, J=8.6 Hz, 2H), 6.87-6.79 (m, 2H), 4.23 (s, 2H).

Step B: 1-fluoro-4-((1-(4-iodophenyl)cyclopentyl) sulfonyl)benzene

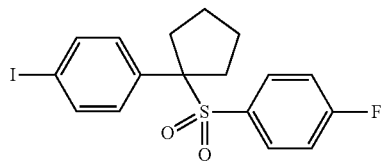 [SMILES: O=S(=O)(c1ccc(F)cc1)C1(c2ccc(I)cc2)CCCC1]

A solution of 1-fluoro-4-((4-iodobenzyl)sulfonyl)benzene (2.190 g, 5.82 mmol) in N,N-dimethylformamide (20 mL) was added over 5 min to a suspension of sodium hydride (1.164 g, 29.1 mmol, 60% suspension in mineral oil) and 1,4-dibromobutane (2.51 g, 11.64 mmol) in N,N-dimethylformamide (40 mL) at 0° C. After 2 h at 0° C., the mixture was quenched with saturated ammonium chloride (20 mL), diluted with water (150 mL) and extracted with ethyl acetate (3×60 mL). The combined extracts were washed with water (30 mL), brine (30 mL), dried (magnesium sulfate), filtered and concentrated under reduced pressure. Silica gel chromatography, eluting with 2-20% ethyl acetate in hexanes, gave 1-fluoro-4-((1-(4-iodophenyl)cyclopentyl)sulfonyl) benzene as white solid (1.853 g, 70% yield). LC/MS (M+23): 453.0; HPLC RT=4.371 min (analytical HPLC Method A); 1H NMR (400 MHz, CDCl₃) δ ppm 7.62-7.52 (m, 2H), 7.36-7.28 (m, 2H), 7.07-6.98 (m, 2H), 6.96-6.88 (m, 2H), 2.83-2.69 (m, 2H), 2.30-2.18 (m, 2H), 2.09-1.96 (m, 2H), 1.73-1.59 (m, 2H).

Step C: 1,1,1-trifluoro-2-(4-(1-((4-fluorophenyl) sulfonyl)cyclopentyl)phenyl)propan-2-ol

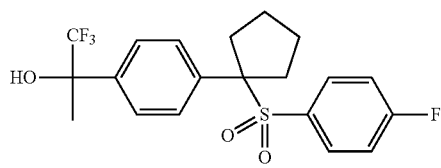 [SMILES: CC(O)(c1ccc(C2(S(=O)(=O)c3ccc(F)cc3)CCCC2)cc1)C(F)(F)F]

A 1.7 M pentane solution of tert-butyllithium (0.342 mL, 0.581 mmol) was added to a solution of 1-fluoro-4-((1-(4-iodophenyl)cyclopentyl)sulfonyl)benzene (100 mg, 0.232 mmol) in tetrahydrofuran (3 mL) at −78° C. The resulting mixture was stirred under nitrogen for 10 min. 1,1,1-Trifluoropropan-2-one (0.083 mL, 0.930 mmol) was added. After stirring for 30 min at −78° C., the mixture was quenched with saturated ammonium chloride (3 mL), diluted with ethyl acetate (30 mL), washed with water (2×5 mL) and brine (5 mL), dried (magnesium sulfate), filtered and concentrated under reduced pressure. Silica gel chromatography, eluting with 5-40% ethyl acetate in hexanes, gave Example 10 as colorless liquid (37.4 mg, 33% yield). LC/MS (M+23): 439.2; HPLC RT=4.045 min (analytical HPLC Method A); 1H NMR (400 MHz, CDCl₃) δ ppm 7.44 (d, J=8.4 Hz, 2H), 7.25-7.16 (m, 4H), 6.99-6.86 (m, 2H), 2.87-2.73 (m, 2H), 2.59 (s, 1H), 2.39-2.23 (m, 2H), 2.13-1.98 (m, 2H), 1.77 (d, J=0.7 Hz, 3H), 1.73-1.65 (m, 2H).

Example 11

1,3-difluoro-2-(((1,1,1-trifluoro-2-(4-(1-((4-fluorophenyl)sulfonyl)cyclopentyl)phenyl)propan-2-yl) oxy)methyl)benzene

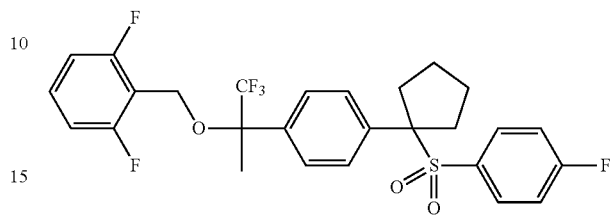

Sodium hydride (14.60 mg, 0.365 mmol, 60% suspension in mineral oil) was added to a solution of 1,1,1-trifluoro-2-(4-(1-((4-fluorophenyl)sulfonyl) cyclopentyl)phenyl)propan-2-ol (15.2 mg, 0.037 mmol, from Example 10) and 2-(bromomethyl)-1,3-difluorobenzene (22.67 mg, 0.110 mmol) in N,N-dimethylformamide (1 mL) at room temperature. After stirring under nitrogen for 18 h, the mixture was quenched with saturated ammonium chloride (2 mL), diluted with ethyl acetate (15 mL), washed with water (2×3 mL), brine (3 mL), dried (magnesium sulfate), filtered and concentrated under reduced pressure. The crude material was purified via preparative LC/MS with the following conditions: Column: Waters XBridge C18, 19×100 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 10 minutes, then a 5-minute hold at 100% B; Flow: 20 mL/min. Fractions containing the desired product were combined and dried via centrifugal evaporation to give Example 11 (15.3 mg, 77% yield). LC/MS (M+18): 560.2; HPLC RT=2.51 min (analytical HPLC Method B); 1H NMR (500 MHz, 1:1 mixture of CDCl₃-CD₃OD) δ ppm 7.48 (d, J=8.4 Hz, 2H), 7.43-7.33 (m, 1H), 7.31-7.22 (m, 4H), 7.05-6.91 (m, 4H), 4.57 (d, J=9.9 Hz, 1H), 4.40-4.32 (m, 1H), 2.83 (td, J=14.7, 7.7 Hz, 2H), 2.47-2.32 (m, 2H), 2.14-2.01 (m, 2H), 1.94 (s, 3H), 1.83-1.67 (m, 2H).

Example 12

1-(difluoro(phenyl)methyl)-4-(1-((4-fluorophenyl) sulfonyl)cyclopentyl)benzene

Step A: (4-(1-((4-fluorophenyl)sulfonyl)cyclopentyl) phenyl)(phenyl)methanol

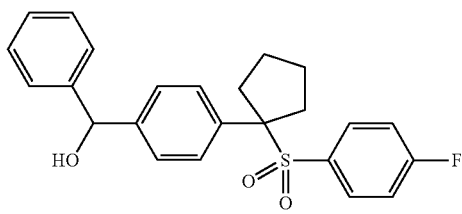 [SMILES: O=S(=O)(c1ccc(F)cc1)C1(c2ccc(C(O)c3ccccc3)cc2)CCCC1]

A 2.0 M ether solution of isopropylmagnesium chloride (0.209 mL, 0.418 mmol) was added to a solution of 1-fluoro-4-((1-(4-iodophenyl)cyclopentyl) sulfonyl)benzene (60 mg, 0.139 mmol, from Step B of Example 10) in tetrahydrofuran (1 mL) at 0° C. After stirring for 30 min at 0° C., benzaldehyde (44.4 mg, 0.418 mmol) was added. The resulting mixture was stirred at 0° C. for 30 min and warmed to room temperature for 1 h. After quenching with water (1 mL), the mixture was concentrated. The residue was purified by silica gel chromatography, eluting with 0 to 30% ethyl acetate in hexanes, to provide (4-(1-((4-fluorophenyl)sulfonyl)cyclopentyl)phenyl)(phenyl)methanol (40 mg, 66% yield). LM/CS (M+18): 428.2; HPLC RT=4.06 min (analytical HPLC Method A); 1H NMR (400 MHz, CDCl$_3$) δ ppm 7.44-7.34 (m, 4H), 7.34-7.21 (m, 3H), 7.21-7.02 (m, 4H), 6.89-6.66 (m, 2H), 5.82 (d, J=1.5 Hz, 1H), 2.81-2.57 (m, 2H), 2.28 (dt, J=13.0, 6.4 Hz, 2H), 2.07-2.01 (m, 2H), 1.75-1.60 (m, 2H).

Step B: (4-(1-((4-fluorophenyl)sulfonyl)cyclopentyl)phenyl)(phenyl)methanone

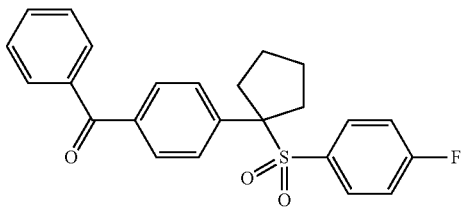 [SMILES: O=C(c1ccccc1)c1ccc(C2(S(=O)(=O)c3ccc(F)cc3)CCCC2)cc1]

Dess-Martin periodinane (43.4 mg, 0.102 mmol) was added to a solution of (4-(1-((4-fluorophenyl)sulfonyl)cyclopentyl)phenyl)(phenyl)methanol (35 mg, 0.085 mmol) in dichloromethane (3 mL) at room temperature. The resultant suspension was stirred at room temperature for 2 h, quenched with saturated sodium bicarbonate (2 mL) and diluted with dichloromethane (60 mL). The resulting mixture was washed with water, brine, dried (magnesium sulfate), filtered and concentrated under reduced pressure. Silica gel chromatography, eluting with 0 to 20% ethyl acetate in hexanes, provided (4-(1-((4-fluorophenyl)sulfonyl)cyclopentyl)phenyl)(phenyl)methanone (25 mg, 68% yield). LC/MS (M+1): 409.1; HPLC RT=4.24 min (analytical HPLC Method A); 1H NMR (400 MHz, CDCl$_3$) δ ppm 7.81-7.71 (m, 2H), 7.71-7.54 (m, 3H), 7.54-7.38 (m, 2H), 7.38-7.28 (m, 4H), 7.10-6.80 (m, 2H), 2.99-2.64 (m, 2H), 2.46-2.19 (m, 2H), 2.16-1.96 (m, 2H), 1.78-1.63 (m, 2H).

Step C: 1-(difluoro(phenyl)methyl)-4-(1-((4-fluorophenyl)sulfonyl)cyclopentyl) benzene

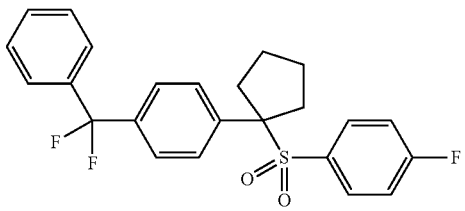 [SMILES: O=S(=O)(c1ccc(F)cc1)C1(c2ccc(C(F)(F)c3ccccc3)cc2)CCCC1]

A mixture of (4-(1-((4-fluorophenyl)sulfonyl)cyclopentyl)phenyl)(phenyl) methanone (20 mg, 0.049 mmol) and Deoxofluor (271 μl, 1.469 mmol) was heated at 90° C. in a sealed tube for 15 h. After cooling to room temperature, the mixture was diluted with dichloromethane (50 mL), washed with saturated sodium bicarbonate, water, brine, dried (magnesium sulfate), filtered and concentrated under reduced pressure. Silica gel chromatography, eluting with 0 to 20% ethyl acetate in hexanes, provided Example 12 (9.0 mg, 43% yield). LC/MS (M+23): 453.0; HPLC RT=4.52 min (analytical HPLC Method A); 1H NMR (400 MHz, CDCl$_3$) δ ppm 7.56-7.30 (m, 7H), 7.30-7.11 (m, 4H), 6.97-6.70 (m, 2H), 2.94-2.68 (m, 2H), 2.42-2.26 (m, 2H), 2.13-1.94 (m, 2H), 1.80-1.55 (m, 2H).

Example 13

1-fluoro-4-((1-(4-(1,1,1,3,3,3-hexafluoro-2-phenoxypropan-2-yl)phenyl)cyclopentyl)sulfonyl)benzene

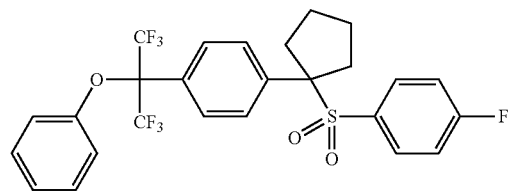 [SMILES: O=S(=O)(c1ccc(F)cc1)C1(c2ccc(C(Oc3ccccc3)(C(F)(F)F)C(F)(F)F)cc2)CCCC1]

Sodium hydride (7.65 mg, 0.191 mmol, 60% suspension in mineral oil) was added to a solution of 1,1,1,3,3,3-hexafluoro-2-(4-(1-((4-fluorophenyl)sulfonyl)cyclopentyl)phenyl)propan-2-ol (15 mg, 0.032 mmol, from Example 5) and diphenyliodonium iodide (26.0 mg, 0.064 mmol) in toluene (1 mL) under nitrogen at room temperature. The resulting mixture was heated to reflux for 4 h, cooled to room temperature and quenched with saturated sodium bicarbonate (1 mL). Following addition of ethyl acetate (60 mL), the mixture was washed with water, brine, dried (magnesium sulfate), filtered and concentrated under reduced pressure. Silica gel chromatography, eluting with 0 to 20% ethyl acetate in hexanes, provided the title compound (3.0 mg, 16% yield). LC/MS (M+23): 569.0; HPLC RT=4.80 min. (analytical HPLC Method A); $^1$H NMR (400 MHz, CDCl$_3$) δ ppm 7.44 (d, J=8.4 Hz, 2H), 7.25-7.09 (m, 4H), 7.00-6.85 (m, 2H), 2.87-2.76 (m, 2H), 2.43-2.26 (m, 2H), 2.14-2.00 (m, 2H), 1.76 (s, 3H), 1.72-1.64 (m, 2H).

Example 14 rac-(1R,3R)-3-(4-(2-(benzyloxy)-1,1,1,3,3,3-hexafluoropropan-2-yl)phenyl)-3-((4-fluorophenyl)sulfonyl)cyclopentanol

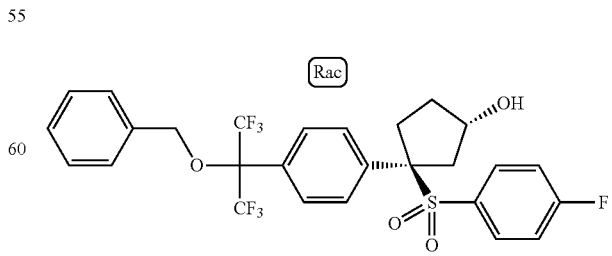

A 1 M tetrahydrofuran solution of borane tetrahydrofuran complex (8.95 mL, 8.95 mmol) was added dropwise to a solution of 1-(2-(benzyloxy)-1,1,1,3,3,3-hexafluoropropan-2-yl)-4-(1-((4-fluorophenyl)sulfonyl)cyclopent-3-en-1-yl)benzene (2.00 g, 3.58 mmol, from Example 1) in tetrahydrofuran (50 mL) at 0° C. The resulting solution was stirred under nitrogen and allowed to slowly warm to room temperature overnight. After 20 h, the mixture was cooled to 0° C., and quenched with dropwise addition of water (20 mL). A 30% hydrogen peroxide solution (3.66 mL, 35.8 mmol) and 1 N sodium hydroxide (17.90 mL, 17.90 mmol) were added dropwise and the mixture allowed to slowly warm to room temperature overnight. The mixture was diluted with brine (80 mL), water (80 mL), and extracted with dichloromethane (3×120 mL). The combined organic extracts were washed with water (50 mL), brine (50 mL), dried (magnesium sulfate), filtered and concentrated under reduced pressure. Silica gel chromatography, eluting with 20-50% ethyl acetate in hexanes, gave Example 14 as white solid (1.801 g, 82% yield, contaminated with approximately 10% of the cis alcohol isomer). LC/MS (M+18): 594.2; LC retention time: 4.510 min (analytical HPLC Method A); 1H NMR (500 MHz, 1:1 mixture of $CDCl_3$-$CD_3OD$) δ ppm 7.90 (dd, J=8.7, 5.2 Hz, 1H), 7.78-7.64 (m, 4H), 7.41 (s, 5H), 7.22 (td, J=8.4, 2.5 Hz, 1H), 7.11 (dd, J=9.4, 2.5 Hz, 1H), 4.68 (s, 2H), 3.63 (t, J=5.4 Hz, 1H), 3.28 (d, J=13.4 Hz, 1H), 3.15-3.04 (m, 1H), 2.67-2.58 (m, 1H), 2.55 (dd, J=13.4, 5.0 Hz, 1H), 2.43-2.30 (m, 1H), 1.92 (dd, J=12.9, 9.4 Hz, 1H).

Example 15 rac-(1R,3R)-3-((4-fluorophenyl)sulfonyl)-3-(4-(1,1,1,3,3,3-hexafluoro-2-hydroxypropan-2-yl)phenyl)cyclopentanol

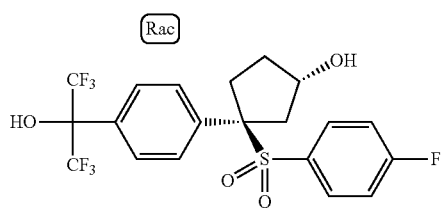 [SMILES: O=S(=O)(c1ccc(F)cc1)[C@@]1(c2ccc(C(O)(C(F)(F)F)C(F)(F)F)cc2)CC[C@H](O)C1]

A mixture of (1S,3S)-3-(4-(2-(benzyloxy)-1,1,1,3,3,3-hexafluoropropan-2-yl)phenyl)-3-((4-fluorophenyl)sulfonyl)cyclopentanol (1.425 g, 2.472 mmol, from Example 14) and 20% palladium hydroxide on carbon (3.82 g, 5.44 mmol) in ethyl acetate (15 mL) and methanol (30 mL) was hydrogenated under hydrogen (40 psi) using a Parr shaker for 15 h. The reaction mixture was filtered and the filter cake rinsed with ethyl acetate. The filtrate was concentrated. Silica gel chromatography, eluting with 20-70% ethyl acetate in hexanes, gave Example 15 as white solid (1.083 g, 90% yield, contaminated with approximately 10% of the cis alcohol isomer). LC/MS (M+23): 509.2; LC retention time: 3.853 min (analytical HPLC Method A); 1H NMR (400 MHz, 1:1 mixture of $CDCl_3$-$CD_3OD$) δ ppm 7.61 (d, J=8.6 Hz, 2H), 7.28-7.21 (m, 2H), 7.21-7.12 (m, 2H), 7.05-6.93 (m, 2H), 4.72-4.63 (m, 1H), 3.16 (dd, J=14.9, 6.1 Hz, 1H), 2.86 (ddd, J=14.1, 7.9, 4.6 Hz, 1H), 2.59 (dt, J=14.3, 8.6 Hz, 1H), 2.44-2.28 (m, 2H), 1.80 (ddt, J=12.5, 8.3, 3.9 Hz, 1H).

Examples 16 and 17

(1S,3S)-3-((4-fluorophenyl)sulfonyl)-3-(4-(1,1,1,3,3,3-hexafluoro-2-hydroxypropan-2-yl)phenyl)cyclopentanol and (1R,3R)-3-((4-fluorophenyl)sulfonyl)-3-(4-(1,1,1,3,3,3-hexafluoro-2-hydroxypropan-2-yl)phenyl)cyclopentanol

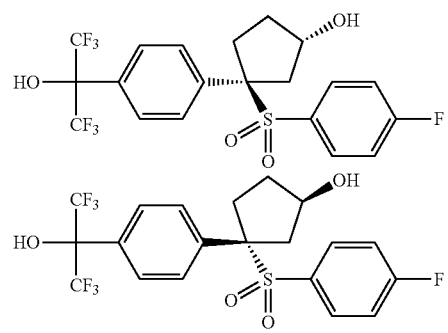

rac-(1R,3R)-3-((4-fluorophenyl)sulfonyl)-3-(4-(1,1,1,3,3,3-hexafluoro-2-hydroxypropan-2-yl)phenyl)cyclopentanol (1.083 g, from Example 15) was separated into its homochiral components using a chiral AS-H column, 10% methanol in $CO_2$, 40° C., 140 bars to afford (1S,3S)-3-((4-fluorophenyl)sulfonyl)-3-(4-(1,1,1,3,3,3-hexafluoro-2-hydroxypropan-2-yl)phenyl)cyclopentanol (493 mg) as the first eluent off the column and (1R,3R)-3-((4-fluorophenyl)sulfonyl)-3-(4-(1,1,1,3,3,3-hexafluoro-2-hydroxypropan-2-yl)phenyl)cyclopentanol (474 mg) as the second eluent off the column. Both examples are contaminated with approximately 10% of cis alcohol isomer.

Example 18

1,3-difluoro-2-(((1,1,1,3,3,3-hexafluoro-2-(4-(1-((4-fluorophenyl)sulfonyl)cyclopent-3-en-1-yl)phenyl)propan-2-yl)oxy)methyl)benzene Step A: 1,3-difluoro-2-(((1,1,1,3,3,3-hexafluoro-2-(4-(((4-fluorophenyl)sulfonyl)methyl)phenyl)propan-2-yl)oxy)methyl)benzene

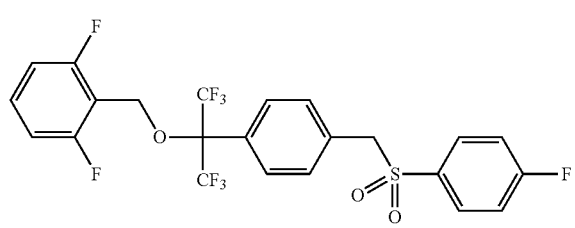 [SMILES: O=S(=O)(Cc1ccc(C(OCc2c(F)cccc2F)(C(F)(F)F)C(F)(F)F)cc1)c1ccc(F)cc1]

A mixture of 1,1,1,3,3,3-hexafluoro-2-(4-(((4-fluorophenyl)sulfonyl)methyl)phenyl)propan-2-ol (12.625 g, 30.3 mmol, from Step A of Example 3), 2-(bromomethyl)-1,3-difluorobenzene (6.59 g, 31.8 mmol) and potassium carbonate (12.57 g, 91 mmol) in N,N-dimethylformamide (120 mL) was stirred under nitrogen at room temperature for 22 h. The mixture was quenched with saturated ammonium chloride (100 mL), diluted with ethyl acetate (800 mL), washed with water (3×100 mL), brine (50 mL), dried (magnesium sulfate), filtered and concentrated under reduced pressure. The residue was treated with dichloromethane (20 mL) and toluene (40 mL), sonicated, triturated with hexanes (500 mL), stirred for 15 min and filtered. The filter cake was washed with hexanes (100 mL) and dried under vacuum to give first batch of 1,3-difluoro-2-(((1,1,1,3,3,3-hexafluoro-2-(4-(((4-fluorophenyl)sulfonyl)methyl)phenyl)propan-2-yl)oxy)methyl)benzene as white solid (14.881 g). The filtrate was concentrated. Silica gel chromatography, eluting with 5-30% ethyl acetate in hexanes, gave second batch of the desired product as white solid (0.735 g). The combined amount of the product is 15.616 g (95% yield). LC/MS (M+18): 560.2; LC retention time: 4.460 min (analytical HPLC Method A); 1H NMR (400 MHz, CDCl$_3$) δ ppm 7.68-7.57 (m, 4H), 7.37 (tt, J=8.4, 6.4 Hz, 1H), 7.28-7.21 (m, 2H), 7.15-7.07 (m, 2H), 7.01-6.91 (m, 2H), 4.68 (s, 2H), 4.36 (s, 2H).

Step B: 1,3-difluoro-2-(((1,1,1,3,3,3-hexafluoro-2-(4-(1-((4-fluorophenyl)sulfonyl)cyclopent-3-en-1-yl)phenyl)propan-2-yl)oxy)methyl)benzene

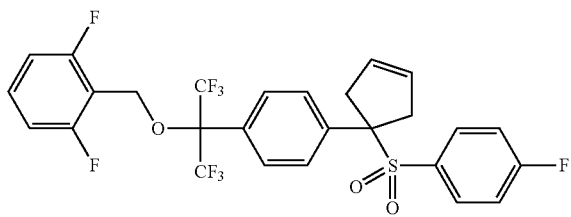 [SMILES: O=S(=O)(c1ccc(F)cc1)C1(c2ccc(C(OCc3c(F)cccc3F)(C(F)(F)F)C(F)(F)F)cc2)CC=CC1]

A solution of 1,3-difluoro-2-(((1,1,1,3,3,3-hexafluoro-2-(4-(((4-fluorophenyl)sulfonyl)methyl)phenyl)propan-2-yl)oxy)methyl)benzene (2.788 g, 5.14 mmol) in N,N-dimethylformamide (20 mL) was added dropwise to a stirred suspension of sodium hydride (0.720 g, 17.99 mmol, 60% suspension in mineral oil) and (Z)-1,4-dichlorobut-2-ene (0.964 g, 7.71 mmol) in N,N-dimethylformamide (30 mL) at 0° C. under nitrogen. After 10 min at 0° C. and 1 h at ambient temperature, the mixture was carefully quenched with saturated ammonium chloride (20 mL), diluted with ethyl acetate (400 mL), washed with water (2×150 mL), brine (50 mL), dried (magnesium sulfate), filtered and concentrated under reduced pressure. The residue was treated with dichloromethane (10 mL), sonicated for 2 min, triturated with hexanes (80 mL), stirred for 1 h and filtered. The filter cake was washed with hexanes (50 mL) and dried under vacuum to give first batch of 1,3-difluoro-2-(((1,1,1,3,3,3-hexafluoro-2-(4-(1-((4-fluorophenyl)sulfonyl)cyclopent-3-en-1-yl)phenyl)propan-2-yl)oxy)methyl)benzene (1.629 g). The filtrate was concentrated. Silica gel chromatography, eluting with 0-30% ethyl acetate in hexanes, gave second batch of the product as yellow solid (0.813 g). The combined amount of Example 18 is 2.441 g (80% yield). LC/MS (M+18): 612.4; LC retention time: 4.696 min (analytical HPLC Method A); 1H NMR (400 MHz, CDCl$_3$) δ ppm 7.60 (d, J=8.4 Hz, 2H), 7.42-7.32 (m, 5H), 7.05-6.90 (m, 4H), 5.74 (s, 2H), 4.71 (s, 2H), 3.68 (d, J=16.3 Hz, 2H), 3.14 (d, J=16.3 Hz, 2H).

Example 19

(1R,3s,5S)-3-(4-(2-(benzyloxy)-1,1,1,3,3,3-hexafluoropropan-2-yl)phenyl)-3-((4-fluorophenyl)sulfonyl)-6-oxabicyclo[3.1.0]hexane

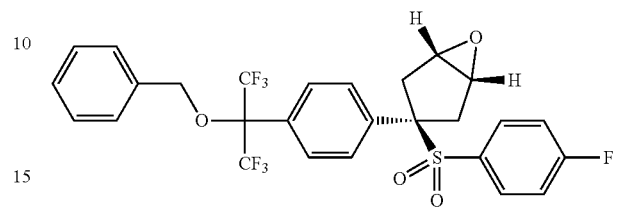

3-Chloroperbenzoic acid (169 mg, 0.752 mmol, 77% pure) was added to a solution of 1-(2-(benzyloxy)-1,1,1,3,3,3-hexafluoropropan-2-yl)-4-(1-((4-fluorophenyl)sulfonyl)cyclopent-3-en-1-yl)benzene (140 mg, 0.251 mmol, from Example 3) in dichloromethane (5 mL). After stirring for 15 h at room temperature, the mixture was diluted with ether (30 mL), washed with 1 M aqueous solution of sodium sulfite (2×5 mL), 1 N aqueous sodium hydroxide (3×5 mL), water (5 mL), brine (5 mL), dried (magnesium sulfate), filtered and concentrated under reduced pressure. Silica gel chromatography, eluting with 5-30% ethyl acetate in hexanes, gave Example 19 as white solid (107.4 mg, 67% yield). LC/MS (M+18): 592.5; LC retention time: 4.533 min (analytical HPLC Method A); 1H NMR (400 MHz, CDCl$_3$) δ ppm 7.48 (d, J=8.4 Hz, 2H), 7.43-7.33 (m, 5H), 7.28-7.22 (m, 2H), 7.18-7.10 (m, 2H), 6.97-6.86 (m, 2H), 4.63 (s, 2H), 3.73 (s, 2H), 3.09 (d, J=15.2 Hz, 2H), 2.85 (d, J=15.2 Hz, 2H).

Example 20

(1R,3s,5S)-3-(4-(2-((2,6-difluorobenzyl)oxy)-1,1,1,3,3,3-hexafluoropropan-2-yl)phenyl)-3-((4-fluorophenyl)sulfonyl)-6-oxabicyclo[3.1.0]hexane

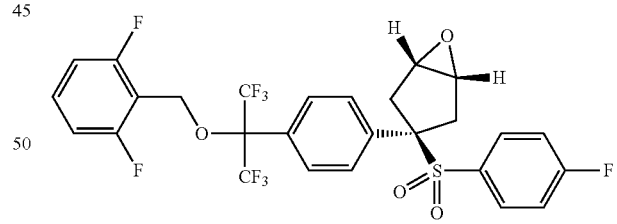

3-Chloroperbenzoic acid (136 mg, 0.606 mmol, 77% pure) was added to a solution of 1,3-difluoro-2-(((1,1,1,3,3,3-hexafluoro-2-(4-(1-((4-fluorophenyl)sulfonyl)cyclopent-3-en-1-yl)phenyl)propan-2-yl)oxy)methyl)benzene (120 mg, 0.202 mmol, from Example 18) in dichloromethane (5 mL). After stirring for 15 h at room temperature, the mixture was diluted with ether (30 mL), washed with 1 M aqueous solution of sodium thiosulfate (2×5 mL), 1 N aqueous sodium hydroxide (3×5 mL), water (5 mL), and brine (5 mL), dried (magnesium sulfate), filtered and concentrated under reduced pressure. Silica gel chromatography, eluting with 5-40% ethyl acetate in hexanes, gave Example 20 as white solid (103.3 mg, 82% yield). LC/MS (M+18): 628.3; LC retention time: 4.480 min (analytical HPLC Method A); 1H NMR (400 MHz, CDCl$_3$) δ ppm 7.55 (d, J=8.4 Hz, 2H), 7.37 (tt, J=8.4, 6.5 Hz, 1H), 7.31-7.24 (m, 2H), 7.21-7.12 (m, 2H), 7.03-6.86 (m, 4H), 4.69 (s, 2H), 3.74 (s, 2H), 3.11 (d, J=15.0 Hz, 2H), 2.87 (d, J=15.2 Hz, 2H).

Example 21

(1R,2S,4s)-4-(4-(2-(benzyloxy)-1,1,1,3,3,3-hexafluoropropan-2-yl)phenyl)-4-((4-fluorophenyl)sulfonyl)cyclopentane-1,2-diol

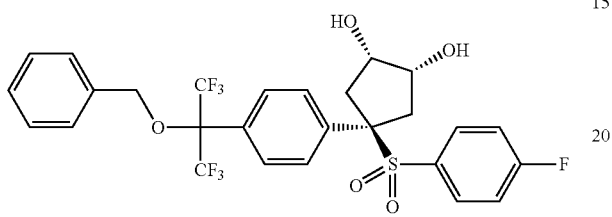

4-Methylmorpholine N-oxide (76 mg, 0.645 mmol) and osmium tetroxide (0.270 mL, 0.021 mmol, 2.5% solution in t-butanol) were added to a solution of 1-(2-(benzyloxy)-1,1,1,3,3,3-hexafluoropropan-2-yl)-4-(1-((4-fluorophenyl)sulfonyl)cyclopent-3-en-1-yl)benzene (120 mg, 0.215 mmol, from Example 3) in acetone (3 mL), tetrahydrofuran (1.5 mL), water (0.75 mL) and tert-butanol (0.75 mL). After stirring for 16 h at room temperature, the mixture was diluted with ethyl acetate (30 mL), washed with water (2×5 mL), brine (5 mL), dried (magnesium sulfate), filtered and concentrated under reduced pressure. Silica gel chromatography, eluting with 20-60% ethyl acetate in hexanes, gave Example 21 as white solid (113.6 mg, 80% yield, contaminated with approximately 10% of the cis alcohol isomer). LC/MS (M+18): 610.7; LC retention time: 4.425 min (analytical HPLC Method A); 1H NMR (400 MHz, CDCl$_3$) δ ppm 7.48 (d, J=8.4 Hz, 2H), 7.44-7.31 (m, 5H), 7.24-7.10 (m, 4H), 6.97-6.86 (m, 2H), 4.70-4.51 (m, 4H), 3.12 (dd, J=14.9, 6.1 Hz, 2H), 2.58-2.41 (m, 4H).

Example 22

(1R,2S,4s)-4-((4-fluorophenyl)sulfonyl)-4-(4-(1,1,1,3,3,3-hexafluoro-2-hydroxypropan-2-yl)phenyl)cyclopentane-1,2-diol

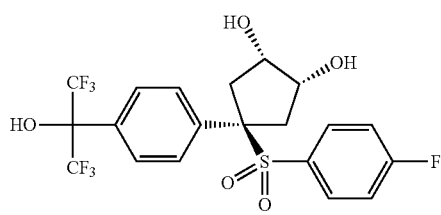 [SMILES: O=S(=O)(c1ccc(F)cc1)[C@]1(c2ccc(C(O)(C(F)(F)F)C(F)(F)F)cc2)C[C@@H](O)[C@@H](O)C1]

A mixture of (1R,2S,4s)-4-(4-(2-(benzyloxy)-1,1,1,3,3,3-hexafluoropropan-2-yl)phenyl)-4-((4-fluorophenyl)sulfonyl)cyclopentane-1,2-diol (110 mg, 0.186 mmol, from Example 21) and 20% palladium hydroxide on carbon (326 mg, 0.464 mmol) in methanol (10 mL) and ethyl acetate (5 mL) was hydrogenated under 40 psi hydrogen using a Parr Shaker for 15 h. The mixture was filtered and the filtrate concentrated. Silica gel chromatography, eluting with 30-100% ethyl acetate in hexanes, gave the desired product as white solid (85.6 mg, contaminated with 6% of the isomer where the diols are cis to the sulfone). The product was dissolved in methanol (1 mL), and triturated with dichloromethane (20 mL), hexanes (10 mL) and stirred for 30 min to give a suspension. The solid was collected by filtration to give Example 22 (55.2 mg, 59% yield). LC/MS (M+18): 520.3; LC retention time: 3.655 min (analytical HPLC Method A); 1H NMR (400 MHz, CD$_3$OD) δ ppm 7.59 (d, J=8.6 Hz, 2H), 7.32-7.17 (m, 4H), 7.11-6.98 (m, 2H), 4.38 (quin, J=4.2 Hz, 2H), 3.04 (dd, J=14.9, 6.3 Hz, 2H), 2.52 (dd, J=14.6, 5.4 Hz, 2H).

Example 23

(3aR,5s,6aS)-5-((4-fluorophenyl)sulfonyl)-5-(4-(1,1,1,3,3,3-hexafluoro-2-hydroxypropan-2-yl)phenyl)tetrahydro-3aH-cyclopenta[d][1,3]dioxol-2-one

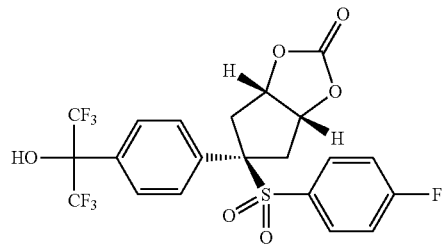 [SMILES: O=C1O[C@H]2C[C@](c3ccc(C(O)(C(F)(F)F)C(F)(F)F)cc3)(S(=O)(=O)c3ccc(F)cc3)C[C@H]2O1]

Hunig's base (0.035 mL, 0.198 mmol) was added to a mixture of (1R,2S,4s)-4-((4-fluorophenyl)sulfonyl)-4-(4-(1,1,1,3,3,3-hexafluoro-2-hydroxypropan-2-yl)phenyl)cyclopentane-1,2-diol (24.9 mg, 0.050 mmol, from Example 22) and 1,1'-carbonyldiimidazole (16.07 mg, 0.099 mmol) in tetrahydrofuran (1 mL). After 5 h at room temperature, LCMS analysis showed that most of the starting material remained unreacted. Triphosgene (14.71 mg, 0.050 mmol) and additional Hunig's base (0.035 mL, 0.198 mmol) were added. After 3 days at room temperature, the mixture was quenched with ammonium hydroxide (2 drops), stirred and filtered. The filtrate was concentrated. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 minutes, then a 10-minute hold at 60% B; Flow: 20 mL/min. Fractions containing the desired product were combined and dried via centrifugal evaporation to give Example 23 (16.7 mg, 63% yield). LC/MS (M+18): 546.4; LC retention time: 1.788 min (analytical HPLC Method B); 1H NMR (500 MHz, 1:1 mixture of CDCl$_3$-CD$_3$OD) δ ppm 7.70-7.59 (m, 2H), 7.31-7.17 (m, 4H), 7.11-6.99 (m, 2H), 5.58-5.43 (m, 2H), 3.38-3.27 (m, 2H), 2.83 (d, J=15.9 Hz, 2H).

Example 24

1,3-difluoro-2-(((1,1,1,3,3,3-hexafluoro-2-(4-(1-((4-fluorophenyl)sulfonyl)-3-methylenecyclopentyl)phenyl)propan-2-1 meth benzene

Step A: 1,3-difluoro-2-(((1,1,1,3,3,3-hexafluoro-2-(4-(1-((4-fluorophenyl)sulfonyl)vinyl)phenyl)propan-2-yl)oxy)methyl)benzene

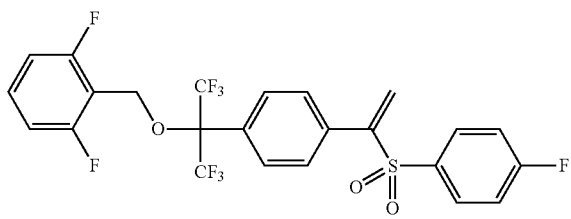 [SMILES: C=C(c1ccc(C(OCc2c(F)cccc2F)(C(F)(F)F)C(F)(F)F)cc1)S(=O)(=O)c1ccc(F)cc1]

Acetic anhydride (10.35 mL, 110 mmol) was added to a solution of 1,3-difluoro-2-(((1,1,1,3,3,3-hexafluoro-2-(4-(((4-fluorophenyl)sulfonyl) methyl)phenyl)propan-2-yl)oxy)methyl)benzene (14.88 g, 27.4 mmol, from Step A of Example 18) and N,N,N',N'-tetramethylmethanediamine (14.97 mL, 110 mmol) in N,N-dimethylformamide (140 mL) at room temperature. The reaction flask was equipped with a condenser, placed in a 60° C. oil bath and stirred under nitrogen for 5 h. Additional N,N,N',N'-tetramethylmethanediamine (14.97 mL, 110 mmol) and acetic anhydride (10.35 mL, 110 mmol) were added dropwise and the mixture stirred at 60° C. for 15 h. Additional acetic anhydride (5 mL) was added. After 1 h at 60° C., the mixture was diluted with ethyl acetate (1.2 L), washed with saturated sodium bicarbonate (3×200 mL), water (200 mL), brine (200 mL), dried (magnesium sulfate), filtered and concentrated under reduced pressure. Silica gel chromatography, eluting with 5-25% ethyl acetate in hexanes, gave impure 1,3-difluoro-2-(((1,1,1,3,3,3-hexafluoro-2-(4-(1-((4-fluorophenyl)sulfonyl)vinyl)phenyl)propan-2-yl)oxy)methyl)benzene as tan solid (8.834 g). This material was taken to the next reaction without further purification.

Step B: 1,3-difluoro-2-(((1,1,1,3,3,3-hexafluoro-2-(4-(1-((4-fluorophenyl)sulfonyl)-3-methylenecyclopentyl)phenyl)propan-2-yl)oxy)methyl)benzene

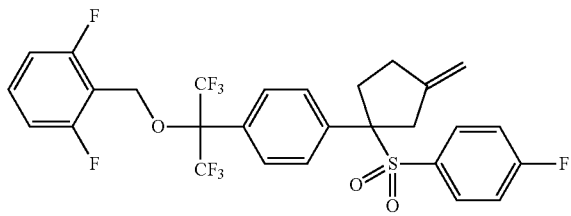

In a 25 mL sealed tube, to a solution of 1,3-difluoro-2-(((1,1,1,3,3,3-hexafluoro-2-(4-(1-((4-fluorophenyl)sulfonyl)vinyl)phenyl)propan-2-yl)oxy)methyl)benzene (500 mg, 0.902 mmol) in toluene (5 mL) was added 2-((trimethylsilyl)methyl)allyl acetate (252 mg, 1.353 mmol), 1,1'-bis(diphenylphosphino)ferrocene (50.0 mg, 0.090 mmol) and tetrakis(triphenylphosphine)palladium(0) (52.1 mg, 0.045 mmol). The reaction mixture was degassed using nitrogen for 15 min. The reaction tube was sealed and heated to 120° C. for 6 h. After cooling to room temperature, the mixture was quenched with water (25 mL) and extracted with ethyl acetate (2×25 mL). The combined organic layer was dried (sodium sulphate), filtered and concentrated under reduced pressure. The residue was purified by silica gel chromatography, eluting with 10-15% ethyl acetate in hexanes, to give 1,3-difluoro-2-(((1,1,1,3,3,3-hexafluoro-2-(4-(1-((4-fluorophenyl)sulfonyl)-3-methylenecyclopentyl) phenyl)propan-2-yl)oxy)methyl)benzene as pale yellow solid (380 mg, 69% yield). LC/MS (M+18): 626.0; LC retention time: 22.28 min (analytical HPLC Method D); 1H NMR (400 MHz, CDCl$_3$): δ 7.60-7.50 (m, 2H), 7.41-7.22 (m, 5H), 6.95 (q, J=8.4 Hz, 4H), 5.03 (t, J=2.4 Hz, 1H), 4.94 (t, J=2.4 Hz, 1H), 4.69 (s, 2H), 3.58 (dd, J=16.8, 2.0 Hz, 1H), 3.10-2.90 (m, 3H), 2.49-2.28 (m, 2H); 19F NMR (376 MHz): δ −70.47, −103.30, −114.43.

Example 25

(3-(4-(2-((2,6-difluorobenzyl)oxy)-1,1,1,3,3,3-hexafluoropropan-2-yl)phenyl)-3-((4-fluorophenyl)sulfonyl)cyclopentyl)methanol

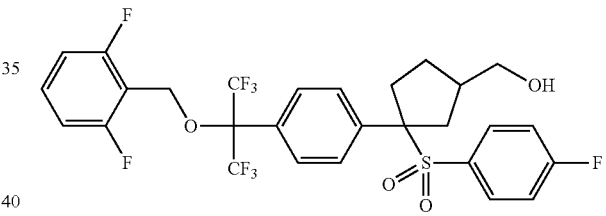

At 0° C., under inert atmosphere, borane-methyl sulfide complex (0.493 mL, 0.986 mmol, 2 M solution) was added to a solution of 1,3-difluoro-2-(((1,1,1,3,3,3-hexafluoro-2-(4-(1-((4-fluorophenyl) sulfonyl)-3-methylenecyclopentyl) phenyl)propan-2-yl)oxy)methyl)benzene (200 mg, 0.329 mmol) in tetrahydrofuran (4 mL). The mixture was allowed to gradually warm to room temperature over 2 h, then cooled to 0° C. Aqueous 1 M sodium hydroxide solution (3.29 mL, 3.29 mmol) was added. After stirring for 20 min at 0° C., 30% hydrogen peroxide (2 mL, 65.3 mmol) was added. The mixture was allowed to gradually warm to room temperature over 2 h, diluted with water (20 mL) and extracted with ethyl acetate (2×20 mL). The combined organic layer was dried (sodium sulphate), filtered and concentrated under reduced pressure to obtain pale yellow gummy solid (210 mg). The crude material was purified in combi-flash (4 g red-sep silica column, eluted with 40-45% ethyl acetate in hexanes) to yield (3-(4-(2-((2,6-difluorobenzyl)oxy)-1,1,1,3,3,3-hexafluoropropan-2-yl)phenyl)-3-((4-fluorophenyl) sulfonyl)cyclopentyl)methanol (110 mg, 0.176 mmol, 53% yield) as off-white solids, as mixture of diastereomers. LC/MS (M−1): 643.8; LC retention time: 11.65 min (analytical HPLC Method D).

Example 26

3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid

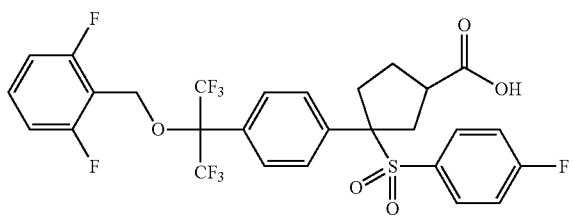 [SMILES: O=C(O)C1CCC(c2ccc(C(OCc3c(F)cccc3F)(C(F)(F)F)C(F)(F)F)cc2)(S(=O)(=O)c2ccc(F)cc2)C1]

To a solution of (3-(4-(2-((2,6-difluorobenzyl)oxy)-1,1,3,3,3-hexafluoropropan-2-yl)phenyl)-3-((4-fluorophenyl)sulfonyl)cyclopentyl)methanol (1.5 g, 2.394 mmol) in acetone (150 mL) at 0° C. was slowly added orange-red colored solution of chromic acid [Preparation of chromic acid solution: sodium dichromate dihydrate (2.14 g, 7.18 mmol) was added to 9.5 mL water and cooled to 0° C., to that was added sulfuric acid (2.8 mL, 52.5 mmol) and stirred for 15 min. Color of the mixture turned orange-red.]. The resulting mixture was stirred at 24° C. for 4 h, quenched with water (200 mL), and extracted with ethyl acetate (2×150 mL). The combined organic layer was washed with brine (50 mL), dried (sodium sulphate), filtered and concentrated under reduced pressure. The pale greenish semi-solid material was treated with ethyl acetate:hexane (25 mL, 1:9 ratio), stirred for 5 min, and allowed to settle for another 5 min. The clear liquid solution was decanted out. Similar wash-treatment was applied to the remaining solids for another two times. Finally the solids were filtered and dried under vacuum to yield 3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid as a mixture of two diastereomers (1.30 g).

Examples 27 and 28 rac-1-(4-((1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarbonyl)piperazin-1-yl)ethanone, and rac-1-(4-((1R,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarbonyl)piperazin-1-yl)ethanone Step A: rac-(1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid, and rac-(1R,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid

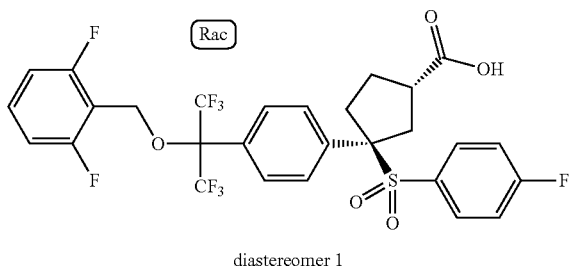

diastereomer 1

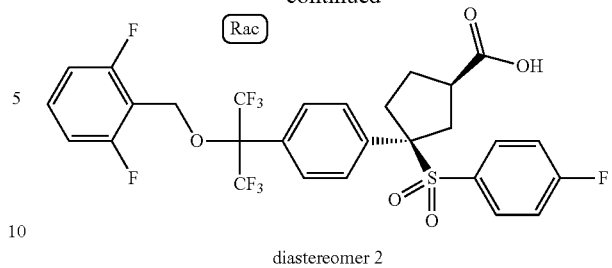

diastereomer 2

The diastereomeric mixture of 3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid from Example 26 was separated by SCF purification to give rac-(1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (diastereomer 1, peak 1, 248 mg) and rac-(1R,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (diastereomer 2, peak 2, 500 mg). Analytical data of diastereomer 1: LC/MS (M−1): 638.8; LC retention time: 13.76 min (analytical HPLC Method D); 1H NMR (400 MHz, DMSO-d6): δ ppm 7.60-7.55 (m, 1H), 7.48 (d, J=8.0 Hz, 2H), 7.36 (d, J=8.8 Hz, 2H), 7.30-7.17 (m, 6H), 4.63 (s, 2H), 3.23-3.17 (m, 1H), 3.08-3.03 (m, 1H), 2.89-2.67 (m, 2H), 2.49-2.43 (m, 1H), 2.33-2.29 (m, 1H), 1.92-1.89 (m, 1H). Analytical data of diastereomer 2: LC/MS (M−1): 638.8; LC retention time: 13.90 min (analytical HPLC Method D); 1H NMR (400 MHz, DMSO-d6): δ ppm 7.62-7.56 (m, 1H), 7.48 (dd, J=17.6, 8.4 Hz, 4H), 7.29-7.19 (m, 6H), 4.64 (s, 2H), 2.96-2.85 (m, 1H), 2.83-2.69 (m, 3H), 2.49-2.39 (m, 1H), 2.19-2.09 (m, 1H), 1.95-1.85 (m, 1H).

Step B: rac-1-(4-((1R,3R)-3-(4-(2-((2,6-difluorobenzyl)oxy)-1,1,1,3,3,3-hexafluoropropan-2-yl)phenyl)-3-((4-fluorophenyl)sulfonyl) cyclopentanecarbonyl) piperazin-1-yl)ethanone

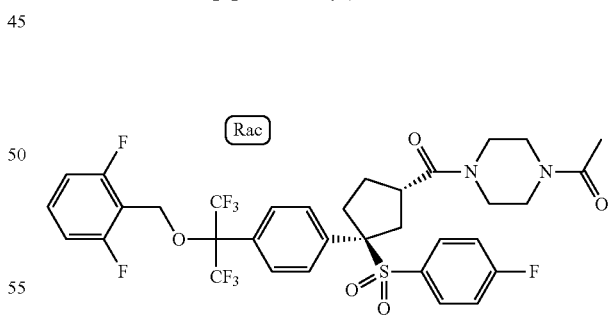

A solution of rac-(1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (10 mg, 0.016 mmol, diastereomer 1 from Step A), 1-(piperazin-1-yl)ethanone (2.401 mg, 0.019 mmol), (benzotriazol-1-yloxy)tris(dimethylamino)phosphonium hexafluorophosphate (8.29 mg, 0.019 mmol) and Hunig's Base (8.18 µl, 0.047 mmol) in acetonitrile (0.5 mL) was stirred at room temperature for 30 min. LCMS analysis showed that the reaction was complete. The crude material was purified via preparative LC/MS with the following conditions: Column: 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-100% B over 25 minutes, then a 5-minute hold at 100% B; Flow: 20 mL/min. Fractions containing the desired product were combined and dried via centrifugal evaporation to give Example 27 (10.3 mg, 87% yield). LC/MS (M+18): 768.3; LC retention time: 2.15 min (analytical HPLC Method B); 1H NMR (500 MHz, 1:1 mixture of CDCl$_3$-CD$_3$OD) δ ppm 7.52 (d, J=8.3 Hz, 2H), 7.46-7.38 (m, 1H), 7.30-7.20 (m, 4H), 7.03-6.94 (m, 4H), 4.67 (s, 2H), 3.79-3.49 (m, 9H), 3.11-2.99 (m, 2H), 2.74 (dd, J=14.6, 9.6 Hz, 1H), 2.56-2.43 (m, 2H), 2.18-2.10 (m, 3H), 1.99-1.88 (m, 1H).

Step C: rac-1-(4-((1R,3S)-3-(4-(2-((2,6-difluorobenzyl)oxy)-1,1,1,3,3,3-hexafluoropropan-2-yl)phenyl)-3-((4-fluorophenyl)sulfonyl) cyclopentanecarbonyl) piperazin-1-yl)ethanone

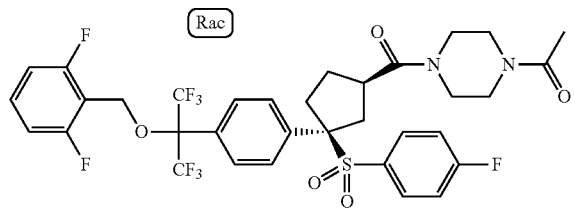 [SMILES: CC(=O)N1CCN(C(=O)[C@@H]2CC[C@](c3ccc(C(OCc4c(F)cccc4F)(C(F)(F)F)C(F)(F)F)cc3)(S(=O)(=O)c3ccc(F)cc3)C2)CC1]

A solution of rac-(1R,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (10 mg, 0.016 mmol, diastereomer 2 from Step A), 1-(piperazin-1-yl)ethanone (2.401 mg, 0.019 mmol), (benzotriazol-1-yloxy)tris(dimethylamino)phosphonium hexafluorophosphate (8.29 mg, 0.019 mmol) and Hunig's Base (8.18 μl, 0.047 mmol) in acetonitrile (0.5 mL) was stirred at room temperature for 30 min. LCMS analysis showed that the reaction was complete. The crude material was purified via preparative LC/MS with the following conditions: Column: 19×250 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-100% B over 25 minutes, then a 5-minute hold at 100% B; Flow: 20 mL/min. Fractions containing the desired product were combined and dried via centrifugal evaporation to give Example 27 (10.3 mg, 87% yield). LC/MS (M+1): 751.2; LC retention time: 2.12 min (analytical HPLC Method B); 1H NMR (500 MHz, 1:1 mixture of CDCl$_3$-CD$_3$OD) δ ppm 7.61-7.56 (m, 2H), 7.48-7.38 (m, 3H), 7.32 (d, J=5.3 Hz, 2H), 7.00 (q, J=8.0 Hz, 4H), 4.69 (s, 2H), 3.72-3.42 (m, 8H), 3.21 (dd, J=13.6, 10.5 Hz, 1H), 3.04 (br. s., 1H), 2.94-2.86 (m, 1H), 2.67 (dd, J=13.6, 7.2 Hz, 1H), 2.51 (dt, J=13.7, 6.7 Hz, 1H), 2.19-2.06 (m, 4H), 2.03-1.92 (m, 1H).

Examples 29 and 30

1-(4-((1S,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarbonyl)piperazin-1-yl)ethanone, and 1-(4-((1R,3R)-3-(4-(2-((2,6-difluorobenzyl)oxy)-1,1,1,3,3,3-hexafluoropropan-2-yl)phenyl)-3-((4-fluorophenyl)sulfonyl) cyclopentanecarbonyl)piperazin-1-yl)ethanone Step A: (1S,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid, and (1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid

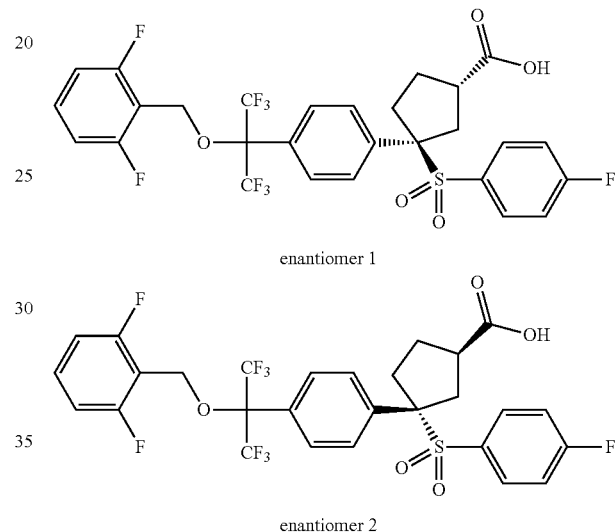

enantiomer 1 enantiomer 2 rac-(1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (267 mg. diastereomer 1 from Step 1 of Examples 27 and 28) was separated into its homochiral components using a chiral Whelk-O1 column (R,R 25×3 cm ID, 5um, 12% methanol in CO2, 85 mL/min) to afford (1S,3S)-3-(4-(2-((2,6-difluorobenzyl)oxy)-1,1,1,3,3,3-hexafluoropropan-2-yl)phenyl)-3-((4-fluorophenyl)sulfonyl) cyclopentanecarboxylic acid (enantiomer 1, 93 mg) as the first eluent off the column and (1R,3R)-3-(4-(2-((2,6-difluorobenzyl)oxy)-1,1,1,3,3,3-hexafluoropropan-2-yl) phenyl)-3-((4-fluorophenyl)sulfonyl)cyclopentanecarboxylic acid (enantiomer 2, 120.4 mg) as the second eluent off the column. Analytical data of enantiomer 1: LC/MS (M+18): 658.3; LC retention time: 4.633 min (analytical HPLC Method A); 1H NMR (400 MHz, 1:1 mixture of CDCl$_3$-CD$_3$OD) δ ppm 7.52 (d, J=8.4 Hz, 2H), 7.41 (tt, J=8.4, 6.5 Hz, 1H), 7.32-7.19 (m, 4H), 7.04-6.89 (m, 4H), 4.70 (s, 2H), 3.43 (quin, J=8.2 Hz, 1H), 3.14 (dd, J=14.5, 8.2 Hz, 1H), 3.04-2.91 (m, 1H), 2.62 (dd, J=14.6, 9.0 Hz, 1H), 2.54-2.38 (m, 2H), 2.12-1.96 (m, 1H). Analytical data of enantiomer 2: LC/MS (M+18): 658.2; LC retention time: 4.638 min (analytical HPLC Method A); 1H NMR (400 MHz, 1:1 mixture of CDCl$_3$-CD$_3$OD) δ ppm 7.52 (d, J=8.4 Hz, 2H), 7.40 (tt, J=8.4, 6.5 Hz, 1H), 7.32-7.19 (m, 4H), 7.03-6.92 (m, 4H), 4.68 (br. s., 2H), 3.43 (quin, J=8.2 Hz, 1H), 3.14 (dd, J=14.5, 8.1 Hz, 1H), 3.06-2.92 (m, 1H), 2.62 (dd, J=14.5, 9.0 Hz, 1H), 2.54-2.40 (m, 2H), 2.11-1.96 (m, 1H).

Step B: 1-(4-((1S,3S)-3-(4-(2-((2,6-difluorobenzyl)oxy)-1,1,1,3,3,3-hexafluoropropan-2-yl)phenyl)-3-((4-fluorophenyl)sulfonyl) cyclopentanecarbonyl) piperazin-1-yl)ethanone

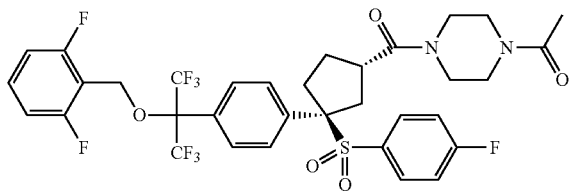 [SMILES: CC(=O)N1CCN(C(=O)[C@H]2CC[C@](c3ccc(C(OCc4c(F)cccc4F)(C(F)(F)F)C(F)(F)F)cc3)(S(=O)(=O)c3ccc(F)cc3)C2)CC1]

A solution of (1S,3S)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (10 mg, 0.016 mmol, enantiomer 1 from Step A), 1-(piperazin-1-yl)ethanone (2.401 mg, 0.019 mmol), (benzotriazol-1-yloxy)tris(dimethylamino)phosphonium hexafluorophosphate (8.29 mg, 0.019 mmol) and Hunig's Base (8.18 µl, 0.047 mmol) in acetonitrile (0.5 mL) was stirred at room temperature for 30 min. LCMS analysis showed that the reaction was complete. The crude material was purified via preparative LC/MS with the following conditions: Column: Waters XBridge C18, 19×100 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-100% B over 10 minutes, then a 5-minute hold at 100% B; Flow: 20 mL/min. Fractions containing the desired product were combined and dried via centrifugal evaporation to give Example 29 (10.2 mg, 82% yield). LC/MS (M+18): 751.3; LC retention time: 2.21 min (analytical HPLC Method B); 1H NMR (500 MHz, 1:1 mixture of CDCl$_3$-CD$_3$OD) δ ppm 7.52 (d, J=8.3 Hz, 2H), 7.46-7.36 (m, 1H), 7.30-7.20 (m, 4H), 7.03-6.93 (m, 4H), 4.67 (s, 2H), 3.78-3.48 (m, 9H), 3.09-2.99 (m, 2H), 2.74 (dd, J=14.4, 9.7 Hz, 1H), 2.55-2.42 (m, 2H), 2.14 (d, J=11.7 Hz, 3H), 1.99-1.88 (m, 1H).

Step C: 1-(4-((1R,3R)-3-(4-(2-((2,6-difluorobenzyl)oxy)-1,1,1,3,3,3-hexafluoropropan-2-yl)phenyl)-3-((4-fluorophenyl)sulfonyl) cyclopentanecarbonyl) piperazin-1-yl)ethanone

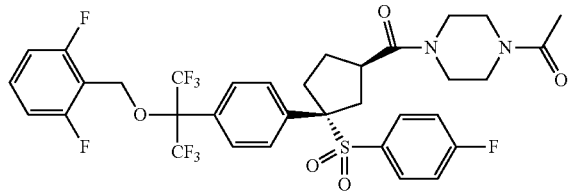 [SMILES: CC(=O)N1CCN(C(=O)[C@@H]2CC[C@@](c3ccc(C(OCc4c(F)cccc4F)(C(F)(F)F)C(F)(F)F)cc3)(S(=O)(=O)c3ccc(F)cc3)C2)CC1]

A solution of (1R,3R)-3-(4-(2-((2,6-difluorobenzyl)oxy)-1,1,1,3,3,3-hexafluoropropan-2-yl)phenyl)-3-((4-fluorophenyl)sulfonyl)cyclopentanecarboxylic acid (10 mg, 0.016 mmol, enantiomer 2 from Step A), 1-(piperazin-1-yl)ethanone (2.401 mg, 0.019 mmol), (benzotriazol-1-yloxy)tris(dimethylamino)phosphonium hexafluorophosphate (8.29 mg, 0.019 mmol) and Hunig's Base (8.18 µl, 0.047 mmol) in acetonitrile (0.5 mL) was stirred at room temperature for 30 min. LCMS analysis showed that the reaction was complete. The crude material was purified via preparative LC/MS with the following conditions: Column: Waters XBridge Phenyl, 19×250 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-100% B over 15 minutes, then a 5-minute hold at 100% B; Flow: 20 mL/min. Fractions containing the desired product were combined and dried via centrifugal evaporation to give Example 30 (10.5 mg, 85% yield). LC/MS (M+18): 751.2; LC retention time: 2.20 min (analytical HPLC Method B); 1H NMR (500 MHz, 1:1 mixture of CDCl$_3$-CD$_3$OD) δ ppm 7.52 (d, J=8.3 Hz, 2H), 7.46-7.36 (m, 1H), 7.30-7.21 (m, 4H), 7.03-6.95 (m, 4H), 4.67 (s, 2H), 3.79-3.47 (m, 9H), 3.09-2.98 (m, 2H), 2.74 (dd, J=14.4, 9.7 Hz, 1H), 2.55-2.42 (m, 2H), 2.14 (d, J=11.7 Hz, 3H), 1.99-1.89 (m, 1H).

Examples 31 and 32 tert-butyl (3-(4-(2-((2,6-difluorobenzyl)oxy)-1,1,1,3,3,3-hexafluoropropan-2-yl)phenyl)-3-((4-fluorophenyl)sulfonyl)cyclopentyl)carbamate (diastereomers 1 and 2)

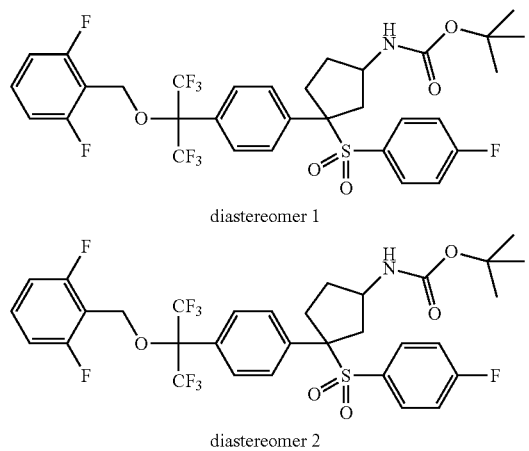

diastereomer 1 diastereomer 2

3-(4-(2-((2,6-difluorobenzyl)oxy)-1,1,1,3,3,3-hexafluoropropan-2-yl)phenyl)-3-((4-fluoro phenyl)sulfonyl)cyclopentanecarboxylic acid (100 mg, 0.156 mmol) was taken in toluene (4 mL) and cooled to 0° C. To that was added triethylamine (0.044 mL, 0.312 mmol) and diphenylphosphonic azide (0.070 mL, 0.312 mmol). The reaction mixture was slowly warmed to room temperature. After 15 min at room temperature, the mixture was heated to 40° C. with continuous stirring for 2 h, cooled to room temperature and quenched with water (10 mL). The aqueous mixture was extracted with ethyl acetate (2×50 mL). Combined organic layer was washed with water (50 mL), brine (50 mL), dried (sodium sulphate), filtered and concentrated under reduced pressure. The residue was taken in tert-butanol (3.0 mL) and heated in microwave at 80° C. for 2 h. After cooling to room temperature, the mixture was diluted with water (2 mL) and extracted with ethyl acetate (3×50 mL). Combined organic layer was dried (sodium sulphate), filtered and concentrated under reduced pressure. The crude material purified by preparative HPLC (ammonium acetate method) to yield two diastereomers of tert-butyl (3-(4-(2-((2,6-difluorobenzyl) oxy)-1,1,1,3,3,3-hexafluoropropan-2-yl)phenyl)-3-((4-fluorophenyl)sulfonyl)cyclopentyl)carbamate. Diastereomer 1 (peak 1, 3.0 mg, 4.22 µmol, 2.7% yield): LC/MS (M+18): 729.2; LC retention time: 16.76 min (analytical HPLC Method D); 1H NMR (400 MHz, DMSO-d6): δ 7.64-7.54 (m, 1H), 7.48 (d, J=8.4 Hz, 2H), 7.34 (d, J=8.7 Hz, 2H), 7.28-7.19 (m, 6H), 6.93-6.88 (m, 1H), 4.64 (s, 2H), 4.24 (d, J=7.5 Hz, 1H), 3.07-2.99 (m, 1H), 2.86-2.77 (m, 1H), 2.32-2.13 (m, 2H), 1.82-1.56 (m, 2H), 1.35 (s, 9H); 19F NMR (376 MHz): δ −70.15, −104.33, −115.03. Diastereomer 2 (peak 2, 3.0 mg, 4.22 µmol, 2.7% yield): LC/MS (M−100): 612; LC retention time: 17.31 min (analytical HPLC Method D); 1H NMR (400 MHz, DMSO-d6): δ 7.63-7.43 (m, 5H), 7.32-7.14 (m, 7H), 4.64 (s, 2H), 3.72 (dd, J=9.2, 1.2 Hz, 1H), 2.81-2.71 (m, 2H), 2.57-2.51 (m, 1H), 2.41-2.31 (m, 1H), 1.96-1.71 (m, 2H), 1.38 (s, 9H); 19F NMR (376 MHz): δ −69.97 (m), −104.38, −115.01.

Examples 33 and 34

N-benzyl-3-(4-(2-((2,6-difluorobenzyl)oxy)-1,1,1,3,3,3-hexafluoropropan-2-yl)phenyl)-3-((4-fluorophenyl)sulfonyl)cyclopentanamine (diastereomers 1 and 2)

Step A: 2-(trimethylsilyl)ethyl (3-(4-(2-((2,6-difluorobenzyl)oxy)-1,1,1,3,3,3-hexafluoropropan-2-yl) phenyl)-3-((4-fluorophenyl)sulfonyl)cyclopentyl) carbamate (diastereomers 1 and 2)

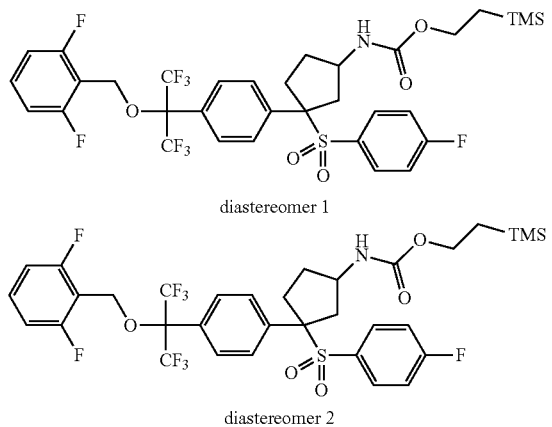

diastereomer 1 diastereomer 2

In a 100 mL round bottomed flask, 3-(4-(2-((2,6-difluorobenzyl)oxy)-1,1,1,3,3,3-hexafluoro propan-2-yl)phenyl)-3-((4-fluorophenyl)sulfonyl) cyclopentanecarboxylic acid (1.20 g, 1.873 mmol) was taken in toluene (40 mL) and cooled to 0° C. To that was added triethylamine (0.783 mL, 5.62 mmol) and diphenylphosphonic azide (1.261 mL, 5.62 mmol). The reaction mixture was gradually warmed to room temperature and then heated to 40° C. After 30 min at 40° C., the mixture was cooled to room temperature, quenched with water (100 mL) and extracted with ethyl acetate (2×100 mL). Combined organic layer was washed with water (2×100 mL), dried (sodium sulphate), filtered and concentrated under reduced pressure. The residue was then taken in 2-(trimethylsilyl)ethanol (2.0 mL) and heated to 80° C. with stirring for 60 min. The reaction mixture was diluted with water (2 mL) and extracted with ethyl acetate (3×100 mL). The combined organic layer was dried (sodium sulphate), filtered and concentrated under reduced pressure. The crude material was purified by prep-HPLC (ammonium acetate method) to yield two diastereomers of 2-(trimethylsilyl) ethyl (3-(4-(2-((2,6-difluorobenzyl)oxy)-1,1,1,3,3,3-hexafluoropropan-2-yl)phenyl)-3-((4-fluorophenyl)sulfonyl) cyclopentyl)carbamate. Diastereomer 1 (peak 1, 0.18 g, 0.238 mmol, 12.7% yield): LC/MS (M+18): 773.4; LC retention time: 19.51 min (analytical HPLC Method D); 1H NMR (400 MHz, DMSO-d6): δ 7.63-7.54 (m, 1H), 7.49 (d, J=8.3 Hz, 2H), 7.34 (d, J=8.7 Hz, 2H), 7.29-7.18 (m, 6H), 7.10 (d, J=6.5 Hz, 1H), 4.64 (s, 2H), 4.28 (q, J=7.3 Hz, 1H), 4.01 (t, J=7.6 Hz, 2H), 3.07 (dd, J=7.1, 14.4 Hz, 1H), 2.82 (m, 1H), 2.53-2.45 (m, 1H), 2.34-2.16 (m, 2H), 1.67-1.58 (m, 1H), 0.87 (t, J=8.1 Hz, 2H), 0.06 (s, 9H). Diastereomer 2 (peak 2, 0.37 g, 0.490 mmol, 26.1% yield): LC/MS (M−1): 754.3; LC retention time: 19.51 min (analytical HPLC Method D); 1H NMR (400 MHz, DMSO-d6): δ 7.60-7.56 (m, 1H), 7.54-7.43 (m, 4H), 7.36 (d, J=7.3 Hz, 1H), 7.31-7.18 (m, 6H), 4.64 (s, 2H), 4.06-4.00 (m, 2H), 3.77 (q, J=7.9 Hz, 2H), 2.83-2.72 (m, 2H), 2.62-2.52 (m, 1H), 2.43-2.31 (m, 1H), 1.85-1.73 (m, 1H), 0.95-0.88 (m, 2H), 0.03 (s, 9H).

Step B: 3-(4-(2-((2,6-difluorobenzyl)oxy)-1,1,1,3,3,3-hexafluoropropan-2-yl)phenyl)-3-((4-fluorophenyl)sulfonyl)cyclopentanamine (diastereomer 1)

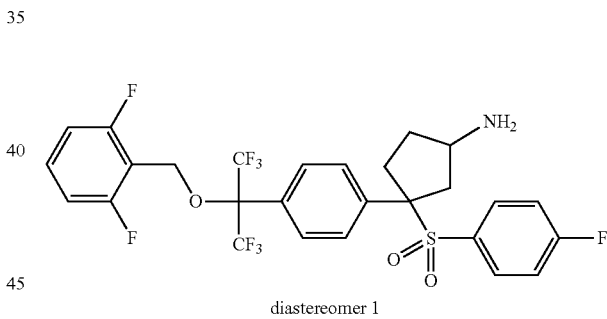

diastereomer 1

Diastereomer 1 of 2-(trimethylsilyl)ethyl (3-(4-(2-((2,6-difluorobenzyl)oxy)-1,1,1,3,3,3-hexafluoropropan-2-yl) phenyl)-3-((4-fluorophenyl)sulfonyl) cyclopentyl)carbamate (0.30 g, 0.397 mmol) was taken in dichloromethane (5 mL) and cooled to 0° C. To that was added trifluoroacetic acid (0.092 mL, 1.191 mmol) at 0° C. After stirring at room temperature for 12 h, the reaction mixture was concentrated under reduced pressure and dried by lyophilization to give 3-(4-(2-((2,6-difluorobenzyl)oxy)-1,1,1,3,3,3-hexafluoropropan-2-yl) phenyl)-3-((4-fluorophenyl)sulfonyl)cyclopentanamine TFA salt as a white solid (310 mg). LC/MS (M+1): 612.3; LC retention time: 9.40 min (analytical HPLC Method D); 1H NMR (400 MHz, DMSO-d6): δ 7.95 (br-s, 2H), 7.64-7.48 (m, 3H), 7.36-7.18 (m, 8H), 4.64 (s, 2H), 4.02 (br-s, 1H), 3.31-3.23 (m, 1H), 2.95-2.84 (m, 1H), 2.63-2.53 (m, 1H), 2.48-2.40 (m, 1H), 2.35 (dd, J=8.2, 15.1 Hz, 1H), 1.87-1.76 (m, 1H).

Step C: N-benzyl-3-(4-(2-((2,6-difluorobenzyl)oxy)-1,1,1,3,3,3-hexafluoropropan-2-yl)phenyl)-3-((4-fluorophenyl)sulfonyl)cyclopentanamine (diastereomer 1)

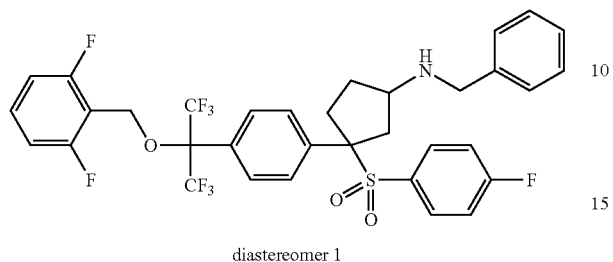

diastereomer 1

Diastereomer 1 of 3-(4-(2-((2,6-difluorobenzyl)oxy)-1,1,1,3,3,3-hexafluoropropan-2-yl)phenyl)-3-((4-fluoro phenyl)sulfonyl)cyclopentanamine (25 mg, 0.041 mmol) was taken in N,N-dimethylformamide (1 mL) and cooled 0° C. To that were added Hunig's Base (10.71 µl, 0.061 mmol) and benzyl bromide (3.89 µl, 0.033 mmol). After stirring for 8 h at room temperature, the mixture was quenched with cold water (5 mL) and extracted with ethyl acetate (2×50 mL). Combined organic layer was washed with water (2×50 mL), brine (50 mL), dried (sodium sulphate), filtered and concentrated under reduced pressure. The crude material was purified by prep-HPLC (ammonium acetate method) to yield white solids of N-benzyl-3-(4-(2-((2,6-difluorobenzyl)oxy)-1,1,1,3,3,3-hexafluoropropan-2-yl)phenyl)-3-((4-fluorophenyl) sulfonyl) cyclopentanamine (4.0 mg, 14% yield). LC/MS (M+1): 702.2; LC retention time: 17.24 min (analytical HPLC Method D); 1H NMR (400 MHz, DMSO-d6): δ 7.64-7.54 (m, 1H), 7.52-7.46 (m, 2H), 7.42-7.36 (m, 2H), 7.29-7.14 (m, 10H), 4.64 (s, 2H), 3.64 (s, 2H), 2.97 (dd, J=14.3, 6.4 Hz, 1H), 2.79-2.72 (m, 1H), 2.57-2.52 (m, 1H), 2.28 (dd, J=14.4, 6.0 Hz, 1H), 2.15-2.04 (m, 1H), 1.82 (s, 3H), 1.63-1.54 (m, 1H); 19F NMR (376 MHz): δ -70.06, -104.53, -115.02.

Step D: N-benzyl-3-(4-(2-((2,6-difluorobenzyl)oxy)-1,1,1,3,3,3-hexafluoropropan-2-yl)phenyl)-3-((4-fluorophenyl)sulfonyl)cyclopentanamine (diastereomer 2)

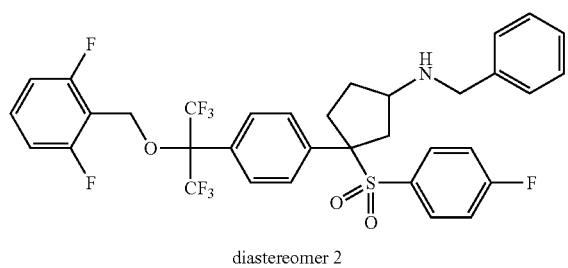 [SMILES: O=S(=O)(c1ccc(F)cc1)C1(c2ccc(C(OCc3c(F)cccc3F)(C(F)(F)F)C(F)(F)F)cc2)CCC(NCc2ccccc2)C1]

diastereomer 2

Following conditions similar to Steps B and C, diastereomer 2 of N-benzyl-3-(4-(2-((2,6-difluorobenzyl)oxy)-1,1,1,3,3,3-hexafluoropropan-2-yl)phenyl)-3-((4-fluorophenyl)sulfonyl)cyclopentanamine (Example 34) was synthesized from diastereomer 2 of 2-(trimethylsilyl)ethyl (3-(4-(2-((2,6-difluorobenzyl)oxy)-1,1,1,3,3,3-hexafluoropropan-2-yl)phenyl)-3-((4-fluorophenyl)sulfonyl) cyclopentyl)carbamate. LC/MS (M+1): 702.2; LC retention time: 17.32 min (analytical HPLC Method D); 1H NMR (400 MHz, DMSO-d6): δ 7.63-7.54 (m, 1H), 7.51-7.41 (m, 4H), 7.36-7.17 (m, 11H), 4.63 (s, 2H), 3.70 (s, 2H), 3.0 (m, 1H), 2.81-2.71 (m, 2H), 2.49-2.42 (m, 1H), 2.38-2.28 (m, 1H), 1.91-1.81 (m, 1H), 1.79 (s, 1H), 1.76-1.65 (m, 1H); 19F NMR (376 MHz): δ -70.05, -104.55, -115.03.

Example 35

1,3-difluoro-2-(((1,1,1,3,3,3-hexafluoro-2-(4-(1-(phenylsulfonyl)cyclopropyl)phenyl)propan-2-yl)oxy)methyl)benzene

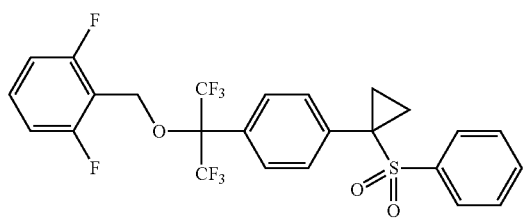 [SMILES: O=S(=O)(c1ccccc1)C1(c2ccc(C(OCc3c(F)cccc3F)(C(F)(F)F)C(F)(F)F)cc2)CC1]

In a 25 mL dry round bottomed flask, a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (50 mg, 0.092 mmol) in dry N,N-dimethylformamide (10 mL) was cooled to 0° C. under inert atmosphere. To that was added sodium hydride (4.87 mg, 0.203 mmol) followed by 1,2-dibromoethane (17.32 mg, 0.092 mmol). The reaction mixture was allowed to reach room temperature and stirred at that temperature for another 1 h followed by 60° C. for 12 h. The reaction mixture was quenched slowly with water (10 mL) and extracted with ethyl acetate (3×15 mL). Combined organic phase was subsequently washed with water (2×20 mL), brine (20 mL), dried (sodium sulphate), filtered and concentrated under reduced pressure to produce yellowish gummy liquid (82 mg). The crude material was purified through prep-HPLC to give 1,3-difluoro-2-(((1,1,1,3,3,3-hexafluoro-2-(4-(1-((4-fluoro phenyl)sulfonyl)cyclopropyl)phenyl)propan-2-yl)oxy)methyl)benzene (12.18 mg, 23% yield) as white solids. LC/MS (M+18): 586.0; LC retention time: 21.0 (analytical HPLC Method D); 1H NMR (CDCl3, 400 MHz): δ 7.54 (d, J=8.4 Hz, 2H), 7.46 (dd, J=8.8, 5.2 Hz, 2H), 7.42-7.32 (m, 1H), 7.28 (d, J=8.8 Hz, 2H), 7.05 (t, J=8.4 Hz, 2H), 6.96 (t, J=7.6 Hz, 2H), 4.66 (s, 2H), 2.00 (d, J=2.0 Hz, 2H), 1.33 (d, J=2.0 Hz, 2H); 19F NMR (376 MHz): δ -70.50, -103.63, -114.43.

Example 36 rac-((1R,2S)-2-(4-(2-((2,6-difluorobenzyl)oxy)-1,1,1,3,3,3-hexafluoropropan-2-yl)phenyl)-2-((4-fluorophenyl)sulfonyl)cyclopropyl)methanol

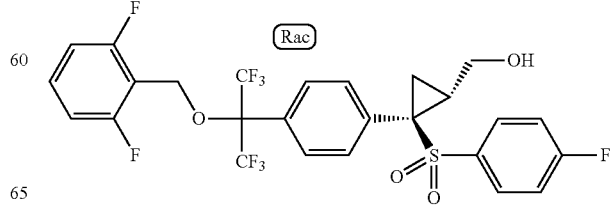

In a 25 mL round bottom flash, a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (50 mg, 0.092 mmol) in dry tetrahydrofuran (2 mL) under inert atmosphere was cooled to −78° C. A 1.6 M solution of tert-butyllithium (0.138 mL, 0.221 mmol) was added. After stirring at −78° C. for 1 h, a solution of 2-(bromomethyl)oxirane (12.63 mg, 0.092 mmol) in tetrahydrofuran (1 mL) and lithium perchlorate (9.81 mg, 0.092 mmol) were added. The resulting mixture was stirred at −78° C. for 2 h, at 25° C. for 8 h and quenched with saturated ammonium chloride (10 mL). After extraction with ethyl acetate (3×10 mL), the combined organic phase was washed with water (15 mL), brine (15 mL), dried (sodium sulphate), filtered and concentrated under reduced pressure. The residue was purified by Prep-HPLC to give rac-((1R,2S)-2-(4-(2-((2,6-difluorobenzyl)oxy)-1,1,1,3,3,3-hexafluoropropan-2-yl)phenyl)-2-((4-fluorophenyl)sulfonyl)cyclopropyl)methanol as white solid (7.55 mg, 14% yield). LC/MS (M+18): 616.6; LC retention time: 18.7 min (analytical HPLC Method D); 1H NMR (DMSO-d6, 400 MHz): δ 7.60-7.55 (m, 1H), 7.50-7.43 (m, 4H), 7.37-7.29 (m, 4H), 7.21 (d, J=8.0 Hz, 2H), 4.88 (dd, J=5.6, 4.4 Hz, 1H), 4.61 (q, J=6.8 Hz, 2H), 3.37-3.28 (m, 1H), 3.08-2.96 (m, 1H), 2.30-2.45 (m, 1H), 1.93 (dd, J=9.6, 5.6 Hz, 1H), 1.37 (t, J=6.4 Hz, 2H); 19F NMR (376 MHz): δ −70.07, −104.67, −115.07.

Example 37 rac-(1R,2S)-tert-butyl 2-(4-(2-((2,6-difluorobenzyl)oxy)-1,1,1,3,3,3-hexafluoropropan-2-yl)phenyl)-2-((4-fluorophenyl)sulfonyl)cyclopropanecarboxylate

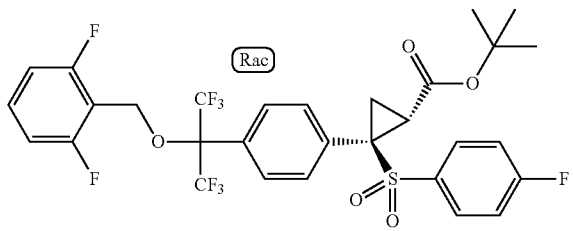 [SMILES: CC(C)(C)OC(=O)[C@H]1C[C@]1(c1ccc(C(OCc2c(F)cccc2F)(C(F)(F)F)C(F)(F)F)cc1)S(=O)(=O)c1ccc(F)cc1]

To a solution of 1,3-difluoro-2-(((1,1,1,3,3,3-hexafluoro-2-(4-(1-((4-fluorophenyl)sulfonyl) vinyl)phenyl)propan-2-yl)oxy)methyl)benzene (500 mg, 0.902 mmol) in dry acetonitrile (10 mL) was added (2-(tert-butoxy)-2-oxoethyl) dimethylsulfonium (192 mg, 1.082 mmol) and DBU (0.299 mL, 1.984 mmol). The reaction mixture was stirred at room temperature for 4 h. After evaporation of acetonitrile under reduced pressure, the residue was purified by silica gel chromatography, eluting 15% ethyl acetate in petroleum ether, to give rac-(1R,2S)-tert-butyl 2-(4-(2-((2,6-difluorobenzyl)oxy)-1,1,1,3,3,3-hexafluoropropan-2-yl)phenyl)-2-((4-fluorophenyl)sulfonyl)cyclopropanecarboxylate as white solid (380 mg, 63% yield). LC/MS (M+18): 686.7; LC retention time: 22.1 min (analytical HPLC Method D); 1H NMR (CDCl3, 400 MHz): δ 7.53 (d, J=8.4 Hz, 2H), 7.48-7.31 (m, 3H), 7.21 (d, J=8.4 Hz, 2H), 7.04 (t, J=8.4 Hz, 2H), 6.95 (t, J=8.0 Hz, 2H), 4.65 (dd, J=14.4, 9.6 Hz, 2H), 3.06 (dd, J=9.2, 6.8 Hz, 1H), 2.15 (dd, J=9.2, 5.2 Hz, 1H), 1.92 (dd, J=6.4, 5.2 Hz, 1H), 1.18 (s, 9H); 19F NMR (376 MHz): δ −70.32, −102.73, −114.47.

Example 38 rac-(1R,2S)-2-(4-(2-((2,6-difluorobenzyl)oxy)-1,1,1,3,3,3-hexafluoropropan-2-yl)phenyl)-2-((4-fluorophenyl)sulfonyl)-N,N-dimethylcyclopropanecarboxamide Step A: rac-(1R,2S)-2-(4-(2-((2,6-difluorobenzyl)oxy)-1,1,1,3,3,3-hexafluoropropan-2-yl)phenyl)-2-((4-fluorophenyl)sulfonyl)cyclopropanecarboxylic acid

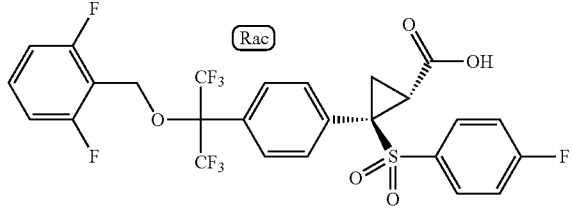 [SMILES: O=C(O)[C@H]1C[C@]1(c1ccc(C(OCc2c(F)cccc2F)(C(F)(F)F)C(F)(F)F)cc1)S(=O)(=O)c1ccc(F)cc1]

Trifluoroacetic acid (0.202 mL, 2.62 mmol) was added to a solution of tert-butyl 2-(4-(2-((2,6-difluorobenzyl)oxy)-1,1,1,3,3,3-hexafluoropropan-2-yl)phenyl)-2-((4-fluorophenyl)sulfonyl)cyclopropanecarboxylate (350 mg, 0.524 mmol, from Example 37) in dry acetonitrile (7 mL) at 0° C. under inert atmosphere. After stirring at room temperature for 12 h, the reaction mixture was concentrated under reduced pressure. The residue was purified by Prep-HPLC to produce rac-(1R,2S)-2-(4-(2-((2,6-difluorobenzyl)oxy)-1,1,1,3,3,3-hexafluoropropan-2-yl)phenyl)-2-((4-fluorophenyl)sulfonyl)cyclopropanecarboxylic acid as white solids (201 mg, 63% yield). LC/MS (M+18): 629.8; LC retention time: 18.7 min (analytical HPLC Method D); 1H NMR (DMSO-d6, 400 MHz): δ 13.02 (br-s, 1H), 7.63-7.55 (m, 1H), 7.53-7.48 (m, 4H), 7.36 (t, J=8.8 Hz, 2H), 7.27-7.20 (m, 4H), 4.60 (dd, J=24, 10 Hz, 2H), 2.97 (dd, J=8.8, 8.0 Hz, 1H), 2.22 (dd, J=9.2, 6.0 Hz, 1H), 1.94 (t, J=6.4 Hz, 1H). 19F NMR (376 MHz): δ −69.89, −103.72, −115.06.

Step B: rac-(1R,2S)-2-(4-(2-((2,6-difluorobenzyl)oxy)-1,1,1,3,3,3-hexafluoropropan-2-yl)phenyl)-2-((4-fluorophenyl)sulfonyl)-N,N-dimethylcyclopropanecarboxamide

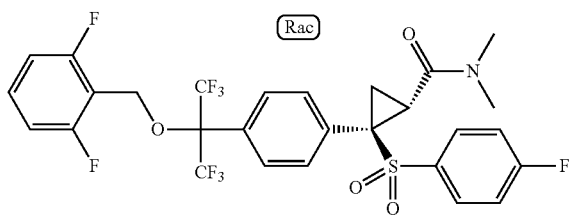 [SMILES: CN(C)C(=O)[C@H]1C[C@]1(c1ccc(C(OCc2c(F)cccc2F)(C(F)(F)F)C(F)(F)F)cc1)S(=O)(=O)c1ccc(F)cc1]

Hunig's Base (0.017 mL, 0.098 mmol) and a 2 M tetrahydrofuran solution of dimethylamine (0.039 mL, 0.078 mmol) were added to a mixture of rac-(1R,2S)-2-(4-(2-((2,6-difluorobenzyl)oxy)-1,1,1,3,3,3-hexafluoropropan-2-yl)phenyl)-2-((4-fluorophenyl)sulfonyl)cyclopropanecarboxylic acid (12 mg, 0.020 mmol) and (benzotriazol-1-yloxy)tris(dimethylamino)phosphonium hexafluorophosphate (17.33 mg, 0.039 mmol) in dichloromethane (1 mL). After 1 h at room temperature, the mixture was quenched with ammonium hydroxide (1 drop), stirred for 5 min and concentrated. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 15 minutes, then a 5-minute hold at 100% B; Flow: 20 mL/min. Fractions containing the desired product were combined and dried via centrifugal evaporation to give Example 38 (9.6 mg, 77% yield). LC/MS (M+1): 640.1; LC retention time: 2.36 min (analytical HPLC Method B); 1H NMR (500 MHz, 1:1 mixture of CDCl$_3$-CD$_3$OD) δ ppm 7.53 (d, J=8.3 Hz, 2H), 7.49-7.38 (m, 3H), 7.19 (d, J=7.8 Hz, 2H), 7.09 (t, J=8.6 Hz, 2H), 7.01 (t, J=7.9 Hz, 2H), 4.74-4.54 (m, 2H), 3.49 (s, 3H), 3.42-3.35 (m, 1H), 2.89 (s, 3H), 2.23-2.09 (m, 2H).

Example 39

1-{2-[(2,6-difluorophenyl)methoxy]-1,1,1,3,3,3-hexafluoropropan-2-yl}-4-[1-(4-fluorobenzenesulfonyl)cyclobutyl]benzene

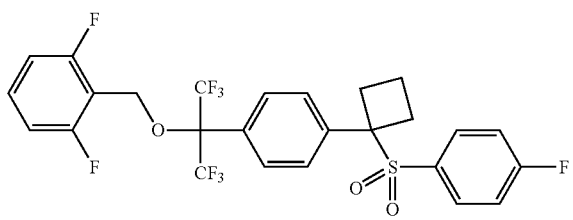 [SMILES: O=S(=O)(c1ccc(F)cc1)C1(c2ccc(C(OCc3c(F)cccc3F)(C(F)(F)F)C(F)(F)F)cc2)CCC1]

Sodium hydride (14.75 mg, 0.369 mmol, 60% suspension in mineral oil) was added to a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (20 mg, 0.037 mmol) and 1,3-diiodopropane (10.91 mg, 0.037 mmol) in N,N-dimethylformamide (1 mL). After 1 h at room temperature, saturated ammonium chloride (2 mL) and ethyl acetate (15 mL) were added. The mixture was washed with water (2×5 mL), brine (5 mL), dried (magnesium sulfate), filtered and concentrated under reduced pressure. The crude material was purified via preparative LC/MS with the following conditions: Column: Waters XBridge C18, 19×150 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 15 minutes, then a 5-minute hold at 100% B; Flow: 20 mL/min. Fractions containing the desired product were combined and dried via centrifugal evaporation to give Example 39 (13.2 mg, 62% yield). LC/MS (M+18): 600.1; LC retention time: 2.296 (analytical HPLC Method B); 1H NMR (500 MHz, 1:1 mixture of CDCl$_3$-CD$_3$OD) δ ppm 7.56 (d, J=8.4 Hz, 2H), 7.50-7.41 (m, 1H), 7.38-7.30 (m, 2H), 7.19 (d, J=8.4 Hz, 2H), 7.11-6.97 (m, 4H), 4.70 (s, 2H), 3.27 (ddd, J=13.9, 9.9, 5.9 Hz, 2H), 2.81-2.67 (m, 2H), 2.45-2.30 (m, 1H), 2.13-1.97 (m, 1H).

Example 40

1,3-difluoro-2-(((1,1,1,3,3,3-hexafluoro-2-(4-(1-((4-fluorophenyl)sulfonyl)-3-methylenecyclobutyl)phenyl)propan-2-yl)oxy)methyl)benzene

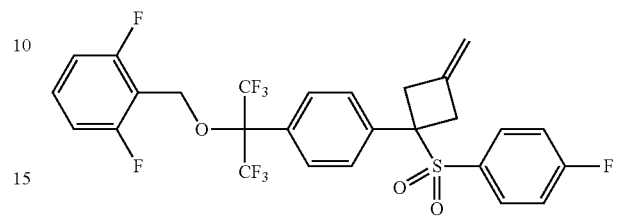

To a solution of 1,3-difluoro-2-(((1,1,1,3,3,3-hexafluoro-2-(4-(((4-fluorophenyl)sulfonyl)methyl)phenyl)propan-2-yl)oxy)methyl)benzene (2.0 g, 3.69 mmol) in N,N-dimethylformamide (30 mL) in a 100 mL round bottom flask under inert atmosphere was added sodium hydride (0.147 g, 3.69 mmol, 60% suspension in mineral oil) and 3-chloro-2-(chloromethyl)prop-1-ene (0.461 g, 3.69 mmol). After stirring at room temperature for 2 h, the reaction mixture was quenched with water (500 mL) and extracted with ethyl acetate (2×100 mL). The combined organic layer was washed with water (2×50 mL), saturated brine (100 mL), dried (sodium sulphate), filtered and concentrated under reduced pressure. The residue was purified by silica gel chromatography, eluting with 15% ethyl acetate in hexanes, to yield 1,3-difluoro-2-(((1,1,1,3,3,3-hexafluoro-2-(4-(1-((4-fluorophenyl)sulfonyl)-3-methylenecyclobutyl)phenyl)propan-2-yl)oxy)methyl)benzene (0.41 g, 19% yield). LC/MS (M+18): 612.2; LC retention time: 22.01 min (analytical HPLC Method D); 1H NMR (400 MHz, DMSO-d6): δ 7.63-7.54 (m, 1H), 7.51 (d, J=8.3 Hz, 2H), 7.44-7.36 (m, 2H), 7.34-7.25 (m, 4H), 7.22 (t, J=8.1 Hz, 2H), 4.93 (s, 2H), 4.63 (s, 2H), 3.82 (dd, J=17.2, 2.8 Hz, 2H), 3.39 (dd, J=17.6, 2.0 Hz, 2H); 19F NMR (376 MHz): δ −70.05, −104.26, −115.08.

Example 41

(3-(4-(2-((2,6-difluorobenzyl)oxy)-1,1,1,3,3,3-hexafluoropropan-2-yl)phenyl)-3-((4-fluorophenyl)sulfonyl)cyclobutyl)methanol

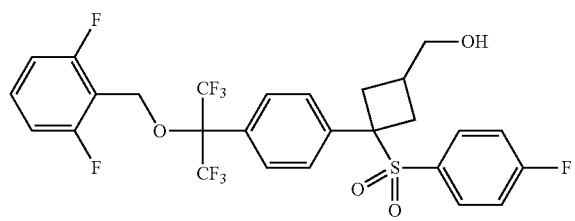 [SMILES: O=S(=O)(c1ccc(F)cc1)C1(c2ccc(C(OCc3c(F)cccc3F)(C(F)(F)F)C(F)(F)F)cc2)CC(CO)C1]

To a solution of 1,3-difluoro-2-(((1,1,1,3,3,3-hexafluoro-2-(4-(1-((4-fluorophenyl)sulfonyl)-3-methylenecyclobutyl)phenyl)propan-2-yl)oxy)methyl)benzene (0.89 g, 1.497 mmol, from Example 40) in tetrahydrofuran (12 mL) under nitrogen atmosphere was added a 1 M solution of borane-dimethylsulfide complex (0.426 mL, 4.26 mmol) at 0° C. The reaction mixture was allowed to reach 25° C. with continuous stirring for 2 h then cooled to 0° C. A 1 M aqueous solution of NaOH (14.97 mL, 14.97 mmol) was added. After stirring for 20 min, hydrogen peroxide (6.12 mL, 59.9 mmol, 30%) was added. The resulting mixture was stirred for 2 h (during this period temperature was gradually brought to 25° C.). The reaction mixture was diluted with water (50 mL) and extracted with ethyl acetate (2×50 mL). The combined organic layer was dried (sodium sulphate), filtered and concentrated under reduced pressure. The white solid residue was washed with a mixture of ethyl acetate: petroleum ether (20 mL, 1:10 ratio) to yield (3-(4-(2-((2,6-difluorobenzyl)oxy)-1,1,1,3,3,3-hexafluoropropan-2-yl)phenyl)-3-((4-fluorophenyl)sulfonyl)cyclobutyl)methanol (0.8 g, 87% yield) as a mixture of two diastereomers based on 1H NMR analysis. LC/MS (M+18): 630.2; LC retention time: 21.32 min (analytical HPLC Method D).

Examples 42 and 43

(1r,3r)-3-(4-(2-((2,6-difluorobenzyl)oxy)-1,1,1,3,3,3-hexafluoropropan-2-yl)phenyl)-3-((4-fluorophenyl)sulfonyl)cyclobutanecarboxylic acid and (1s,3s)-3-(4-(2-((2,6-difluorobenzyl)oxy)-1,1,1,3,3,3-hexafluoropropan-2-yl)phenyl)-3-((4-fluorophenyl)sulfonyl)cyclobutanecarboxylic acid

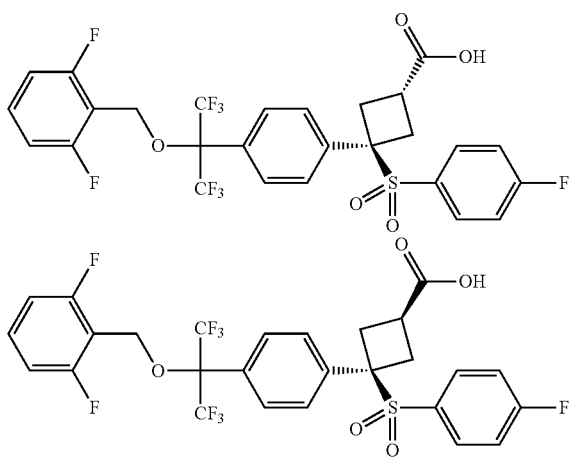

Sulfuric acid (1.5 mL, 28.7 mmol) was added to a solution of sodium dichromate dihydrate (1.16 g, 1.306 mmol) in water (8 mL) at 0° C. After stirring for 15 min at 0° C., the color of the mixture turned orange red. A solution of (3-(4-(2-((2,6-difluorobenzyl)oxy)-1,1,1,3,3,3-hexafluoropropan-2-yl)phenyl)-3-((4-fluorophenyl)sulfonyl)cyclobutyl)methanol (800 mg, 1.306 mmol) in acetone (55 mL) was added slowly. The resulting mixture was stirred at room temperature for 3 h, quenched with water (100 mL), and extracted with ethyl acetate (3×100 mL). The combined organic layer was washed with saturated brine (50 mL), dried (sodium sulphate), filtered and concentrated under reduced pressure to give a crude mixture (780 mg). The two diastereomers were separated by SFC purification to give (1r,3r)-3-(4-(2-((2,6-difluorobenzyl)oxy)-1,1,1,3,3,3-hexafluoropropan-2-yl)phenyl)-3-((4-fluorophenyl)sulfonyl)cyclobutanecarboxylic acid (Example 42, peak 1, 120 mg, 15% yield) and (1s,3s)-3-(4-(2-((2,6-difluorobenzyl)oxy)-1,1,1,3,3,3-hexafluoropropan-2-yl)phenyl)-3-((4-fluorophenyl)sulfonyl)cyclobutanecarboxylic acid (Example 43, peak 2, 300 mg, 37% yield), both as white solid. Analytical data for Example 42: LC/MS (M+18): 644.2; LC retention time: 16.30 min (analytical HPLC Method D); 1H NMR (400 MHz, DMSO-d6): δ 12.48 (br-s, 1H), 7.63-7.54 (m, 1H), 7.49 (d, J=8.2 Hz, 2H), 7.42-7.34 (m, 2H), 7.32-7.14 (m, 6H), 4.62 (s, 2H), 3.40-3.32 (m, 3H), 2.90-2.81 (m, 2H); 19F NMR (376 MHz): δ 70.04, −103.92, −115.03. Analytical data for Example 43: LC/MS (M+18): 644.2; LC retention time: 16.38 min (analytical HPLC Method D); 1H NMR (400 MHz, DMSO-d6): δ 12.50 (br-s, 1H), 7.63-7.54 (m, 1H), 7.51 (d, J=8.3 Hz, 2H), 7.37 (d, J=8.7 Hz, 2H), 7.33-7.18 (m, 6H), 4.62 (s, 2H), 3.29-3.26 (m, 2H), 3.11-3.06 (m, 1H), 2.97-2.88 (m, 2H); 19F NMR (376 MHz): −70.03, −104.11, −115.05.

Example 44

(1s,3s)-3-((4-fluorophenyl)sulfonyl)-3-(4-(perfluoropropan-2-yl)phenyl)-N-(tetrahydro-2H-pyran-4-yl)cyclobutanecarboxamide Step A: 1-(2-(benzyloxy)-1,1,1,3,3,3-hexafluoropropan-2-yl)4-(1-((4-fluorophenylsulfonyl)-3-methylenecyclobutyl)benzene

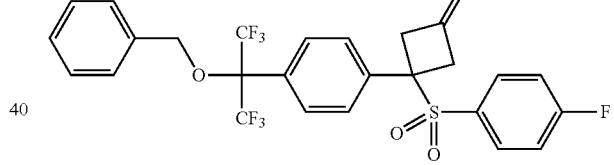

To a solution of 1-(2-(benzyloxy)-1,1,1,3,3,3-hexafluoropropan-2-yl)-4-((4-fluorophenyl)sulfonyl)methyl)benzene (5.00 g, 9.87 mmol, from Step B of Example 3) in N,N-dimethylformamide (45 mL) was added sodium hydride (0.395 g, 9.87 mmol, 60% suspension in mineral oil) and 3-chloro-2-(chloromethyl)prop-1-ene (1.234 g, 9.87 mmol). After 2 h at room temperature, the mixture was quenched with water (500 mL) and extracted with ethyl acetate (3×100 mL). the combined organic layer was washed with saturated brine solution (100 mL), dried (sodium sulphate), filtered and concentrated under reduced pressure. The crude product was purified by column chromatography, using combi-flash (40 g Red-Sep column) and eluting with 18% ethyl acetate in hexanes, to give 1-(2-(benzyloxy)-1,1,1,3,3,3-hexafluoropropan-2-yl)4-(1-((4-fluorophenylsulfonyl)-3-methylenecyclobutyl)benzene as cream colored solid (1.0 g, 18% yield). 1H NMR (400 MHz, DMSO-d6): δ 7.45 (d, J=8.8 Hz, 2H), 7.44-7.37 (m, 7H), 7.29-7.24 (m, 4H), 4.91 (t, J=2 Hz, 2H), 4.59 (s, 2H), 3.82-3.78 (dd, J=17.8, 2.8 Hz, 2H), 3.38-3.33 (dd, J=17.2, 2.4 Hz, 2H); 19F NMR (376 MHz): −70.15, −103.88.

Step B: (3-(4-(2-(benzyloxy)-1,1,1,3,3,3-hexafluoropropan-2-yl)phenyl)-3-((4-fluorophenyl)sulfonyl)cyclobutyl)methanol

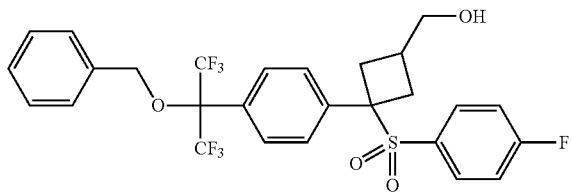 [SMILES: O=S(=O)(c1ccc(F)cc1)C1(c2ccc(C(OCc3ccccc3)(C(F)(F)F)C(F)(F)F)cc2)CC(CO)C1]

To a solution of 1-(2-(benzyloxy)-1,1,1,3,3,3-hexafluoropropan-2-yl)4-(1-((4-fluorophenylsulfonyl)-3-methylenecyclobutyl)benzene (2.6 g, 4.66 mmol) in tetrahydrofuran (100 mL) under nitrogen atmosphere was added borane-methyl sulfide complex (13.97 mmol, 1.326 mL) at 0° C. The mixture was stirred for 2 h while allowing the reaction mixture to gradually reach room temperature, then cooled to 0° C. A 1 M aqueous sodium hydroxide solution (46.6 mmol, 46.6 mL) was added. After stirring for 20 min, a 35% solution of hydrogen peroxide (186 mmol, 19.02 mL) was added. The mixture was stirred for 2 h while allowing the reaction mixture to gradually reach room temperature, diluted with water (100 mL) and extracted with ethyl acetate (2×100 mL). The combined organic layer was dried (sodium sulphate), filtered and concentrated under reduced pressure. The white solid residue was washed with 10% ethyl acetate in petroleum ether (20 mL) to yield (3-(4-(2-(benzyloxy)-1,1,1,3,3,3-hexafluoropropan-2-yl)phenyl)-3-((4-fluorophenylsulfonyl)cyclobutyl)methanol (2.4 g crude) as white solid. LC/MS (M+18): 594.2.

Step C: 3-(4-(2-(benzyloxy)-1,1,1,3,3,3-hexafluoropropan-2-yl)phenyl)-3-((4-fluorophenyl)sulfonyl)cyclobutanecarboxylic acid

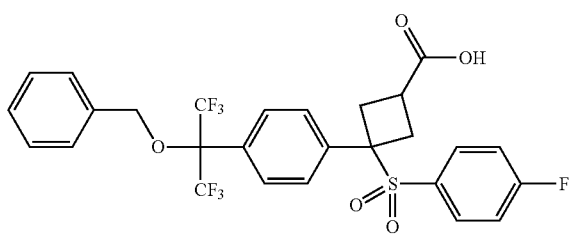 [SMILES: O=C(O)C1CC(c2ccc(C(OCc3ccccc3)(C(F)(F)F)C(F)(F)F)cc2)(S(=O)(=O)c2ccc(F)cc2)C1]

Sulfuric acid (34.3 mmol, 1.831 mL) was added to a solution of sodium dichromate dihydrate (4.68 mmol, 1396 mg) in water (12 mL) at 0° C. The resulting solution was stirred for 15 min at 0° C. The color of the mixture turned orange-red. A solution of (3-(4-(2-(benzyloxy)-1,1,1,3,3,3-hexafluoropropan-2-yl)phenyl)-3-((4-fluorophenylsulfonyl)cyclobutyl)methanol (1.561 mmol, 900 mg) in acetone (95 mL) was added slowly to the above prepared orange red solution at 0° C. The resulting reaction mixture was stirred at room temperature for 3 h, quenched with water (100 mL) and extracted with ethyl acetate (3×100 mL). The combined organic layer was dried (sodium sulphate), filtered and concentrated under reduced pressure to give 3-(4-(2-(benzyloxy)-1,1,1,3,3,3-hexafluoropropan-2-yl)phenyl)-3-(4-fluorophenylsulfonyl)cyclobutanecarboxylic acid (850 mg) as off white gummy solid. LC/MS (M−1): 589.0.

Step D: (1r,3r)-3-((4-fluorophenyl)sulfonyl)-3-(4-(1,1,1,3,3,3-hexafluoro-2-hydroxypropan-2-yl)phenyl)cyclobutanecarboxylic acid and (1s,3s)-3-((4-fluorophenyl)sulfonyl)-3-(4-(1,1,1,3,3,3-hexafluoro-2-hydroxypropan-2-yl)phenyl)cyclobutanecarboxylic acid

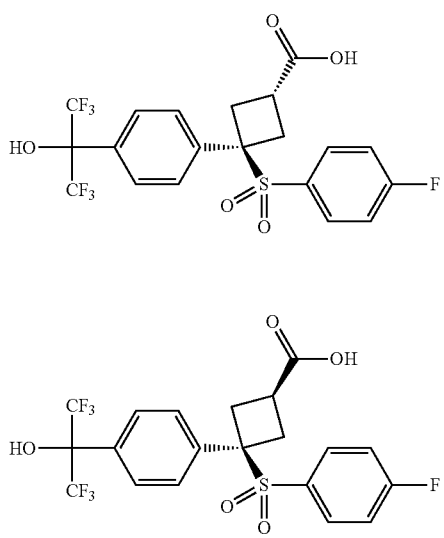

To a solution of 3-(4-(2-(benzyloxy)-1,1,1,3,3,3-hexafluoropropan-2-yl)phenyl)-3-(4-fluorophenylsulfonyl)cyclobutanecarboxylic acid (1.524 mmol, 900 mg) in methanol (45 mL) was added palladium on carbon (1.677 mmol, 178 mg). The resulting mixture was stirred at room temperature under hydrogen atmosphere through bladder for 3 h, then filtered through celite bed. The celite bed was rinsed with methanol (50 mL). The combined organic layer was concentrated to give the crude product. The crude material was purified by preparative HPLC and SFC to yield (1r,3r)-3-((4-fluorophenyl)sulfonyl)-3-(4-(1,1,1,3,3,3-hexafluoro-2-hydroxypropan-2-yl)phenyl)cyclobutanecarboxylic acid (diastereomer 1, 295 mg, 38.7% yield) and (1s,3s)-3-((4-fluorophenyl)sulfonyl)-3-(4-(1,1,1,3,3,3-hexafluoro-2-hydroxypropan-2-yl)phenyl)cyclobutanecarboxylic acid (diastereomer 2, 470 mg, 61.6% yield). Analytical data for enantiomer 1: LC/MS (M+18): 518.0; LC retention time: 10.28 min (analytical HPLC Method F); 1H NMR (400 MHz, DMSO-d6): δ 7.55 (d, J=8.0 Hz, 2H), 7.40-7.37 (m, 2H), 7.27-7.23 (m, 2H), 7.07 (d, J=8.4 Hz, 2H), 3.25-3.07 (m, 3H), 2.80-2.75 (m, 2H); 19F NMR (376 MHz): −73.93, −104.06. Analytical data for enantiomer 2: LC/MS (M+18): 518.0; LC retention time: 10.11 min (analytical HPLC Method F); 1H NMR (400 MHz, DMSO-d6): δ 7.55 (d, J=8.0 Hz, 2H), 7.29-7.22 (m, 6H), 3.25-3.16 (m, 2H), 2.79-2.71 (m, 3H); 19F NMR (376 MHz): −73.93, −104.44.

Step E: (1s,3s)-methyl 3-((4-fluorophenyl)sulfonyl)-3-(4-(1,1,1,3,3,3-hexafluoro-2-hydroxypropan-2-yl)phenyl)cyclobutanecarboxylate

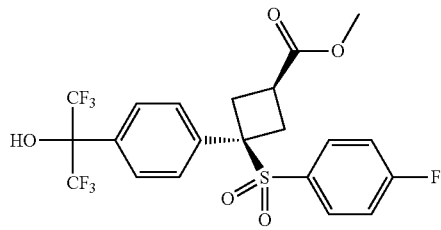 [SMILES: COC(=O)[C@H]1C[C@@](c2ccc(C(O)(C(F)(F)F)C(F)(F)F)cc2)(S(=O)(=O)c2ccc(F)cc2)C1]

Thionyl chloride (0.066 mL, 0.899 mmol) was added dropwise to a stirred solution of (1s,3s)-3-((4-fluorophenyl)sulfonyl)-3-(4-(1,1,1,3,3,3-hexafluoro-2-hydroxypropan-2-yl)phenyl)cyclobutanecarboxylic acid (150 mg, 0.300 mmol) in methanol (2 mL) at 0° C. Reaction vial was sealed and stirred at 70° C. for 1 h. After evaporation of solvent under reduced pressure, the residue was dried under vacuum to give crude (1s,3s)-methyl 3-((4-fluorophenyl)sulfonyl)-3-(4-(1,1,1,3,3,3-hexafluoro-2-hydroxypropan-2-yl)phenyl)cyclobutanecarboxylate, which was used in the next reaction without purification. LC/MS (M+18): 532.3.

Step F: (1s,3s)-methyl 3-((4-fluorophenyl)sulfonyl)-3-(4-(perfluoropropan-2-yl)phenyl)cyclobutanecarboxylate

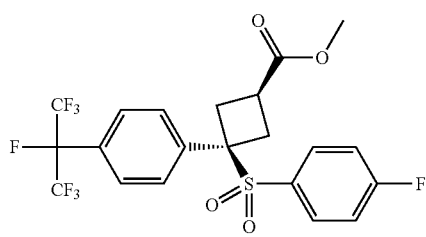 [SMILES: COC(=O)[C@H]1C[C@@](c2ccc(C(F)(C(F)(F)F)C(F)(F)F)cc2)(S(=O)(=O)c2ccc(F)cc2)C1]

(Diethylamino)sulfur trifluoride (0.119 mL, 0.899 mmol) was added to a suspension of crude (1s,3s)-methyl 3-((4-fluorophenyl)sulfonyl)-3-(4-(1,1,1,3,3,3-hexafluoro-2-hydroxypropan-2-yl)phenyl)cyclobutanecarboxylate from Step E in dichloromethane (2 mL). The reaction vial was sealed and stirred at 50° C. for 15 h. LCMS analysis showed that the reaction was about 50% complete. Additional (diethylamino)sulfur trifluoride (0.119 mL) was added. After 3.5 h at 50° C., another portion of (diethylamino)sulfur trifluoride (0.119 mL) was added. After another 18 h, the mixture was carefully quenched by slowly adding it into a stirred methanol (2 mL) solution. The resulting solution was concentrated. Silica gel chromatography, eluting with 0-100% ethyl acetate in hexanes, gave (1s,3s)-methyl 3-((4-fluorophenyl)sulfonyl)-3-(4-(perfluoropropan-2-yl)phenyl)cyclobutanecarboxylate as off-white solid (0.122 g, 79% yield over 2 steps). LC/MS (M+23): 539.3; 1H NMR (400 MHz, CDCl$_3$) δ ppm 7.52 (d, J=8.4 Hz, 2H), 7.30-7.20 (m, 4H), 6.99 (t, J=8.6 Hz, 2H), 3.79 (s, 3H), 3.62-3.53 (m, 2H), 3.07 (quin, J=8.9 Hz, 1H), 2.89-2.80 (m, 2H); 19F NMR (400 MHz, CDCl$_3$) d −75.67, −102.50, −182.73.

Step G: (1s,3s)-3-((4-fluorophenyl)sulfonyl)-3-(4-(perfluoropropan-2-yl)phenyl)cyclobutanecarboxylic acid

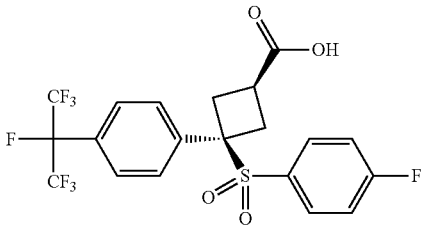 [SMILES: O=C(O)[C@H]1C[C@@](c2ccc(C(F)(C(F)(F)F)C(F)(F)F)cc2)(S(=O)(=O)c2ccc(F)cc2)C1]

A 1 N aqueous solution of sodium hydroxide (1 mL, 1.00 mmol) was added to a solution of (1s,3s)-methyl 3-((4-fluorophenyl)sulfonyl)-3-(4-(perfluoropropan-2-yl)phenyl)cyclobutanecarboxylate (122 mg, 0.236 mmol) in tetrahydrofuran (1 mL) at room temperature. After 2 h at room temperature, the volatile tetrahydrofuran was evaporated under reduced pressure. Following addition of 1 N hydrochloric acid (1 mL), the resulting suspension was filtered. The solid was washed with water (2 mL) and dried under vacuum to give (1s,3s)-3-((4-fluorophenyl)sulfonyl)-3-(4-(perfluoropropan-2-yl)phenyl)cyclobutanecarboxylic acid as white solid (0.118 g, 100% yield). LC/MS (M+18): 520.3; 1H NMR (400 MHz, CDCl$_3$) δ ppm 7.54 (d, J=8.3 Hz, 2H), 7.32-7.28 (m, 2H), 7.25 (d, J=8.4 Hz, 2H), 7.00 (t, J=8.5 Hz, 2H), 3.67-3.59 (m, 2H), 3.16 (quin, J=9.0 Hz, 1H), 2.94-2.86 (m, 2H); 19F NMR (400 MHz, CDCl$_3$) d −75.66, −102.30, −182.71.

Step H: (1s,3s)-3-((4-fluorophenyl)sulfonyl)-3-(4-(perfluoropropan-2-yl)phenyl)-N-(tetrahydro-2H-pyran-4-yl)cyclobutanecarboxamide

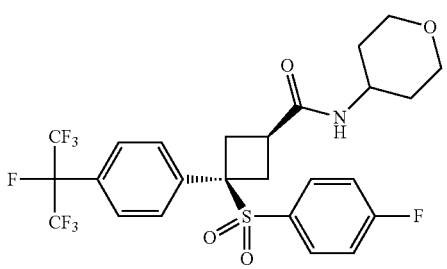 [SMILES: O=C(NC1CCOCC1)[C@H]1C[C@@](c2ccc(C(F)(C(F)(F)F)C(F)(F)F)cc2)(S(=O)(=O)c2ccc(F)cc2)C1]

Hunig's Base (0.014 mL, 0.080 mmol) was added to a stirred solution of (1s,3s)-3-((4-fluorophenyl)sulfonyl)-3-(4-(perfluoropropan-2-yl)phenyl)cyclobutanecarboxylic acid (8 mg, 0.016 mmol), tetrahydro-2H-pyran-4-amine hydrochloride (2.191 mg, 0.016 mmol) and (benzotriazol-1-yloxy)tris(dimethylamino)phosphonium hexafluorophosphate (7.04 mg, 0.016 mmol) in acetonitrile (0.5 mL) at room temperature. After 16 h at room temperature, the reaction was complete. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 15 minutes, then a 5-minute hold at 100% B; Flow: 20 mL/min. Fractions containing the desired product were combined and dried via centrifugal evaporation to give Example 44 (7.1 mg, 75% yield). LC/MS (M+1): 586.3; LC retention time: 2.03 min (analytical HPLC Method B); 1H NMR (500 MHz, 1:1 mixture of CDCl$_3$-CD$_3$OD) δ ppm 7.53 (d, J=8.4 Hz, 2H), 7.37-7.26 (m, 4H), 7.06 (t, J=8.5 Hz, 2H), 3.97-3.86 (m, 3H), 3.53-3.43 (m, 4H), 2.95-2.85 (m, 1H), 2.83-2.75 (m, 2H), 1.83 (dd, J=12.7, 2.1 Hz, 2H), 1.56-1.45 (m, 2H).

Examples 45 and 46

3-(4-(2-((2,6-difluorobenzyl)oxy)-1,1,1,3,3,3-hexafluoropropan-2-yl)phenyl)-3-((4-fluorophenyl)sulfonyl)cyclobutanamine (diastereomers 1 and 2, respectively)

Step A: 2-(trimethylsilyl)ethyl (3-(4-(2-((2,6-difluorobenzyl)oxy)-1,1,1,3,3,3-hexafluoropropan-2-yl)phenyl)-3-((4-fluorophenyl)sulfonyl)cyclobutyl)carbamate

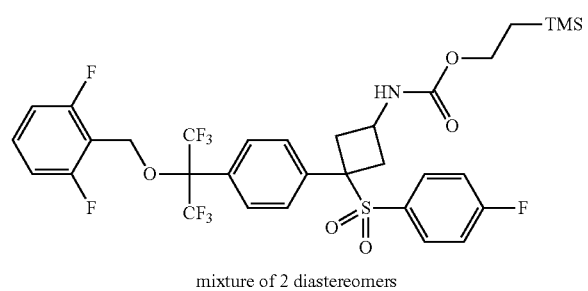 [SMILES: C[Si](C)(C)CCOC(=O)NC1CC(c2ccc(C(OCc3c(F)cccc3F)(C(F)(F)F)C(F)(F)F)cc2)(S(=O)(=O)c2ccc(F)cc2)C1]

mixture of 2 diastereomers

To a solution of 3-(4-(2-((2,6-difluorobenzyl)oxy)-1,1,1,3,3,3-hexafluoropropan-2-yl)phenyl)-3-((4-fluorophenyl)sulfonyl)cyclobutanecarboxylic acid (1.00 g, 1.59 mmol, mixture of diastereomers) in toluene (20 mL) in a 100 mL round bottom flask under nitrogen atmosphere was added triethylamine (0.667 ml, 4.79 mmol) at 0° C. After 5 min at 0° C., diphenylphosphoryl azide (1.31 g, 4.79 mmol) was added and the mixture was stirred at 25° C. for 30 min. After quenching with water (100 mL), the mixture was extracted with ethyl acetate (2×100 mL). Combined organic layer was washed with brine (100 mL), dried (sodium sulphate), filtered and concentrated under reduced pressure. The crude material was dissolved in 2-(trimethylsilyl)ethanol (4.9 ml, 31.9 mmol) and heated to 80° C. for 1 h. The resulting mixture was concentrated at reduced pressure. The crude yellow oil was diluted with water (50 mL) and extracted with ethyl acetate (2×50 mL). The combined organic layer was washed with water (50 mL) and brine (50 mL), dried (sodium sulphate), filtered and concentrated under reduced pressure to give crude 2-(trimethylsilyl)ethyl (3-(4-(2-((2,6-difluorobenzyl)oxy)-1,1,1,3,3,3-hexafluoropropan-2-yl)phenyl)-3-(4-fluorophenSulfonyl)cyclobutyl)carbamate (1.30 g), which was directly used for next step without further purification. LC/MS (M−1): 740.3.

Step B: 3-(4-(2-((2,6-difluorobenzyl)oxy)-1,1,1,3,3,3-hexafluoropropan-2-yl)phenyl)-3-((4-fluorophenyl)sulfonyl)cyclobutanamine (diastereomers 1 and 2)

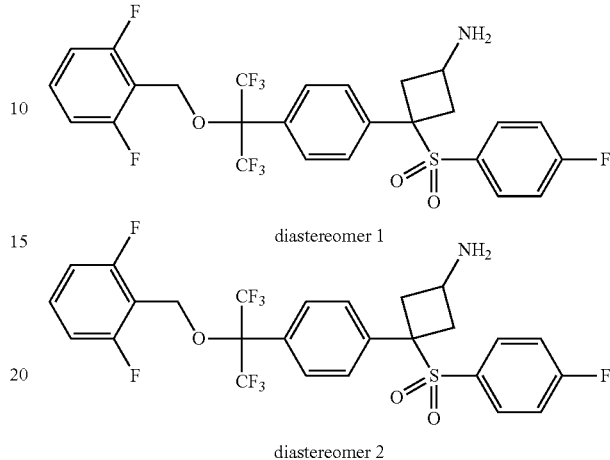

diastereomer 1 diastereomer 2

A solution of crude 2-(trimethylsilyl)ethyl-(3-(4-(2-((2,6-difluorobenzyl)oxy)-1,1,1,3,3,3-hexafluoropropan-2-yl)phenyl)-3-(4-fluorophenSulfonyl)cyclobutyl) carbamate from Step A (1.30 g) in dichloromethane (20 mL) and trifluoroacetic acid (1.42 mL, 18.2 mmol) was stirred for 2 h and concentrated under reduced pressure. The crude yellow oil was diluted with water (50 mL) and extracted with ethyl acetate (2×50 mL). The combined organic layer was dried (sodium sulphate), filtered and concentrated under reduced pressure. The crude mixture was purified by SFC to give two diastereomers of 3-(4-(2-((2,6-difluorobenzyl)oxy)-1,1,1,3,3,3-hexafluoropropan-2-yl)phenyl)-3-((4-fluorophenyl)sulfonyl)cyclobutanamine. Diastereomer 1 (Example 45, peak 1, 270 mg, 25% yield): LC/MS (M+1): 598.2; LC retention time: 9.368 min (analytical HPLC Method D); 1H NMR (400 MHz, DMSO-d6): δ 8.21 (s, 2H), 7.64-7.55 (m, 1H), 7.50 (d, J=8.4 Hz, 2H), 7.41 (d, J=8.8 Hz, 2H), 7.27 (m, 6H), 4.62 (s, 2H), 3.69-3.60 (m, 1H), 3.27-3.18 (m, 2H), 3.10-3.02 (m, 2H); 19F NMR (376 MHz): −70.03, −103.74, −115.07. Diastereomer 2 (Example 46, peak 2, 100 mg, 9.2% yield): LC/MS (M+1): 598.2; LC retention time: 9.39 min (analytical HPLC Method D); 1H NMR (400 MHz, DMSO-d6): δ 8.04 (s, 2H), 7.65-7.54 (m, 1H), 7.51 (d, J=8.5 Hz, 2H), 7.39-7.35 (m, 2H), 7.32-7.16 (m, 6H), 4.62 (s, 2H), 4.06-3.98 (m, 1H), 3.43-3.34 (m, 2H), 2.95-2.86 (m, 2H); 19F NMR (376 MHz): −70.07, −103.46, −115.08.

Example 47

4-(2-(4-(2-((2,6-difluorobenzyl)oxy)-1,1,1,3,3,3-hexafluoropropan-2-yl)phenyl)-2-((4-fluorophenyl)sulfonyl)-2,3-dihydro-1H-inden-5-yl)-1-methyl-1H-pyrazole Step A: 4-bromo-1,2-bis(bromomethyl)benzene

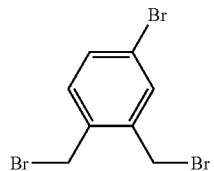

A solution of 4-bromo-1,2-dimethylbenzene (2.0 g, 10.81 mmol) in carbon tetrachloride (70 mL) in a 250 mL round bottom flask was stirred at room temperature until all solids were dissolved. N-bromosuccinimide (4.81 g, 27.0 mmol) and 2,2'-azobis(2-methylpropionitrile) (0.044 g, 0.270 mmol) were added and mixture was heated to 70° C. for 1 h. After cooling to room temperature, the mixture was filtered through celite bed. Celite bed was rinsed with carbon tetrachloride (3×50 mL). Combined filtrate was dried (sodium sulphate), filtered and concentrated under reduced pressure. The crude material was purified by combi-flash column chromatography (Column: 120 gm Red-Sep; eluent: hexane). The fractions were collected and concentrated under reduced pressure to yield 4-bromo-1,2-bis(bromomethyl) benzene (2.1 g, 56.7% yield) as colorless gummy oil. 1H NMR (400 MHz, CDCl$_3$): δ 7.56-7.51 (m, 1H), 7.44-7.41 (m, 1H), 7.25-7.22 (m, 1H), 4.59 (s, 2H), 4.578 (s, 2H).

Step B: 5-bromo-2-(4-(2-((2,6-difluorobenzyl)oxy)-1,1,1,3,3,3-hexafluoropropan-2-yl)phenyl)-2-((4-fluorophenyl)sulfonyl)-2,3-dihydro-1H-indene

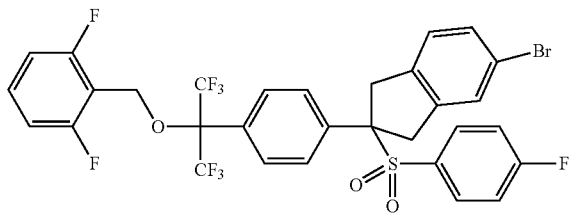 [SMILES: O=S(=O)(c1ccc(F)cc1)C1(c2ccc(C(OCc3c(F)cccc3F)(C(F)(F)F)C(F)(F)F)cc2)Cc2ccc(Br)cc2C1]

A solution of 1,3-difluoro-2-(((1,1,1,3,3,3-hexafluoro-2-(4-(((4-fluorophenyl)sulfonyl)methyl)phenyl)propan-2-yl) oxy)methyl)benzene (0.6 g, 1.106 mmol) in N,N-dimethylformamide (5 mL) in a 50 mL round bottom flask was cooled to 0° C. Sodium hydride (44.2 mg, 1.10 mmol, 60% suspension in mineral oil) and 4-bromo-1,2-bis(bromomethyl) benzene (379 mg, 1.10 mmol) were added sequentially. The reaction mixture was allowed to reach 25° C. and stirred at that temperature for 2 h. After quenching by slow addition of cold water (100 mL), the mixture was extracted with ethyl acetate (3×100 mL). The combined organic layer was washed with brine (50 mL), dried (sodium sulphate), filtered and concentrated under reduced pressure. The crude mixture was purified by Prep-HPLC to give 5-bromo-2(4-(2-((2,6-difluorobenzyl)oxy)-1,1,1,3,3,3-hexafluoropropan-2-yl) phenyl)-2-((4-fluorophenyl)sulfonyl)2,3-dihydro-1H-indene as white solid (120 mg, 15% yield). LC/MS (M+18): 740.0; LC retention time: 23.17 min (analytical HPLC Method D); 1H NMR (400 MHz, DMSO-d6): δ 7.64-7.56 (m, 5H), 7.55-7.44 (m, 2H), 7.36 (s, 1H), 7.29-7.20 (m, 5H), 7.13 (d, J=8.1 Hz, 1H), 4.67 (s, 2H), 4.15 (dd, J=17.8, 11.4 Hz, 2H), 3.75 (dd, J=23.6, 17.6 Hz, 2H); 19F NMR (376 MHz): δ −69.98, −104.14, −115.00.

Step C: 4-(2-(4-(2-((2,6-difluorobenzyl)oxy)-1,1,1,3,3,3-hexafluoropropan-2-yl)phenyl)-2-((4-fluorophenyl)sulfonyl)-2,3-dihydro-1H-inden-5-yl)-1-methyl-1H-pyrazole

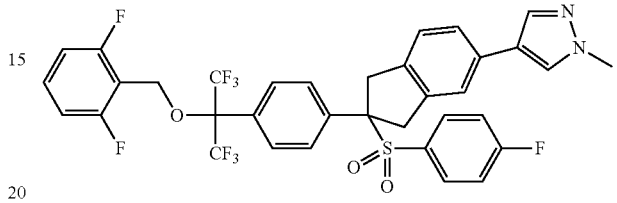

A mixture of 5-bromo-2-(4-(2-((2,6-difluorobenzyl)oxy)-1,1,1,3,3,3-hexafluoropropan-2-yl)phenyl)-2-((4-fluorophenyl)sulfonyl)-2,3-dihydro-1H-indene (15 mg, 0.021 mmol), 1-methyl-4-(4,4,5,5-tetramethyl-1,3,2-dioxaborolan-2-yl)-1H-pyrazole (8.63 mg, 0.041 mmol), Pd2(dba)3.CHCl$_3$ (1.9 mg, 2.073 μmol), dicyclohexyl(2',4',6'-triisopropyl-[1,1'-biphenyl]-3-yl)phosphine (2.0 mg, 4.15 μmol) and 2 M aqueous potassium phosphate tribasic (0.031 mL, 0.062 mmol) was dissolved in dioxane (0.5 mL). The reaction vial was flushed with nitrogen, sealed and heated at 90° C. for 3 h. After cooling to room temperature, the reaction mixture was diluted with N,N-dimethylformamide (1 mL) and filtered. The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 35-100% B over 25 minutes, then a 5-minute hold at 100% B; Flow: 20 mL/min. Fractions containing the desired product were combined and dried via centrifugal evaporation to give Example 47 (11.8 mg, 78% yield). LC/MS (M+1): 725.3; LC retention time: 2.47 min (analytical HPLC Method B); 1H NMR (400 MHz, 1:1 mixture of CDCl$_3$-CD$_3$OD) δ ppm 7.73-7.62 (m, 4H), 7.54 (d, J=8.5 Hz, 2H), 7.48-7.36 (m, 3H), 7.28-7.21 (m, 2H), 7.12 (d, J=7.8 Hz, 1H), 7.04-6.91 (m, 4H), 4.70 (s, 2H), 4.25-4.14 (m, 2H), 3.91 (s, 3H), 3.80-3.70 (m, 2H).

The Examples in TABLE 1 below were prepared in the same manner as outlined in the examples above, substituting the appropriate amine, alcohol, acid, bromide or sulfone intermediates.

TABLE 1

| Example number | Structure | MS observed (M + 1) | HPLC ret. time (min.) | HPLC method |
|---|---|---|---|---|
| 48 | 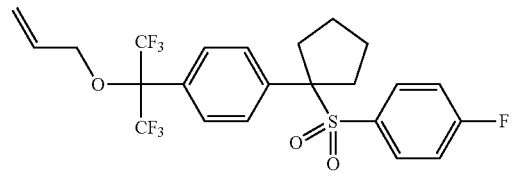 [SMILES: C=CCOC(c1ccc(C2(S(=O)(=O)c3ccc(F)cc3)CCCC2)cc1)(C(F)(F)F)C(F)(F)F] | 528.2 (M + 18) | 2.563 | B |

TABLE 1-continued

| Example number | Structure | MS observed (M + 1) | HPLC ret. time (min.) | HPLC method |
|---|---|---|---|---|
| 49 | 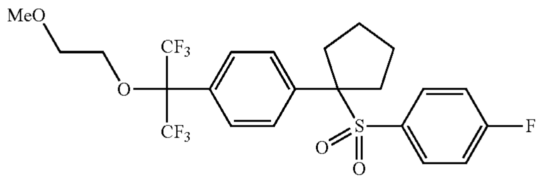 [SMILES: COCCOC(c1ccc(C2(S(=O)(=O)c3ccc(F)cc3)CCCC2)cc1)(C(F)(F)F)C(F)(F)F] | 546.0 (M + 18) | 2.06 | C |
| 50 | 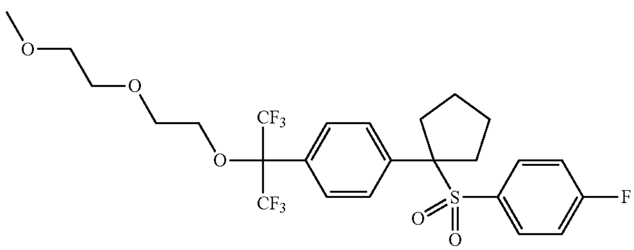 [SMILES: COCCOCCOC(c1ccc(C2(S(=O)(=O)c3ccc(F)cc3)CCCC2)cc1)(C(F)(F)F)C(F)(F)F] | 590.1 (M + 18) | 2.35 | C |
| 51 | 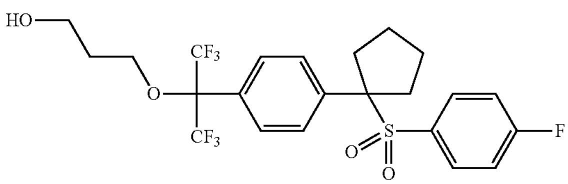 [SMILES: O=S(=O)(c1ccc(F)cc1)C1(c2ccc(C(OCCCO)(C(F)(F)F)C(F)(F)F)cc2)CCCC1] | 546.0 (M + 18) | 2.11 | B |
| 52 | 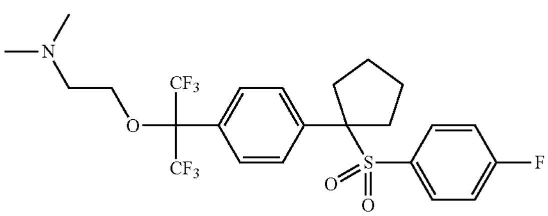 [SMILES: CN(C)CCOC(c1ccc(C2(S(=O)(=O)c3ccc(F)cc3)CCCC2)cc1)(C(F)(F)F)C(F)(F)F] | 541.9 | 1.68 | C |
| 53 | 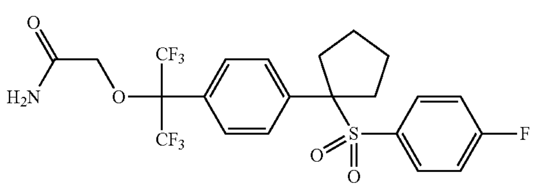 [SMILES: NC(=O)COC(c1ccc(C2(S(=O)(=O)c3ccc(F)cc3)CCCC2)cc1)(C(F)(F)F)C(F)(F)F] | 545.1 (M + 18) | 1.680 | B |
| 54 | 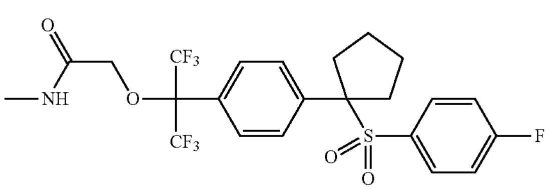 [SMILES: CNC(=O)COC(c1ccc(C2(S(=O)(=O)c3ccc(F)cc3)CCCC2)cc1)(C(F)(F)F)C(F)(F)F] | 559.1 (M + 18) | 2.056 | B |
| 55 | 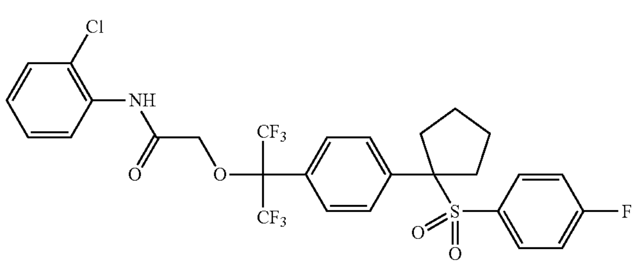 [SMILES: O=C(COC(c1ccc(C2(S(=O)(=O)c3ccc(F)cc3)CCCC2)cc1)(C(F)(F)F)C(F)(F)F)Nc1ccccc1Cl] | 655.1 (M + 18) | 2.58 | C |

TABLE 1-continued

| Example number | Structure | MS observed (M + 1) | HPLC ret. time (min.) | HPLC method |
|---|---|---|---|---|
| 56 | 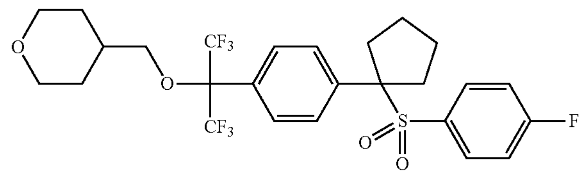 [SMILES: O=S(=O)(c1ccc(F)cc1)C1(c2ccc(C(OCC3CCOCC3)(C(F)(F)F)C(F)(F)F)cc2)CCCC1] | 591.0 (M + 23) | 2.14 | C |
| 57 | 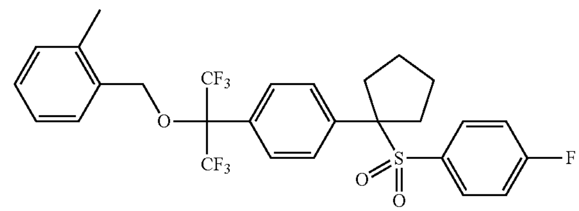 [SMILES: Cc1ccccc1COC(c1ccc(C2(S(=O)(=O)c3ccc(F)cc3)CCCC2)cc1)(C(F)(F)F)C(F)(F)F] | 592.1 (M + 18) | 2.40 | C |
| 58 | 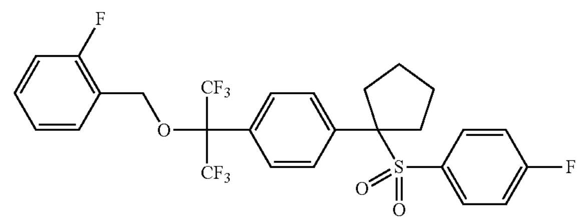 [SMILES: O=S(=O)(c1ccc(F)cc1)C1(c2ccc(C(OCc3ccccc3F)(C(F)(F)F)C(F)(F)F)cc2)CCCC1] | 595.5 (M + 18) | 3.316 | B |
| 59 | 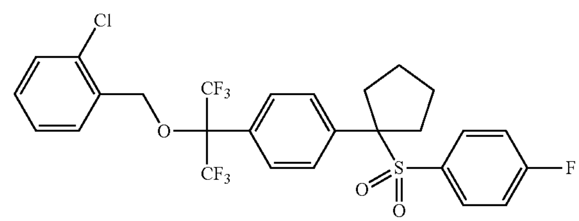 [SMILES: O=S(=O)(c1ccc(F)cc1)C1(c2ccc(C(OCc3ccccc3Cl)(C(F)(F)F)C(F)(F)F)cc2)CCCC1] | 612.0 (M + 18) | 2.42 | C |
| 60 | 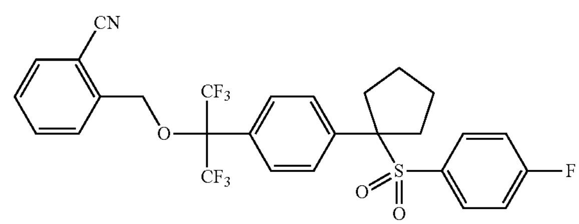 [SMILES: N#Cc1ccccc1COC(c1ccc(C2(S(=O)(=O)c3ccc(F)cc3)CCCC2)cc1)(C(F)(F)F)C(F)(F)F] | 603.1 (M + 18) | 2.15 | C |
| 61 | 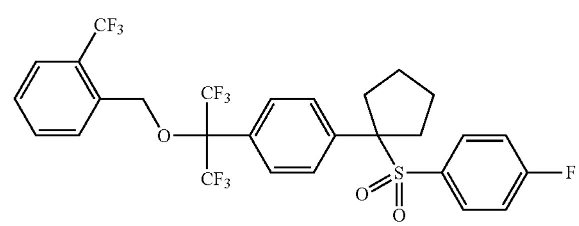 [SMILES: O=S(=O)(c1ccc(F)cc1)C1(c2ccc(C(OCc3ccccc3C(F)(F)F)(C(F)(F)F)C(F)(F)F)cc2)CCCC1] | 646.1 (M + 18) | 3.13 | C |
| 62 | 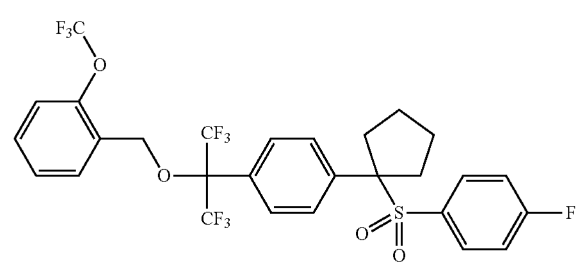 [SMILES: O=S(=O)(c1ccc(F)cc1)C1(c2ccc(C(OCc3ccccc3OC(F)(F)F)(C(F)(F)F)C(F)(F)F)cc2)CCCC1] | 662.1 (M + 18) | 2.44 | B |

TABLE 1-continued

| Example number | Structure | MS observed (M + 1) | HPLC ret. time (min.) | HPLC method |
|---|---|---|---|---|
| 63 | 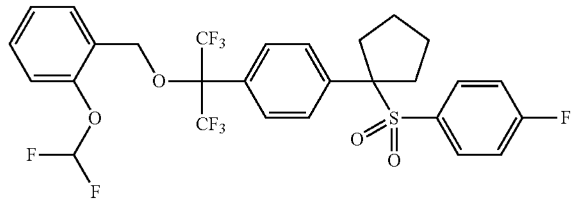 [SMILES: O=S(=O)(c1ccc(F)cc1)C1(c2ccc(C(OCc3ccccc3OC(F)F)(C(F)(F)F)C(F)(F)F)cc2)CCCC1] | 644.1 (M + 18) | 2.62 | C |
| 64 | 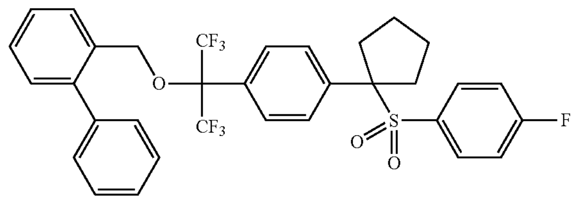 [SMILES: O=S(=O)(c1ccc(F)cc1)C1(c2ccc(C(OCc3ccccc3-c3ccccc3)(C(F)(F)F)C(F)(F)F)cc2)CCCC1] | 654.1 (M + 18) | 2.65 | C |
| 65 | 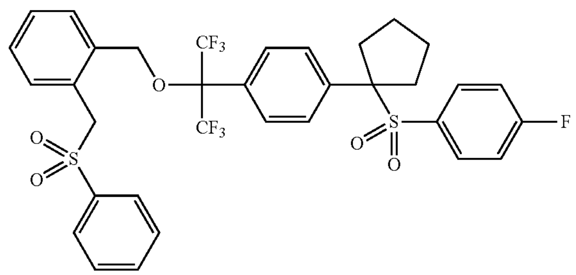 [SMILES: O=S(=O)(Cc1ccccc1COC(c1ccc(C2(S(=O)(=O)c3ccc(F)cc3)CCCC2)cc1)(C(F)(F)F)C(F)(F)F)c1ccccc1] | 731.2 (M + 18) | 2.34 | B |
| 66 | 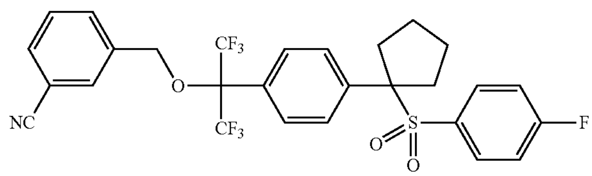 [SMILES: N#Cc1cccc(COC(c2ccc(C3(S(=O)(=O)c4ccc(F)cc4)CCCC3)cc2)(C(F)(F)F)C(F)(F)F)c1] | 603.1 (M + 18) | 2.518 | B |
| 67 | 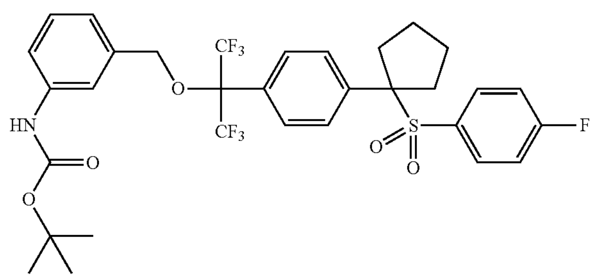 [SMILES: CC(C)(C)OC(=O)Nc1cccc(COC(c2ccc(C3(S(=O)(=O)c4ccc(F)cc4)CCCC3)cc2)(C(F)(F)F)C(F)(F)F)c1] | 676.2 | 2.64 | C |
| 68 | 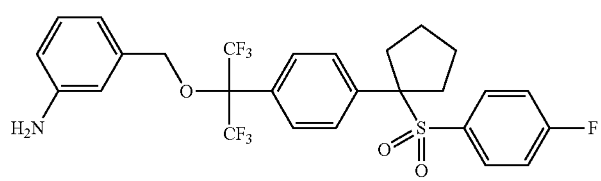 [SMILES: Nc1cccc(COC(c2ccc(C3(S(=O)(=O)c4ccc(F)cc4)CCCC3)cc2)(C(F)(F)F)C(F)(F)F)c1] | 576.1 | 2.190 | B |
| 69 | 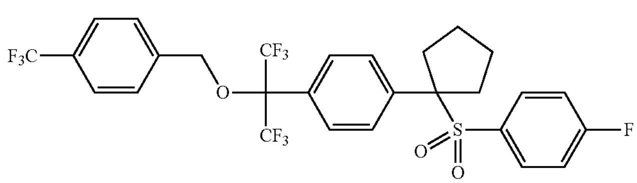 [SMILES: O=S(=O)(c1ccc(F)cc1)C1(c2ccc(C(OCc3ccc(C(F)(F)F)cc3)(C(F)(F)F)C(F)(F)F)cc2)CCCC1] | 646.0 (M + 18) | 2.768 | B |

TABLE 1-continued

| Example number | Structure | MS observed (M + 1) | HPLC ret. time (min.) | HPLC method |
|---|---|---|---|---|
| 70 | 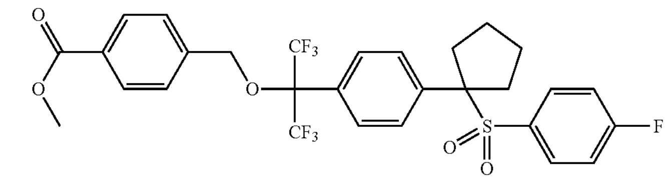 [SMILES: COC(=O)c1ccc(COC(c2ccc(C3(S(=O)(=O)c4ccc(F)cc4)CCCC3)cc2)(C(F)(F)F)C(F)(F)F)cc1] | 636.2 (M + 18) | 2.610 | B |
| 71 | 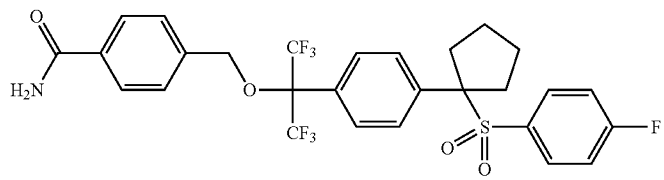 [SMILES: NC(=O)c1ccc(COC(c2ccc(C3(S(=O)(=O)c4ccc(F)cc4)CCCC3)cc2)(C(F)(F)F)C(F)(F)F)cc1] | 604.1 | 2.156 | B |
| 72 | 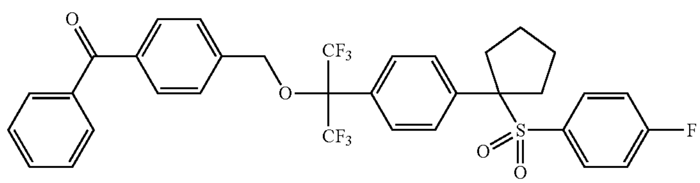 [SMILES: O=C(c1ccccc1)c1ccc(COC(c2ccc(C3(S(=O)(=O)c4ccc(F)cc4)CCCC3)cc2)(C(F)(F)F)C(F)(F)F)cc1] | 665.2 | 2.67 | C |
| 73 | 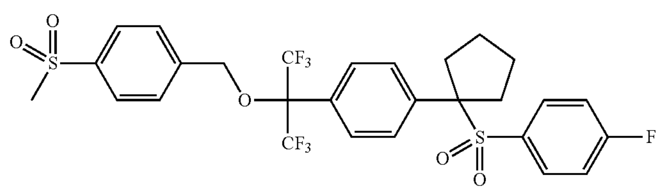 [SMILES: CS(=O)(=O)c1ccc(COC(c2ccc(C3(S(=O)(=O)c4ccc(F)cc4)CCCC3)cc2)(C(F)(F)F)C(F)(F)F)cc1] | 656.0 (M + 18) | 2.32 | C |
| 74 | 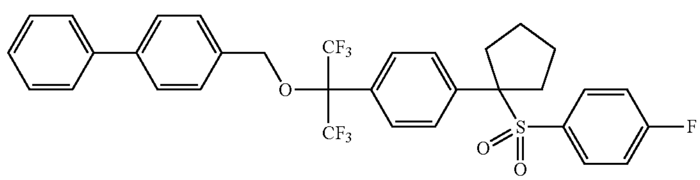 [SMILES: O=S(=O)(c1ccc(F)cc1)C1(c2ccc(C(OCc3ccc(-c4ccccc4)cc3)(C(F)(F)F)C(F)(F)F)cc2)CCCC1] | 655.1 (M + 18) | 2.55 | C |
| 75 | 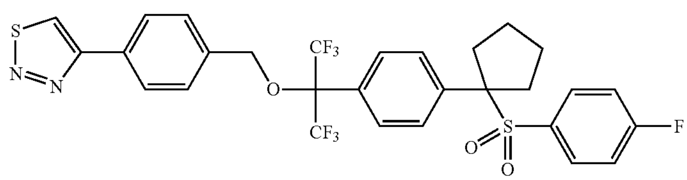 [SMILES: O=S(=O)(c1ccc(F)cc1)C1(c2ccc(C(OCc3ccc(-c4csnn4)cc3)(C(F)(F)F)C(F)(F)F)cc2)CCCC1] | 645.0 | 2.57 | B |
| 76 | 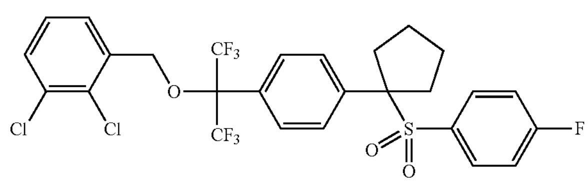 [SMILES: O=S(=O)(c1ccc(F)cc1)C1(c2ccc(C(OCc3cccc(Cl)c3Cl)(C(F)(F)F)C(F)(F)F)cc2)CCCC1] | 646.0 (M + 18) | 2.86 | C |
| 77 | 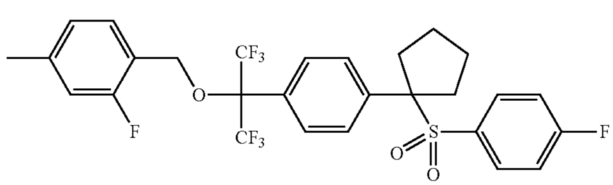 | 611.1 (M + 18) | 2.73 | B |

TABLE 1-continued

| Example number | Structure | MS observed (M + 1) | HPLC ret. time (min.) | HPLC method |
|---|---|---|---|---|
| 78 | 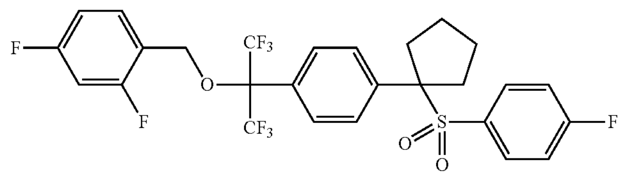 [SMILES: O=S(=O)(c1ccc(F)cc1)C1(c2ccc(C(OCc3ccc(F)cc3F)(C(F)(F)F)C(F)(F)F)cc2)CCCC1] | 614.0 (M + 18) | 2.671 | B |
| 79 | 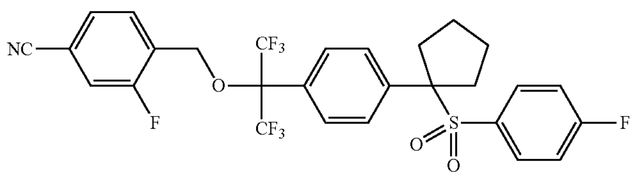 [SMILES: N#Cc1ccc(COC(c2ccc(C3(S(=O)(=O)c4ccc(F)cc4)CCCC3)cc2)(C(F)(F)F)C(F)(F)F)c(F)c1] | 621.2 (M + 18) | 2.552 | B |
| 80 | 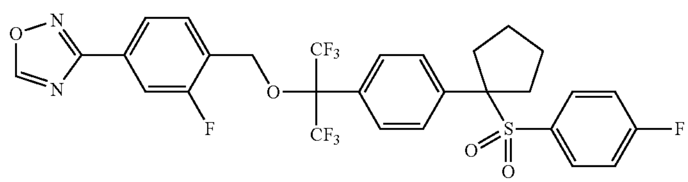 [SMILES: O=S(=O)(c1ccc(F)cc1)C1(c2ccc(C(OCc3ccc(-c4ncon4)cc3F)(C(F)(F)F)C(F)(F)F)cc2)CCCC1] | 664.5 (M + 18) | 2.52 | B |
| 81 | 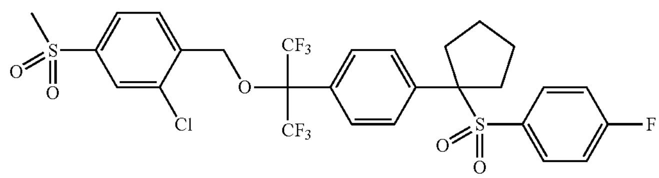 [SMILES: CS(=O)(=O)c1ccc(COC(c2ccc(C3(S(=O)(=O)c4ccc(F)cc4)CCCC3)cc2)(C(F)(F)F)C(F)(F)F)c(Cl)c1] | 690.0 (M + 18) | 2.44 | B |
| 82 | 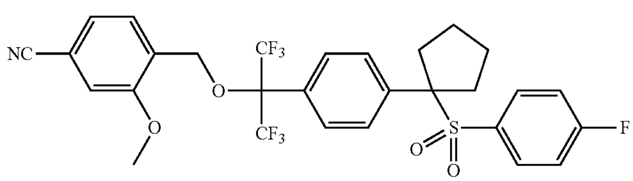 | 633.1 (M + 18) | 2.54 | B |
| 83 | 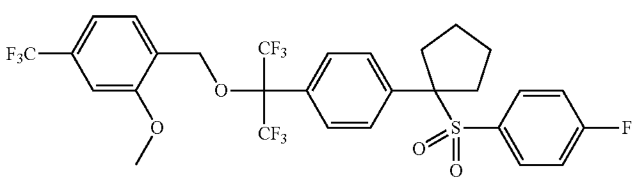 [SMILES: COc1cc(C(F)(F)F)ccc1COC(c1ccc(C2(S(=O)(=O)c3ccc(F)cc3)CCCC2)cc1)(C(F)(F)F)C(F)(F)F] | 676.1 (M + 18) | 2.80 | B |
| 84 | 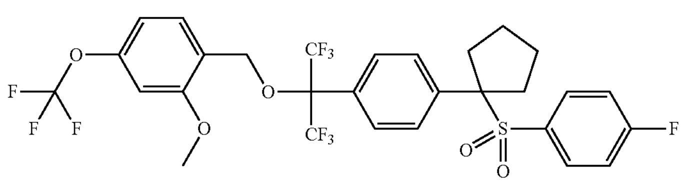 [SMILES: COc1cc(OC(F)(F)F)ccc1COC(c1ccc(C2(S(=O)(=O)c3ccc(F)cc3)CCCC2)cc1)(C(F)(F)F)C(F)(F)F] | 692.1 (M + 18) | 2.79 | B |
| 85 | 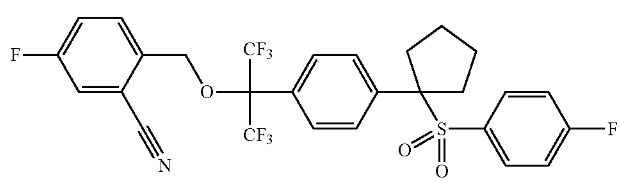 [SMILES: N#Cc1cc(F)ccc1COC(c1ccc(C2(S(=O)(=O)c3ccc(F)cc3)CCCC2)cc1)(C(F)(F)F)C(F)(F)F] | 621.1 (M + 18) | 2.49 | C |

TABLE 1-continued

| Example number | Structure | MS observed (M + 1) | HPLC ret. time (min.) | HPLC method |
|---|---|---|---|---|
| 86 | 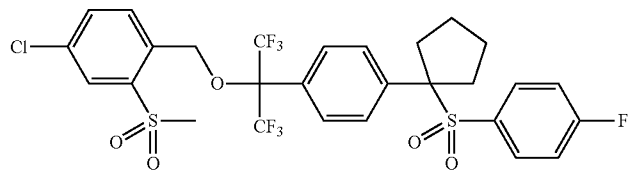 [SMILES: CS(=O)(=O)c1cc(Cl)ccc1COC(c1ccc(C2(S(=O)(=O)c3ccc(F)cc3)CCCC2)cc1)(C(F)(F)F)C(F)(F)F] | 690.2 (M + 18) | 2.55 | B |
| 87 | 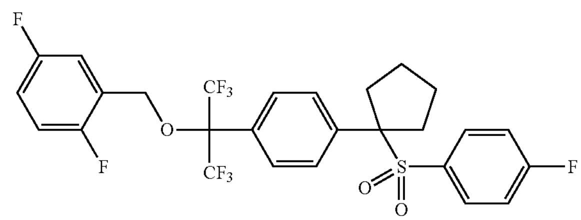 | 614.2 (M + 18) | 2.667 | B |
| 88 | 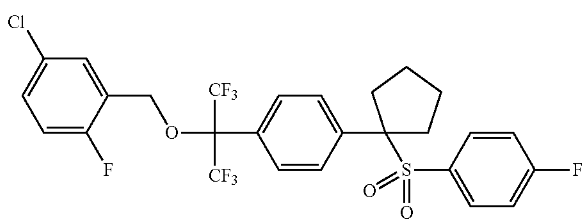 [SMILES: O=S(=O)(c1ccc(F)cc1)C1(c2ccc(C(OCc3cc(Cl)ccc3F)(C(F)(F)F)C(F)(F)F)cc2)CCCC1] | 632.0 (M + 18) | 3.18 | C |
| 89 | 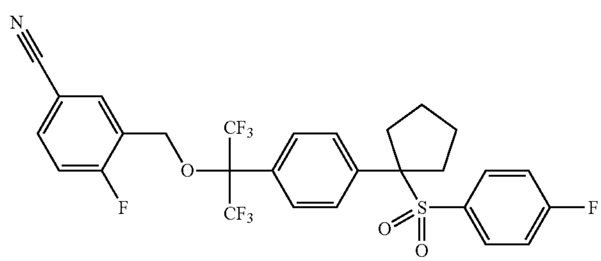 [SMILES: N#Cc1ccc(F)c(COC(c2ccc(C3(S(=O)(=O)c4ccc(F)cc4)CCCC3)cc2)(C(F)(F)F)C(F)(F)F)c1] | 621.1 (M + 18) | 2.46 | B |
| 90 | 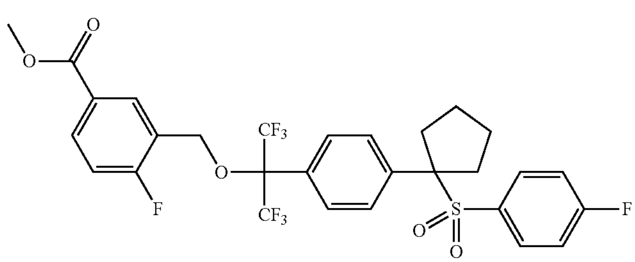 [SMILES: COC(=O)c1ccc(F)c(COC(c2ccc(C3(S(=O)(=O)c4ccc(F)cc4)CCCC3)cc2)(C(F)(F)F)C(F)(F)F)c1] | 653.6 (M + 18) | 2.59 | B |
| 91 | 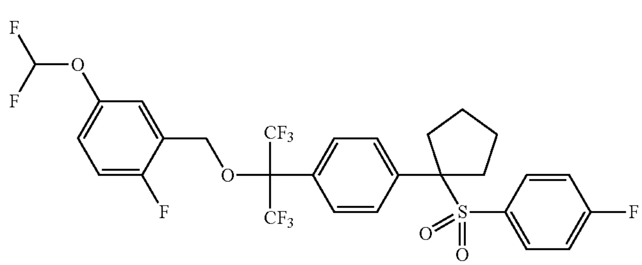 [SMILES: O=S(=O)(c1ccc(F)cc1)C1(c2ccc(C(OCc3cc(OC(F)F)ccc3F)(C(F)(F)F)C(F)(F)F)cc2)CCCC1] | 662.1 (M + 18) | 2.37 | B |

TABLE 1-continued

| Example number | Structure | MS observed (M + 1) | HPLC ret. time (min.) | HPLC method |
|---|---|---|---|---|
| 92 | 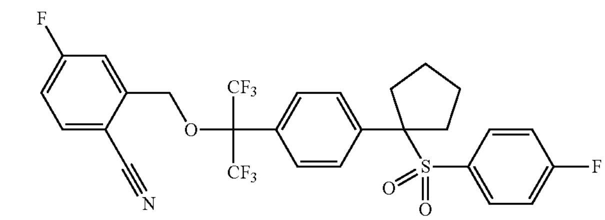 [SMILES: N#Cc1ccc(F)cc1COC(c1ccc(C2(S(=O)(=O)c3ccc(F)cc3)CCCC2)cc1)(C(F)(F)F)C(F)(F)F] | 622.1 (M + 18) | 2.29 | C |
| 93 | 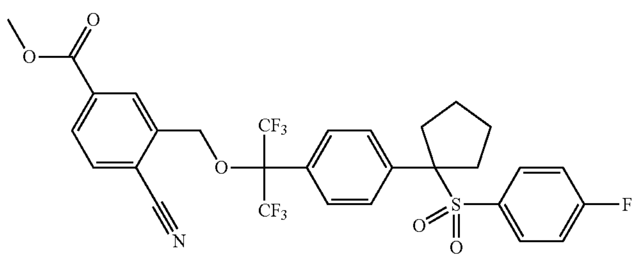 [SMILES: COC(=O)c1ccc(C#N)c(COC(c2ccc(C3(S(=O)(=O)c4ccc(F)cc4)CCCC3)cc2)(C(F)(F)F)C(F)(F)F)c1] | 661.0 | 2.47 | C |
| 94 | 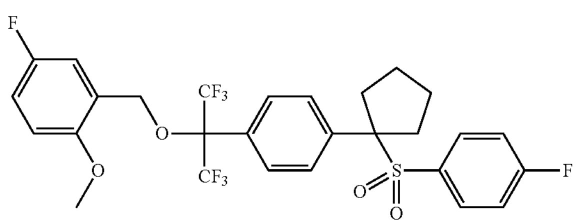 [SMILES: COc1ccc(F)cc1COC(c1ccc(C2(S(=O)(=O)c3ccc(F)cc3)CCCC2)cc1)(C(F)(F)F)C(F)(F)F] | 625.8 (M + 18) | 2.63 | B |
| 95 | 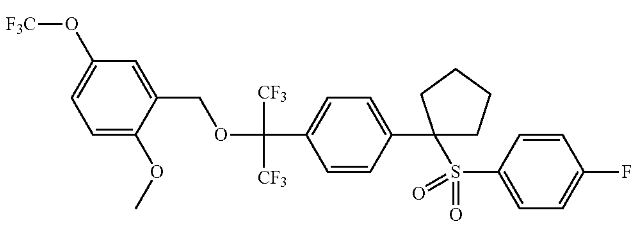 | 693.1 (M + 18) | 2.80 | B |
| 96 | 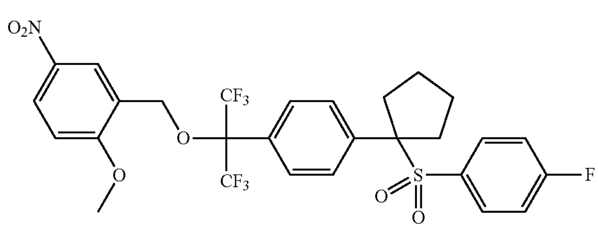 [SMILES: COc1ccc([N+](=O)[O-])cc1COC(c1ccc(C2(S(=O)(=O)c3ccc(F)cc3)CCCC2)cc1)(C(F)(F)F)C(F)(F)F] | 652.5 (M + 18) | 2.56 | B |
| 97 | 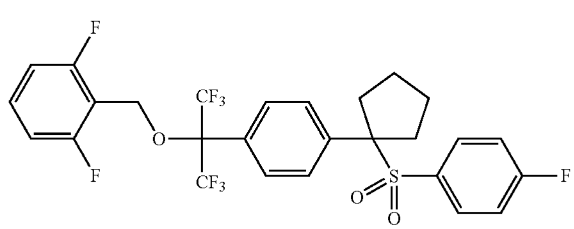 [SMILES: O=S(=O)(c1ccc(F)cc1)C1(c2ccc(C(OCc3c(F)cccc3F)(C(F)(F)F)C(F)(F)F)cc2)CCCC1] | 614.8 (M + 18) | 4.808 | A |

TABLE 1-continued

| Example number | Structure | MS observed (M + 1) | HPLC ret. time (min.) | HPLC method |
|---|---|---|---|---|
| 98 | 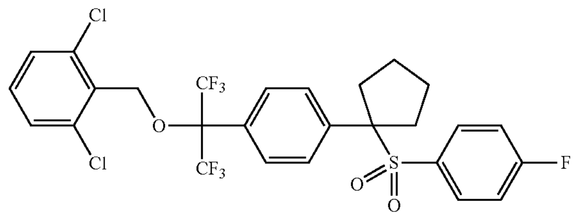 | 646.0 (M + 18) | 2.785 | B |
| 99 | 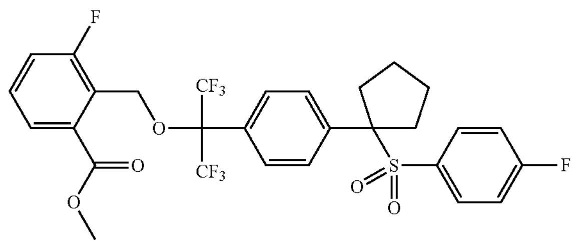 [SMILES: COC(=O)c1cccc(F)c1COC(c1ccc(C2(S(=O)(=O)c3ccc(F)cc3)CCCC2)cc1)(C(F)(F)F)C(F)(F)F] | 653.6 (M + 18) | 2.56 | B |
| 100 | 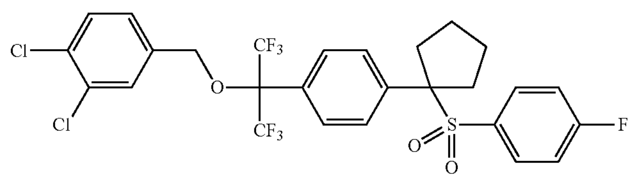 [SMILES: O=S(=O)(c1ccc(F)cc1)C1(c2ccc(C(OCc3ccc(Cl)c(Cl)c3)(C(F)(F)F)C(F)(F)F)cc2)CCCC1] | 646.2 (M + 18) | 2.862 | B |
| 101 | 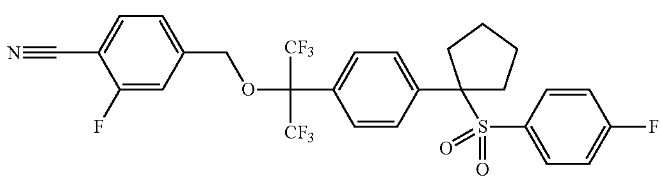 [SMILES: N#Cc1ccc(COC(c2ccc(C3(S(=O)(=O)c4ccc(F)cc4)CCCC3)cc2)(C(F)(F)F)C(F)(F)F)cc1F] | 621.2 (M + 18) | 2.55 | B |
| 102 | 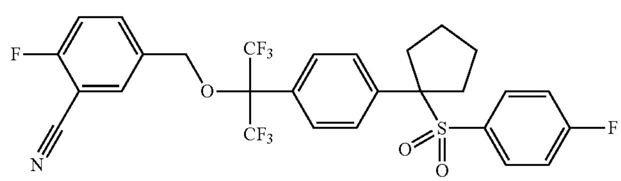 [SMILES: N#Cc1cc(COC(c2ccc(C3(S(=O)(=O)c4ccc(F)cc4)CCCC3)cc2)(C(F)(F)F)C(F)(F)F)ccc1F] | 620.8 (M + 18) | 2.45 | B |
| 103 | 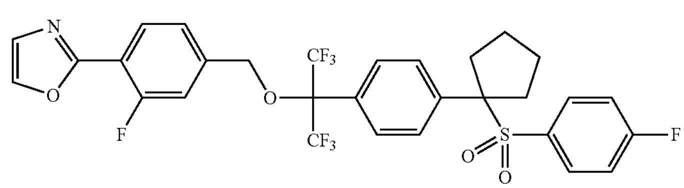 [SMILES: O=S(=O)(c1ccc(F)cc1)C1(c2ccc(C(OCc3ccc(-c4ncco4)c(F)c3)(C(F)(F)F)C(F)(F)F)cc2)CCCC1] | 646.0 | 2.29 | C |
| 104 | 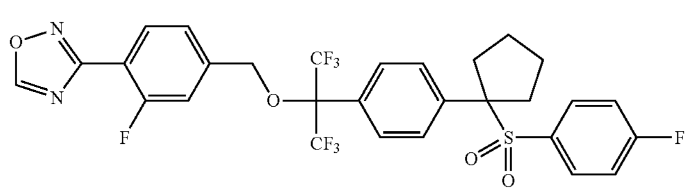 [SMILES: O=S(=O)(c1ccc(F)cc1)C1(c2ccc(C(OCc3ccc(-c4ncon4)c(F)c3)(C(F)(F)F)C(F)(F)F)cc2)CCCC1] | 647.1 | 2.46 | C |

TABLE 1-continued

| Example number | Structure | MS observed (M + 1) | HPLC ret. time (min.) | HPLC method |
|---|---|---|---|---|
| 105 | 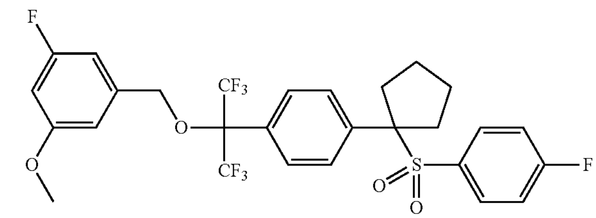 [SMILES: COc1cc(F)cc(COC(c2ccc(C3(S(=O)(=O)c4ccc(F)cc4)CCCC3)cc2)(C(F)(F)F)C(F)(F)F)c1] | 625.8 (M + 18) | 2.60 | B |
| 106 | 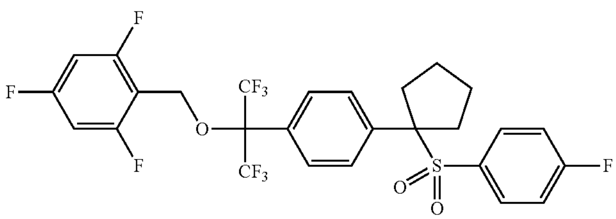 [SMILES: O=S(=O)(c1ccc(F)cc1)C1(c2ccc(C(OCc3c(F)cc(F)cc3F)(C(F)(F)F)C(F)(F)F)cc2)CCCC1] | 632.1 (M + 18) | 2.662 | B |
| 107 | 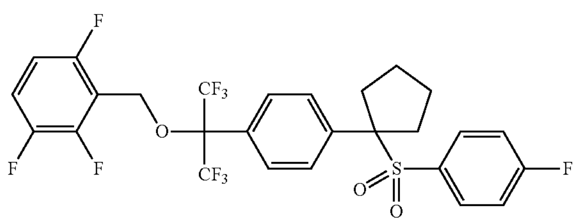 [SMILES: O=S(=O)(c1ccc(F)cc1)C1(c2ccc(C(OCc3c(F)ccc(F)c3F)(C(F)(F)F)C(F)(F)F)cc2)CCCC1] | 632.0 (M + 18) | 2.61 | C |
| 108 | 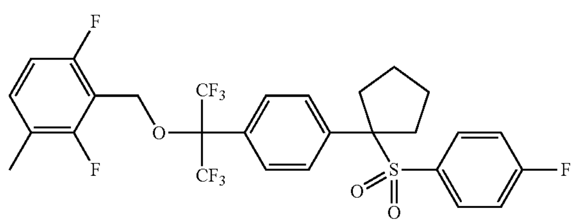 | 627.6 (M + 18) | 2.71 | C |
| 109 | 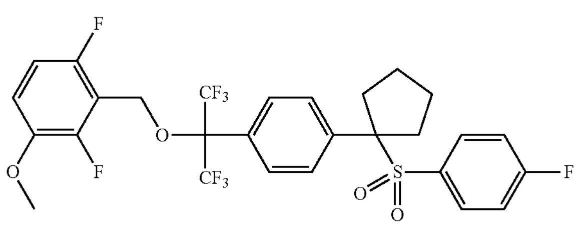 [SMILES: COc1ccc(F)c(COC(c2ccc(C3(S(=O)(=O)c4ccc(F)cc4)CCCC3)cc2)(C(F)(F)F)C(F)(F)F)c1F] | 644.0 (M + 18) | 2.58 | B |
| 110 | 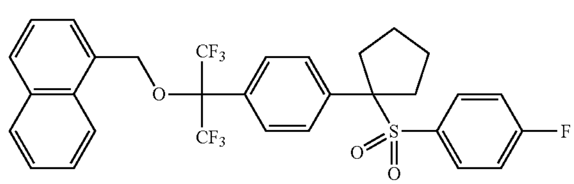 [SMILES: O=S(=O)(c1ccc(F)cc1)C1(c2ccc(C(OCc3cccc4ccccc34)(C(F)(F)F)C(F)(F)F)cc2)CCCC1] | 628.2 (M + 18) | 2.80 | B |
| 111 | 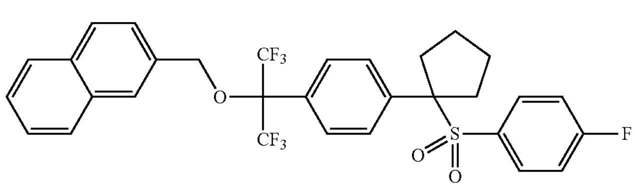 [SMILES: O=S(=O)(c1ccc(F)cc1)C1(c2ccc(C(OCc3ccc4ccccc4c3)(C(F)(F)F)C(F)(F)F)cc2)CCCC1] | 628.1 (M + 18) | 2.805 | B |

TABLE 1-continued

| Example number | Structure | MS observed (M + 1) | HPLC ret. time (min.) | HPLC method |
|---|---|---|---|---|
| 112 | 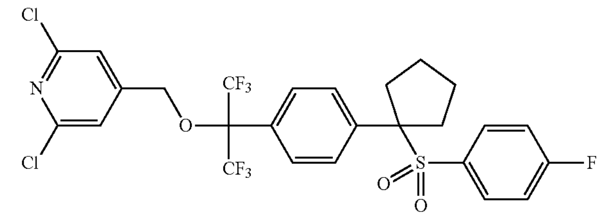 [SMILES: O=S(=O)(c1ccc(F)cc1)C1(c2ccc(C(OCc3cc(Cl)nc(Cl)c3)(C(F)(F)F)C(F)(F)F)cc2)CCCC1] | 630.0 | 2.704 | B |
| 113 | 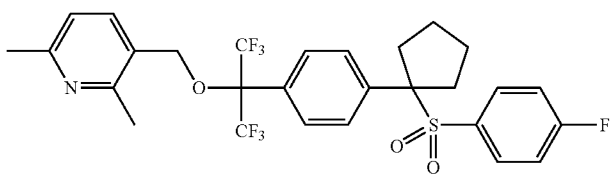 [SMILES: Cc1ccc(COC(c2ccc(C3(S(=O)(=O)c4ccc(F)cc4)CCCC3)cc2)(C(F)(F)F)C(F)(F)F)c(C)n1] | 590.1 | 1.83 | C |
| 114 | 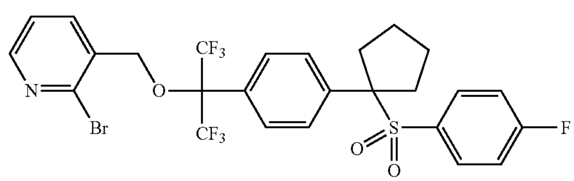 [SMILES: O=S(=O)(c1ccc(F)cc1)C1(c2ccc(C(OCc3cccnc3Br)(C(F)(F)F)C(F)(F)F)cc2)CCCC1] | 642.0 | 2.51 | B |
| 115 | 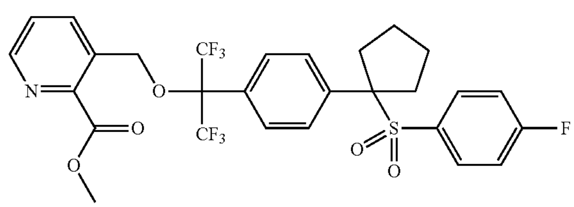 [SMILES: COC(=O)c1ncccc1COC(c1ccc(C2(S(=O)(=O)c3ccc(F)cc3)CCCC2)cc1)(C(F)(F)F)C(F)(F)F] | 620.1 | 2.27 | B |
| 116 | 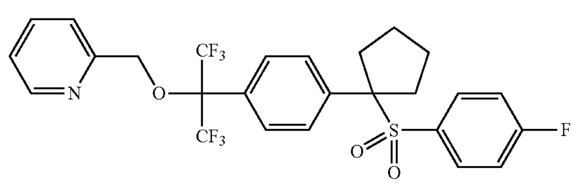 | 561.8 | 2.20 | C |
| 117 | 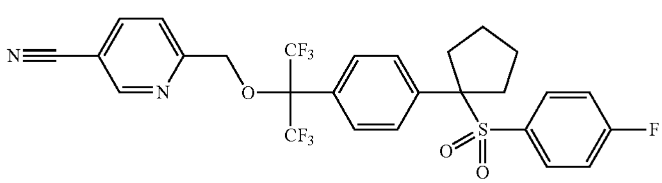 [SMILES: N#Cc1ccc(COC(c2ccc(C3(S(=O)(=O)c4ccc(F)cc4)CCCC3)cc2)(C(F)(F)F)C(F)(F)F)nc1] | 587.1 | 2.96 | B |
| 118 | 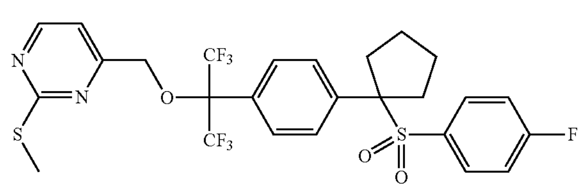 [SMILES: CSc1nccc(COC(c2ccc(C3(S(=O)(=O)c4ccc(F)cc4)CCCC3)cc2)(C(F)(F)F)C(F)(F)F)n1] | 609.0 | 2.53 | C |
| 119 | 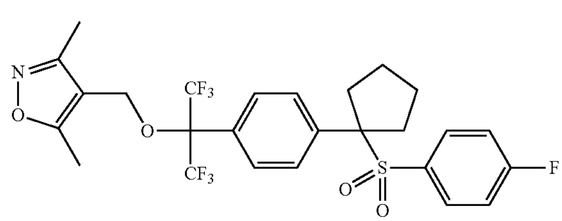 [SMILES: Cc1noc(C)c1COC(c1ccc(C2(S(=O)(=O)c3ccc(F)cc3)CCCC2)cc1)(C(F)(F)F)C(F)(F)F] | 580.1 | 2.420 | B |

TABLE 1-continued

| Example number | Structure | MS observed (M + 1) | HPLC ret. time (min.) | HPLC method |
|---|---|---|---|---|
| 120 | 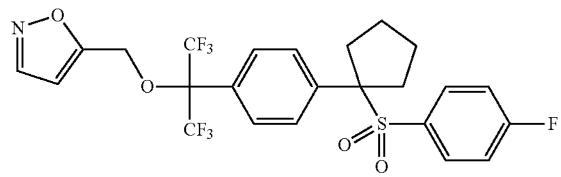 [SMILES: O=S(=O)(c1ccc(F)cc1)C1(c2ccc(C(OCc3ccno3)(C(F)(F)F)C(F)(F)F)cc2)CCCC1] | 551.7 | 2.24 | C |
| 121 | 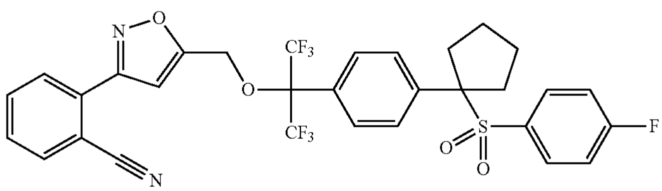 [SMILES: N#Cc1ccccc1-c1cc(COC(c2ccc(C3(S(=O)(=O)c4ccc(F)cc4)CCCC3)cc2)(C(F)(F)F)C(F)(F)F)on1] | 670.0 (M + 18) | 2.30 | C |
| 122 | 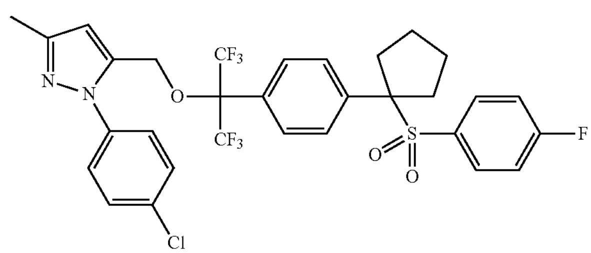 [SMILES: Cc1cc(COC(c2ccc(C3(S(=O)(=O)c4ccc(F)cc4)CCCC3)cc2)(C(F)(F)F)C(F)(F)F)n(-c2ccc(Cl)cc2)n1] | 675.1 | 2.65 | C |
| 123 | 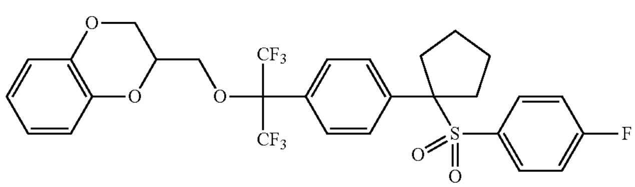 [SMILES: O=S(=O)(c1ccc(F)cc1)C1(c2ccc(C(OCC3COc4ccccc4O3)(C(F)(F)F)C(F)(F)F)cc2)CCCC1] | 636.1 (M + 18) | 2.28 | C |
| 124 | 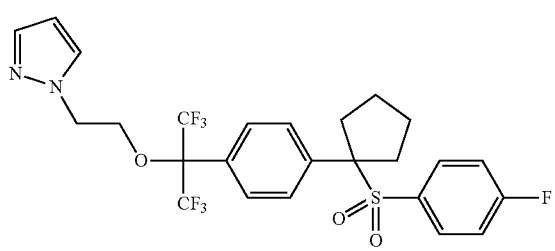 [SMILES: O=S(=O)(c1ccc(F)cc1)C1(c2ccc(C(OCCn3cccn3)(C(F)(F)F)C(F)(F)F)cc2)CCCC1] | 564.8 | 2.29 | C |
| 125 | 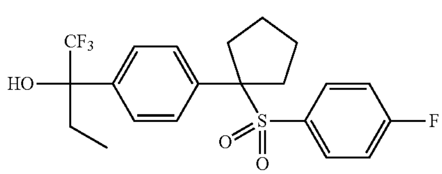 [SMILES: CCC(O)(c1ccc(C2(S(=O)(=O)c3ccc(F)cc3)CCCC2)cc1)C(F)(F)F] | 453.3 (M + 18) | 4.146 | A |
| 126 | 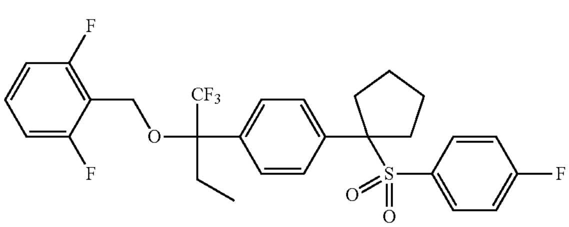 [SMILES: CCC(OCc1c(F)cccc1F)(c1ccc(C2(S(=O)(=O)c3ccc(F)cc3)CCCC2)cc1)C(F)(F)F] | 574.1 (M + 18) | 2.358 | B |

TABLE 1-continued

| Example number | Structure | MS observed (M + 1) | HPLC ret. time (min.) | HPLC method |
|---|---|---|---|---|
| 127 | 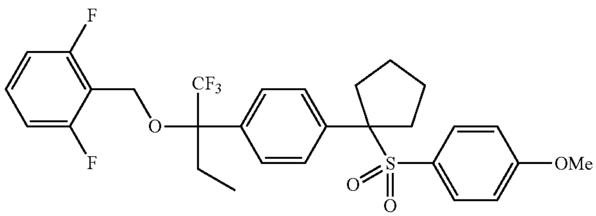 [SMILES: CCC(OCc1c(F)cccc1F)(c1ccc(C2(S(=O)(=O)c3ccc(OC)cc3)CCCC2)cc1)C(F)(F)F] | 586.1 (M + 18) | 2.51 | B |
| 128 | 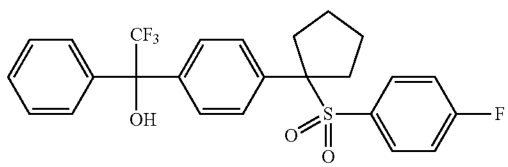 [SMILES: O=S(=O)(c1ccc(F)cc1)C1(c2ccc(C(O)(c3ccccc3)C(F)(F)F)cc2)CCCC1] | 496.1 (M + 18) | 2.14 | B |
| 129 | 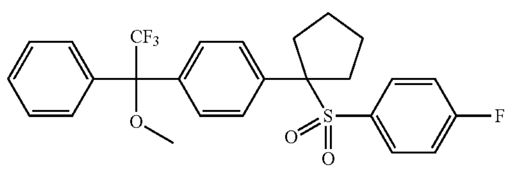 [SMILES: COC(c1ccccc1)(c1ccc(C2(S(=O)(=O)c3ccc(F)cc3)CCCC2)cc1)C(F)(F)F] | 510.1 (M + 18) | 2.61 | B |
| 130 | 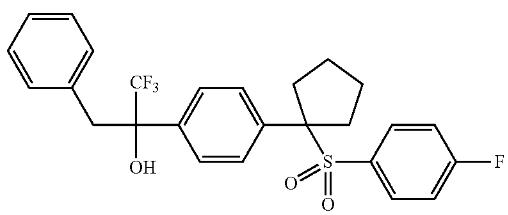 [SMILES: O=S(=O)(c1ccc(F)cc1)C1(c2ccc(C(O)(Cc3ccccc3)C(F)(F)F)cc2)CCCC1] | — | 3.975 | A |
| 131 | 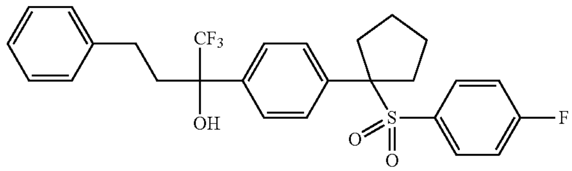 [SMILES: O=S(=O)(c1ccc(F)cc1)C1(c2ccc(C(O)(CCc3ccccc3)C(F)(F)F)cc2)CCCC1] | — | 3.963 | A |
| 132 | 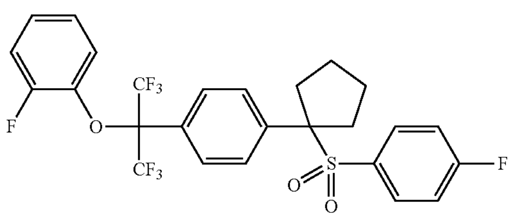 [SMILES: O=S(=O)(c1ccc(F)cc1)C1(c2ccc(C(Oc3ccccc3F)(C(F)(F)F)C(F)(F)F)cc2)CCCC1] | 586.9 (M + 23) | 2.63 | B |
| 133 | 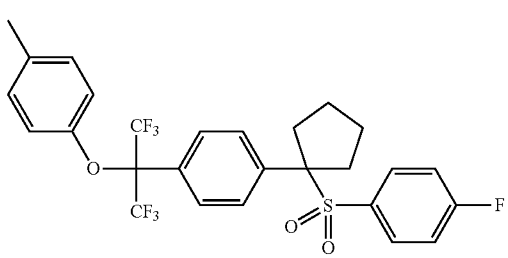 [SMILES: Cc1ccc(OC(c2ccc(C3(S(=O)(=O)c4ccc(F)cc4)CCCC3)cc2)(C(F)(F)F)C(F)(F)F)cc1] | 582.9 (M + 23) | 2.79 | B |

TABLE 1-continued

| Example number | Structure | MS observed (M + 1) | HPLC ret. time (min.) | HPLC method |
|---|---|---|---|---|
| 134 | 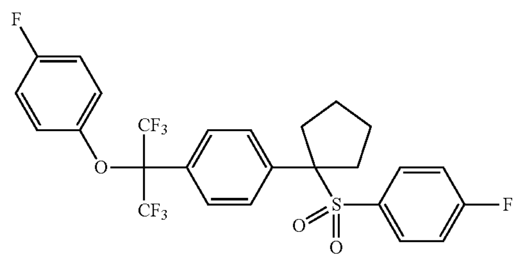 [SMILES: O=S(=O)(c1ccc(F)cc1)C1(c2ccc(C(Oc3ccc(F)cc3)(C(F)(F)F)C(F)(F)F)cc2)CCCC1] | 586.9 (M + 23) | 4.80 | A |
| 135 | 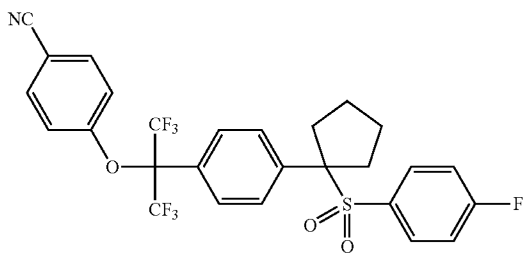 [SMILES: N#Cc1ccc(OC(c2ccc(C3(S(=O)(=O)c4ccc(F)cc4)CCCC3)cc2)(C(F)(F)F)C(F)(F)F)cc1] | 594.1 (M + 23) | 2.39 | B |
| 136 | 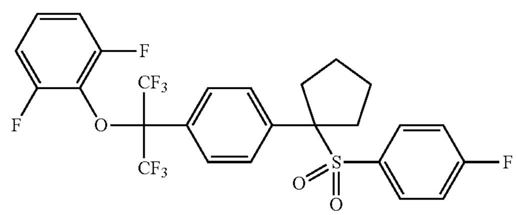 [SMILES: O=S(=O)(c1ccc(F)cc1)C1(c2ccc(C(Oc3c(F)cccc3F)(C(F)(F)F)C(F)(F)F)cc2)CCCC1] | 600.1 (M + 18) | 2.55 | B |
| 137 | 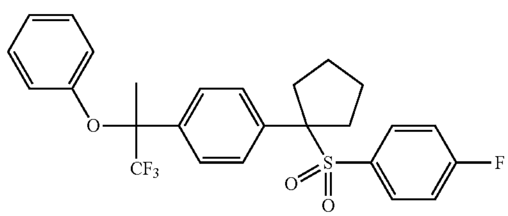 | 510.2 (M + 18) | 2.45 | B |
| 138 | 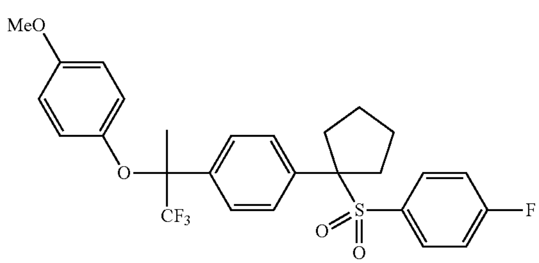 [SMILES: COc1ccc(OC(C)(c2ccc(C3(S(=O)(=O)c4ccc(F)cc4)CCCC3)cc2)C(F)(F)F)cc1] | 540.2 (M + 18) | 2.57 | B |
| 139 | 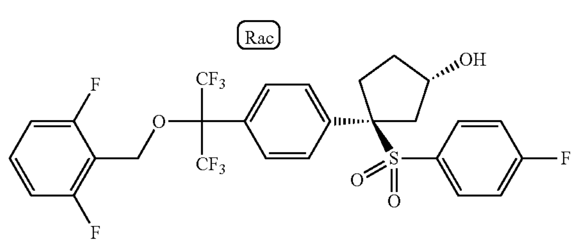 [SMILES: O=S(=O)(c1ccc(F)cc1)[C@@]1(c2ccc(C(OCc3c(F)cccc3F)(C(F)(F)F)C(F)(F)F)cc2)CC[C@H](O)C1] | 630.1 (M + 18) | 2.266 | B |

TABLE 1-continued
| Example number | Structure | MS observed (M + 1) | HPLC ret. time (min.) | HPLC method |
|---|---|---|---|---|
| 140 | 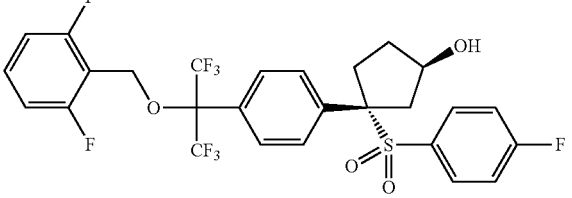 | 630.3 (M + 18) | 4.470 | A |
| 141 | 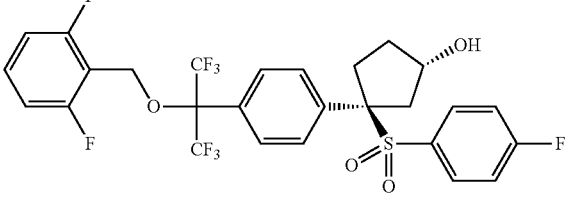 | 630.3 (M + 18) | 4.451 | A |
| 142 | 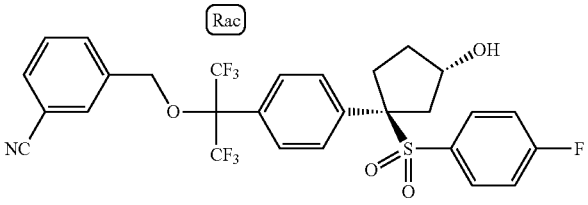 [SMILES: N#Cc1cccc(COC(c2ccc([C@]3(S(=O)(=O)c4ccc(F)cc4)CC[C@H](O)C3)cc2)(C(F)(F)F)C(F)(F)F)c1] | 619.1 (M + 18) | 1.995 | B |
| 143 | 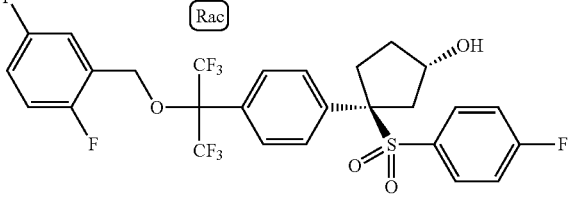 | 630.0 (M + 18) | 2.079 | B |
| 144 | 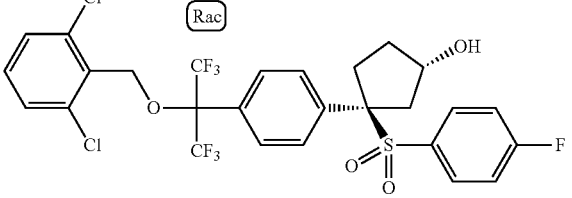 | 663.9 (M + 18) | 2.172 | B |
| 145 | 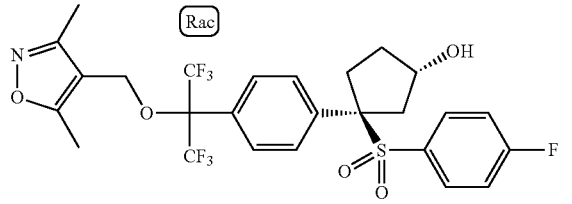 [SMILES: Cc1noc(C)c1COC(c1ccc([C@]2(S(=O)(=O)c3ccc(F)cc3)CC[C@H](O)C2)cc1)(C(F)(F)F)C(F)(F)F] | 596.1 | 1.891 | B |
| 146 | 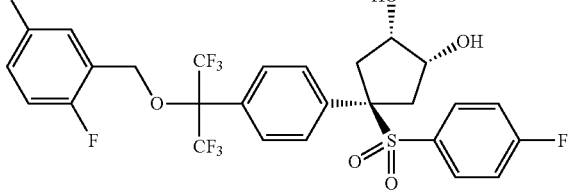 | 646.0 (M + 18) | 2.001 | B |

TABLE 1-continued

| Example number | Structure | MS observed (M + 1) | HPLC ret. time (min.) | HPLC method |
|---|---|---|---|---|
| 147 | 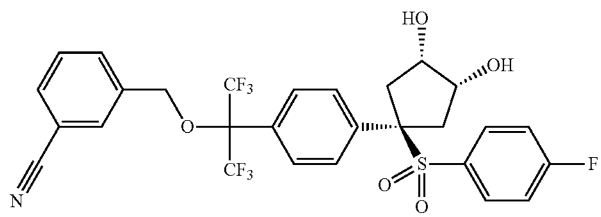 [SMILES: N#Cc1cccc(COC(c2ccc([C@@]3(S(=O)(=O)c4ccc(F)cc4)C[C@@H](O)[C@@H](O)C3)cc2)(C(F)(F)F)C(F)(F)F)c1] | 635.1 (M + 18) | 1.893 | B |
| 148 | 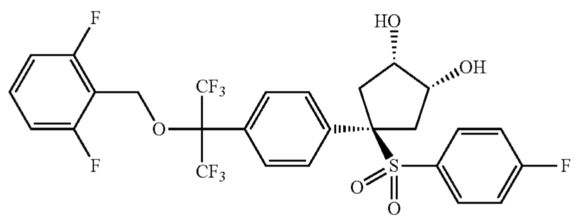 [SMILES: O=S(=O)(c1ccc(F)cc1)[C@]1(c2ccc(C(OCc3c(F)cccc3F)(C(F)(F)F)C(F)(F)F)cc2)C[C@@H](O)[C@@H](O)C1] | 646.2 (M + 18) | 2.138 | B |
| 149 | 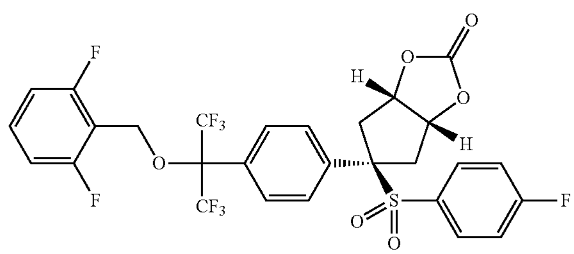 [SMILES: O=C1O[C@H]2C[C@](c3ccc(C(OCc4c(F)cccc4F)(C(F)(F)F)C(F)(F)F)cc3)(S(=O)(=O)c3ccc(F)cc3)C[C@H]2O1] | 671.8 | 2.25 | B |
| 150 | 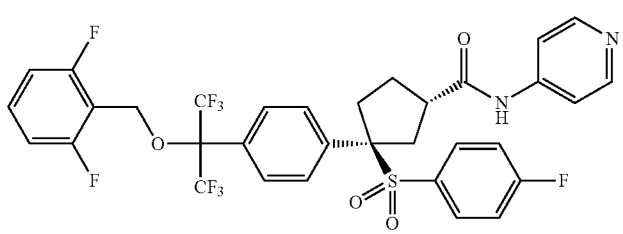 [SMILES: O=C(Nc1ccncc1)[C@H]1CC[C@](c2ccc(C(OCc3c(F)cccc3F)(C(F)(F)F)C(F)(F)F)cc2)(S(=O)(=O)c2ccc(F)cc2)C1] | 717.4 | 2.35 | B |
| 151 | 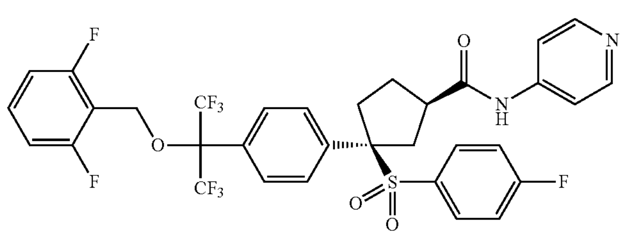 [SMILES: O=C(Nc1ccncc1)[C@@H]1CC[C@](c2ccc(C(OCc3c(F)cccc3F)(C(F)(F)F)C(F)(F)F)cc2)(S(=O)(=O)c2ccc(F)cc2)C1] | 717.3 | 2.33 | B |
| 152 | 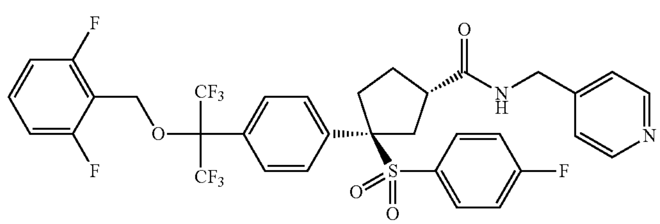 [SMILES: O=C(NCc1ccncc1)[C@H]1CC[C@](c2ccc(C(OCc3c(F)cccc3F)(C(F)(F)F)C(F)(F)F)cc2)(S(=O)(=O)c2ccc(F)cc2)C1] | 731.3 | 2.26 | B |

TABLE 1-continued

| Example number | Structure | MS observed (M + 1) | HPLC ret. time (min.) | HPLC method |
|---|---|---|---|---|
| 153 | 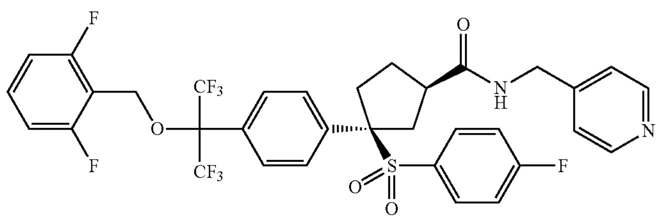 [SMILES: O=C(NCc1ccncc1)[C@@H]1CC[C@](c2ccc(C(OCc3c(F)cccc3F)(C(F)(F)F)C(F)(F)F)cc2)(S(=O)(=O)c2ccc(F)cc2)C1] | 731.3 | 2.25 | B |
| 154 | 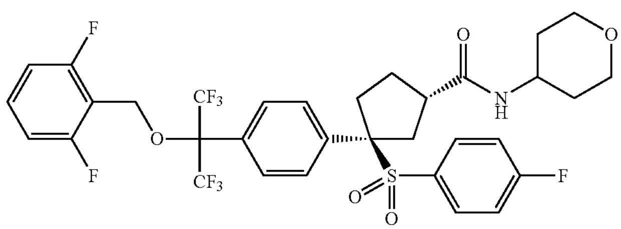 [SMILES: O=C(NC1CCOCC1)[C@H]1CC[C@](c2ccc(C(OCc3c(F)cccc3F)(C(F)(F)F)C(F)(F)F)cc2)(S(=O)(=O)c2ccc(F)cc2)C1] | 724.4 | 2.32 | B |
| 155 | 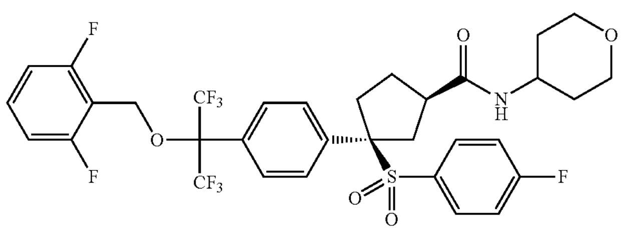 [SMILES: O=C(NC1CCOCC1)[C@@H]1CC[C@](c2ccc(C(OCc3c(F)cccc3F)(C(F)(F)F)C(F)(F)F)cc2)(S(=O)(=O)c2ccc(F)cc2)C1] | 724.4 | 2.31 | B |
| 156 | (diastereomer 1) | 752.1 | 1.906 | B |
| 157 | (diastereomer 2) | 752.0 | 1.950 | B |
| 158 | 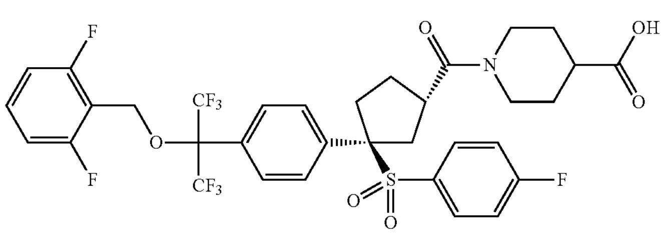 [SMILES: O=C(O)C1CCN(C(=O)[C@H]2CC[C@](c3ccc(C(OCc4c(F)cccc4F)(C(F)(F)F)C(F)(F)F)cc3)(S(=O)(=O)c3ccc(F)cc3)C2)CC1] | 752.4 | 1.98 | B |

TABLE 1-continued

| Example number | Structure | MS observed (M + 1) | HPLC ret. time (min.) | HPLC method |
|---|---|---|---|---|
| 159 | 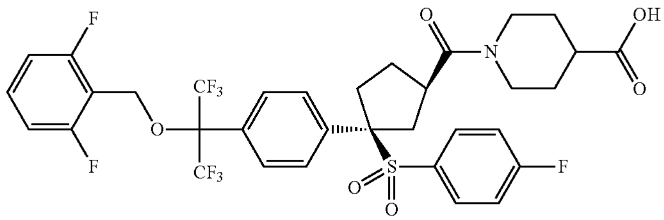 [SMILES: O=C(O)C1CCN(C(=O)[C@@H]2CC[C@](c3ccc(C(OCc4c(F)cccc4F)(C(F)(F)F)C(F)(F)F)cc3)(S(=O)(=O)c3ccc(F)cc3)C2)CC1] | 752.4 | 1.95 | B |
| 160 | diastereomer 1 | 738.2 | 2.36 | B |
| 161 | diastereomer 2 | 738.2 | 2.38 | B |
| 162 | 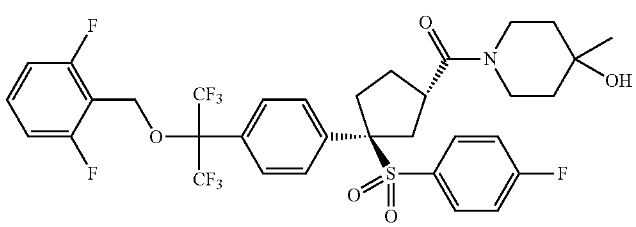 [SMILES: CC1(O)CCN(C(=O)[C@H]2CC[C@](c3ccc(C(OCc4c(F)cccc4F)(C(F)(F)F)C(F)(F)F)cc3)(S(=O)(=O)c3ccc(F)cc3)C2)CC1] | 738.4 | 2.31 | B |
| 163 | 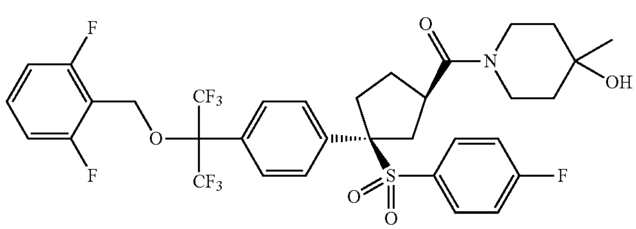 [SMILES: CC1(O)CCN(C(=O)[C@@H]2CC[C@](c3ccc(C(OCc4c(F)cccc4F)(C(F)(F)F)C(F)(F)F)cc3)(S(=O)(=O)c3ccc(F)cc3)C2)CC1] | 738.4 | 2.28 | B |
| 164 | diastereomer 1 | 754.2 | 2.102 | B |

TABLE 1-continued
| Example number | Structure | MS observed (M + 1) | HPLC ret. time (min.) | HPLC method |
|---|---|---|---|---|
| 165 | 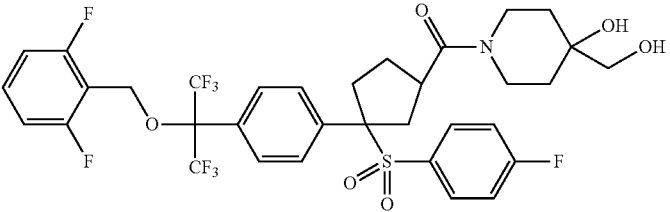 [SMILES: O=C(C1CCC(c2ccc(C(OCc3c(F)cccc3F)(C(F)(F)F)C(F)(F)F)cc2)(S(=O)(=O)c2ccc(F)cc2)C1)N1CCC(O)(CO)CC1] diastereomer 2 | 754.1 | 2.136 | B |
| 166 | 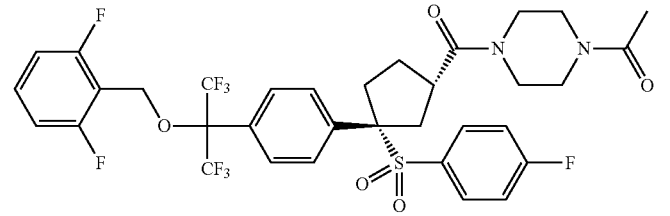 [SMILES: CC(=O)N1CCN(C(=O)[C@H]2CC[C@@](c3ccc(C(OCc4c(F)cccc4F)(C(F)(F)F)C(F)(F)F)cc3)(S(=O)(=O)c3ccc(F)cc3)C2)CC1] | 751.3 | 2.17 | B |
| 167 | 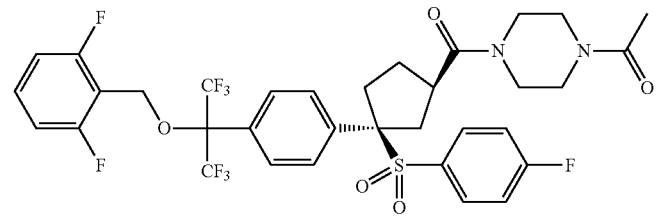 [SMILES: CC(=O)N1CCN(C(=O)[C@@H]2CC[C@](c3ccc(C(OCc4c(F)cccc4F)(C(F)(F)F)C(F)(F)F)cc3)(S(=O)(=O)c3ccc(F)cc3)C2)CC1] | 751.4 | 2.16 | B |
| 168 | 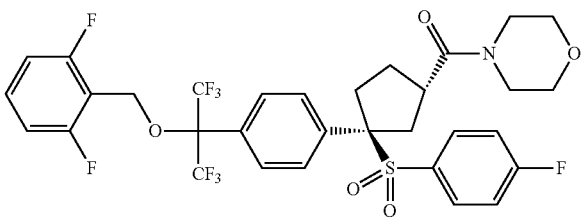 [SMILES: O=C([C@H]1CC[C@](c2ccc(C(OCc3c(F)cccc3F)(C(F)(F)F)C(F)(F)F)cc2)(S(=O)(=O)c2ccc(F)cc2)C1)N1CCOCC1] | 710.3 | 2.35 | B |
| 169 | 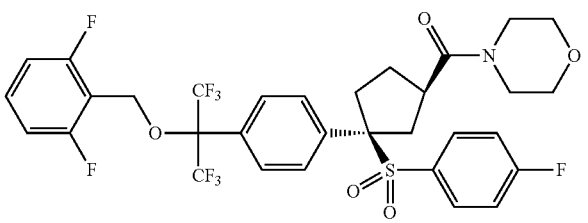 [SMILES: O=C([C@@H]1CC[C@](c2ccc(C(OCc3c(F)cccc3F)(C(F)(F)F)C(F)(F)F)cc2)(S(=O)(=O)c2ccc(F)cc2)C1)N1CCOCC1] | 710.4 | 2.35 | B |
| 170 | 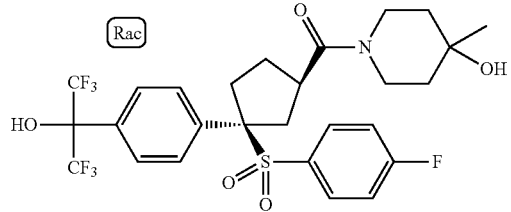 [SMILES: CC1(O)CCN(C(=O)[C@@H]2CC[C@](c3ccc(C(O)(C(F)(F)F)C(F)(F)F)cc3)(S(=O)(=O)c3ccc(F)cc3)C2)CC1] | 612.2 | 1.67 | B |

TABLE 1-continued

| Example number | Structure | MS observed (M + 1) | HPLC ret. time (min.) | HPLC method |
|---|---|---|---|---|
| 171 | 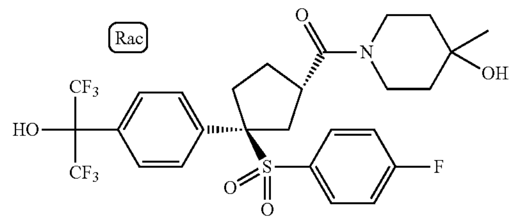 [SMILES: CC1(O)CCN(C(=O)[C@H]2CC[C@](c3ccc(C(O)(C(F)(F)F)C(F)(F)F)cc3)(S(=O)(=O)c3ccc(F)cc3)C2)CC1] | 612.2 | 1.72 | B |
| 172 | 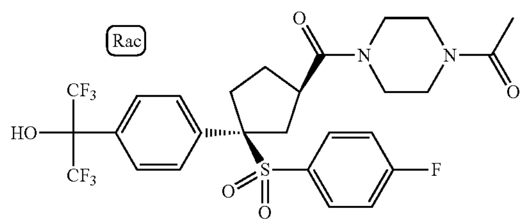 [SMILES: CC(=O)N1CCN(C(=O)[C@@H]2CC[C@](c3ccc(C(O)(C(F)(F)F)C(F)(F)F)cc3)(S(=O)(=O)c3ccc(F)cc3)C2)CC1] | 625.2 | 1.65 | B |
| 173 | 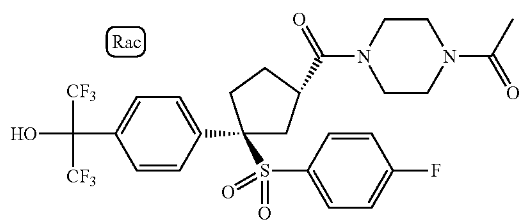 [SMILES: CC(=O)N1CCN(C(=O)[C@H]2CC[C@](c3ccc(C(O)(C(F)(F)F)C(F)(F)F)cc3)(S(=O)(=O)c3ccc(F)cc3)C2)CC1] | 625.2 | 1.69 | B |
| 174 | 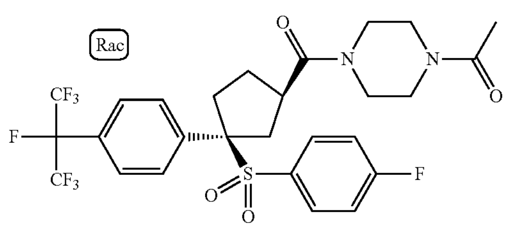 [SMILES: CC(=O)N1CCN(C(=O)[C@@H]2CC[C@](c3ccc(C(F)(C(F)(F)F)C(F)(F)F)cc3)(S(=O)(=O)c3ccc(F)cc3)C2)CC1] | 627.3 | 1.94 | B |
| 175 | 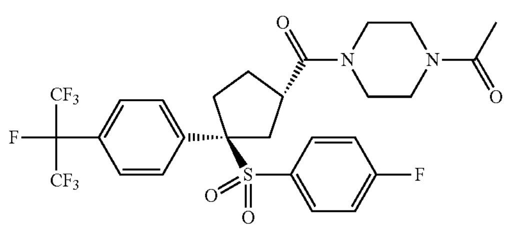 [SMILES: CC(=O)N1CCN(C(=O)[C@H]2CC[C@](c3ccc(C(F)(C(F)(F)F)C(F)(F)F)cc3)(S(=O)(=O)c3ccc(F)cc3)C2)CC1] | 627.2 | 1.99 | B |
| 176 | 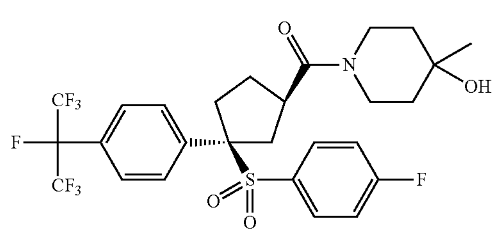 [SMILES: CC1(O)CCN(C(=O)[C@@H]2CC[C@](c3ccc(C(F)(C(F)(F)F)C(F)(F)F)cc3)(S(=O)(=O)c3ccc(F)cc3)C2)CC1] | 614.2 | 2.03 | B |

TABLE 1-continued

| Example number | Structure | MS observed (M + 1) | HPLC ret. time (min.) | HPLC method |
|---|---|---|---|---|
| 177 | 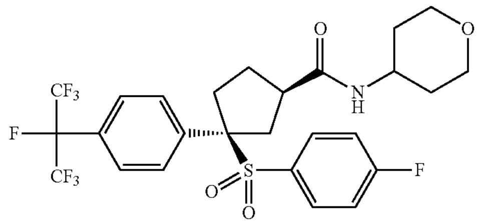 [SMILES: O=C(NC1CCOCC1)[C@@H]1CC[C@](c2ccc(C(F)(C(F)(F)F)C(F)(F)F)cc2)(S(=O)(=O)c2ccc(F)cc2)C1] | 600.3 | 2.03 | B |
| 178 | 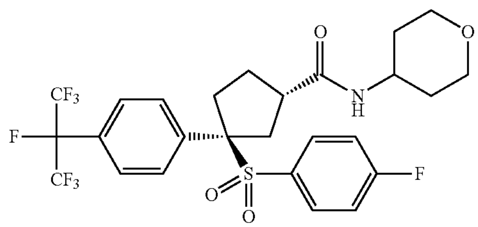 [SMILES: O=C(NC1CCOCC1)[C@H]1CC[C@](c2ccc(C(F)(C(F)(F)F)C(F)(F)F)cc2)(S(=O)(=O)c2ccc(F)cc2)C1] | 600.2 | 2.06 | B |
| 179 | 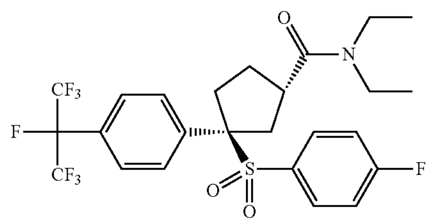 [SMILES: CCN(CC)C(=O)[C@H]1CC[C@](c2ccc(C(F)(C(F)(F)F)C(F)(F)F)cc2)(S(=O)(=O)c2ccc(F)cc2)C1] | 572.2 | 2.31 | B |
| 180 | diastereomer 1 | 654.2 | 19.44 | D |
| 181 | diastereomer 2 | 654.2 | 20.32 | D |
| 182 | diastereomer 1 | 668 | 19.53 | D |

TABLE 1-continued

| Example number | Structure | MS observed (M + 1) | HPLC ret. time (min.) | HPLC method |
|---|---|---|---|---|
| 183 | diastereomer 2 | 668 | 17.09 | D |
| 184 | diastereomer 1 | 718.2 | 20.56 | D |
| 185 | diastereomer 2 | 718.2 | 20.93 | D |
| 186 | diastereomer 1 | 736 | 16.06 | D |
| 187 | diastereomer 2 | 736 | 17.98 | D |

TABLE 1-continued

| Example number | Structure | MS observed (M + 1) | HPLC ret. time (min.) | HPLC method |
|---|---|---|---|---|
| 188 | diastereomer 1 | 682.3 | 2.29 | B |
| 189 | diastereomer 2 | 682.2 | 2.29 | B |
| 190 | diastereomer 1 | 671.2 (M + 18) | 2.11 | B |
| 191 | diastereomer 2 | 654.2 | 2.13 | B |
| 192 | diastereomer 1 | 766.3 | 1.93 | B |

TABLE 1-continued

| Example number | Structure | MS observed (M + 1) | HPLC ret. time (min.) | HPLC method |
|---|---|---|---|---|
| 193 | diastereomer 2 | 766.2 | 1.98 | B |
| 194 | enantiomer 1 of diastereomer 2 | 766.2 | 1.95 | B |
| 195 | enantiomer 2 of diastereomer 2 | 766.3 | 1.95 | B |
| 196 | diastereomer 1 | 724.2 | 2.14 | B |

TABLE 1-continued

| Example number | Structure | MS observed (M + 1) | HPLC ret. time (min.) | HPLC method |
|---|---|---|---|---|
| 197 | diastereomer 2 | 724.2 | 2.19 | B |
| 198 | diastereomer 1 | 765.2 | 2.04 | B |
| 199 | diastereomer 2 | 765.3 | 2.10 | B |
| 200 | diastereomer 1 | 717.2 | 2.14 | B |
| 201 | diastereomer 2 | 717.2 | 2.22 | B |

TABLE 1-continued

| Example number | Structure | MS observed (M + 1) | HPLC ret. time (min.) | HPLC method |
|---|---|---|---|---|
| 202 | enantiomer 1 of diastereomer 2 | 717.3 | 2.22 | B |
| 203 | enantiomer 2 of diastereomer 2 | 717.3 | 2.22 | B |
| 204 | diastereomer 1 | 697.3 | 2.24 | B |
| 205 | diastereomer 2 | 680.2 | 2.22 | B |
| 206 | Rac | 612.1 | 2.14 | B |

TABLE 1-continued

| Example number | Structure | MS observed (M + 1) | HPLC ret. time (min.) | HPLC method |
|---|---|---|---|---|
| 207 | 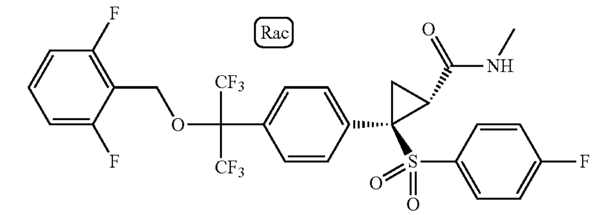 [SMILES: CNC(=O)[C@H]1C[C@]1(c1ccc(C(OCc2c(F)cccc2F)(C(F)(F)F)C(F)(F)F)cc1)S(=O)(=O)c1ccc(F)cc1] | 626.1 | 2.22 | B |
| 208 | 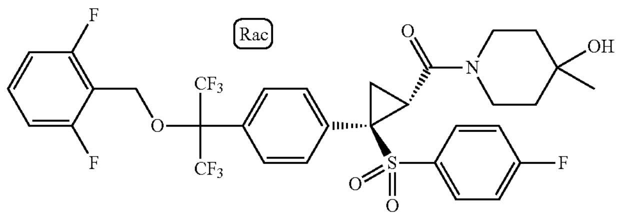 [SMILES: CC1(O)CCN(C(=O)[C@H]2C[C@]2(c2ccc(C(OCc3c(F)cccc3F)(C(F)(F)F)C(F)(F)F)cc2)S(=O)(=O)c2ccc(F)cc2)CC1] | 710.2 | 2.28 | B |
| 209 | 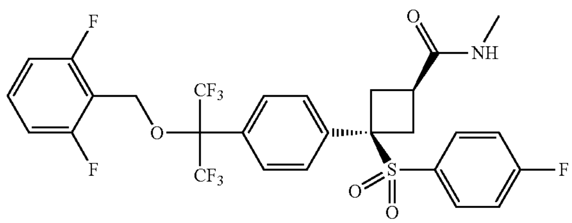 [SMILES: CNC(=O)[C@H]1C[C@@](c2ccc(C(OCc3c(F)cccc3F)(C(F)(F)F)C(F)(F)F)cc2)(S(=O)(=O)c2ccc(F)cc2)C1] | 640.2 | 2.11 | B |
| 210 | 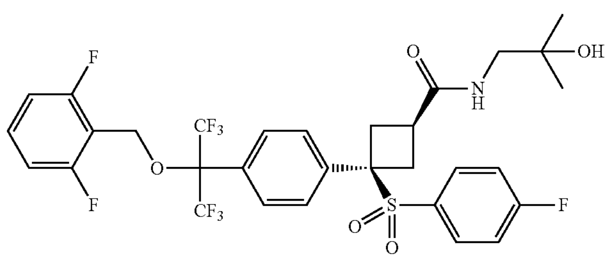 [SMILES: CC(C)(O)CNC(=O)[C@H]1C[C@@](c2ccc(C(OCc3c(F)cccc3F)(C(F)(F)F)C(F)(F)F)cc2)(S(=O)(=O)c2ccc(F)cc2)C1] | 698.2 | 2.12 | C |
| 211 | 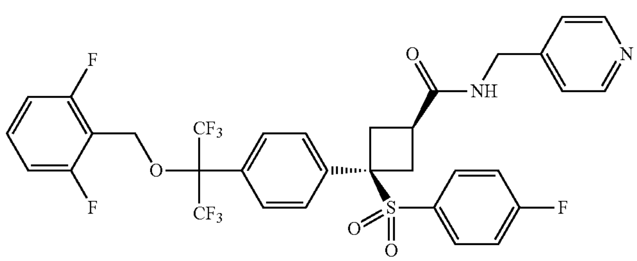 [SMILES: O=C(NCc1ccncc1)[C@H]1C[C@@](c2ccc(C(OCc3c(F)cccc3F)(C(F)(F)F)C(F)(F)F)cc2)(S(=O)(=O)c2ccc(F)cc2)C1] | 717.2 | 2.12 | B |
| 212 | 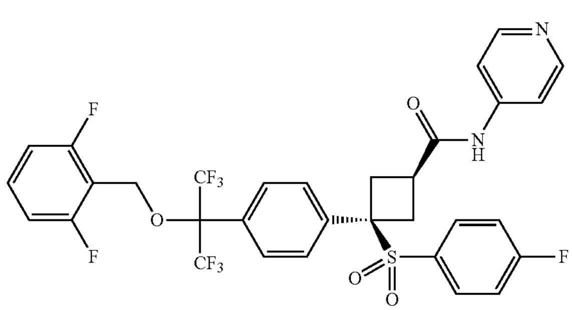 [SMILES: O=C(Nc1ccncc1)[C@H]1C[C@@](c2ccc(C(OCc3c(F)cccc3F)(C(F)(F)F)C(F)(F)F)cc2)(S(=O)(=O)c2ccc(F)cc2)C1] | 703.2 | 2.19 | B |

TABLE 1-continued

| Example number | Structure | MS observed (M + 1) | HPLC ret. time (min.) | HPLC method |
|---|---|---|---|---|
| 213 | 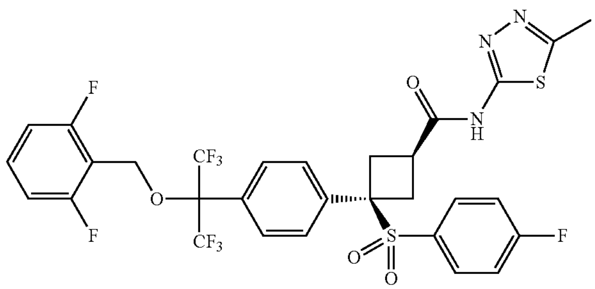 [SMILES: Cc1nnc(NC(=O)[C@H]2C[C@@](c3ccc(C(OCc4c(F)cccc4F)(C(F)(F)F)C(F)(F)F)cc3)(S(=O)(=O)c3ccc(F)cc3)C2)s1] | 724.4 | 2.21 | C |
| 214 | 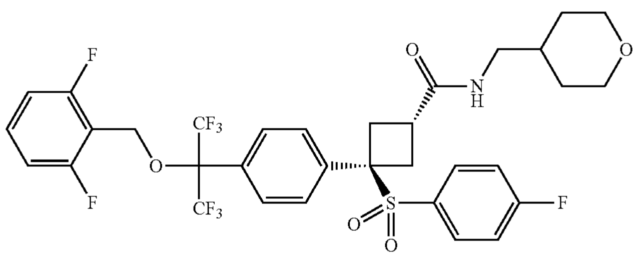 [SMILES: O=C(NCC1CCOCC1)[C@H]1C[C@](c2ccc(C(OCc3c(F)cccc3F)(C(F)(F)F)C(F)(F)F)cc2)(S(=O)(=O)c2ccc(F)cc2)C1] | 724.3 | 2.19 | B |
| 215 | 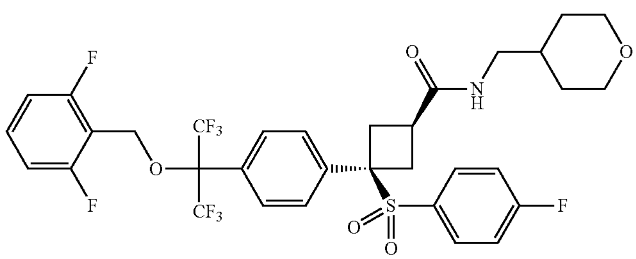 [SMILES: O=C(NCC1CCOCC1)[C@H]1C[C@@](c2ccc(C(OCc3c(F)cccc3F)(C(F)(F)F)C(F)(F)F)cc2)(S(=O)(=O)c2ccc(F)cc2)C1] | 724.2 | 2.16 | B |
| 216 | 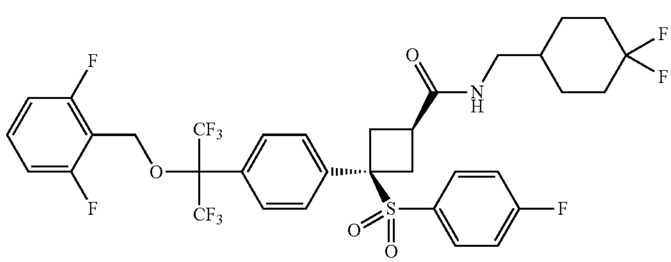 [SMILES: O=C(NCC1CCC(F)(F)CC1)[C@H]1C[C@@](c2ccc(C(OCc3c(F)cccc3F)(C(F)(F)F)C(F)(F)F)cc2)(S(=O)(=O)c2ccc(F)cc2)C1] | 758.5 | 2.44 | B |
| 217 | 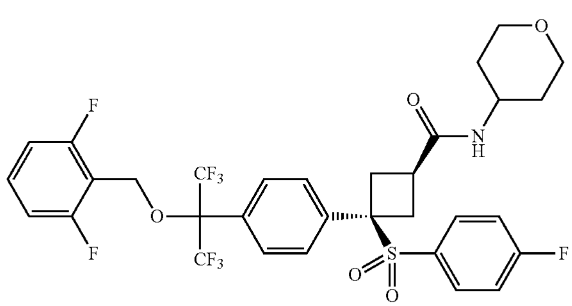 [SMILES: O=C(NC1CCOCC1)[C@H]1C[C@@](c2ccc(C(OCc3c(F)cccc3F)(C(F)(F)F)C(F)(F)F)cc2)(S(=O)(=O)c2ccc(F)cc2)C1] | 710.2 | 2.17 | B |

TABLE 1-continued

| Example number | Structure | MS observed (M + 1) | HPLC ret. time (min.) | HPLC method |
|---|---|---|---|---|
| 218 | 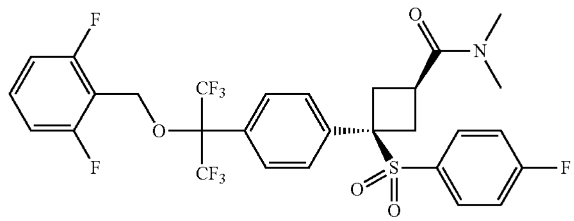 [SMILES: CN(C)C(=O)[C@H]1C[C@@](c2ccc(C(OCc3c(F)cccc3F)(C(F)(F)F)C(F)(F)F)cc2)(S(=O)(=O)c2ccc(F)cc2)C1] | 654.1 | 2.23 | B |
| 219 | 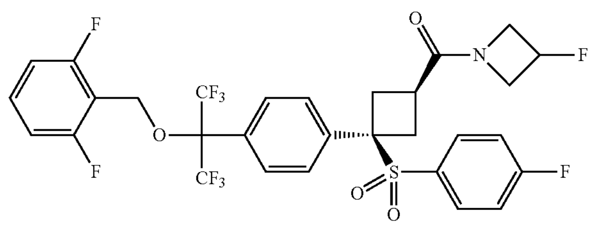 [SMILES: O=C([C@H]1C[C@@](c2ccc(C(OCc3c(F)cccc3F)(C(F)(F)F)C(F)(F)F)cc2)(S(=O)(=O)c2ccc(F)cc2)C1)N1CC(F)C1] | 684.2 | 2.29 | B |
| 220 | 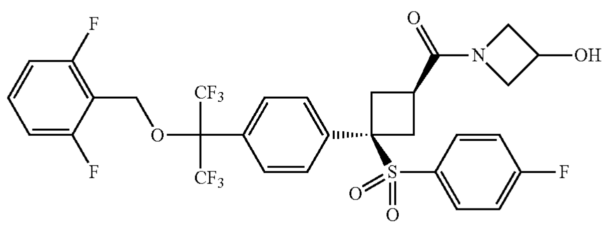 [SMILES: O=C([C@H]1C[C@@](c2ccc(C(OCc3c(F)cccc3F)(C(F)(F)F)C(F)(F)F)cc2)(S(=O)(=O)c2ccc(F)cc2)C1)N1CC(O)C1] | 682.3 | 2.10 | B |
| 221 | 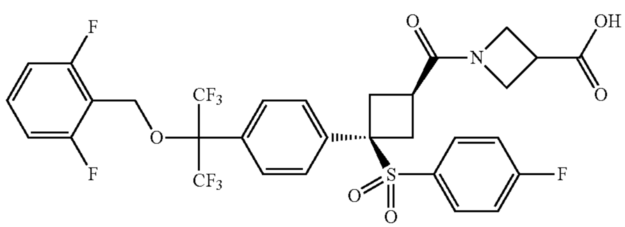 [SMILES: O=C(O)C1CN(C(=O)[C@H]2C[C@@](c3ccc(C(OCc4c(F)cccc4F)(C(F)(F)F)C(F)(F)F)cc3)(S(=O)(=O)c3ccc(F)cc3)C2)C1] | 710.4 | 1.74 | B |
| 222 | 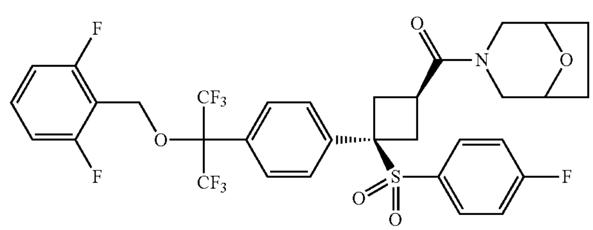 [SMILES: O=C([C@H]1C[C@@](c2ccc(C(OCc3c(F)cccc3F)(C(F)(F)F)C(F)(F)F)cc2)(S(=O)(=O)c2ccc(F)cc2)C1)N1CC2CCC(C1)O2] | 722.4 | 2.32 | B |
| 223 | 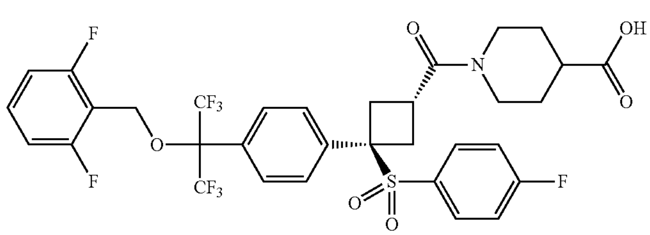 [SMILES: O=C(O)C1CCN(C(=O)[C@H]2C[C@](c3ccc(C(OCc4c(F)cccc4F)(C(F)(F)F)C(F)(F)F)cc3)(S(=O)(=O)c3ccc(F)cc3)C2)CC1] | 738.2 | 1.79 | B |

TABLE 1-continued

| Example number | Structure | MS observed (M + 1) | HPLC ret. time (min.) | HPLC method |
|---|---|---|---|---|
| 224 | 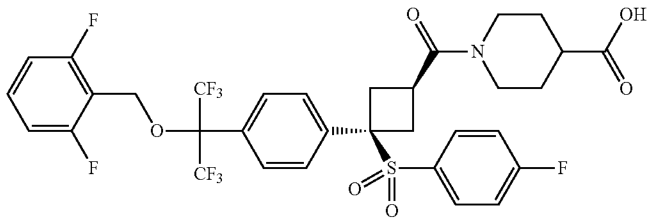 [SMILES: O=C(O)C1CCN(C(=O)[C@H]2C[C@@](c3ccc(C(OCc4c(F)cccc4F)(C(F)(F)F)C(F)(F)F)cc3)(S(=O)(=O)c3ccc(F)cc3)C2)CC1] | 738.2 | 1.83 | B |
| 225 | 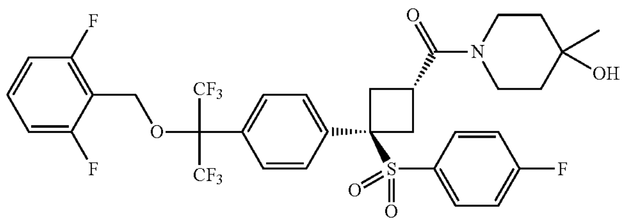 [SMILES: CC1(O)CCN(C(=O)[C@H]2C[C@](c3ccc(C(OCc4c(F)cccc4F)(C(F)(F)F)C(F)(F)F)cc3)(S(=O)(=O)c3ccc(F)cc3)C2)CC1] | 724.2 | 2.17 | B |
| 226 | 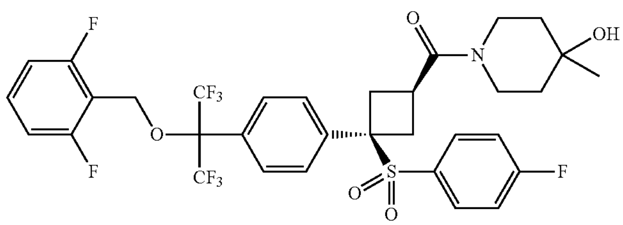 [SMILES: CC1(O)CCN(C(=O)[C@H]2C[C@@](c3ccc(C(OCc4c(F)cccc4F)(C(F)(F)F)C(F)(F)F)cc3)(S(=O)(=O)c3ccc(F)cc3)C2)CC1] | 724.4 | 2.18 | B |
| 227 | 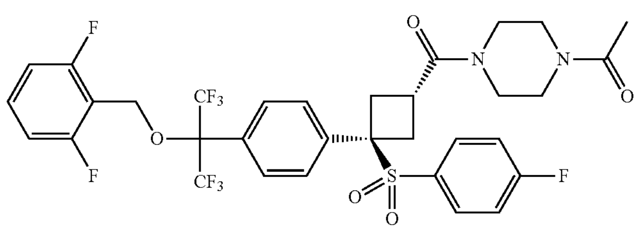 [SMILES: CC(=O)N1CCN(C(=O)[C@H]2C[C@](c3ccc(C(OCc4c(F)cccc4F)(C(F)(F)F)C(F)(F)F)cc3)(S(=O)(=O)c3ccc(F)cc3)C2)CC1] | 737.4 | 2.15 | B |
| 228 | 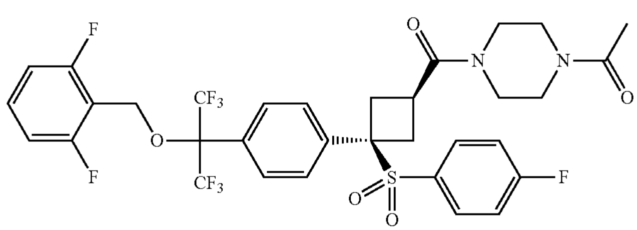 [SMILES: CC(=O)N1CCN(C(=O)[C@H]2C[C@@](c3ccc(C(OCc4c(F)cccc4F)(C(F)(F)F)C(F)(F)F)cc3)(S(=O)(=O)c3ccc(F)cc3)C2)CC1] | 737.4 | 2.12 | B |
| 229 | 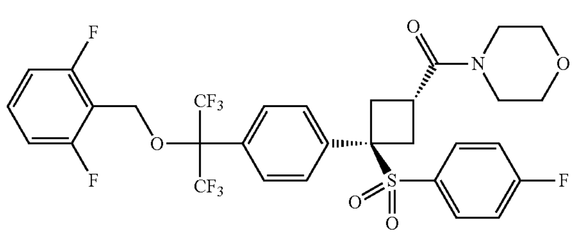 [SMILES: O=C([C@H]1C[C@](c2ccc(C(OCc3c(F)cccc3F)(C(F)(F)F)C(F)(F)F)cc2)(S(=O)(=O)c2ccc(F)cc2)C1)N1CCOCC1] | 696.4 | 2.27 | B |

| Example number | Structure | MS observed (M + 1) | HPLC ret. time (min.) | HPLC method |
|---|---|---|---|---|
| 230 | 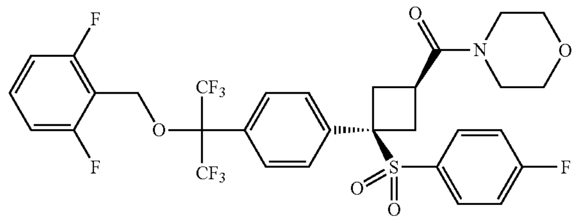 [SMILES: O=C([C@H]1C[C@@](c2ccc(C(OCc3c(F)cccc3F)(C(F)(F)F)C(F)(F)F)cc2)(S(=O)(=O)c2ccc(F)cc2)C1)N1CCOCC1] | 696.4 | 2.24 | B |
| 231 | 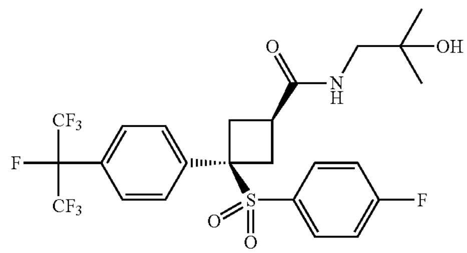 [SMILES: CC(C)(O)CNC(=O)[C@H]1C[C@@](c2ccc(C(F)(C(F)(F)F)C(F)(F)F)cc2)(S(=O)(=O)c2ccc(F)cc2)C1] | 574.2 | 1.87 | B |
| 232 | 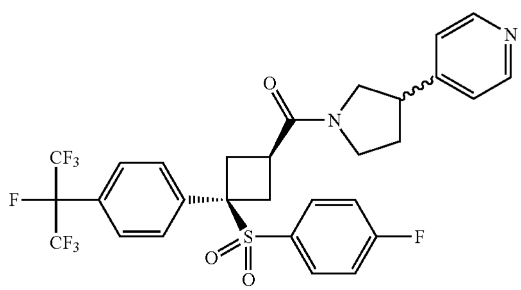 [SMILES: O=C([C@H]1C[C@@](c2ccc(C(F)(C(F)(F)F)C(F)(F)F)cc2)(S(=O)(=O)c2ccc(F)cc2)C1)N1CCC(c2ccncc2)C1] | 633.2 | 1.98 | B |
| 233 | 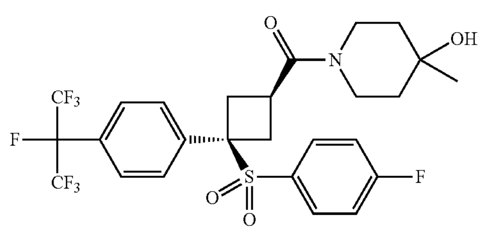 [SMILES: CC1(O)CCN(C(=O)[C@H]2C[C@@](c3ccc(C(F)(C(F)(F)F)C(F)(F)F)cc3)(S(=O)(=O)c3ccc(F)cc3)C2)CC1] | 600.3 | 2.05 | B |
| 234 | 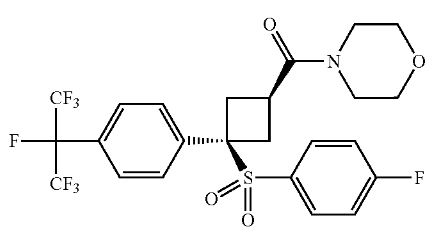 [SMILES: O=C([C@H]1C[C@@](c2ccc(C(F)(C(F)(F)F)C(F)(F)F)cc2)(S(=O)(=O)c2ccc(F)cc2)C1)N1CCOCC1] | 572.2 | 1.98 | B |
| 235 | diastereomer 1 | 640.2 | 16.06 | D |

TABLE 1-continued

| Example number | Structure | MS observed (M + 1) | HPLC ret. time (min.) | HPLC method |
|---|---|---|---|---|
| 236 | diastereomer 2 | 640.2 | 16.18 | D |
| 237 | diastereomer 1 | 654.0 | 16.80 | D |
| 238 | diastereomer 2 | 654.0 | 16.77 | D |
| 239 | diastereomer 1 | 704.0 | 16.52 | D |
| 240 | diastereomer 2 | 704.0 | 16.33 | D |

TABLE 1-continued

| Example number | Structure | MS observed (M + 1) | HPLC ret. time (min.) | HPLC method |
|---|---|---|---|---|
| 241 | diastereomer 1 | 688.0 | 17.07 | D |
| 242 | diastereomer 1 | 722 | 17.70 | D |
| 243 | diastereomer 1 | 668.2 | 2.29 | B |
| 244 | diastereomer 2 | 668.2 | 2.32 | B |
| 245 | diastereomer 1 | 640.2 | 2.13 | B |

TABLE 1-continued
| Example number | Structure | MS observed (M + 1) | HPLC ret. time (min.) | HPLC method |
|---|---|---|---|---|
| 246 | 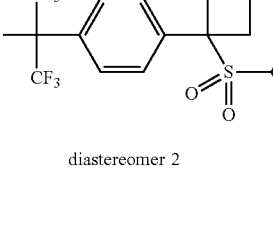  diastereomer 2 | 657.2 (M + 18) | 2.10 | B |
| 247 | 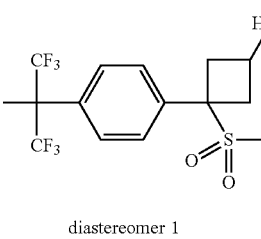  diastereomer 1 | 682.3 | 2.13 | B |
| 248 | 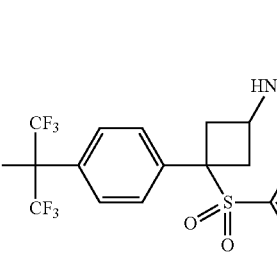  diastereomer 1 | 710.3 (M + 18) | 2.31 | B |
| 249 | 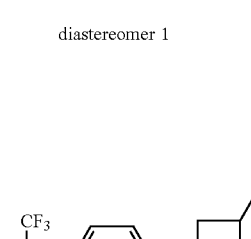  diastereomer 1 | 703.2 | 2.18 | B |
| 250 | 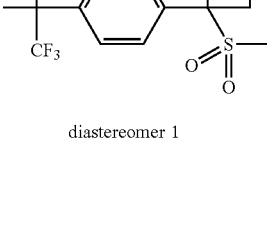  diastereomer 2 | 703.2 | 2.15 | B |

TABLE 1-continued
| Example number | Structure | MS observed (M + 1) | HPLC ret. time (min.) | HPLC method |
|---|---|---|---|---|
| 251 | 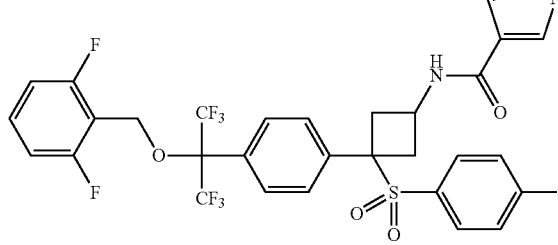<br>diastereomer 1 | 692.2 | 2.09 | C |
| 252 | 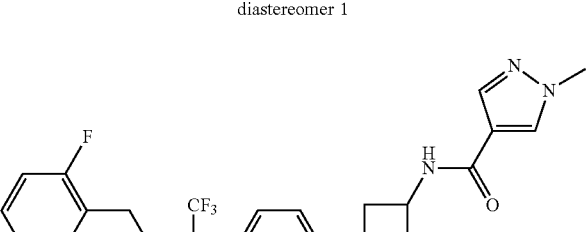<br>diastereomer 1 | 706.4 | 2.21 | B |
| 253 | 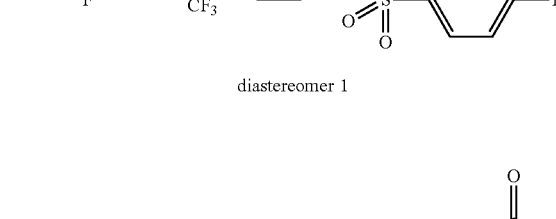<br>diastereomer 1 | 723.4 | 2.13 | B |
| 254 | 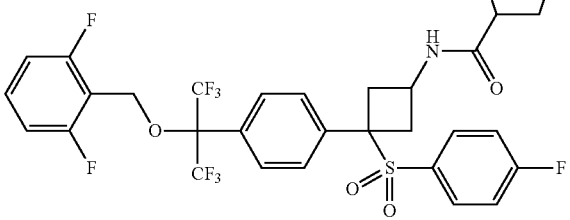<br>diastereomer 1, alcohol isomer 1 | 724.3 | 2.16 | B |

TABLE 1-continued
| Example number | Structure | MS observed (M + 1) | HPLC ret. time (min.) | HPLC method |
|---|---|---|---|---|
| 255 | 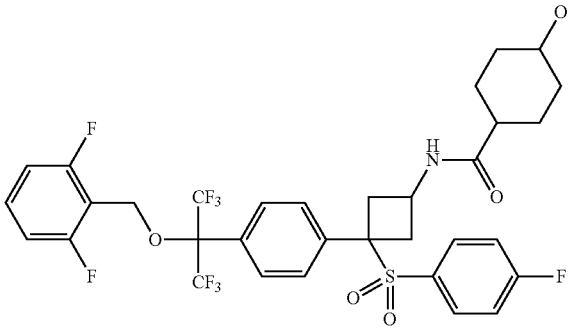 diastereomer 1, alcohol isomer 2 | 724.3 | 2.14 | B |
| 256 | 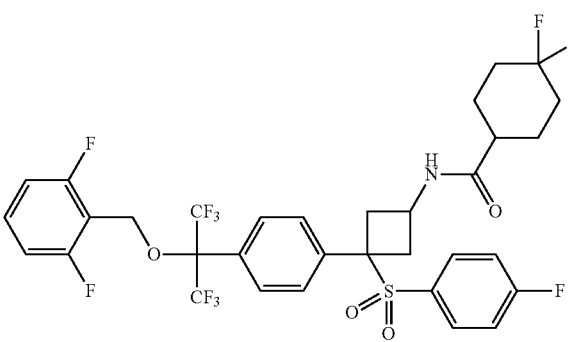 diastereomer 1 | 744.4 | 2.46 | B |
| 257 | 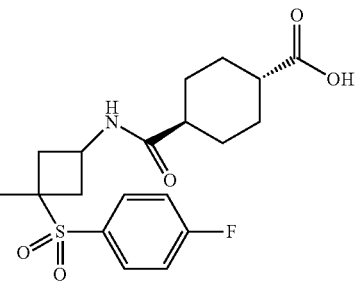 diastereomer 1 | 752.2 | 1.95 | B |
| 258 | 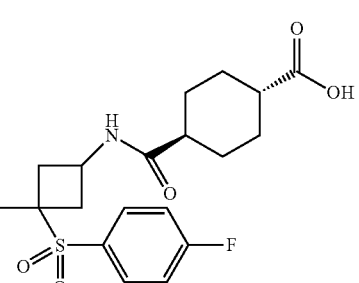 diastereomer 2 | 752.2 | 1.93 | B |

TABLE 1-continued

| Example number | Structure | MS observed (M + 1) | HPLC ret. time (min.) | HPLC method |
|---|---|---|---|---|
| 259 | diastereomer 1 | 751.3 | 2.10 | B |
| 260 | diastereomer 1 | 710.2 | 2.15 | B |
| 261 | diastereomer 2 | 710.2 | 2.14 | B |
| 262 | diastereomer 1 | 673.2 (M + 18) | 2.27 | B |
| 263 | diastereomer 1 | 669.2 | 2.16 | B |

TABLE 1-continued

| Example number | Structure | MS observed (M + 1) | HPLC ret. time (min.) | HPLC method |
|---|---|---|---|---|
| 264 | diastereomer 1 | 711.2 | 2.14 | B |
| 265 | diastereomer 1 | 666.2 | 2.18 | B |
| 266 | diastereomer 2 | 666.2 | 2.21 | B |
| 267 | diastereomer 1 | 693.2 (M + 18) | 2.19 | B |
| 268 | 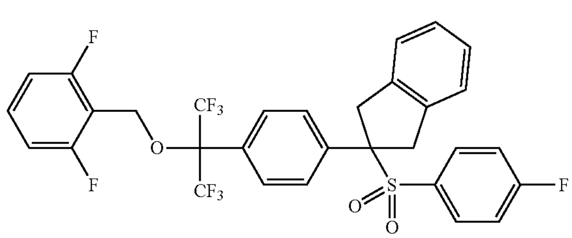 | 662.1 (M + 18) | 2.422 | B |

TABLE 1-continued

| Example number | Structure | MS observed (M + 1) | HPLC ret. time (min.) | HPLC method |
|---|---|---|---|---|
| 269 | 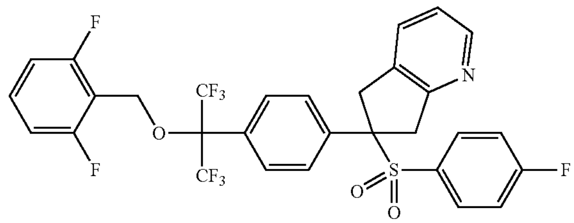 [SMILES: O=S(=O)(c1ccc(F)cc1)C1(c2ccc(C(OCc3c(F)cccc3F)(C(F)(F)F)C(F)(F)F)cc2)Cc2ccccc2C1] | 646.2 | 2.164 | B |
| 270 | 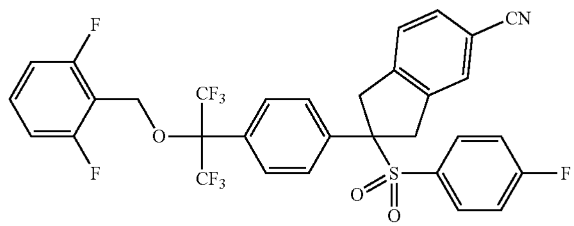 [SMILES: N#Cc1ccc2c(c1)CC(c1ccc(C(OCc3c(F)cccc3F)(C(F)(F)F)C(F)(F)F)cc1)(S(=O)(=O)c1ccc(F)cc1)C2] | 687.2 | 4.683 | A |
| 271 | 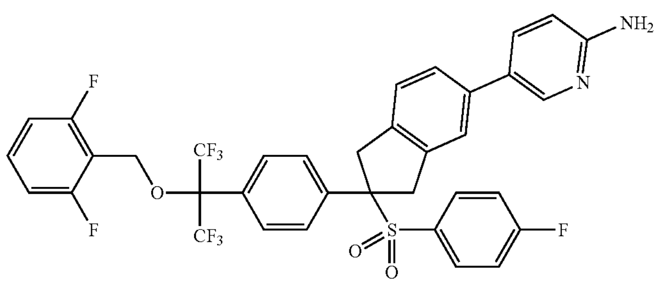 [SMILES: Nc1ccc(-c2ccc3c(c2)CC(c2ccc(C(OCc4c(F)cccc4F)(C(F)(F)F)C(F)(F)F)cc2)(S(=O)(=O)c2ccc(F)cc2)C3)cn1] | 737.3 | 2.43 | B |
| 272 | 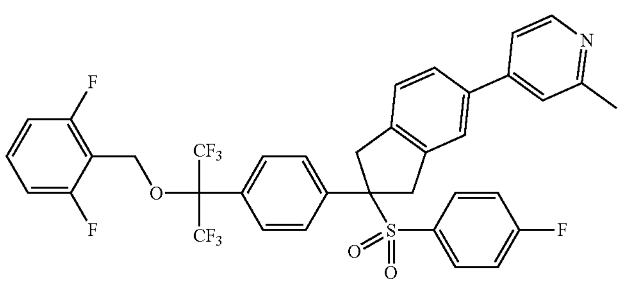 [SMILES: Cc1cc(-c2ccc3c(c2)CC(c2ccc(C(OCc4c(F)cccc4F)(C(F)(F)F)C(F)(F)F)cc2)(S(=O)(=O)c2ccc(F)cc2)C3)ccn1] | 736.3 | 2.60 | B |
| 273 | diastereomer 1 | 757 | 10.05 | D |

TABLE 1-continued
| Example number | Structure | MS observed (M + 1) | HPLC ret. time (min.) | HPLC method |
|---|---|---|---|---|
| 274 | 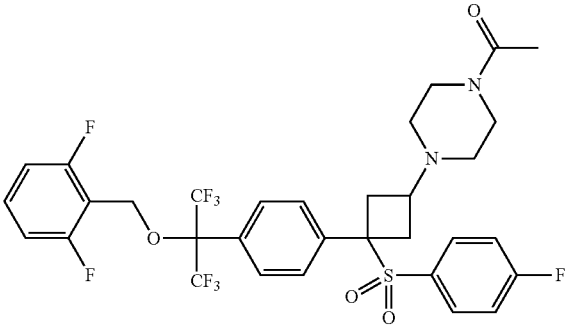 [SMILES: CC(=O)N1CCN(C2CC(c3ccc(C(OCc4c(F)cccc4F)(C(F)(F)F)C(F)(F)F)cc3)(S(=O)(=O)c3ccc(F)cc3)C2)CC1] diastereomer 1 | 709.2 | 9.59 | D |
| 275 | 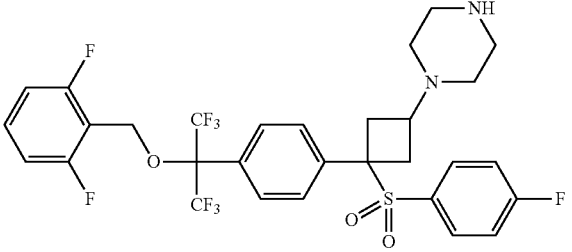 diastereomer 1 | 667.2 | 9.49 | D |
| 276 | 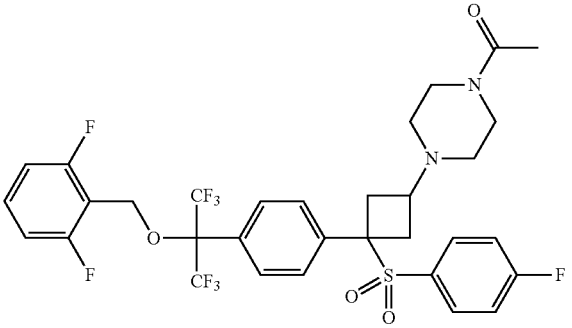 [SMILES: CC(=O)N1CCN(C2CC(c3ccc(C(OCc4c(F)cccc4F)(C(F)(F)F)C(F)(F)F)cc3)(S(=O)(=O)c3ccc(F)cc3)C2)CC1] diastereomer 2 | 709.2 | 9.60 | D |
| 277 | 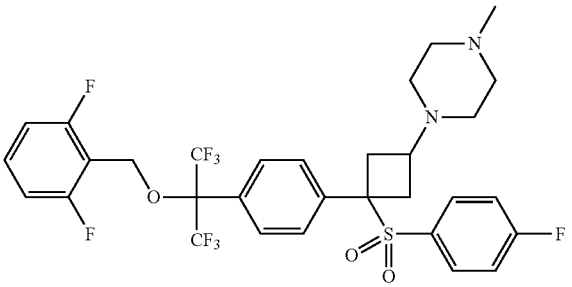 [SMILES: CN1CCN(C2CC(c3ccc(C(OCc4c(F)cccc4F)(C(F)(F)F)C(F)(F)F)cc3)(S(=O)(=O)c3ccc(F)cc3)C2)CC1] diastereomer 2 | 681.2 | 9.76 | D |

TABLE 1-continued

| Example number | Structure | MS observed (M + 1) | HPLC ret. time (min.) | HPLC method |
|---|---|---|---|---|
| 278 | diastereomer 1 | 681.2 | 9.73 | D |
| 279 | diastereomer 1 | 745.0 | 15.81 | F |
| 280 | diastereomer 2 | 771.2 | 18.69 | D |
| 281 | diastereomer 2 | 695.2 | 14.94 | D |
| 282 | diastereomer 2 | 723.2 | 9.58 | D |

TABLE 1-continued

| Example number | Structure | MS observed (M + 1) | HPLC ret. time (min.) | HPLC method |
|---|---|---|---|---|
| 283 | diastereomer 1 | 723.2 | 9.60 | D |
| 284 | diastereomer 2 | 681.2 | 8.86 | D |
| 285 | diastereomer 1 | 695.2 | 9.27 | D |
| 286 | diastereomer 1 | 753.2 | 9.66 | D |
| 287 | diastereomer 2 | 753.2 | 9.66 | D |

TABLE 1-continued

| Example number | Structure | MS observed (M + 1) | HPLC ret. time (min.) | HPLC method |
|---|---|---|---|---|
| 288 | diastereomer 1 | 752.2 | 9.83 | D |
| 289 | diastereomer 2 | 752.2 | 9.82 | D |
| 290 | diastereomer 2 | 738.2 | 10.05 | D |
| 291 | diastereomer 1 | 759.0 | 9.96 | D |

Example 292

1-fluoro-4-(1-(4-(perfluoroethyl)phenyl)cyclopentyl-sulfonyl)benzene

Step A: 2,2,2-trifluoro-1-(4-(((4-fluorophenyl)sulfonyl)methyl)phenyl)ethanone

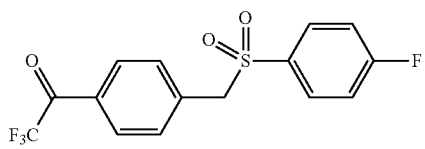

A DMF (6.24 ml) solution of 1-(4-(bromomethyl)phenyl)-2,2,2-trifluoroethanone (1 g, 3.74 mmol, prepared according to the literature procedure: Numata, Tatsuo et al, Jpn. Kokai Tokkyo Koho, 63159375, 2 Jul. 1988) and sodium 4-fluorobenzenesulfinate (0.955 g, 5.24 mmol) was stirred at room temperature for 17 h. The mixture was diluted with water (162 mL) and stayed at room temperature overnight. Colorless crystal precipitated out as the first crop of product (0.0942 g, 7%). Additional product (0.2508 g, 19%) was obtained by further concentrations and filtrations. 1H NMR (400 MHz, CDCl$_3$) δ 7.68-7.61 (m, 4H), 7.19 (d, J=8.4 Hz, 2H), 7.13 (t, J=8.6 Hz, 2H), 4.34 (s, 2H); 19F NMR (376 MHz, CDCl$_3$) δ −84.69, −102.88.

Step B: 1-fluoro-4-(4-(perfluoroethyl)benzylsulfonyl)benzene

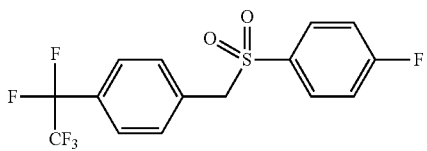

(Diethylamino)sulfur trifluoride (0.036 mL, 0.270 mmol) was added to a ClCH$_2$CH$_2$Cl (0.5 mL) solution of 2,2,2-trifluoro-1-(4-(((4-fluorophenyl)sulfonyl)methyl)phenyl)ethanone (15.6 mg, 0.045 mmol) at room temperature. The mixture was then heated to 50° C. overnight in a sealed safety vial. After cooled to ambient temperature, the crude was added slowly to MeOH (2 mL). The resulting solution was concentrated. Silica gel chromatography, eluting with 0-100% ethyl acetate in hexanes, gave 1-fluoro-4-(4-(perfluoroethyl)benzylsulfonyl) benzene as white solid (5.1 mg, 31% yield). 1H NMR (400 MHz, CDCl$_3$) δ 7.69-7.62 (m, 2H), 7.54 (d, J=8.3 Hz, 2H), 7.30-7.24 (m, 2H), 7.19-7.11 (m, 2H), 4.37 (s, 2H); 19F NMR (376 MHz, CDCl$_3$) δ −84.75, −102.47, −115.20.

Step C: 1-fluoro-4-(1-(4-(perfluoroethyl)phenyl)cyclopentylsulfonyl)benzene

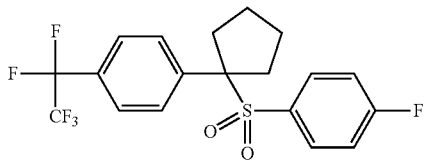 [SMILES: O=S(=O)(c1ccc(F)cc1)C1(c2ccc(C(F)(F)C(F)(F)F)cc2)CCCC1]

A DMF (0.25 mL) solution of 1-fluoro-4-((4-(perfluoroethyl)benzyl) sulfonyl)benzene (5.1 mg, 0.014 mmol) was added dropwise to a stirred DMF (0.25 mL) suspension of 1,4-dibromobutane (3.28 μL, 0.028 mmol) and NaH (2.77 mg, 0.069 mmol) at 0° C. under N2. After 1 hr at 0° C., the reaction was quenched by adding 1M HCl (0.2 mL) and extracted with EtOAc (2 mL). The EtOAc solution was concentrated. Silica gel chromatography, eluting with 0-20% ethyl acetate in hexanes, gave 1-fluoro-4-(1-(4-(perfluoroethyl)phenyl)cyclopentylsulfonyl)benzene as white solid (5.2 mg, 88% yield). LC/MS (M+23): 445.1; LC retention time: 1.11 min (analytical HPLC Method I); 1H NMR (400 MHz, CDCl$_3$) δ 7.47 (d, J=8.4 Hz, 2H), 7.35 (d, J=8.7 Hz, 2H), 7.29-7.23 (m, 2H), 7.02-6.94 (m, 2H), 2.90-2.81 (m, 2H), 2.37-2.26 (m, 2H), 2.15-2.02 (m, 2H), 1.78-1.65 (m, 2H); 19F NMR (376 MHz, CDCl$_3$) δ −84.76, −103.35, −115.30.

Example 293

1-fluoro-4-(1-(4-(1,1,1,3,3,3-hexafluoro-2-methylpropan-2-yl)phenyl)cyclopentylsulfonyl)benzene Step A: 1-methyl-4-(perfluoroprop-1-en-2-yl)benzene

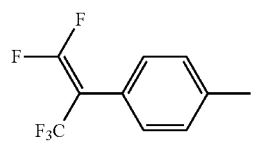

A DMF (100 mL) solution of 2,2,2-trifluoro-1-(p-tolyl)ethanone (9.41 g, 50.0 mmol), sodium 2-chloro-2,2-difluoroacetate (15.25 g, 100 mmol) and triphenylphosphine (13.12 g, 50.0 mmol) was heated at 80° C. for 1 h under N2. Hexane (400 mL) was added and the mixture was stirred at ambient temperature overnight. The hexane layer was separated, washed with water (2×50 mL) and brine (50 mL) respectively, dried (MgSO$_4$) and concentrated. Silica gel chromatography, eluting with 0-5% ethyl acetate in hexanes, gave 1-methyl-4-(perfluoroprop-1-en-2-yl)benzene (3.95 g, 36%) as colorless oil. 1H NMR (400 MHz, CDCl$_3$) δ 7.24 (s, 4H), 2.40 (s, 3H); 19F NMR (376 MHz, CDCl$_3$) δ −59.46, −76.00, −77.88.

Step B: 1-(1,1,1,3,3,3-hexafluoro-2-methylpropan-2-yl)-4-methylbenzene

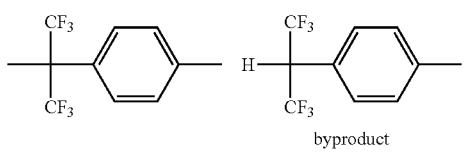

byproduct

Cesium fluoride (1.368 g, 9.00 mmol) was added to a stirred DMF (9.00 mL) solution of 1-methyl-4-(perfluoroprop-1-en-2-yl)benzene (1 g, 4.50 mmol) and iodomethane (0.563 mL, 9.00 mmol) at room temperature. The mixture was heated at 60° C. for 5 h in a sealed safety vial. The crude was poured into ice-water (200 mL) and extracted with hexanes (150 mL). The hexanes solution was washed with 10% LiCl (20 mL), dried over $Na_2SO_4$ and concentrated to give yellow oil. Silica gel chromatography, eluting with 0-5% ethyl acetate in hexanes, gave a 1:1 mixture (by 1H NMR analysis) of desired 1-(1,1,1,3,3,3-hexafluoro-2-methylpropan-2-yl)-4-methylbenzene and byproduct 1-(1,1,1,3,3,3-hexafluoropropan-2-yl)-4-methylbenzene as colorless oil. The mixture was used in the step C without further purification, assuming 50% purity of the desired 1-(1,1,1,3,3,3-hexafluoro-2-methylpropan-2-yl)-4-methylbenzene (0.427 g, 19%).

Step C: 1-(bromomethyl)-4-(1,1,1,3,3,3-hexafluoro-2-methylpropan-2-yl)benzene

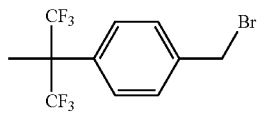

A stirred carbon tetrachloride (1 mL) suspension of impure 1-(1,1,1,3,3,3-hexafluoro-2-methylpropan-2-yl)-4-methylbenzene (0.427 g, assuming 50% purity, 0.833 mmol), NBS (0.3284 g, 1.845 mmol) and AIBN (1.2 mg, 7.31 μmol) was heated at 90° C. in a sealed safety vial for 18 h. Additional NBS (0.35 g) and AIBN (5 mg) were added. The mixture was heated at 90° C. for additional 4 h. It was cooled to ambient temperature and filtered. The filtrate was concentrated. The resulting residue (0.279 g) was used in the step D without further purification.

Step D: 1-fluoro-4-(4-(1,1,1,3,3,3-hexafluoro-2-methylpropan-2-yl)benzylsulfonyl)benzene

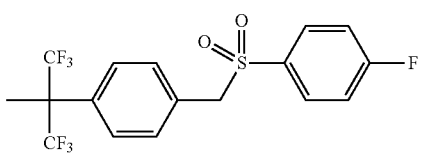

A DMF (0.75 mL) solution of crude 1-(bromomethyl)-4-(1,1,1,3,3,3-hexafluoro-2-methylpropan-2-yl)benzene (0.279 g, assuming 50% purity, 0.416 mmol) and sodium 4-fluorobenzenesulfinate (0.367 g, 2.015 mmol) was stirred at room temperature for 16 h. The resulting suspension was filtered. The filtrate was diluted with EtOAc (10 mL) and 10% LiCl (4 mL). After phase separation, the EtOAc layer was washed with 10% LiCl (2 mL) then concentrated. Silica gel chromatography, eluting with 0-35% ethyl acetate in hexanes, gave a mixture of desired 1-fluoro-4-(4-(1,1,1,3,3,3-hexafluoro-2-methylpropan-2-yl)benzylsulfonyl)benzene and byproduct 1-fluoro-4-(4-(1,1,1,3,3,3-hexafluoropropan-2-yl)benzylsulfonyl)benzene as white solid (0.2537 g). Part of the mixture (0.054 g) was further purified by a second silica gel chromatography, eluting with 0-30% ethyl acetate in hexanes, gave pure 1-fluoro-4-(4-(1,1,1,3,3,3-hexafluoro-2-methylpropan-2-yl)benzylsulfonyl)benzene as white solid (0.0157 g). 1H NMR (400 MHz, $CDCl_3$) δ 7.63-7.57 (m, 2H), 7.55 (d, J=8.3 Hz, 2H), 7.21-7.15 (m, 2H), 7.14-7.07 (m, 2H), 4.33 (s, 2H), 1.86 (s, 3H); 19F NMR (376 MHz, $CDCl_3$) δ −69.53, −102.85.

Step E: 1-fluoro-4-(1-(4-(1,1,1,3,3,3-hexafluoro-2-methylpropan-2-yl)phenyl)cyclopentylsulfonyl)benzene

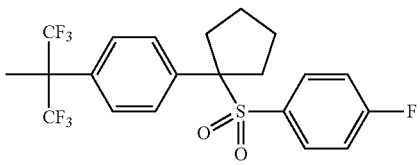 [SMILES: CC(c1ccc(C2(S(=O)(=O)c3ccc(F)cc3)CCCC2)cc1)(C(F)(F)F)C(F)(F)F]

A DMF (0.3 mL) solution of 1-fluoro-4-((4-(1,1,1,3,3,3-hexafluoro-2-methylpropan-2-yl)benzyl)sulfonyl)benzene (15 mg, 0.036 mmol) was added dropwise to a stirred DMF (0.2 mL) solution of 1,4-dibromobutane (25 mg, 0.116 mmol) and NaH (13.4 mg, 0.335 mmol) at 0° C. After 1 h at 0° C., the reaction was quenched by adding 2M HCl (180 μL) and the crude was extracted with EtOAc (3 mL). The EtOAc phase was concentrated. Silica gel chromatography, eluting with 0-20% ethyl acetate in hexanes, gave a 3:1 mixture (by 1H NMR analysis) of desired 1-fluoro-4-(1-(4-(1,1,1,3,3,3-hexafluoro-2-methylpropan-2-yl)phenyl)cyclopentylsulfonyl)benzene and uncyclized intermediate 1-(5-bromo-1-((4-fluorophenyl)sulfonyl)pentyl)-4-(1,1,1,3,3,3-hexafluoro-2-methylpropan-2-yl)benzene. The material was further purified by preparative chiral HPLC (Chiralcel OJ column, 20×250 mm, 20-μm particles, 10% EtOH in heptane with 0.1% diethylamine, 20 mL/min). Fractions containing the desired product were combined and dried via centrifugal evaporation to give 1-fluoro-4-(1-(4-(1,1,1,3,3,3-hexafluoro-2-methylpropan-2-yl)phenyl)cyclopentylsulfonyl)benzene (6.2 mg). LC/MS (M+18): 486.3; LC retention time: 2.46 min (analytical HPLC Method B); 1H NMR (400 MHz, 1:1 mixture of $CDCl_3$-$CD_3OD$) δ 7.51 (d, J=8.5 Hz, 2H), 7.32-7.25 (m, 2H), 7.25-7.18 (m, 2H), 7.04-6.93 (m, 2H), 2.86-2.72 (m, 2H), 2.42-2.30 (m, 2H), 2.10-1.95 (m, 2H), 1.87 (s, 3H), 1.78-1.64 (m, 2H).

Example 294

1-acetyl-N-((1s,3s)-3-(4-fluorophenylsulfonyl)-3-(4-(perfluoropropan-2-yl)phenyl)cyclobutyl)piperidine-4-carboxamide Step A: 1-acetyl-N-((1s,3s)-3-(4-fluorophenylsulfonyl)-3-(4-(1,1,1,3,3,3-hexafluoro-2-hydroxypropan-2-yl)phenyl)cyclobutyl)piperidine-4-carboxamide

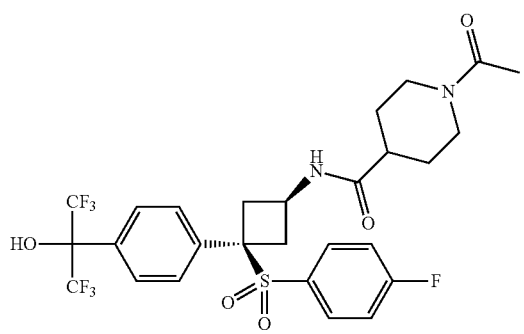 [SMILES: CC(=O)N1CCC(C(=O)N[C@H]2C[C@@](c3ccc(C(O)(C(F)(F)F)C(F)(F)F)cc3)(S(=O)(=O)c3ccc(F)cc3)C2)CC1]

A MeCN (0.5 mL) solution of 2-(4-((1s,3s)-3-amino-1-((4-fluorophenyl)sulfonyl)cyclobutyl)phenyl)-1,1,1,3,3,3-hexafluoropropan-2-ol (15 mg, 0.032 mmol from intermediate 1), 1-acetylpiperidine-4-carbonyl chloride (14 mg, 0.074 mmol) and Hunig's base (0.028 mL, 0.159 mmol) was stirred at room temperature for 45 minute. Silica gel chromatography, eluting with 0-10% MeOH in $CH_2Cl_2$, gave 1-acetyl-N-((1s,3s)-3-(4-fluorophenylsulfonyl)-3-(4-(1,1,1,3,3,3-hexafluoro-2-hydroxypropan-2-yl)phenyl)cyclobutyl)piperidine-4-carboxamide (17.6 mg, 89% yield) as white solid. LC/MS (M+1): 625.2; LC retention time: 0.84 min (analytical HPLC Method I); 1H NMR (400 MHz, 1:1 mixture of $CDCl_3$-$CD_3OD$) δ 7.61 (d, J=8.4 Hz, 2H), 7.25-7.17 (m, 2H), 7.14 (d, J=8.6 Hz, 2H), 7.04-6.95 (m, 2H), 4.51 (d, J=13.4 Hz, 1H), 4.22 (quin, J=8.1 Hz, 1H), 3.90 (d, J=13.9 Hz, 1H), 3.19-3.07 (m, 3H), 3.05-2.94 (m, 2H), 2.68 (td, J=12.7, 2.8 Hz, 1H), 2.43 (tt, J=11.4, 3.9 Hz, 1H), 2.08 (s, 3H), 1.90-1.77 (m, 2H), 1.73-1.51 (m, 2H).

Step B: 1-acetyl-N-((1s,3s)-3-(4-fluorophenylsulfonyl)-3-(4-(perfluoropropan-2-yl)phenyl)cyclobutyl)piperidine-4-carboxamide

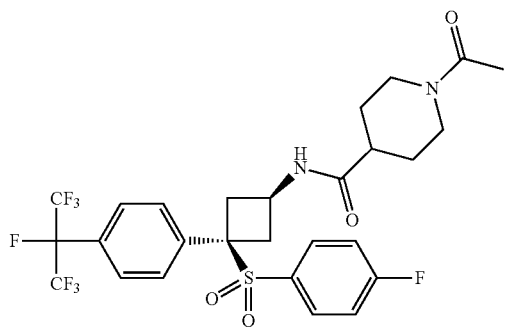 [SMILES: CC(=O)N1CCC(C(=O)N[C@H]2C[C@@](c3ccc(C(F)(C(F)(F)F)C(F)(F)F)cc3)(S(=O)(=O)c3ccc(F)cc3)C2)CC1]

A $ClCH_2CH_2Cl$ (0.3 mL) solution of 1-acetyl-N-((1s,3s)-3-(4-fluorophenylsulfonyl)-3-(4-(1,1,1,3,3,3-hexafluoro-2-hydroxypropan-2-yl)phenyl)cyclobutyl)piperidine-4-carboxamide (9 mg, 0.014 mmol) and (diethylamino)sulfur trifluoride (11 μL, 0.086 mmol) was stirred at 50° C. in a sealed safety vial. Additional (diethylamino)sulfur trifluoride (11 μL) was added twice after 2 and 18 h. After total heating of 25 h, the crude was cooled to ambient temperature and slowly added to MeOH (1 mL). The material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 34-74% B over 20 minutes, then a 6-minute hold at 100% B; Flow: 20 mL/min. Fractions containing the desired product were combined and dried via centrifugal evaporation to give 1-acetyl-N-((1s,3s)-3-(4-fluorophenylsulfonyl)-3-(4-(perfluoropropan-2-yl)phenyl)cyclobutyl)piperidine-4-carboxamide (3.1 mg, 32% yield). LC/MS (M+1): 627.3; LC retention time: 1.98 min (analytical HPLC Method B); 1H NMR (500 MHz, 1:1 mixture of $CDCl_3$-$CD_3OD$) δ 7.52 (d, J=8.4 Hz, 2H), 7.32-7.22 (m, 4H), 7.04 (t, J=8.5 Hz, 2H), 4.52 (d, J=13.4 Hz, 1H), 4.20 (quin, J=8.2 Hz, 1H), 3.92 (d, J=13.9 Hz, 1H), 3.20-3.10 (m, 3H), 3.06-2.96 (m, 2H), 2.73-2.64 (m, 1H), 2.45 (tt, J=11.4, 3.8 Hz, 1H), 2.09 (s, 3H), 1.88-1.78 (m, 2H), 1.72-1.52 (m, 2H).

The examples in TABLE 2 below were prepared from 2-(4-((1s,3s)-3-amino-1-((4-fluorophenyl)sulfonyl)cyclobutyl)phenyl)-1,1,1,3,3,3-hexafluoropropan-2-ol (intermediate 1) or 2-(4-((1r,3r)-3-amino-1-(4-fluorophenylsulfonyl)cyclobutyl)phenyl)-1,1,1,3,3,3-hexafluoropropan-2-ol (intermediate 2) or (1s,3s)-3-(4-fluorophenylsulfonyl)-3-(4-(perfluoropropan-2-yl)phenyl)cyclobutanamine (intermediate 3) in the same manner as outlined in the step A of Example 294 above, substituting the appropriate acid or chlorocarbamate reagents.

TABLE 2

| Example number | Structure | MS observed (M + 1) | HPLC ret. time (min.) | HPLC method |
|---|---|---|---|---|
| 295 | 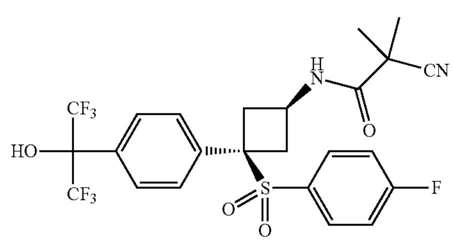 [SMILES: CC(C)(C#N)C(=O)N[C@H]1C[C@@](c2ccc(C(O)(C(F)(F)F)C(F)(F)F)cc2)(S(=O)(=O)c2ccc(F)cc2)C1] | 567.1 | 1.91 | B |
| 296 | 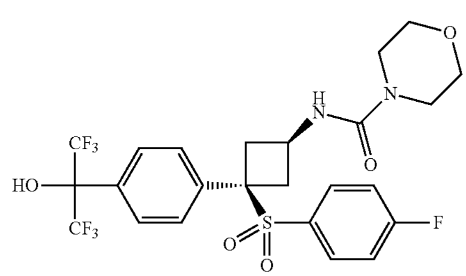 [SMILES: O=C(N[C@H]1C[C@@](c2ccc(C(O)(C(F)(F)F)C(F)(F)F)cc2)(S(=O)(=O)c2ccc(F)cc2)C1)N1CCOCC1] | 585.2 | 1.73 | B |

TABLE 2-continued

| Example number | Structure | MS observed (M + 1) | HPLC ret. time (min.) | HPLC method |
|---|---|---|---|---|
| 297 | 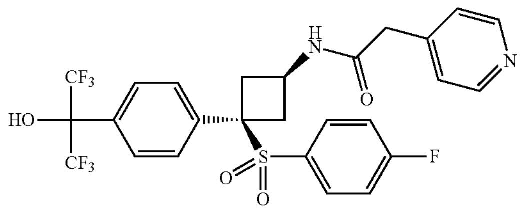 [SMILES: O=C(Cc1ccncc1)N[C@H]1C[C@@](c2ccc(C(O)(C(F)(F)F)C(F)(F)F)cc2)(S(=O)(=O)c2ccc(F)cc2)C1] | 591.2 | 1.71 | B |
| 298 | 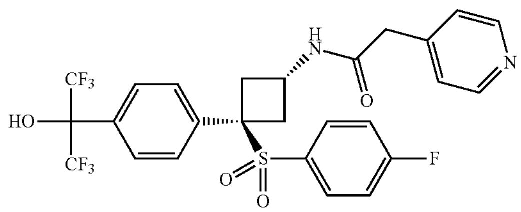 [SMILES: O=C(Cc1ccncc1)N[C@H]1C[C@](c2ccc(C(O)(C(F)(F)F)C(F)(F)F)cc2)(S(=O)(=O)c2ccc(F)cc2)C1] | 591.3 | 1.70 | B |
| 299 | 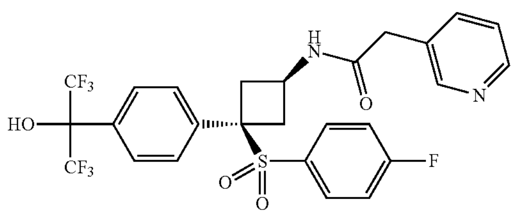 [SMILES: O=C(Cc1cccnc1)N[C@H]1C[C@@](c2ccc(C(O)(C(F)(F)F)C(F)(F)F)cc2)(S(=O)(=O)c2ccc(F)cc2)C1] | 591.2 | 1.69 | B |
| 300 | 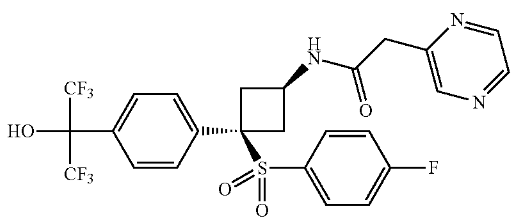 [SMILES: O=C(Cc1cnccn1)N[C@H]1C[C@@](c2ccc(C(O)(C(F)(F)F)C(F)(F)F)cc2)(S(=O)(=O)c2ccc(F)cc2)C1] | 592.2 | 1.54 | B |
| 301 | 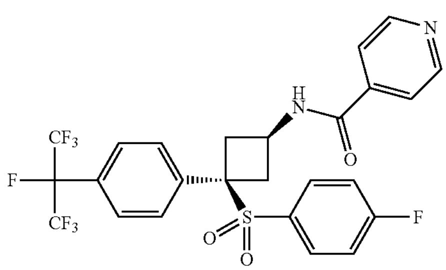 [SMILES: O=C(N[C@H]1C[C@@](c2ccc(C(F)(C(F)(F)F)C(F)(F)F)cc2)(S(=O)(=O)c2ccc(F)cc2)C1)c1ccncc1] | 579.2 | 2.20 | B |
| 302 | 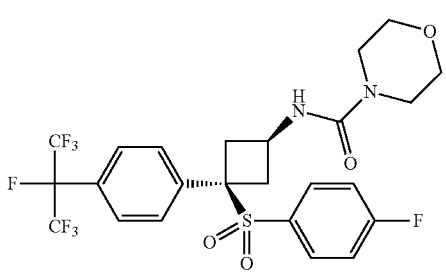 [SMILES: O=C(N[C@H]1C[C@@](c2ccc(C(F)(C(F)(F)F)C(F)(F)F)cc2)(S(=O)(=O)c2ccc(F)cc2)C1)N1CCOCC1] | 587.2 | 2.14 | B |

TABLE 2-continued

| Example number | Structure | MS observed (M + 1) | HPLC ret. time (min.) | HPLC method |
|---|---|---|---|---|
| 303 | 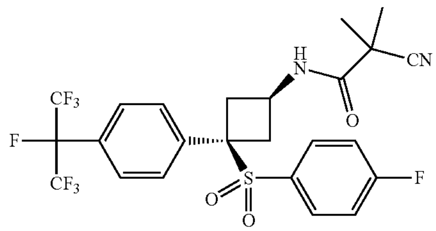 [SMILES: CC(C)(C#N)C(=O)N[C@H]1C[C@@](c2ccc(C(F)(C(F)(F)F)C(F)(F)F)cc2)(S(=O)(=O)c2ccc(F)cc2)C1] | 569.2 | 2.34 | B |
| 304 | 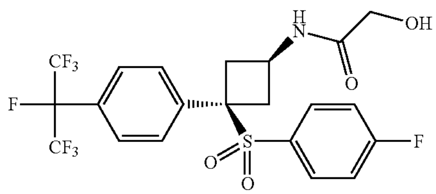 [SMILES: O=C(CO)N[C@H]1C[C@@](c2ccc(C(F)(C(F)(F)F)C(F)(F)F)cc2)(S(=O)(=O)c2ccc(F)cc2)C1] | 532.2 | 1.97 | B |
| 305 | 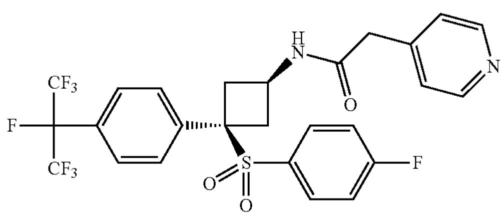 | 593.2 | 2.06 | B |
| 306 | 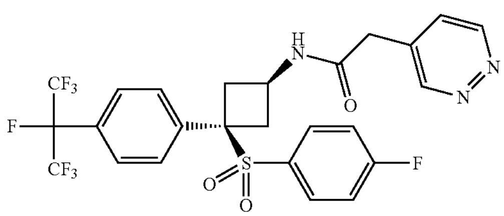 [SMILES: O=C(Cc1ccncc1)N[C@H]1C[C@@](c2ccc(C(F)(C(F)(F)F)C(F)(F)F)cc2)(S(=O)(=O)c2ccc(F)cc2)C1] | 594.1 | 4.10 | A |
| 307 | 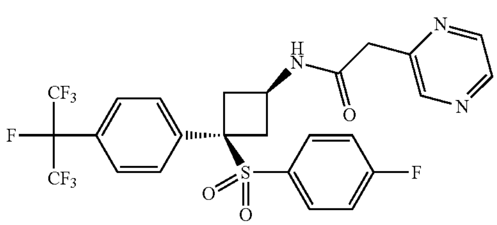 [SMILES: O=C(Cc1cnccn1)N[C@H]1C[C@@](c2ccc(C(F)(C(F)(F)F)C(F)(F)F)cc2)(S(=O)(=O)c2ccc(F)cc2)C1] | 594.1 | 1.93 | B |
| 308 | 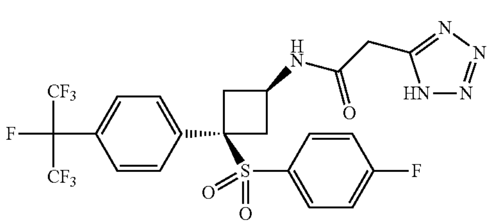 [SMILES: O=C(Cc1nnn[nH]1)N[C@H]1C[C@@](c2ccc(C(F)(C(F)(F)F)C(F)(F)F)cc2)(S(=O)(=O)c2ccc(F)cc2)C1] | 584.2 | 1.51 | B |
| 309 | 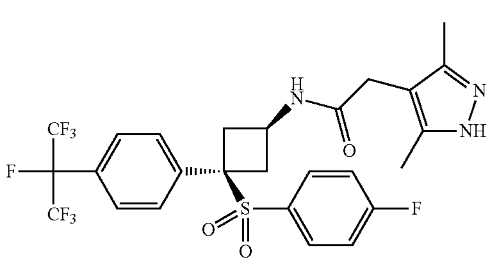 [SMILES: Cc1n[nH]c(C)c1CC(=O)N[C@H]1C[C@@](c2ccc(C(F)(C(F)(F)F)C(F)(F)F)cc2)(S(=O)(=O)c2ccc(F)cc2)C1] | 610.2 | 1.89 | B |

TABLE 2-continued

| Example number | Structure | MS observed (M + 1) | HPLC ret. time (min.) | HPLC method |
|---|---|---|---|---|
| 310 | 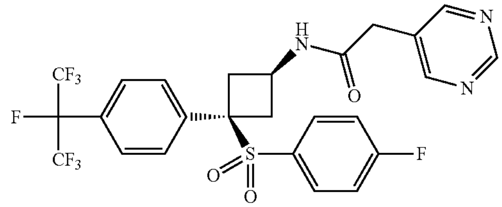 [SMILES: O=C(Cc1cncnc1)N[C@H]1C[C@@](c2ccc(C(F)(C(F)(F)F)C(F)(F)F)cc2)(S(=O)(=O)c2ccc(F)cc2)C1] | 594.1 | 1.87 | B |

The examples in TABLE 3 below were prepared from (1s,3s)-3-(4-fluorophenylsulfonyl)-3-(4-(1,1,1,3,3,3-hexafluoro-2-hydroxypropan-2-yl)phenyl)cyclobutanecarboxylic acid (diastereomer 2 from Step D of Example 44) or (1r,3r)-3-(4-fluorophenylsulfonyl)-3-(4-(1,1,1,3,3,3-hexafluoro-2-hydroxypropan-2-yl)phenyl)cyclobutanecarboxylic acid (diastereomer 1 from Step D of Example 44) or (1s,3 s)-3-(4-fluorophenylsulfonyl)-3-(4-(perfluoropropan-2-yl)phenyl)cyclobutanecarboxylic acid (from Step G of Example 44) or (1s,3s)-3-(4-(2-(2,6-difluorobenzyloxy)-1,1,1,3,3,3-hexafluoropropan-2-yl)phenyl)-3-(4-fluorophenylsulfonyl)cyclobutanecarboxylic acid (Example 43) in the same manner as outlined in the step A of Example 294 above, substituting the appropriate amine reagents.

TABLE 3

| Example number | Structure | MS observed (M + 1) | HPLC ret. time (min.) | HPLC method |
|---|---|---|---|---|
| 311 | 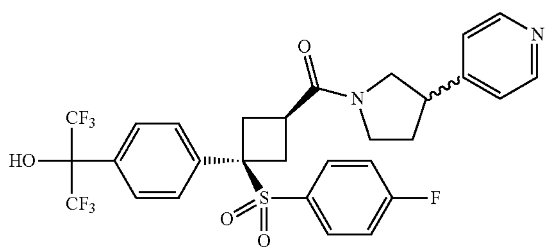 [SMILES: O=C([C@H]1C[C@@](c2ccc(C(O)(C(F)(F)F)C(F)(F)F)cc2)(S(=O)(=O)c2ccc(F)cc2)C1)N1CCC(c2ccncc2)C1] | 631.3 | 1.78 | B |
| 312 | 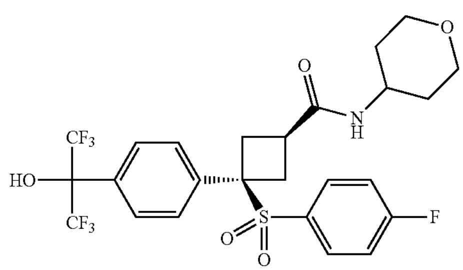 [SMILES: O=C(NC1CCOCC1)[C@H]1C[C@@](c2ccc(C(O)(C(F)(F)F)C(F)(F)F)cc2)(S(=O)(=O)c2ccc(F)cc2)C1] | 584.2 | 1.72 | B |
| 313 | 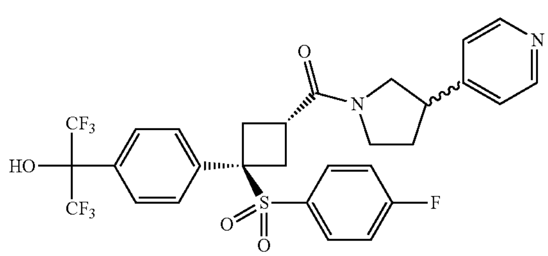 [SMILES: O=C([C@H]1C[C@](c2ccc(C(O)(C(F)(F)F)C(F)(F)F)cc2)(S(=O)(=O)c2ccc(F)cc2)C1)N1CCC(c2ccncc2)C1] | 631.3 | 1.86 | B |

TABLE 3-continued

| Example number | Structure | MS observed (M + 1) | HPLC ret. time (min.) | HPLC method |
|---|---|---|---|---|
| 314 | 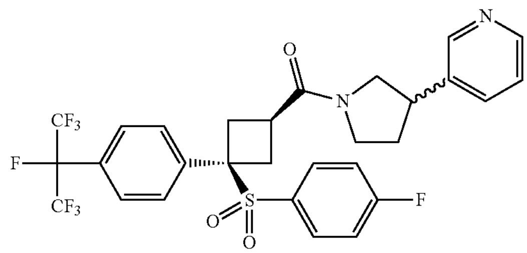 [SMILES: O=C([C@H]1C[C@@](c2ccc(C(F)(C(F)(F)F)C(F)(F)F)cc2)(S(=O)(=O)c2ccc(F)cc2)C1)N1CCC(c2cccnc2)C1] | 633.3 | 2.14 | B |
| 315 | 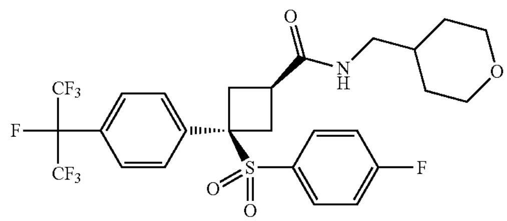 [SMILES: O=C(NCC1CCOCC1)[C@H]1C[C@@](c2ccc(C(F)(C(F)(F)F)C(F)(F)F)cc2)(S(=O)(=O)c2ccc(F)cc2)C1] | 600.2 | 2.08 | B |
| 316 | 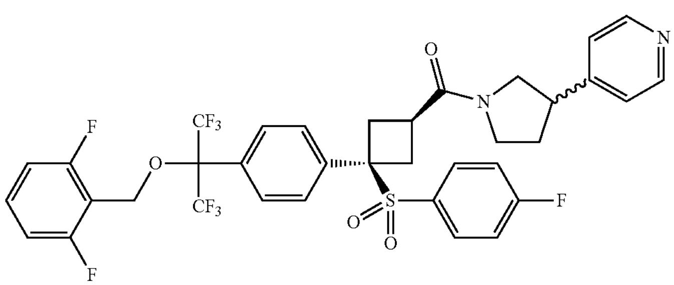 [SMILES: O=C([C@H]1C[C@@](c2ccc(C(OCc3c(F)cccc3F)(C(F)(F)F)C(F)(F)F)cc2)(S(=O)(=O)c2ccc(F)cc2)C1)N1CCC(c2ccncc2)C1] | 757.3 | 2.29 | B |
| 317 | 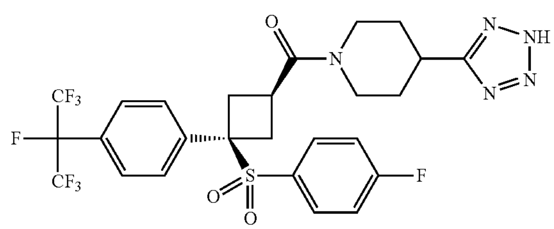 [SMILES: O=C([C@H]1C[C@@](c2ccc(C(F)(C(F)(F)F)C(F)(F)F)cc2)(S(=O)(=O)c2ccc(F)cc2)C1)N1CCC(c2nn[nH]n2)CC1] | 638.1 | 1.73 | B |
| 318 | 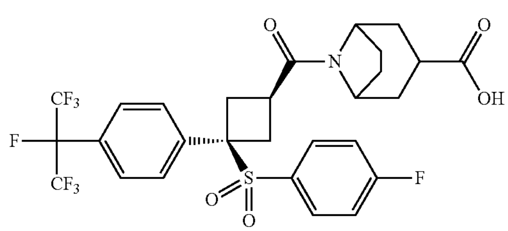 [SMILES: O=C(O)C1CC2CCC(C1)N2C(=O)[C@H]1C[C@@](c2ccc(C(F)(C(F)(F)F)C(F)(F)F)cc2)(S(=O)(=O)c2ccc(F)cc2)C1] | 640.1 | 1.68 | B |
| 319 | 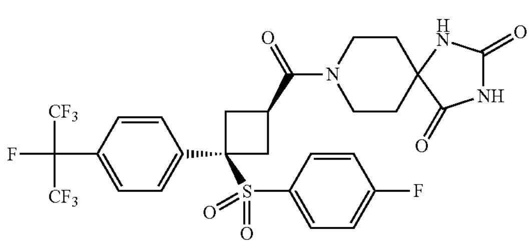 [SMILES: O=C1NC(=O)C2(CCN(C(=O)[C@H]3C[C@@](c4ccc(C(F)(C(F)(F)F)C(F)(F)F)cc4)(S(=O)(=O)c4ccc(F)cc4)C3)CC2)N1] | 654.1 | 1.86 | B |

TABLE 3-continued

| Example number | Structure | MS observed (M + 1) | HPLC ret. time (min.) | HPLC method |
|---|---|---|---|---|
| 320 | 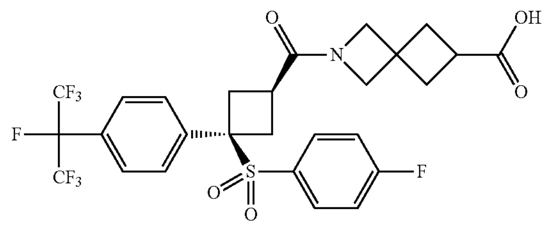 [SMILES: O=C(O)C1CC2(C1)CN(C(=O)[C@H]1C[C@@](c3ccc(C(F)(C(F)(F)F)C(F)(F)F)cc3)(S(=O)(=O)c3ccc(F)cc3)C1)C2] | 626.1 | 1.63 | B |
| 321 | 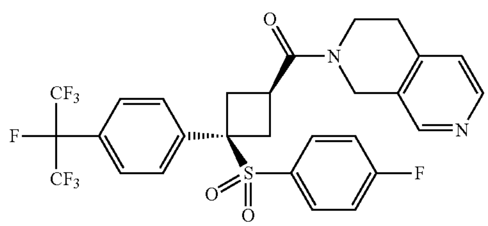 [SMILES: O=C([C@H]1C[C@@](c2ccc(C(F)(C(F)(F)F)C(F)(F)F)cc2)(S(=O)(=O)c2ccc(F)cc2)C1)N1CCc2ccncc2C1] | 619.1 | 2.03 | B |
| 322 | 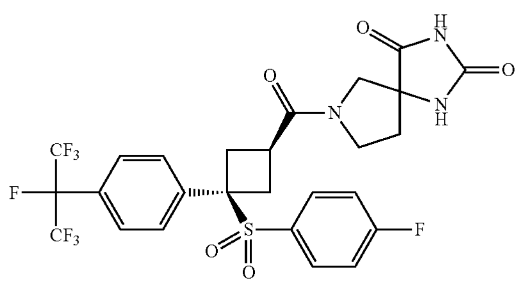 [SMILES: O=C1NC(=O)C2(CCN(C(=O)[C@H]3C[C@@](c4ccc(C(F)(C(F)(F)F)C(F)(F)F)cc4)(S(=O)(=O)c4ccc(F)cc4)C3)C2)N1] | 640.2 | 1.80 | B |
| 323 | 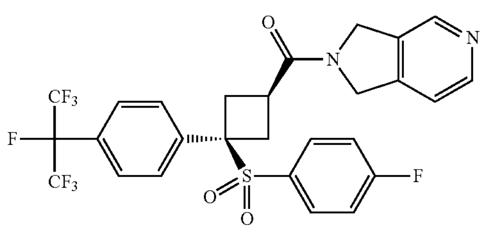 [SMILES: O=C([C@H]1C[C@@](c2ccc(C(F)(C(F)(F)F)C(F)(F)F)cc2)(S(=O)(=O)c2ccc(F)cc2)C1)N1Cc2ccncc2C1] | 605.2 | 1.97 | B |
| 324 | 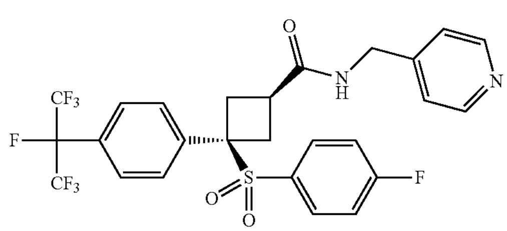 [SMILES: O=C(NCc1ccncc1)[C@H]1C[C@@](c2ccc(C(F)(C(F)(F)F)C(F)(F)F)cc2)(S(=O)(=O)c2ccc(F)cc2)C1] | 593.2 | 1.93 | B |
| 325 | 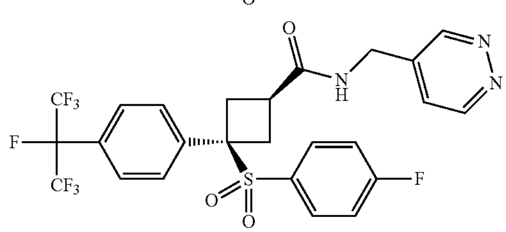 | 594.2 | 1.82 | B |

The examples in TABLE 4 below were prepared from rac-2-(4-((1S,3R)-3-amino-1-(4-fluorophenylsulfonyl)cyclopentyl)phenyl)-1,1,1,3,3,3-hexafluoropropan-2-ol (prepared using procedure similar to synthesis of Example 26 and Intermediate 1) or rac-(1R,3S)-3-(4-fluorophenylsulfonyl)-3-(4-(perfluoropropan-2-yl)phenyl)cyclopentanamine (prepared using procedure similar to synthesis of intermediate 3) in the same manner as outlined in the step A of Example 294 above, substituting the appropriate acid or chlorocarbamate intermediates.

TABLE 4

| Example number | Structure | MS observed (M + 1) | HPLC ret. time (min.) | HPLC method |
|---|---|---|---|---|
| 326 | (Rac) | 639.4 | 1.77 | B |
| 327 | (Rac) | 591.2 | 1.85 | B |
| 328 | (Rac) | 593.1 | 2.04 | B |
| 329 | (Rac) | 572.1 | 1.99 | B |
| 330 | (Rac) | 601.3 | 2.20 | B |

TABLE 4-continued

| Example number | Structure | MS observed (M + 1) | HPLC ret. time (min.) | HPLC method |
|---|---|---|---|---|
| 331 | (Rac) | 607.3 | 2.15 | B |
| 332 | (Rac) | 546.2 | 2.05 | B |
| 333 | (Rac) | 607.2 | 1.95 | B |

Example 334 rac-1-Acetyl-N-((1R,3S)-3-(4-fluorophenylsulfonyl)-3-(4-(perfluoropropan-2-yl)phenyl)cyclopentyl)piperidine-4-carboxamide

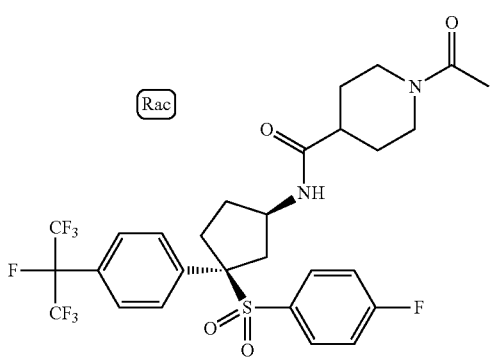 [SMILES: CC(=O)N1CCC(C(=O)N[C@@H]2CC[C@](c3ccc(C(F)(C(F)(F)F)C(F)(F)F)cc3)(S(=O)(=O)c3ccc(F)cc3)C2)CC1]

Similar to the step B of Example 294, rac-1-Acetyl-N-((1R,3S)-3-(4-fluorophenylsulfonyl)-3-(4-(perfluoropropan-2-yl)phenyl)cyclopentyl)piperidine-4-carboxamide was prepared from Example 326. LC/MS (M+1): 641.3; LC retention time: 2.06 min (analytical HPLC Method B); 1H NMR (400 MHz, 1:1 mixture of $CDCl_3$-$CD_3OD$) δ 7.50 (d, J=8.3 Hz, 2H), 7.37 (d, J=8.8 Hz, 2H), 7.26-7.20 (m, 2H), 7.01 (t, J=8.5 Hz, 2H), 4.52 (d, J=11.0 Hz, 1H), 4.25 (quin, J=7.6 Hz, 1H), 3.92 (d, J=13.8 Hz, 1H), 3.20-3.09 (m, 1H), 2.98-2.81 (m, 2H), 2.75-2.63 (m, 2H), 2.50-2.34 (m, 2H), 2.15-2.06 (m, 4H), 2.04-1.53 (m, 5H).

General RORγ SPA Binding Assay

The binding of potential ligands to RORγ is measured by competition with [$^3$H] 25-hydroxycholesterol (Perkin Elmer NET674250UC) using a scintillation proximity assay (SPA) binding assay. The ligand binding domain of human RORγ (A262-S507) with an N-terminal His tag is expressed in *E. coli* and purified using nickel affinity chromatography. 15 ug/well RORγ (A262-S507) is incubated with test compound at varying concentrations in 3-fold serial dilution, with final concentrations ranging from 16.6 μM to 0.28 nM for 10 min at room temperature in PBS buffer (Invitrogen #14190-144) containing 0.5% fatty acid free BSA (Gemini Bio-Products, Cat. #700-107P) and 0.1% Glycerol (Sigma Cat# G5516). 10 nM of [$^3$H] 25-hydroxycholesterol is then added, and the reaction is incubated for 10 min. 10 mg/mL of Copper-His Tag-PVT beads (Perkin Elmer cat # RPNQ0095) are added, and the mixture is incubated for 60 min. The reaction is read on a TopCount Microplate scintillation plate reader (Perkin Elmer). The competition data of the test compound over a range of concentrations was plotted as percentage inhibition of radioligand specifically bound in the absence of test compound (percent of total signal). After correcting for non-specific binding, $IC_{50}$ values were determined. The $IC_{50}$ value is defined as the concentration of test compound needed to reduce [$^3$H] 25-hydroxycholesterol specific binding by 50% and is calculated using the four parameter logistic equation to fit the normalized data.

$IC_{50}$ values of the compounds of the invention in the RORγ binding assay are provided below.

| Example # | RORγ Binding $IC_{50}$, uM |
|---|---|
| 1 | 0.199 |
| 2 | 0.069 |
| 3 | 0.057 |
| 4 | 0.044 |
| 5 | 0.034 |
| 6 | 0.077 |
| 7 | 0.088 |
| 8 | 0.078 |
| 9 | 0.089 |
| 10 | 0.076 |
| 11 | 0.111 |
| 12 | 0.071 |
| 13 | 0.157 |
| 14 | 0.113 |
| 15 | 0.157 |
| 16 | 0.042 |
| 17 | 0.172 |
| 18 | 0.040 |
| 19 | 0.017 |
| 20 | 0.007 |
| 21 | 0.179 |
| 22 | 0.053 |
| 23 | 0.059 |
| 24 | 0.115 |
| 25 | 0.074 |
| 26 | 0.581 |
| 27 | 0.156 |
| 28 | 0.110 |
| 29 | 0.121 |
| 30 | 0.385 |
| 31 | 1.111 |
| 32 | 0.104 |
| 33 | 0.496 |
| 34 | 0.179 |
| 35 | 0.093 |
| 36 | 0.214 |
| 37 | 3.357 |
| 38 | 1.281 |
| 39 | 0.027 |
| 40 | 0.036 |
| 41 | 0.011 |
| 42 | 0.661 |
| 43 | 0.069 |
| 44 | 0.086 |
| 45 | 0.161 |
| 46 | 0.902 |
| 47 | 0.279 |
| 48 | 0.047 |
| 49 | 0.055 |
| 50 | 0.085 |
| 51 | 0.078 |
| 52 | 0.200 |
| 53 | 0.088 |
| 54 | 0.102 |
| 55 | 1.103 |
| 56 | 0.137 |
| 57 | 0.048 |
| 58 | 0.031 |
| 59 | 0.083 |
| 60 | 0.021 |
| 61 | 0.063 |
| 62 | 0.076 |
| 63 | 0.067 |
| 64 | 0.136 |
| 65 | 0.110 |
| 66 | 0.053 |
| 67 | 0.068 |
| 68 | 0.032 |
| 69 | 0.131 |
| 70 | 0.073 |
| 71 | 0.140 |
| 72 | 0.086 |
| 73 | 0.099 |
| 74 | 0.152 |
| 75 | 0.095 |
| 76 | 0.300 |
| 77 | 0.093 |
| 78 | 0.022 |
| 79 | 0.113 |
| 80 | 0.153 |
| 81 | 0.192 |
| 82 | 0.092 |
| 83 | 0.085 |
| 84 | 0.238 |
| 85 | 0.060 |
| 86 | 0.234 |
| 87 | 0.044 |
| 88 | 0.087 |
| 89 | 0.077 |
| 90 | 0.164 |
| 91 | 0.084 |
| 92 | 0.124 |
| 93 | 0.063 |
| 94 | 0.048 |
| 95 | 0.647 |
| 96 | 0.017 |
| 97 | 0.028 |
| 98 | 0.048 |
| 99 | 0.055 |
| 100 | 0.119 |
| 101 | 0.129 |
| 102 | 0.220 |
| 103 | 0.183 |
| 104 | 0.233 |
| 105 | 0.067 |
| 106 | 0.100 |
| 107 | 0.056 |
| 108 | 0.068 |
| 109 | 0.106 |
| 110 | 0.221 |
| 111 | 0.068 |
| 112 | 0.126 |
| 113 | 0.195 |
| 114 | 0.098 |
| 115 | 0.169 |
| 116 | 0.101 |
| 117 | 0.185 |
| 118 | 0.095 |
| 119 | 0.050 |
| 120 | 0.063 |
| 121 | 0.180 |
| 122 | 0.220 |
| 123 | 0.119 |
| 124 | 0.608 |
| 125 | 0.098 |
| 126 | 0.148 |
| 127 | 0.123 |
| 128 | 0.159 |
| 129 | 0.130 |
| 130 | 1.944 |
| 131 | 2.323 |
| 132 | 0.170 |
| 133 | 0.607 |
| 134 | 1.298 |
| 135 | 0.152 |
| 136 | 0.263 |
| 137 | 0.279 |
| 138 | 0.153 |

| Example # | RORγ Binding IC$_{50}$, uM |
|---|---|
| 139 | 0.021 |
| 140 | 0.034 |
| 141 | 0.009 |
| 142 | 0.239 |
| 143 | 0.205 |
| 144 | 0.078 |
| 145 | 0.049 |
| 146 | 0.196 |
| 147 | 0.454 |
| 148 | 0.128 |
| 149 | 0.156 |
| 150 | 0.071 |
| 151 | 0.067 |
| 152 | 0.062 |
| 153 | 0.063 |
| 154 | 0.045 |
| 155 | 0.063 |
| 156 | 0.086 |
| 157 | 0.180 |
| 158 | 0.068 |
| 159 | 0.079 |
| 160 | 0.094 |
| 161 | 0.247 |
| 162 | 0.022 |
| 163 | 0.074 |
| 164 | 0.062 |
| 165 | 0.219 |
| 166 | 0.762 |
| 167 | 0.222 |
| 168 | 0.049 |
| 169 | 0.022 |
| 170 | 0.044 |
| 171 | 0.141 |
| 172 | 0.242 |
| 173 | 0.178 |
| 174 | 0.214 |
| 175 | 0.118 |
| 176 | 0.075 |
| 177 | 0.064 |
| 178 | 0.039 |
| 179 | 0.046 |
| 180 | 0.329 |
| 181 | 0.148 |
| 182 | 4.702 |
| 183 | 0.422 |
| 184 | 0.623 |
| 185 | 0.064 |
| 186 | 4.296 |
| 187 | 0.331 |
| 188 | 0.050 |
| 189 | 0.261 |
| 190 | 0.167 |
| 191 | 0.085 |
| 192 | 0.206 |
| 193 | 0.109 |
| 194 | 0.144 |
| 195 | 0.175 |
| 196 | 0.356 |
| 197 | 0.043 |
| 198 | 1.353 |
| 199 | 0.107 |
| 200 | 0.321 |
| 201 | 0.069 |
| 202 | 0.123 |
| 203 | 0.074 |
| 204 | 0.056 |
| 205 | 0.054 |
| 206 | 2.222 |
| 207 | 0.378 |
| 208 | 2.840 |
| 209 | 0.028 |
| 210 | 0.105 |
| 211 | 0.053 |
| 212 | 1.696 |
| 213 | 0.792 |
| 214 | 0.096 |
| 215 | 0.040 |
| 216 | 0.242 |
| 217 | 0.068 |
| 218 | 0.219 |
| 219 | 0.056 |
| 220 | 0.039 |
| 221 | 0.041 |
| 222 | 0.051 |
| 223 | 0.545 |
| 224 | 0.089 |
| 225 | 0.260 |
| 226 | 0.038 |
| 227 | 0.243 |
| 228 | 0.270 |
| 229 | 0.095 |
| 230 | 0.077 |
| 231 | 0.133 |
| 232 | 0.076 |
| 233 | 0.112 |
| 234 | 0.107 |
| 235 | 0.064 |
| 236 | 0.897 |
| 237 | 0.170 |
| 238 | 1.448 |
| 239 | 0.152 |
| 240 | 0.445 |
| 241 | 0.184 |
| 242 | 0.164 |
| 243 | 0.094 |
| 244 | 0.133 |
| 245 | 0.039 |
| 246 | 0.277 |
| 247 | 0.114 |
| 248 | 0.035 |
| 249 | 0.096 |
| 250 | 0.642 |
| 251 | 0.991 |
| 252 | 0.067 |
| 253 | 0.077 |
| 254 | 0.314 |
| 255 | 0.114 |
| 256 | 0.473 |
| 257 | 0.078 |
| 258 | 0.095 |
| 259 | 0.171 |
| 260 | 0.043 |
| 261 | 0.264 |
| 262 | 0.041 |
| 263 | 0.082 |
| 264 | 0.063 |
| 265 | 0.096 |
| 266 | 0.244 |
| 267 | 0.110 |
| 268 | 3.058 |
| 269 | 0.150 |
| 270 | 0.353 |
| 271 | 0.545 |
| 272 | 0.931 |
| 273 | 1.694 |
| 274 | 0.054 |
| 275 | 0.754 |
| 276 | 1.375 |
| 277 | 4.006 |
| 278 | 0.467 |
| 279 | 0.083 |
| 280 | 0.290 |
| 281 | 0.498 |
| 282 | 0.115 |
| 283 | 0.869 |
| 284 | 0.343 |
| 285 | 1.997 |
| 286 | 1.190 |
| 287 | 0.683 |
| 288 | 0.840 |
| 289 | 0.292 |
| 290 | 0.247 |

-continued

| Example # | RORγ Binding IC$_{50}$, uM |
|---|---|
| 291 | 0.235 |
| 292 | 0.140 |
| 293 | 0.296 |
| 294 | 0.199 |
| 295 | 0.085 |
| 296 | 0.225 |
| 297 | 0.062 |
| 298 | 0.757 |
| 299 | 0.060 |
| 300 | 0.218 |
| 301 | 0.114 |
| 302 | 0.062 |
| 303 | 0.070 |
| 304 | 0.116 |
| 305 | 0.025 |
| 306 | 0.061 |
| 307 | 0.173 |
| 308 | 0.436 |
| 309 | 0.069 |
| 310 | 0.067 |
| 311 | 0.035 |
| 312 | 0.134 |
| 313 | 0.671 |
| 314 | 0.081 |
| 315 | 0.085 |
| 316 | 0.100 |
| 317 | 0.139 |
| 318 | 0.330 |
| 319 | 0.048 |
| 320 | 0.480 |
| 321 | 0.736 |
| 322 | 0.123 |
| 323 | 2.060 |
| 324 | 0.058 |
| 325 | 0.064 |
| 326 | 0.189 |
| 327 | 0.285 |
| 328 | 0.084 |
| 329 | 0.138 |
| 330 | 0.060 |
| 331 | 0.040 |
| 332 | 0.047 |
| 333 | 0.054 |
| 334 | 0.139 |

What is claimed is:
1. The compound having the following formula (I):

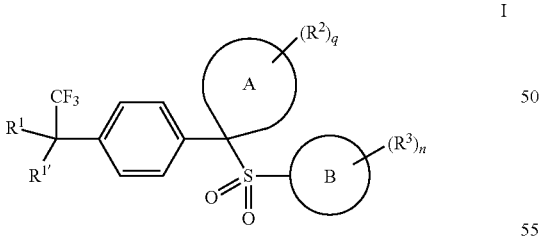

or a stereoisomer or pharmaceutically-acceptable salt thereof, wherein:
A is a 3-, 4- or 5-membered cycloalkyl or cycloalkenyl ring;
B is a, —(CH$_2$)$_r$-3-14 membered carbocycle, or —(CH$_2$)$_r$-5-12 membered heterocycle comprising carbon atoms, and 1-4 heteroatoms selected from N, O, and S(O)$_p$;
$R^1$ and $R^{1'}$ are, independently at each occurrence, hydrogen, halo, CF$_3$, OCF$_3$, CN, NO$_2$, —(CH$_2$)$_r$OR$^{1b}$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^{1a}$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;
$R^{1a}$ is, independently at each occurrence, hydrogen, =O, halo, OCF$_3$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;
$R^{1b}$ is, independently at each occurrence, hydrogen, CF$_3$, —(CH$_2$)$_r$OR$^b$, —(CH$_2$)$_r$S(O)$_p$R$^b$, —(CH2)$_r$C(O)R$^{1d}$, —(CH$_2$)$_r$C(O)OR$^b$, —(CH$_2$)$_r$OC(O)R$^b$, —(CH2)rNR$^{11}$R$^{11}$, —(CH$_2$)$_r$C(O)NR$^{11}$R$^{11}$, —(CH2)rNR$^b$C(O)R$^{1c}$, —(CH2)rNR$^b$C(O)OR$^c$, —(CH2)rNR$^b$C(O)NR$^{11}$R$^{11}$, —(CH2)rS(O)$_2$NR$^{11}$R$^{11}$, —(CH2)rNR$^b$S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-2 R$^a$;
$R^2$ is, independently at each occurrence, hydrogen, C$_{1-6}$ alkyl substituted with 0-3 R$^{2a}$, =CR$^{2a}$R$^{2a}$, C$_{2-6}$ alkenyl substituted with 0-3 R$^{2a}$, —(CH$_2$)$_r$OR$^{2b}$, —(CH$_2$)$_r$C(O)R$^{2b}$, —(CH$_2$)$_r$C(O)OR$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)NR$^{11}$R$^{11}$, —(CH$_2$)$_r$C(O)NR$^{11}$R$^{11}$, —(CH$_2$)$_r$NR$^{2b}$C(O)R$^{2c}$, —(CH$_2$)$_r$NR$^{2b}$C(O)OR$^2$, —(CH$_2$)$_r$NR$^{11}$R$^{11}$, —NR$^{2b}$S(O)$_p$R$^c$, —(CH$_2$)$_r$NR$^{2b}$S(O)$_p$NR$^{11}$R$^{11}$, —(CH2)r-3-10 membered carbocycle substituted with 0-3 R2a or —(CH$_2$)$_r$-4-10 membered heterocycle comprising carbon atoms, and 1-4 heteroatoms selected from N, O, and S(O)$_p$ substituted with 0-3 R$^{2a}$; or one R$^2$ together with an R$^2$ on an adjacent carbon combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, and S(O)$_p$ substituted with 0-3 R$^{2a}$;
$R^{2a}$ is, independently at each occurrence, hydrogen, =O, halo, OCF$_3$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{2b}$ is, independently at each occurrence, hydrogen, $CF_3$, —$(CH_2)_rOR^b$, —$(CH_2)_rS(O)_pR^b$, —$(CH2)_rC(O)R^{1d}$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —(CH2)r$NR^bC(O)R^{1c}$, —(CH2)r$NR^bC(O)OR^c$, —(CH2)r$NR^bC(O)NR^{11}R^{11}$, —$(CH_2)_rS(O)_2NR^{11}R^{11}$, —(CH2)r$NR^bS(O)_2R^c$, $C_{1-6}$ alkyl substituted with 0-2 $R^a$, $C_{1-6}$ haloalkyl, —$(CH_2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-2 $R^a$;

$R^{2c}$ is, independently at each occurrence, hydrogen, $C_{1-6}$ alkyl substituted with 0-3 $R^a$, $C_{2-6}$ alkenyl substituted with 0-3 $R^a$, $C_{3-10}$ cycloalkyl substituted with 0-3 $R^a$, $C_{6-10}$ aryl substituted with 0-3 $R^a$, or —$(CH_2)_r$ 5-10 membered heterocycle comprising carbon atoms and 1-4 heteroatoms selected from N, O, and $S(O)_p$, substituted with 0-3 $R^a$;

$R^{2d}$ is, independently at each occurrence, hydrogen, $C_{1-6}$ alkyl substituted with 0-2 $R^d$, $C_{1-6}$ haloalkyl, $C(O)NR^{11}R^{11}$, $C_{3-6}$ cycloalkyl substituted with 0-2 $R^d$, or $(CH_2)_r$-phenyl substituted with 0-2 $R^a$, a 5-10 membered heterocycle comprising carbon atoms and 1-4 heteroatoms selected from N, O, and $S(O)_p$, substituted with 0-3 $R^a$;

$R^3$ is selected from hydrogen, halo, $N_3$, CN, —$(CH_2)_rOR^{3b}$, —$(CH_2)_rNR^{11}R^{11}$, $C_{1-6}$ alkyl substituted with 0-3 $R^{3a}$, and $C_{3-10}$ cycloalkyl substituted with 0-3 $R^{3a}$; 4-10 membered heterocycle comprising carbon atoms and 1-4 heteroatoms selected from N, O, and $S(O)_p$, substituted with 0-3 $R^a$, or together with the carbon atoms to which they are attached, one $R^3$ combines with a second $R^3$ located on an adjacent atom to form a 5-7 membered carbocycle or a 5-7 membered heterocycle comprising carbon atoms and 1-4 heteroatom selected from N, O and $S(O)_p$, each optionally substituted with 0-3 $R^{3a}$;

$R^{3a}$ is, independently at each occurrence, hydrogen, =O, halo, $OCF_3$, $OCHF_2$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, $C_{1-6}$ alkyl substituted with 0-3 $R^a$, $C_{2-6}$ alkenyl substituted with 0-3 $R^a$, $C_{2-6}$ alkynyl substituted with 0-3 $R^a$, $C_{1-6}$ haloalkyl, —$(CH_2)_r$-3-14 membered carbocycle substituted with 0-3 $R^a$, or a —$(CH_2)_r$-5-10 membered heterocycle comprising carbon atoms and 1-4 heteroatoms selected from N, O, and $S(O)_p$ substituted with 0-3 $R^a$;

$R^{3b}$ is, independently at each occurrence, hydrogen, $CF_3$, —(CH2)r$OR^b$, —$(CH_2)_rS(O)_pR^b$, —$(CH_2)_rC(O)R^{1d}$, —$(CH_2)_rC(O)OR^b$, —(CH2)r$OC(O)R^b$, —(CH2)r$NR^{11}R^{11}$, —$(CH_2)_rC(O)NR^{11}R^{11}$, —$(CH_2)_rNR^bC(O)R^{1c}$, —$(CH_2)_rNR^bC(O)OR^c$, —$(CH_2)_rNR^bC(O)NR^{11}R^{11}$, —$(CH_2)_rS(O)_2NR^{11}R^{11}$, —(CH2)r$NR^bS(O)_2R^c$, $C_{1-6}$ alkyl substituted with 0-3 $R^a$, $C_{1-6}$ haloalkyl, —$(CH2)_r$-3-14 membered carbocycle substituted with 0-3 $R^a$, or —$(CH_2)_r$-5-7 membered heterocycle comprising carbon atoms and 1-4 heteroatoms selected from N, O, and $S(O)_p$ substituted with 0-3 $R^a$;

$R^{11}$ is, independently at each occurrence, hydrogen, $C_{1-6}$ alkyl substituted with 0-3 $R^d$, $CF_3$, $C_{3-10}$ cycloalkyl substituted with 0-3 $R^d$, $(CH)_r$-phenyl substituted with 0-3 $R^d$, or —$(CH_2)_r$-5-7 membered heterocycle comprising carbon atoms and 1-4 heteroatoms selected from N, O, and $S(O)_p$ substituted with 0-3 $R^d$; or, together with the nitrogen atom to which they are attached, one $R^1$ combines with a second $R^{11}$ to form a 4-12 membered[DJ1] heterocycle comprising carbon atoms and 1-4 heteroatoms selected from N, O, and $S(O)_p$ substituted with 0-3 $R^d$;

$R^a$ is, independently at each occurrence, hydrogen, =O, halo, $OCF_3$, $CF_3$, $CHF_2$, CN, $NO_2$, —$(CH_2)_rOR^b$, —$(CH_2)_rS(O)_pR^b$, —$(CH_2)_rC(O)R^b$, —$(CH_2)_rC(O)OR^b$, —$(CH_2)_rOC(O)R^b$, —$(CH_2)_rNR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11R}$, —$S(O)_pNR^{11}R^{11}$, —$NR^bS(O)_pR^c$, $C_{1-6}$ alkyl substituted with 0-3 $R^f$, $C_{1-6}$ haloalkyl, $C_{2-6}$ alkenyl substituted with 0-3 $R^f$, $C_{2-6}$ alkynyl substituted with 0-3 $R^f$, —$(CH_2)_r$-3-14 membered carbocycle substituted with 0-3 $R^f$, or —$(CH_2)_r$-5-7 membered heterocycle comprising carbon atoms and 1-4 heteroatoms selected from N, O, and $S(O)_p$ substituted with 0-3 $R^f$;

$R^b$ is, independently at each occurrence, hydrogen, $C_{1-6}$ alkyl substituted with 0-3 $R^d$, $C_{1-6}$ haloalkyl, $C_{2-6}$ alkenyl substituted with 0-3 $R^d$, $C_{3-6}$ cycloalkyl substituted with 0-3 $R^d$, —$(CH_2)_r$-5-7 membered heterocycle comprising carbon atoms and 1-4 heteroatoms selected from N, O, and $S(O)_p$ substituted with 0-3 $R^f$, or $(CH_2)_r$-6-10 atom carbocycle substituted with 0-3 $R^d$;

$R^c$ is, independently at each occurrence, $C_{1-6}$ alkyl substituted with 0-3 $R^f$, $(CH_2)_r$-$C_{3-6}$ cycloalkyl substituted with 0-3 $R^f$, —$(CH_2)_r$-5-7 membered heterocycle comprising carbon atoms and 1-4 heteroatoms selected from N, O, and $S(O)_p$ substituted with 0-3 $R^f$, or $(CH_2)_r$-phenyl substituted with 0-3 $R^f$;

$R^d$ is, independently at each occurrence, hydrogen, =O, halo, $OCF_3$, $CF_3$, CN, $NO_2$, —$OR^e$, —$(CH_2)_rC(O)R^c$, —$NR^eR^e$, —$NR^eC(O)OR^c$, $C(O)NR^eR^e$, —$NR^eC(O)R^c$, $CO_2R$, —$NR^eSO_2R^c$, $SO_2R^c$, $C_{1-6}$ alkyl substituted with 0-3 $R^f$, $C_{3-6}$ cycloalkyl substituted with 0-3 $R^f$, $(CH_2)_r$-phenyl substituted with 0-3 $R^f$ or —$(CH_2)_r$-5-7 membered heterocycle comprising carbon atoms and 1-4 heteroatoms selected from N, O, and $S(O)_p$ substituted with 0-3 $R^f$;

$R^e$ is, independently at each occurrence, selected from hydrogen, $C(O)NR^fR^f$, $C_{1-6}$ alkyl, $C_{3-6}$ cycloalkyl, or $(CH_2)_r$-phenyl substituted with 0-3 $R^f$;

$R^f$ is, independently at each occurrence, hydrogen, =O, halo, CN, $NH_2$, $NH(C_{1-6}$ alkyl), $N(C_{1-6}$ alkyl$)_2$, $SO_2(C_{1-6}$ alkyl), $CO_2H$, $CO_2(C_{1-6}$ alkyl), OH, $C_{3-6}$ cycloalkyl, $CF_3$ or $O(C_{1-6}$ alkyl);

or $R^f$ is, independently at each occurrence, an optionally substituted —$(CH_2)_r$-5-10 membered heterocycle comprising carbon atoms and 1-4 heteroatoms selected from N, O, and S(O), phenyl or $C_{3-6}$ cycloalkyl, each group optionally substituted with 1-3 groups selected from halo, CN, CF$_3$, C$_{1-6}$ alkyl and O(C$_{1-6}$ alkyl);
q and n are independently selected from 0, 1, 2 and 3;
p is 0, 1, or 2; and
r is 0, 1, 2, 3, or 4.

2. A compound according to claim 1, or a stereoisomer or pharmaceutically-acceptable salt thereof, wherein B is a phenyl ring.

3. The compound according to claim 1, or a stereoisomer or pharmaceutically-acceptable salt thereof, wherein:
R$^{1'}$ is halo, CF$_3$, or C$_{1-6}$ alkyl; and
R$^1$ is hydrogen, NH$_2$, CF$_3$, halo, C$_{1-6}$ alkyl substituted with 0-3 R$^{1a}$, —(CH$_2$)$_r$OR$^{1b}$, or (CH$_2$)$_r$-phenyl substituted with 0-3 R$^{1a}$.

4. The compound according to claim 1, or a stereoisomer or pharmaceutically-acceptable salt thereof, wherein
R$^3$ is hydrogen, halo, N$_3$, CN, OR$^{3b}$, —NH$_2$, NH(C$_{1-6}$ alkyl), N(C$_{1-6}$alkyl)$_2$, C$_{1-6}$ alkyl substituted with 0-3 R$^{3a}$ or C$_{3-10}$ cycloalkyl substituted with 0-3 R$^{3a}$;
R$^{3a}$ is, independently at each occurrence, hydrogen, =O, halo, OCF$_3$, OCHF$_2$, CF$_3$, CHF$_2$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^a$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH$_2$)$_r$-3-14 membered carbocycle substituted with 0-3 R$^a$, a —(CH$_2$)$_r$-5-7 membered heteroaryl comprising carbon atoms and 1-4 heteroatoms selected from N, S or O substituted with 0-3 R$^a$, or a —(CH$_2$)$_r$-5-10 membered heterocycle comprising carbon atoms and 1-4 heteroatoms selected from N, O, and S(O)$_p$ substituted with 0-3 R$^a$; and
R$^{3b}$ is, independently at each occurrence, hydrogen, C$_{1-6}$ alkyl substituted with 0-3 R$^a$ or phenyl substituted with 0-3 R$^a$.

5. A compound according to claim 1 having the following formula

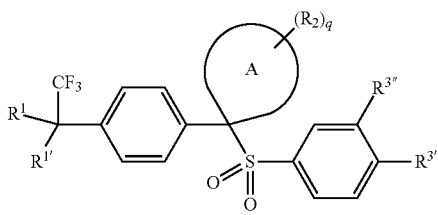

or a stereoisomer or pharmaceutically-acceptable salt thereof, wherein:
R$^{1'}$ is halo, CF$_3$, or C$_{1-6}$ alkyl;
R$^1$ is hydrogen, NH$_2$, CF$_3$, halo, C$_{1-6}$ alkyl substituted with 0-3 R$^{1a}$, —(CH$_2$)$_r$OR$^{1b}$, or (CH$_2$)$_r$-phenyl substituted with 0-3 R$^{1a}$;
R$^{1a}$ is, independently at each occurrence, hydrogen, =O, halo, OCF$_3$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle substituted with 0-3 R$^a$, or —(CH$_2$)$_r$-5-7 membered heterocycle comprising carbon atoms and 1-4 heteroatoms selected from N, O, and S(O)$_p$ substituted with 0-3 R$^a$;
R$^{1b}$ is, independently at each occurrence, hydrogen, CF$_3$, —(CH$_2$)$_r$OR$^b$, —(CH$_2$)$_r$S(O)$_p$R$^b$, —(CH$_2$)$_r$C(O)R$^{1d}$, —(CH$_2$)$_r$C(O)OR$^b$, —(CH$_2$)$_r$OC(O)R$^b$, —(CH2)rNR$^{11}$R$^{11}$, —(CH$_2$)$_r$C(O)NR$^{11}$R$^{11}$, —(CH2)rNR$^b$C(O)R$^{1c}$, —(CH2)rNR$^b$C(O)OR$^c$, —(CH2)rNR$^b$C(O)NR$^{11}$R$^{11}$, —(CH2)rS(O)$_2$NR$^{11}$R$^{11}$, —(CH2)rNR$^b$S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-3 R$^a$, or —(CH2)$_r$-5-7 membered heterocycle comprising carbon atoms and 1-4 heteroatoms selected from N, O, and S(O)$_p$ substituted with 0-2 R$^a$;
R$^2$ is, independently at each occurrence, hydrogen, C$_{1-6}$ alkyl substituted with 0-3 R$^{2a}$, =CR$^{2a}$R$^{2a}$, C$_{2-6}$ alkenyl substituted with 0-3 R$^{2a}$, —(CH$_2$)$_r$OR$^{2b}$, —(CH$_2$)$_r$C(O)R$^{2b}$, —(CH$_2$)$_r$C(O)OR$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)NR$^{11}$R$^{11}$, —(CH$_2$)$_r$C(O)NR$^{11}$R$^{11}$, —(CH$_2$)$_r$NR$^{2b}$C(O)R$^{2c}$, —(CH$_2$)$_r$NR$^{2b}$C(O)OR$^{2c}$, —(CH$_2$)$_r$NR$^{11}$R$^{11}$, NR$^{2b}$S(O)$_p$R$^c$, or —(CH2)$_r$-5-7 membered heterocycle comprising carbon atoms, and 1-4 heteroatoms selected from N, O, and S(O)$_p$ substituted with 0-3 R$^{2a}$; or one R$^2$ together with an R$^2$ on an adjacent carbon combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, and S(O)$_p$ substituted with 0-3 R$^{2a}$;
R$^{2a}$ is hydrogen, NR$^{11}$R$^{11}$, or C$_{1-6}$ alkyl substituted with 0-3 R$^a$, or 3-10 membered carbocycle substituted with 0-3 R$^a$;
R$^{2b}$ is hydrogen, C$_{1-6}$ alkyl substituted with 0-3 R$^a$, C$_{3-6}$ cycloalkyl substituted with 0-3 R$^a$, or 5-7 membered heterocycle comprising carbon atoms and 1-4 heteroatoms selected from N, O, and S(O)$_p$ substituted with 0-3 R$^a$, or (CH$_2$)$_r$-phenyl substituted with 0-3 R$^a$;
R$^{2c}$ is independently at each occurrence hydrogen, C$_{1-6}$ alkyl substituted with 0-3 R$^a$, C$_{2-6}$ alkenyl substituted with 0-3 R$^a$, C$_{3-6}$ cycloalkyl substituted with 0-3 R$^a$, C$_{6-10}$ aryl substituted with 0-3 R$^a$, or a 5-10 membered heterocycle comprising carbon atoms and 1-4 heteroatoms selected from N, O, and S, substituted with 0-3 R$^a$;
R$^{2d}$ is, independently at each occurrence, hydrogen, C$_{1-6}$ alkyl substituted with 0-2 R$^d$, C$_{1-6}$ haloalkyl, C(O)NR$^{11}$R$^{11}$, C$_{3-6}$ cycloalkyl substituted with 0-2 R$^d$, or (CH$_2$)$_r$-phenyl substituted with 0-2 R$^a$, a 5-10 membered heterocycle comprising carbon atoms and 1-4 heteroatoms selected from N, O, and S, substituted with 0-3 R$^a$;
R$^{3'}$ and R$^{3''}$ are, independently, hydrogen, halo, N$_3$, CN, OR$^{3b}$, —NH$_2$, NH(C$_{1-6}$ alkyl), N(C$_1$-6 alkyl)$_2$, C$_{1-6}$ alkyl substituted with 0-3 R$^{3a}$ or C$_{3-10}$ cycloalkyl substituted with 0-3 R$^{3a}$;
R$^{3a}$ is, independently at each occurrence, hydrogen, =O, halo, OCF$_3$, OCHF$_2$, CF$_3$, CHF$_2$, CN, NO$_2$, —(CH$_2$)$_r$OR$^b$, —(CH$_2$)$_r$S(O)$_p$R$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{2-6}$ alkenyl substituted with 0-3 R$^a$, C$_{2-6}$ alkynyl substituted with 0-3 R$^a$, C$_{1-6}$ haloalkyl, —(CH₂)ᵣ-3-14 membered carbocycle substituted with 0-3 Rᵃ, or a —(CH₂)ᵣ-5-10 membered heterocycle comprising carbon atoms and 1-4 heteroatoms selected from N, O, and S(O)ₚ substituted with 0-3 Rᵃ;

R³ᵇ is, independently at each occurrence, hydrogen, C₁₋₆ alkyl substituted with 0-3 Rᵃ or phenyl substituted with 0-3 Rᵃ;

R¹¹ is, independently at each occurrence, hydrogen, C₁₋₆ alkyl substituted with 0-3 Rᵈ, CF₃, C₃₋₁₀ cycloalkyl substituted with 0-3 Rᵈ, (CH)ᵣ-phenyl substituted with 0-3 Rᵈ, or —(CH₂)ᵣ-5-7 membered heterocycle comprising carbon atoms and 1-4 heteroatoms selected from N, O, and S(O)ₚ substituted with 0-3 Rᵈ; or, together with the nitrogen atom to which they are attached, one R¹¹ combines with a second R¹¹ to form a 4-7 membered heterocycle comprising carbon atoms and 1-4 heteroatoms selected from N, O, and S(O)ₚ substituted with 0-3 Rᵈ;

Rᵃ is, independently at each occurrence, hydrogen, =O, halo, OCF₃, CF₃, CHF₂, CN, NO₂, —(CH₂)ᵣORᵇ, —(CH₂)ᵣS(O)ₚRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, C₁₋₆ alkyl substituted with 0-3 Rᶠ, C₁₋₆ haloalkyl, C₂₋₆ alkenyl substituted with 0-3 Rᶠ, C₂₋₆ alkynyl substituted with 0-3 Rᶠ, —(CH₂)ᵣ-3-14 membered carbocycle, or —(CH₂)ᵣ-5-7 membered heterocycle comprising carbon atoms and 1-4 heteroatoms selected from N, O, and S(O)ₚ substituted with 0-3 Rᶠ;

Rᵇ is, independently at each occurrence, hydrogen, C₁₋₆ alkyl substituted with 0-3 Rᵈ, C₁₋₆ haloalkyl, C₃₋₆ cycloalkyl substituted with 0-3 Rᵈ, or —(CH₂)ᵣ-5-7 membered heterocycle comprising carbon atoms and 1-4 heteroatoms selected from N, O, and S(O)ₚ substituted with 0-3 Rᶠ, or (CH₂)ᵣ-6-10 carbocycle substituted with 0-3 Rᵈ;

Rᶜ is, independently at each occurrence, C₁₋₆ alkyl substituted with 0-3 Rᶠ, (CH₂)ᵣ—C₃₋₆ cycloalkyl substituted with 0-3 Rᶠ, —(CH₂)ᵣ-5-7 membered heterocycle comprising carbon atoms and 1-4 heteroatoms selected from N, O, and S(O)ₚ substituted with 0-3 Rᶠ, or (CH₂)ᵣ-phenyl substituted with 0-3 Rᶠ;

Rᵈ is, independently at each occurrence, hydrogen, =O, halo, OCF₃, CF₃, CN, NO₂, —ORᵉ(CH₂)ᵣC(O)Rᶜ, —NRᵉRᵉ, —NRᵉC(O)ORᶜ, C(O)NRᵉRᵉ, —NRᵉC(O)Rᶜ, CO₂Rᶜ, —NRᵉSO₂Rᶜ, SO₂Rᶜ, C₁₋₆ alkyl substituted with 0-3 Rᶠ, C₃₋₆ cycloalkyl substituted with 0-3 Rᶠ, (CH₂)ᵣ-phenyl substituted with 0-3 Rᶠ or —(CH₂)ᵣ-5-7 membered heterocycle comprising carbon atoms and 1-4 heteroatoms selected from N, O, and S(O)ₚ substituted with 0-3 Rᶠ;

Rᵉ is, independently at each occurrence, selected from hydrogen, C(O)NRᶠRᶠ, C₁₋₆ alkyl, C₃₋₆ cycloalkyl, and (CH₂)ᵣ-phenyl substituted with 0-3 Rᶠ;

Rᶠ is, independently at each occurrence, hydrogen, =O, halo, CN, NH₂, NH(C₁₋₆alkyl), N(C₁₋₆alkyl)₂, SO₂(C₁₋₆alkyl), CO₂H, CO₂(C₁₋₆alkyl), OH, C₃₋₆ cycloalkyl, CF₃ or O(C₁₋₆alkyl);

or Rᶠ is, independently at each occurrence, an optionally substituted —(CH₂)ᵣ-5-10 membered heterocycle comprising carbon atoms and 1-4 heteroatoms selected from N, O, and S(O), phenyl or C₃₋₆ cycloalkyl, each group optionally substituted with 1-3 groups selected from halo, CN, CF₃, C₁₋₆ alkyl or O(C₁₋₆alkyl);

p and q are, independently at each occurrence, 0, 1, or 2; and r is 0, 1, 2, 3, or 4.

6. A compound according to claim 5, or a stereoisomer or pharmaceutically-acceptable salt thereof, wherein R¹' is CF₃; and R¹ is OR¹ᵇ or halo.

7. A compound according to claim 5, or a stereoisomer or pharmaceutically-acceptable salt thereof, wherein:

R¹' is F, CF₃, CH₃, and CH₂CH₃; and

R¹ is:

OH, OMe, F, Cl, NH₂, CH₃, Ph, Bz, (CH₂)₂Ph,

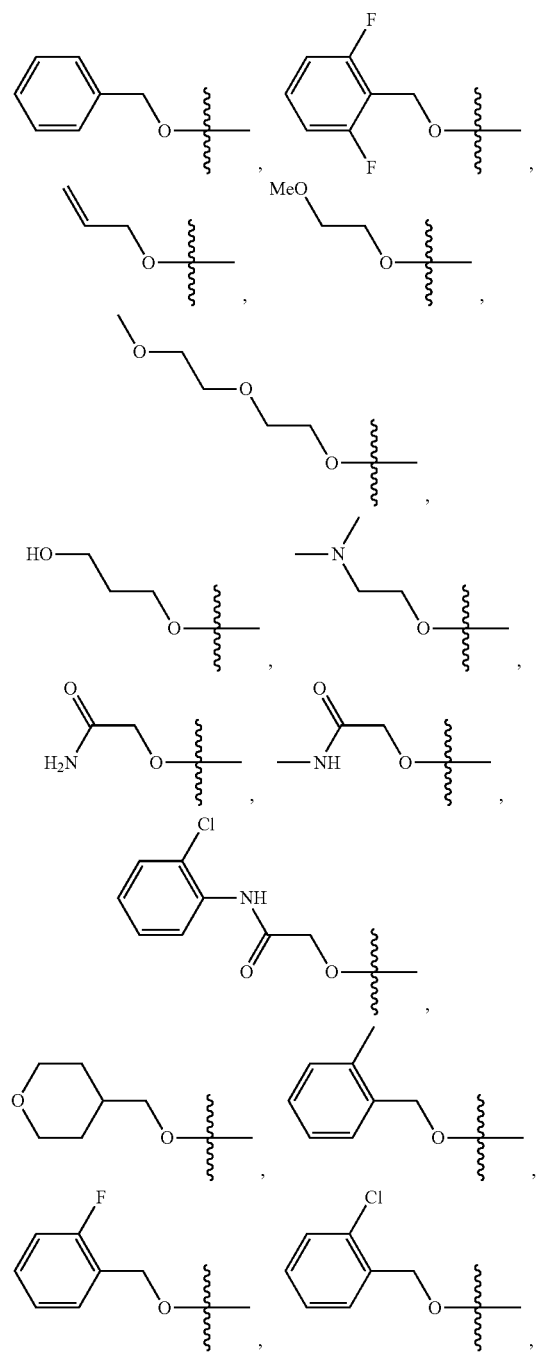

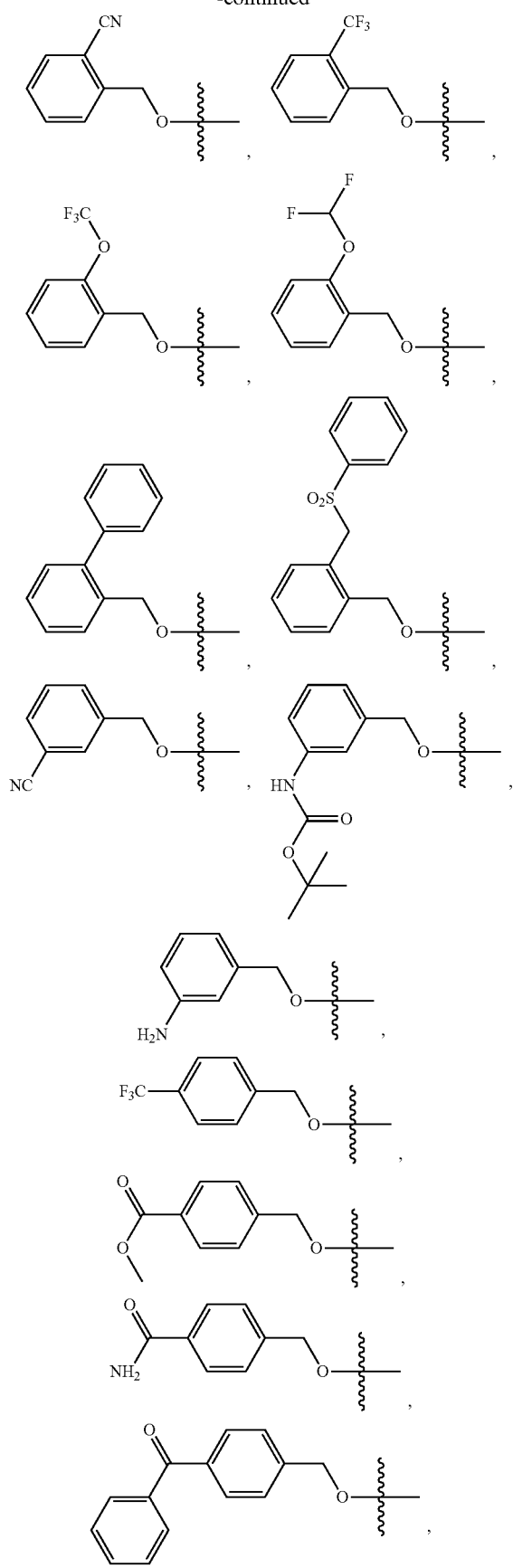
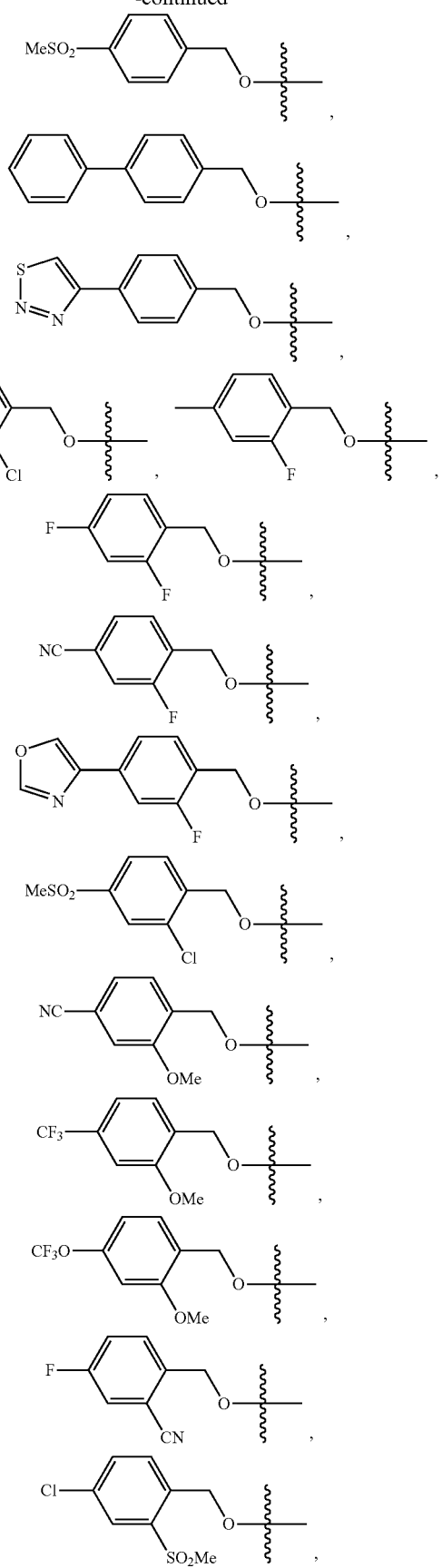

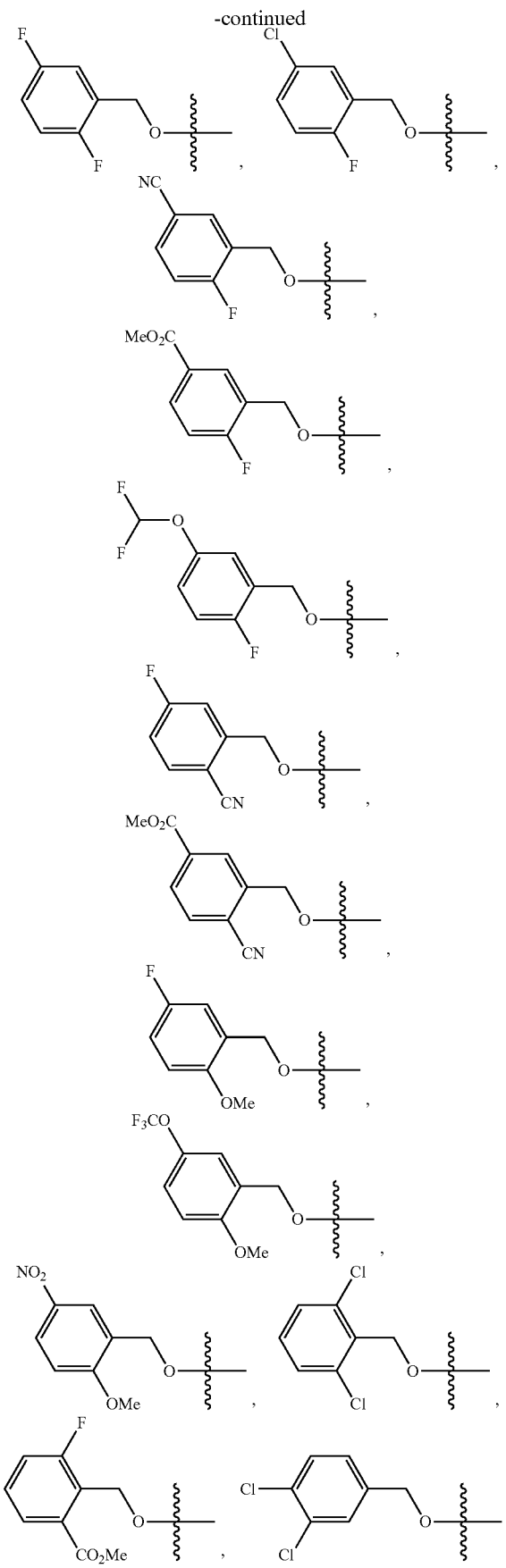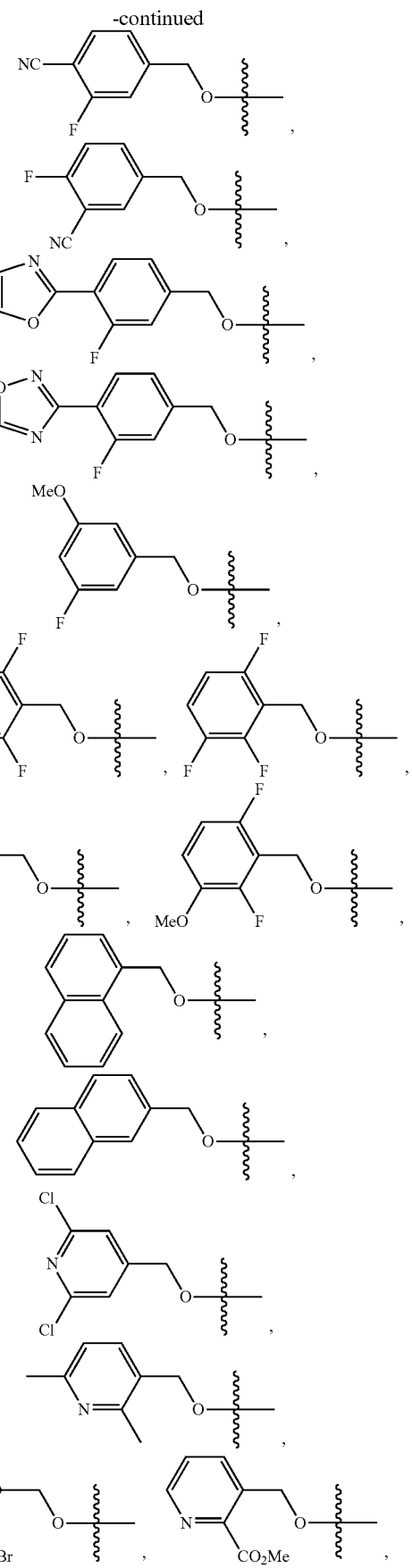

-continued

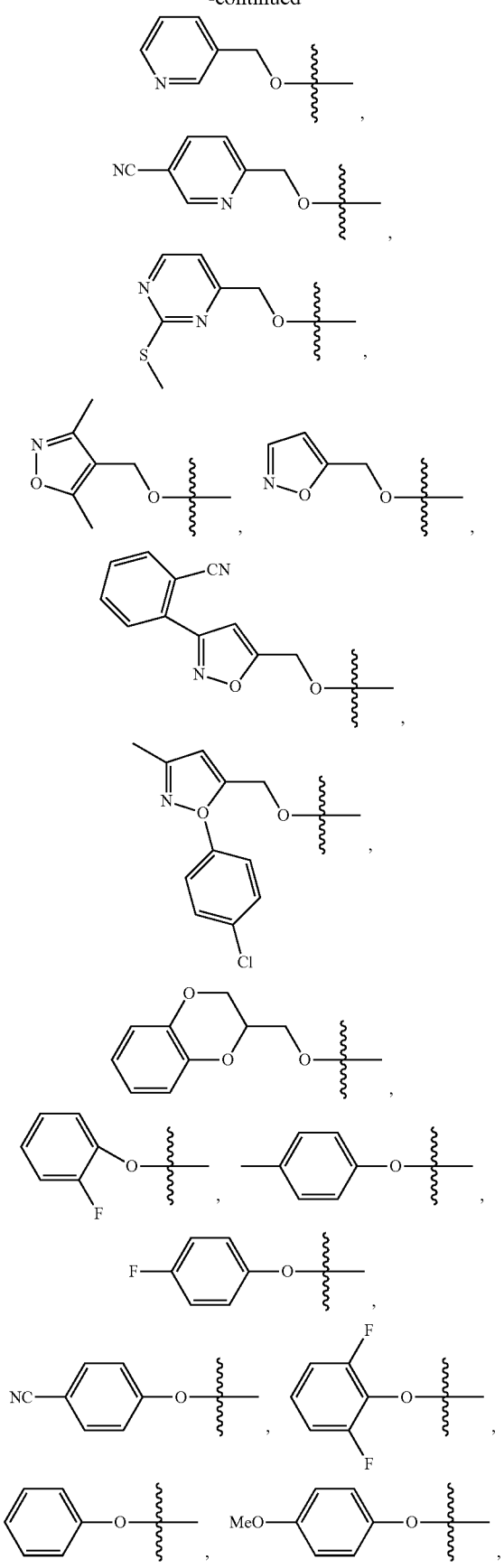

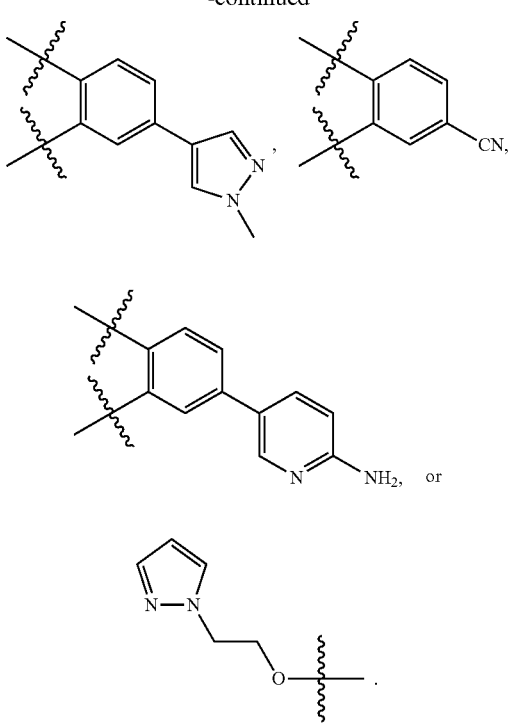

8. A compound according to claim 5, or a stereoisomer or pharmaceutically-acceptable salt thereof, wherein:

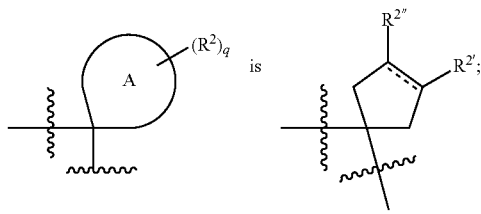

and

R$^{2'}$ and R$^{2''}$ are, independently at each occurrence, hydrogen, =CR$^{2a}$R$^{2a}$, —(CH$_2$)$_r$OR$^{2b}$, —(CH$_2$)$_r$C(O)R$^{2b}$, —(CH$_2$)$_r$C(O)OR$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O) NR$^{11}$R$^{11}$, —(CH$_2$)$_r$C(O)NR$^{11}$R$^{11}$, —(CH$_2$)$_r$NR$^{2b}$C(O) R$^{2c}$, —(CH$_2$)$_r$NR$^{2b}$C(O)OR$^{2}$, —(CH$_2$)$_r$NR$^{11}$R$^{11}$, NR$^{2b}$S(O)$_p$R$^c$, or —(CH$_2$)$_r$-5-7 membered heterocycle comprising carbon atoms, and 1-4 heteroatoms selected from N, O, and S(O)$_p$ substituted with 0-3 R$^{2a}$; or together with the atoms to which they are attached, R$^{2'}$ and R$^{2''}$ combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, and S(O)$_p$ substituted with 0-3 R$^{2a}$.

9. A compound according to claim 5, or a stereoisomer or pharmaceutically-acceptable salt thereof, wherein:

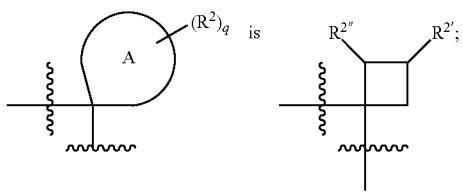

and

R[2'] and R[2'''] are, independently at each occurrence, hydrogen, =CR$^{2a}$R$^{2a}$, —(CH$_2$)$_r$OR$^{2b}$, —(CH$_2$)$_r$C(O)R$^{2b}$, —(CH$_2$)$_r$C(O)OR$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)NR$^{11}$R$^{11}$, —(CH$_2$)$_r$C(O)NR$^{11}$R$^{11}$, —(CH$_2$)$_r$NR$^{2b}$C(O)R$^{2c}$, —(CH$_2$)$_r$NR$^{2b}$C(O)OR$^{2C}$, —(CH$_2$)$_r$NR$^{11}$R$^{11}$, —NR$^{2b}$S(O)$_p$R$^c$, or —(CH2)$_r$-5-7 membered heterocycle comprising carbon atoms, and 1-4 heteroatoms selected from N, O, and S(O)$_p$ substituted with 0-3 R$^{2a}$; or together with the atoms to which they are attached, R$^{2'}$ and R$^{2'''}$ combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, and S(O)$_p$ substituted with 0-3 R$^{2a}$.

10. A compound according to claim 5, or a stereoisomer or pharmaceutically-acceptable salt thereof, wherein:

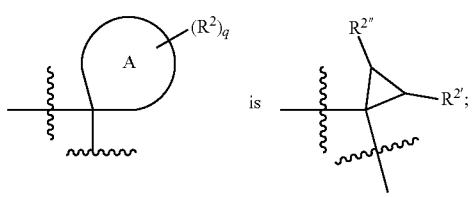

and

R[2'] and R[2'''] are, independently at each occurrence, hydrogen, =CR$^{2a}$R$^{2a}$, —(CH$_2$)$_r$OR$^{2b}$, —(CH$_2$)$_r$C(O)R$^{2b}$, —(CH$_2$)$_r$C(O)OR$^{2b}$, —(CH$_2$)$_r$OC(O)OR$^{2b}$, —(CH$_2$)$_r$OC(O)NR$^{11}$R$^{11}$, —(CH$_2$)$_r$NR$^{2b}$C(O)NR$^{11}$R$^{11}$, —(CH$_2$)$_r$C(O)NR$^{11}$R$^{11}$, —(CH$_2$)$_r$NR$^{2b}$C(O)R$^{2c}$, —(CH$_2$)$_r$NR$^{2b}$C(O)OR$^{2}$, —(CH$_2$)$_r$NR$^{11}$R$^{11}$, —NR$^{2b}$S(O)$_p$R$^c$, or —(CH$_2$)$_r$-5-7 membered heterocycle comprising carbon atoms, and 1-4 heteroatoms selected from N, O, and S(O)$_p$ substituted with 0-3 R$^{2a}$; or together with the atoms to which they are attached, R$^{2'}$ and R$^{2'''}$ combine to form a fused ring substituted with 0-3 R$^{2a}$, wherein the fused ring is selected from 3-10 membered carbocycle substituted with 0-3 R$^{2a}$, or 3-7 membered heterocycle comprising carbon atoms and 1-4 heteroatoms selected from N, O, and S(O)$_p$ substituted with 0-3 R$^{2a}$.

11. A compound according to claim 5, or a stereoisomer or pharmaceutically-acceptable salt thereof, wherein R$^{2'''}$ is hydrogen and R$^{2'}$ is CO$_2$R$^{2b}$, C(O)NR$^{11}$R$^{11}$, —NR$^{11}$R$^{11}$, —NR$^{2b}$C(O)R$^{2c}$, —NR$^{2b}$C(O)OR$^{2c}$, or —NR$^{2b}$C(O)NR$^{11}$R$^{11}$.

12. A compound according to claim 5, or a stereoisomer or pharmaceutically-acceptable salt thereof, wherein R$^{2'}$ is: hydrogen, OH, NH$_2$, =CH$_2$, CO$_2$H, —C(O)OMe, —NHSO$_2$Me,

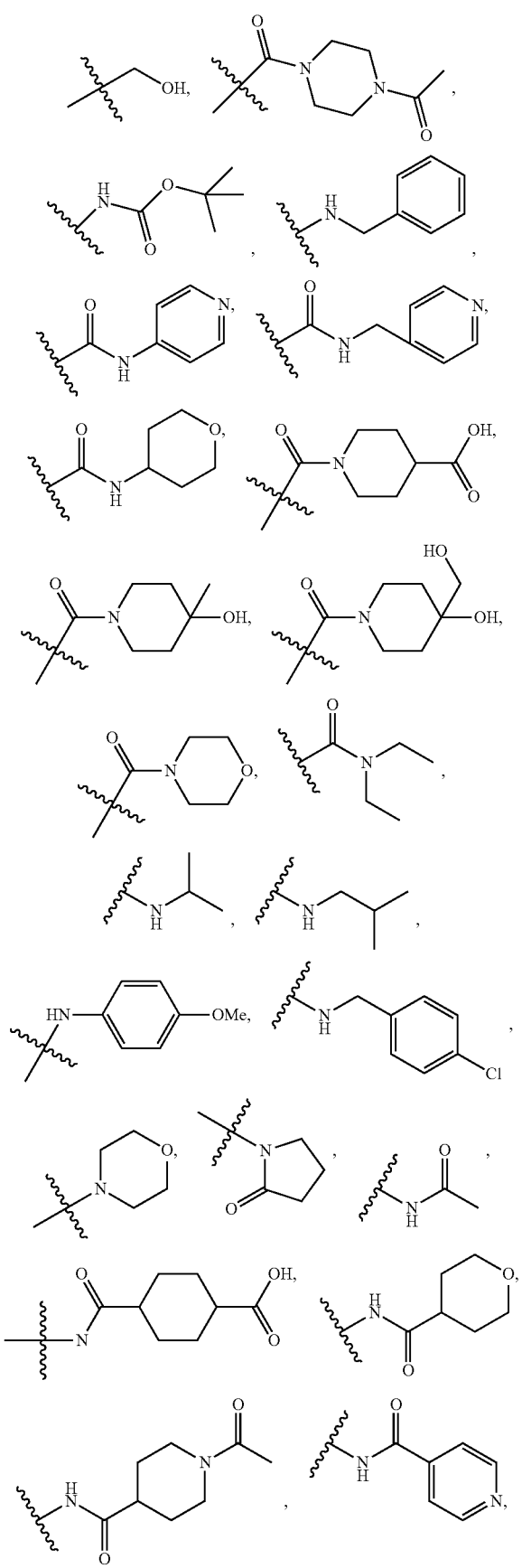

225
-continued
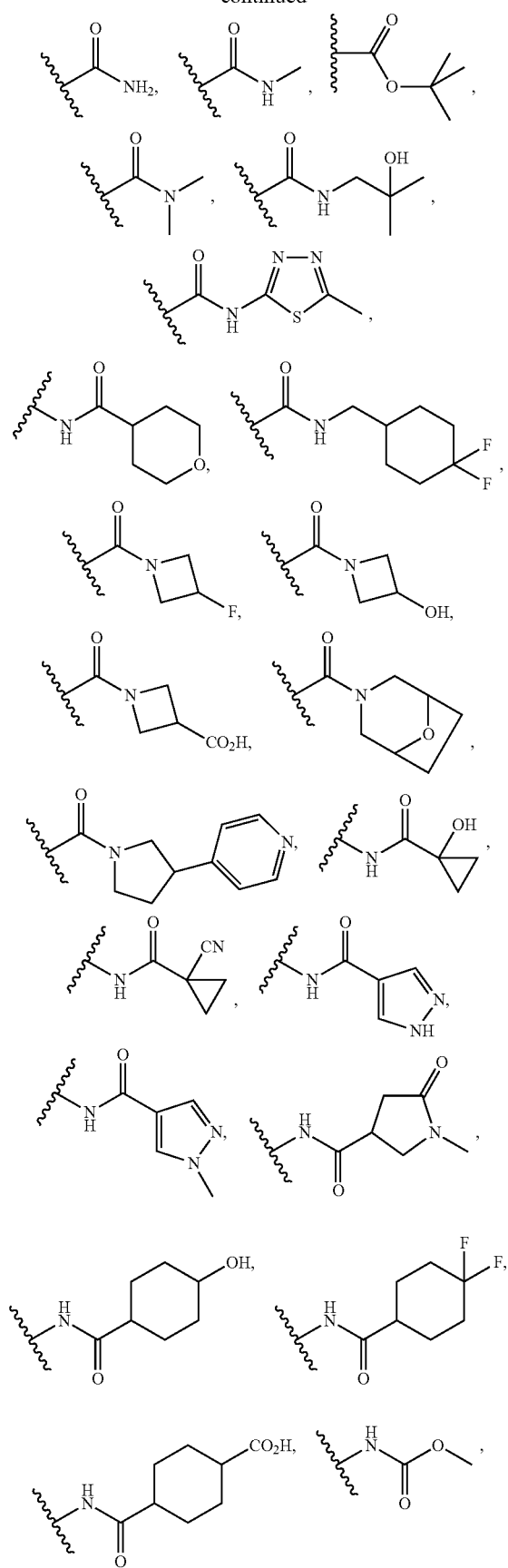
226
-continued
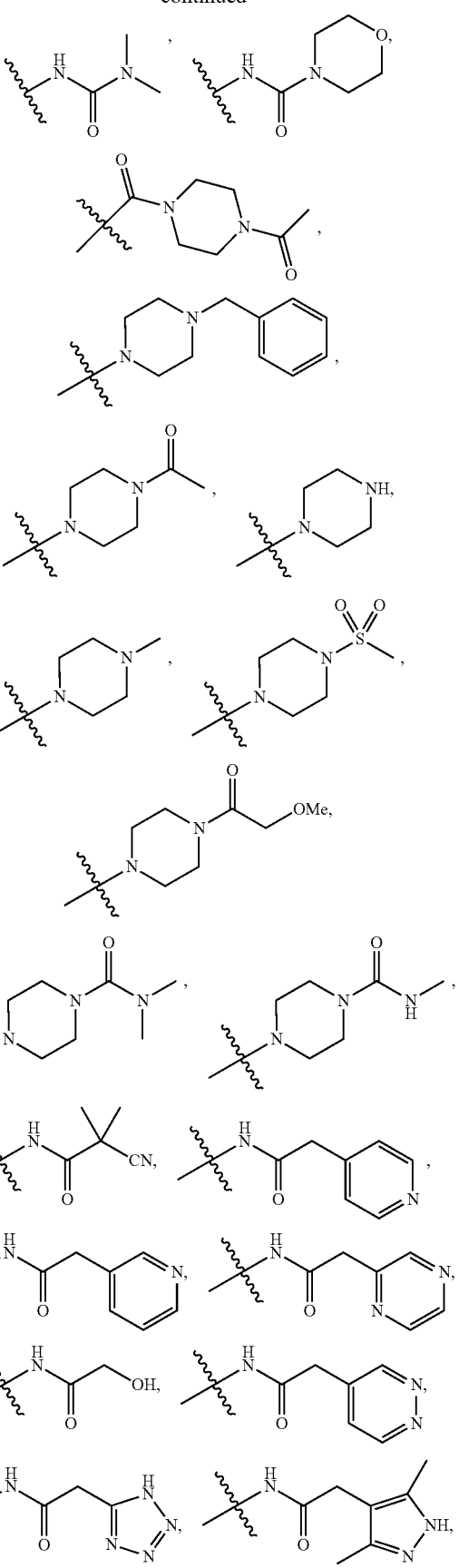

-continued

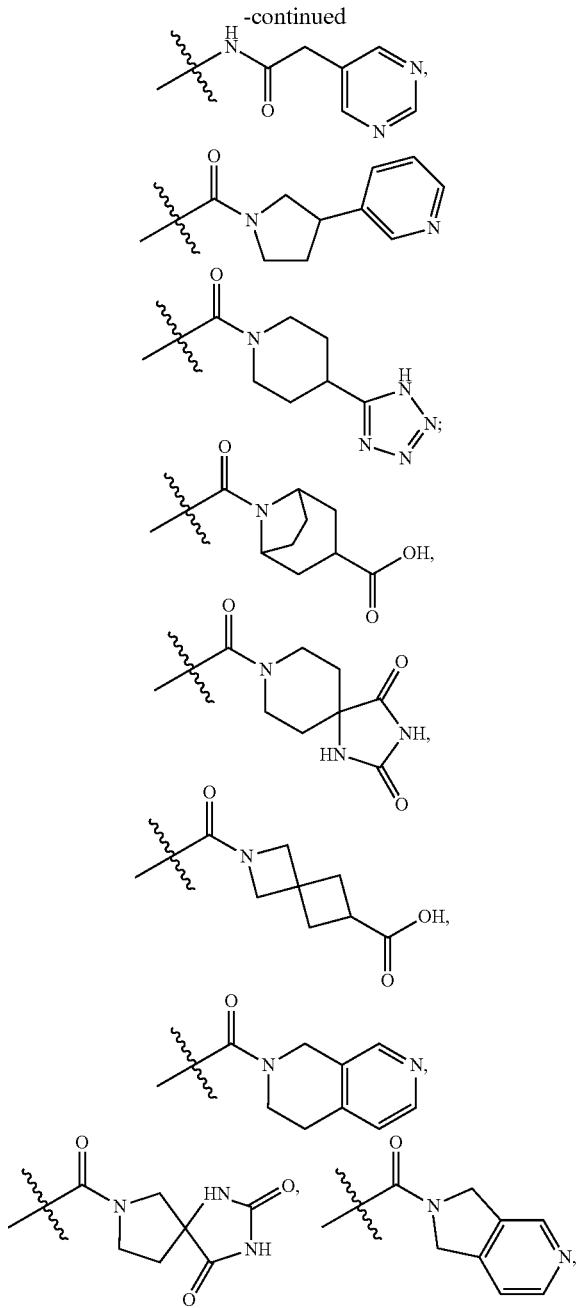

-continued

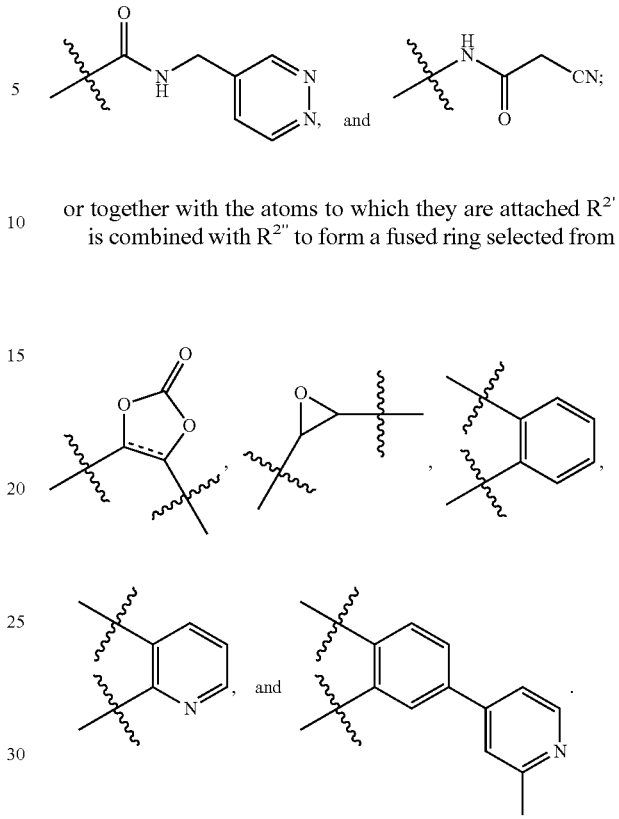

or together with the atoms to which they are attached $R^{2'}$ is combined with $R^{2''}$ to form a fused ring selected from 13. A compound according to claim 5, or a stereoisomer or pharmaceutically-acceptable salt thereof, wherein $R^{3'''}$ and $R^{3'}$ are, independently, hydrogen, halo, $N_3$, CN, —O(phenyl), —$NH_2$, —NH($C_{1-6}$ alkyl), —N($C_{1-6}$ alkyl)$_2$, $C_{1-6}$ alkyl or $C_{3-6}$ cycloalkyl.

14. A pharmaceutical composition comprising one or more compounds according to claim 1 and a pharmaceutically acceptable carrier or diluent.

15. A method of diagnosing or treating a disease or disorder selected from an autoimmune disease or disorder, asthma, an allergic disease or disorder, a metabolic disease or disorder, and cancer in a subject, said method comprising administering to the subject a therapeutically-effective amount of a compound according to claim 1.

* * * * *